US009651553B2

(12) United States Patent
Wang et al.

(10) Patent No.: US 9,651,553 B2
(45) Date of Patent: *May 16, 2017

(54) IMMUNO-BASED RETARGETED ENDOPEPTIDASE ACTIVITY ASSAYS

(71) Applicant: Allergan, Inc., Irvine, CA (US)

(72) Inventors: Joanne Wang, Irvine, CA (US); Hong Zhu, San Diego, CA (US); Dianne D. Hodges, Tustin, CA (US); Ester Fernandez-Salas, Fullerton, CA (US)

(73) Assignee: Allergan, Inc., Irvine, CA (US)

( * ) Notice: Subject to any disclaimer, the term of this patent is extended or adjusted under 35 U.S.C. 154(b) by 44 days.

This patent is subject to a terminal disclaimer.

(21) Appl. No.: 14/695,938

(22) Filed: Apr. 24, 2015

(65) Prior Publication Data

US 2015/0301050 A1 Oct. 22, 2015

Related U.S. Application Data

(63) Continuation of application No. 13/801,711, filed on Mar. 13, 2013, now abandoned, which is a continuation of application No. 12/723,595, filed on Mar. 12, 2010, now Pat. No. 8,455,203.

(60) Provisional application No. 61/160,217, filed on Mar. 13, 2009.

(51) Int. Cl.

| | |
|---|---|
| ***C12N 9/00*** | (2006.01) |
| ***C12Q 1/37*** | (2006.01) |
| ***G01N 33/573*** | (2006.01) |
| ***G01N 33/50*** | (2006.01) |
| ***G01N 33/53*** | (2006.01) |
| ***C12N 9/50*** | (2006.01) |
| ***C07K 16/18*** | (2006.01) |

(52) U.S. Cl.

CPC ........... *G01N 33/573* (2013.01); *C07K 16/18* (2013.01); *C12N 9/50* (2013.01); *C12Q 1/37* (2013.01); *G01N 33/5014* (2013.01); *G01N 33/5035* (2013.01); *G01N 33/53* (2013.01); *C07K 2317/34* (2013.01); *C07K 2317/92* (2013.01); *G01N 2333/33* (2013.01); *G01N 2333/96425* (2013.01)

(58) Field of Classification Search

CPC .................................... C12N 9/50; C12Q 1/37

See application file for complete search history.

(56) References Cited

U.S. PATENT DOCUMENTS

| | | | | |
|---|---|---|---|---|
| 5,962,637 | A | 10/1999 | Shone et al. | |
| 6,043,042 | A | 3/2000 | Shone et al. | |
| 6,337,386 | B1 | 1/2002 | Shone et al. | |
| 7,183,066 | B2 | 2/2007 | Fernandez-Salas et al. | |
| 7,208,285 | B2 | 4/2007 | Steward et al. | |
| 7,244,437 | B2 | 7/2007 | Donovan | |
| 7,332,567 | B2 | 2/2008 | Steward et al. | |
| 7,399,607 | B2 | 7/2008 | Williams et al. | |
| 7,413,742 | B2 | 8/2008 | Donovan | |
| 7,598,027 | B2 | 10/2009 | Fernandez-Salas et al. | |
| 7,645,570 | B2 | 1/2010 | Fernandez-Salas et al. | |
| 7,658,933 | B2 | 2/2010 | Foster et al. | |
| 7,749,514 | B2 | 7/2010 | Steward et al. | |
| 7,897,157 | B2 | 3/2011 | Steward et al. | |
| 7,998,489 | B2 | 8/2011 | Steward et al. | |
| 8,021,859 | B2 | 9/2011 | Steward et al. | |
| 8,067,200 | B2 | 11/2011 | Foster et al. | |
| 8,187,834 | B2 | 5/2012 | Foster et al. | |
| 8,198,034 | B2 * | 6/2012 | Fernandez-Salas | C07K 16/1282 435/325 |
| 8,273,358 | B2 | 9/2012 | Steward et al. | |
| 8,399,401 | B2 | 3/2013 | Foster et al. | |
| 8,455,203 | B2 * | 6/2013 | Wang ........................ | C12Q 1/37 435/325 |
| 8,512,984 | B2 | 8/2013 | Foster et al. | |
| 8,603,779 | B2 | 12/2013 | Foster et al. | |
| 2004/0219619 | A1 | 11/2004 | Fernandez-Salas et al. | |
| 2008/0160561 | A1 | 7/2008 | Fernandez-Salas et al. | |
| 2008/0220456 | A1 | 9/2008 | Williams et al. | |

FOREIGN PATENT DOCUMENTS

| | | |
|---|---|---|
| WO | WO 95/33850 | 12/1995 |
| WO | WO 96/33273 | 10/1996 |
| WO | WO 2006/042149 | 4/2006 |

OTHER PUBLICATIONS

U.S. Appl. No. 12/403,531, filed Mar. 13, 2009, Allergan, Inc.

U.S. Appl. No. 12/722,801, filed Mar. 12, 2010, Allergan, Inc.

Williamson, L.C., et al., Clostridial Neurotoxins and Substrate Proteolysis in Intact Neurons, J. 8ioi Chem. 271(13) : 7694-7699 (1996).

Shimazaki, Y., et al., Phosphphorylation of 25-kDa Synaptosome-Associated Protein, J. Biol. Chem. 271(24): 14548-14533 (1996).

Schulte-Baukloh, H., et al., Persistence of the Synaptosomal-Associated Protein-25 Cleavage Product After Intradetrusor Botulinum Toxin A Injections in Patients with Myelomeningocele Showing an Inadequate Response to Treatment, BJU Int. 100(5):1075-1080 (2007).

Rasooly R. and Do, P.M., Development of an In Vitro Assay as an Alternative to the Mouse Bioassay for Clostridium botulinum Neurotoxin Type A, App. Environ. Microbiol. 74(14): 4309-4313 (2008).

Nabokina, G. et al., Intracellular Location of SNAP-25 in Human Neutrophils, Biochem Biophys, Res. Comm. 239: 592-597 (1997).

Marini, P., et al., SiMa, a New Neuroblastoma Cell Line Combining Poor Prognostic Cytogenetic Markers with High Adrenergic Differentiation, Cancer Genet. Cytogenet. 112: 161-164 (1999).

Marconi, S., et al., A protein-chip Membrane-Capture Assay for Botulinum Neurotoxin Activity, Toxicol. App. Pharmacol. 233: 439-446 (2008).

Hallis, B., et al., Development of Novel Assays for Botulinum Type A and B Neurotoxins Based on Their Endopeptidase Activities, J. Clin. Microbiol 34(8): 1934-1938 (1996).

(Continued)

*Primary Examiner* — Karen Cochrane Carlson

(74) *Attorney, Agent, or Firm* — Brigitte C. Phan; Ted A. Chan

(57) ABSTRACT

The present specification discloses a retargeted endopeptidase pharmaceutical wherein the activity has been determined by the methods disclosed.

4 Claims, 9 Drawing Sheets

(56) References Cited

OTHER PUBLICATIONS

Jones R.G.A., et al., Development of Improved SNAP-25 Endopeptidase Immunoassays for Botulinum Type A and E Toxins, J. Immunol. Methods 329: 92-101 (2008).

Garcia-Rodriguez, C., et al., Molecular Evolution of Antibody Cross-Reactivity for Two Subtypes of Type A Botulinum Neurotoxin, Nature Bioltech 25(1): 107-116 (2007).

Foran, P., et al., Botulinum Neurotoxin C1 Cleaves Both Syntaxin and SNAP-25 in Intact and Permeabilized Chromaffin Cells: Correlation With Its Blockade of Catecholamine Release, Biochemistry 35: 2630-2636 1996.

Boyd. R.S., et al., The Effect of Botulinum Neurotoxins on the Release of Insulin from the Insulinoma Cell Lines HIT-5 and RINm5F, J. Biol. Chem. 270(31): 18216-18218 (1995).

Amersdorfer, P., et al., Molecular Characterization of Murine Humoral Immune Response to Botulinum Neurotoxin Type A Binding Domain as Assessed by Using Phage Antibody Libraries, Infect. Immun. 65(9): 3743-3752 (1997).

* cited by examiner

IMMUNO-BASED RETARGETED ENDOPEPTIDASE ACTIVITY ASSAYS

CROSS REFERENCE TO RELATED APPLICATIONS

This application is a continuation and claims priority pursuant to 35 U.S.C. §120 to U.S. patent application Ser. No. 13/801,711, filed Mar. 13, 2013, which is a continuation of U.S. patent application Ser. No. 12/723,595, filed Mar. 12, 2010, which is now U.S. Pat. No. 8,455,203, which claims priority pursuant to 35 U.S.C. §119(e) to U.S. Provisional Patent Application Ser. No. 61/160,217 filed Mar. 13, 2009, each of which is incorporated entirely by reference.

The sequences disclosed in the present specification are contained in the Sequence Listing submitted with the present specification which is hereby incorporated by reference in its entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A (Biogen-tech Ltd., University, Yantai, Shandong, China); and BoNT/B preparations, such as, e.g., MYOBLOC®/NEUROBLOC® (Solstice Neurosciences, Inc., South San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

A Clostridial toxin treatment inhibits neurotransmitters and neuropeptide release by disrupting the exocytotic process used to secrete the neurotransmitters and neuropeptides into the synaptic cleft. There is a great desire by the pharmaceutical industry to expand the use of Clostridial toxin therapies beyond its current myo-relaxant applications to treat sensory nerve-based ailment, such as, e.g., various kinds of chronic pain, neurogenic inflammation and urogenital disorders, as well as other disorders, such as, e.g., pancreatitis. One approach that is currently being exploited to expand Clostridial toxin-based therapies involves modifying a Clostridial toxin so that the modified toxin has an altered cell targeting capability for a neuronal or non-neuronal cell of interest. Called either re-targeted endopeptidase or Targeted Vesicular Exocytosis Modulator Proteins (TVEMPs), these molecules achieve their exocytosis inhibitory effects by using a target receptor present on the neuronal or non-neuronal target cell of interest. This re-targeted capability is achieved by replacing a naturally-occurring binding domain of a Clostridial toxin with a targeting domain showing a selective binding activity for a non-Clostridial toxin receptor present in a neuronal or non-neuronal target cell of interest. Such modifications to a binding domain result in a molecule that is able to selectively bind to a non-Clostridial toxin receptor present on the target cell. A re-targeted endopeptidase can bind to a target receptor, translocate into the cytoplasm, and exert its proteolytic effect on the SNARE complex of the neuronal or non-neuronal target cell of interest.

One group of re-targeted endopeptidase comprises molecules having an opioid targeting domain. These opioid re-targeted endopeptidases comprise an opioid targeting domain, a Clostridial toxin translocation domain, and a Clostridial toxin enzymatic domain. Non-limiting examples of opioid re-targeted endopeptidase, or opioid-TVEMPs, are described in, e.g., Keith A. Foster et al., Clostridial Toxin Derivatives Able To Modify Peripheral Sensory Afferent Functions, U.S. Pat. No. 5,989,545; J. Oliver Dolly et al., Activatable Recombinant Neurotoxins, U.S. Pat. No. 7,132,259; Stephan Donovan, Clostridial Toxin Derivatives and Methods For Treating Pain, U.S. Pat. No. 7,244,437; Stephan Donovan, Clostridial Toxin Derivatives and Methods For Treating Pain, U.S. Pat. No. 7,413,742; Stephan Donovan, Clostridial Toxin Derivatives and Methods For Treating Pain, U.S. Pat. No. 7,415,338; Lance E. Steward et al., Multivalent Clostridial Toxin Derivatives and Methods of Their Use, U.S. Pat. No. 7,514,088; Keith A. Foster, Fusion Proteins, U.S. Patent Publication 2008/0064092; Keith A. Foster, Fusion Proteins, U.S. Patent Publication 2009/0035822; Lance E. Steward et al., Multivalent Clostridial Toxin Derivatives and Methods of Their Use, U.S. Patent Publication 2009/0048431; Keith A. Foster, Non-Cytotoxic Protein Conjugates, U.S. Patent Publication 2009/0162341; Keith A. Foster et al., Re-targeted Toxin Conjugates, International Patent Publication WO 2005/023309; and Lance E. Steward, Modified Clostridial Toxins with Enhanced Translocation Capabilities and Altered Targeting Capabilities for Non-Clostridial Toxin Target Cells, International Patent Application WO 2008/008805; each of which is hereby incorporated by reference in its entirety.

One general difference between re-targeted endopeptidases and Clostridial toxins is that because re-targeted endopeptidases typically do not target motor neurons, the lethality associated with over-dosing a mammal with a re-targeted endopeptidase is greatly minimized, if not avoided altogether. For example, opioid re-targeted endopeptidases can be administered at 10,000 times the therapeutically effective dose before evidence of lethality is observed, and this lethality is due to the passive diffusion of the molecule and not via the intoxication process. Thus, for all practical purposes re-targeted endopeptidases are non-lethal molecules. Although this non-lethal property is of great therapeutic benefit, a manufacturing problem arises because the standard activity assay used to manufacture Clostridial toxin-based biologics is a mouse $LD_{50}$ bioassay, a lethality test. S. S. Arnon et al., JAMA 285: 1059-1070 (2001). Currently a mouse $LD_{50}$ bioassay is used by all pharmaceutical manufacturers to express the potency of their Clostridial toxin preparations. In fact, the activity units for Clostridial toxins are mouse $LD_{50}$ units. However, because re-targeted endopeptidases are essentially non-lethal, a mouse $LD_{50}$ bioassay cannot be used to assess the potency of these molecules. Thus, a simple, reliable, validated, and governmental agency acceptable activity assay that can evaluate the integrity of all the steps necessary in re-targeted endopeptidase uptake would be of significant value.

The present specification provides novel compositions, cells, and methods for assaying the activity of re-targeted endopeptidases useful for various industries, such as, e.g., the pharmaceutical and food industries, and provides related advantages as well. Such compositions, cells, and methods do not use live animals or tissues taken from live animals, but can evaluate all the steps necessary for re-targeted endopeptidase action.

DETAILED DESCRIPTION OF THE DRAWINGS

FIGS. 1A and 1B show a schematic of the current paradigm of neurotransmitter release and Clostridial toxin intoxication in a central and peripheral neuron. FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 1B shows a schematic of the intoxication mechanism for tetanus and botulinum toxin activity in a central and peripheral neuron. This intoxication process can be described as comprising four steps: 1) receptor binding, where Clostridial toxin binds to a Clostridial receptor complex and initiates the intoxication process; 2) complex internalization, where after toxin binding, a vesicle containing a toxin/receptor system complex is endocytosed into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, and release of the light chain and 4) enzymatic target modification, where the light chain of Clostridial toxin proteolytically cleaves its target SNARE substrates, such as, e.g., SNAP-25, VAMP or Syntaxin, thereby preventing vesicle docking and neurotransmitter release.

FIG. 2 shows a full dose response to the re-targeted endopeptidase Noc/A in the ORL-1 Clone #6 clonal cell line overexpressing ORL-1. Specific uptake of Noc/A can be observed in the ORL-1Clone #6 clonal cell line overexpressing ORL-1. The treatment with Noc/A (LHN/A plus binding ligand nociceptin variant) and $LH_N$/A (LC/A and $H_N$ without any binding domain) performed on ORL-1 stable cell line clone #6 in the ECL ELISA for cleaved SNAP-$25_{197}$ demonstrated that uptake of Noc/A is specific in this clonal cell line. The clonal cell line also show great sensitivity for Noc/A with an $EC_{50}$ of 1.2 nM.

FIG. 3 shows a full dose response to Noc/A in the SK-N-DZ single-cell derived clones #3 and #22. Specific uptake of Noc/A on SK-N-DZ clones #3 and #22 when compared to $LH_N$/A (n=4 independent experiments run). Cells were plated on poly-D-lysine 96-well plates in RPMI SFM+N2+B27+NGF. Treatment with compounds was for 22 hours. ECL ELISA for cleaved SNAP-$25_{197}$ demonstrated that uptake of Noc/A is specific in this clonal cell lines. The clonal cell lines also show great sensitivity for Noc/A with an $EC_{50}$ of 0.3 nM for clone #3 and an $EC_{50}$ of 0.9 nM for clone #22.

FIG. 4 shows an ECL sandwich ELISA assay results from ORL1 ND7 clones 1C11, 4B7, and 4C9 treated with re-targeted endopeptidase Noc/A. Parental ND7 and ORL1 ND7 clones were treated for 24 hours with Noc/A followed by two days of incubation. Parental ND7 $EC_{50}$ could not be calculated since it only reached approximately 50% SNAP-$25_{197}$ cleavage. Clones 4B7 and 1C11 reach more than 80% SNAP-$25_{197}$ cleavage. $EC_{50}$ values were calculated to be 5.7±0.5, 6.7±1, and 8.6±2 nM respectively.

Figure 7A:
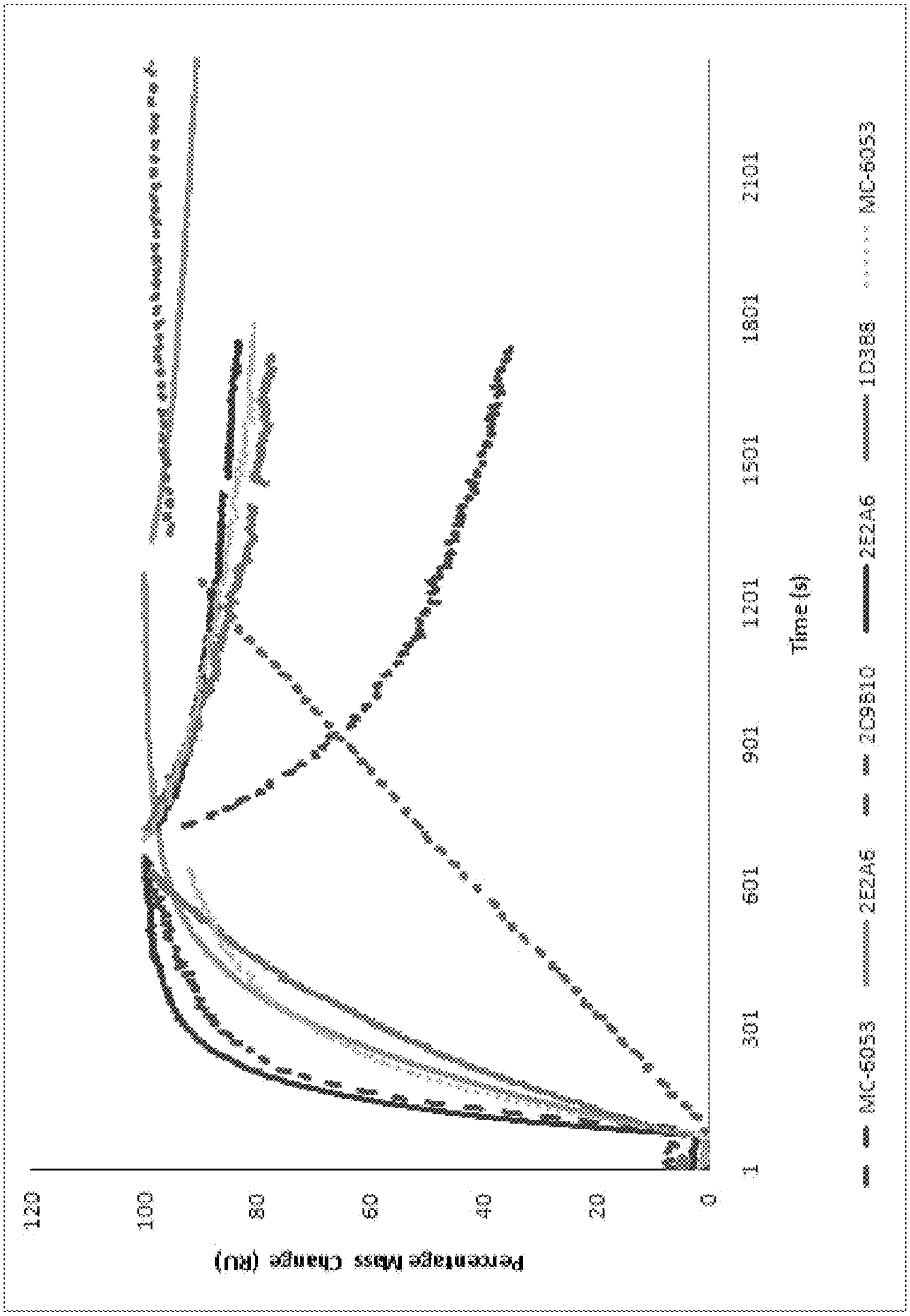
Figure 7B:
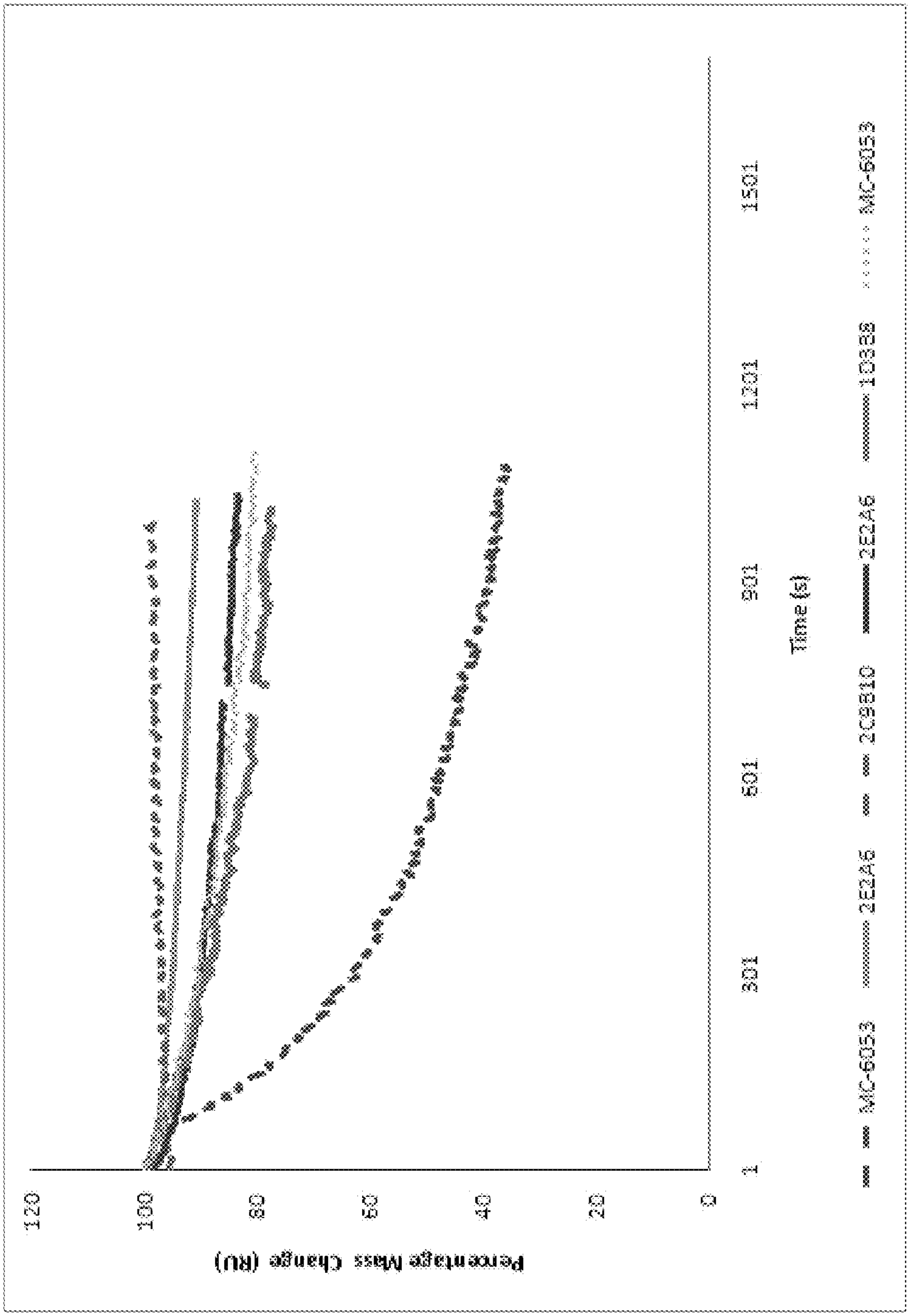

FIGS. 7A and 7B show normalized BIAcore SPR curves of 7.8 nM of the antibodies 2E2A6, 1D3B8, 3C1A5 and 2C9B10 and commercial MC-6050 and MC-6053. FIG. 7A shows the normalized data for the on-rate of each antibody. FIG. 7B shows the normalized data for the off-rate of each antibody.

DETAILED DESCRIPTION

The present specification provides novel assays for determining the presence or absence of an active retargeted endopeptidase in a sample and for determining the activity/potency of a re-targeted endopeptidase. The novel cell-based assays disclosed in the present specification rely on cells, reagents and detection methods that enable the assay to detect nanomolar quantities of a re-targeted endopeptidase in a sample. The cell-based assays disclosed in the present specification serve to analyze multiple functions a re-targeted endopeptidase, namely, re-targeted endopeptidase binding to a cell surface receptor, internalization of the endopeptidase-receptor complex, enzymatic domain translocation into the cytoplasm, enzymatic domain cleavage of substrate. As discussed further below, the novel methods and compositions can be used to analyze crude and bulk samples as well as highly purified di-chain re-targeted endopeptidases and formulated re-targeted endopeptidase products and further are amenable to automated high throughput assay formats.

Thus, one aspect disclosed in the present specification provides immune response inducing compositions for producing α-SNAP-25 antibodies that can selectively bind to an epitope comprising a SNAP-25 cleavage product having a carboxyl-terminus at the $P_1$ residue of the BoNT/A cleavage site scissile bond. Immune response inducing compositions can comprise an adjuvant and an immune response inducing composition including a SNAP-25 antigen, a carrier linked to a SNAP-25 antigen, or a carrier linked to a flexible spacer linked to a SNAP-25 antigen, where the flexible linker intervenes between the SNAP-25 antigen and the carrier. It is envisioned that any and all SNAP-25 antigens that triggers an immune response that produce a α-SNAP-25 antibody that can selectively bind to a SNAP-25 epitope having a carboxyl-terminus at the $P_1$ residue of the BoNT/A cleavage site scissile bond can be useful as a SNAP-25 antigen, including, without limitation, a SNAP-25 antigen derived from a naturally occurring SNAP-25, a SNAP-25 antigen derived from a non-naturally occurring SNAP-25, and a SNAP-25 antigen comprising an immunoreactive fragment of the SNAP-25, the SNAP-25 from a naturally occurring SNAP-25 or a non-naturally occurring SNAP-25. SNAP-25 antigens useful for producing α-SNAP-25 antibodies that can selectively bind to a SNAP-25 epitope having a carboxyl-terminus at the $P_1$ residue of the BoNT/A cleavage site scissile bond include, without limitation, SNAP-25 antigens comprising a SNAP-25 peptide having a carboxylated C-terminal glutamine linked to a carrier peptide, including, without limitation SEQ ID NO:38. Other Immune response inducing compositions useful for making α-SNAP-25 antibodies that can selectively bind to a SNAP-25 epitope having a carboxyl-terminus at the $P_1$ residue of the BoNT/A cleavage site scissile bond include, without limitation, an immune response inducing composition comprising a carrier linked to a flexible linker linked to a SNAP-25 antigen a carboxylated C-terminal glutamine, wherein the flexible linker intervenes between the SNAP-25 antigen and the carrier. It is envisioned that any and all adjuvants can be useful in such an immune response inducing composition, including, without limitation, polyethylene glycol (PEG), monomethoxypolyethylene glycol (mPEG), polyvinyl alcohol (PVA), complete and incomplete Freund's adjuvant.

Another aspect disclosed in the present specification provides methods of producing an α-SNAP-25 antibody that can selectively bind to an epitope comprising a SNAP-25 cleavage product having a carboxyl-terminus at the $P_1$ residue of the BoNT/A cleavage site scissile bond. Aspects of this method comprise the steps of (a) administering to an animal a SNAP-25 immune response inducing composition disclosed in the present specification; (b) collecting from the animal a sample containing an α-SNAP-25 antibody or α-SNAP-25 antibody-producing cell; and (c) isolating the α-SNAP-25 antibody from the sample. The methods disclosed are useful for making either α-SNAP-25 monoclonal antibodies that can selectively bind to an epitope comprising a SNAP-25 cleavage product having a carboxyl-terminus at the $P_1$ residue of the BoNT/A cleavage site scissile bond or α-SNAP-25 polyclonal antibodies that can selectively bind to an epitope comprising a SNAP-25 cleavage product having a carboxyl-terminus at the $P_1$ residue of the BoNT/A cleavage site scissile bond.

Still another aspect disclosed in the present specification provides α-SNAP-25 antibodies that selectively bind to an epitope comprising a SNAP-25 having a carboxyl-terminus at the $P_1$ residue of the BoNT/A cleavage site scissile bond. Such α-SNAP-25 antibodies include both naturally-occurring and non-naturally-occurring antibodies, as well as, monoclonal α-SNAP-25 antibodies or polyclonal α-SNAP-25 antibodies. Monoclonal α-SNAP-25 antibodies useful as α-SNAP-25 antibodies that selectively bind to a SNAP-25 antigen having a carboxyl-terminus at the $P_1$ residue of the BoNT/A cleavage site scissile bond, include, without limitation, the monoclonal α-SNAP-25 antibodies produced from hybridoma cell lines 1D3B8, 2C9B10, 2E2A6, 3C1A5 and 3C3E2.

Yet another aspect disclosed in the present specification provides immuno-based methods of detecting re-targeted endopeptidase activity. Aspects of this method comprise the steps of (a) treating a cell from an established cell line with a sample comprising a re-targeted endopeptidase, wherein the cell from an established cell line is susceptible to re-targeted endopeptidase activity by the re-targeted endopeptidase; (b) isolating from the treated cell a SNAP-25 component comprising a SNAP-25 cleavage product having a carboxyl-terminus at the $P_1$ residue of the BoNT/A cleavage site scissile bond; (c) contacting the SNAP-25 component with an α-SNAP-25 antibody disclosed in the present specification; and (d) detecting the presence of an antibody-antigen complex comprising the α-SNAP-25 antibody and the SNAP-25 cleavage product having a carboxyl-terminus at the $P_1$ residue of the BoNT/A cleavage site scissile bond; wherein detection by the antibody-antigen complex is indicative of re-targeted endopeptidase activity. The α-SNAP-25 antibody of step (c) can optionally be linked to a solid phase support.

Yet another aspect disclosed in the present specification provides immuno-based methods of detecting opioid-TVEMP activity. Aspects of this method comprise the steps of (a) treating a cell from an established cell line with a sample comprising a re-targeted endopeptidase, wherein the cell from an established cell line can uptake a re-targeted endopeptidase; (b) isolating from the treated cell a SNAP-25 component comprising a SNAP-25 having a carboxyl-terminus at the $P_1$ residue of the BoNT/A cleavage site scissile bond; (c) contacting the SNAP-25 component with an α-SNAP-25 antibody disclosed in the present specification; and (d) detecting the presence of an antibody-antigen complex comprising the α-SNAP-25 antibody and the SNAP-25 having a carboxyl-terminus at the $P_1$ residue of the BoNT/A cleavage site scissile bond; wherein detection by the antibody-antigen complex is indicative of re-targeted endopeptidase activity. The α-SNAP-25 antibody of step (c) can optionally be linked to a solid phase support.

A further aspect disclosed in the present specification provides methods of determining re-targeted endopeptidase immunoresistance in a mammal. Aspects of this method comprise the steps of (a) adding a re-targeted endopeptidase to a test sample obtained from a mammal being tested for the presence or absence of α-re-targeted endopeptidase neutralizing antibodies; (b) treating a cell from an established cell line with the test sample, wherein the cell from an established cell line is susceptible to re-targeted endopeptidase activity; (c) isolating from the treated cells a SNAP-25 component comprising a SNAP-25 cleavage product having a carboxyl-terminus at the $P_1$ residue of the BoNT/A cleavage site scissile bond; (d) contacting the SNAP-25 component with an α-SNAP-25 antibody disclosed in the present specification; (e) detecting the presence of an antibody-antigen complex comprising the α-SNAP-25 antibody and the SNAP-25 cleavage product having a carboxyl-terminus at the $P_1$ residue of the BoNT/A cleavage site scissile bond; (f) repeating steps a-e with a negative control sample instead of a test sample; and (g) comparing the amount of antibody-antigen complex detected in step (e) to the amount of antibody-antigen complex detected in step (f), wherein detection of a lower amount of antibody-antigen complex detected in step (e) relative to the amount of antibody-antigen complex detected in step (f) is indicative of the presence of α-re-targeted endopeptidase neutralizing antibodies. The α-SNAP-25 antibody of step (d) can optionally be linked to a solid phase support. The control sample in step (f) can also include a positive control sample, in addition to the negative control sample.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct serotypes of botulinum toxins (BoNTs), which have been identified by investigating botulism outbreaks in man (BoNT/A, BoNT/B, BoNT/E and BoNT/F), animals (BoNT/C1 and BoNT/D), or isolated from soil (BoNT/G). While all seven botulinum toxin serotypes have similar structure and biological properties, each also displays heterogeneous characteristics, such as, e.g., different pharmacological properties. In contrast, tetanus toxin (TeNT) is produced by a uniform group of *C. tetani*. Two other species of Clostridia, *C. baratii* and *C. butyricum*, also produce toxins similar to BoNT/F and BoNT/E, respectively.

Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment. This posttranslational processing yields a di-chain molecule comprising an approximately 50 kDa light chain (LC) and an approximately 100 kDa heavy chain (HC) held together by a single disulfide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell.

Figure 1A:
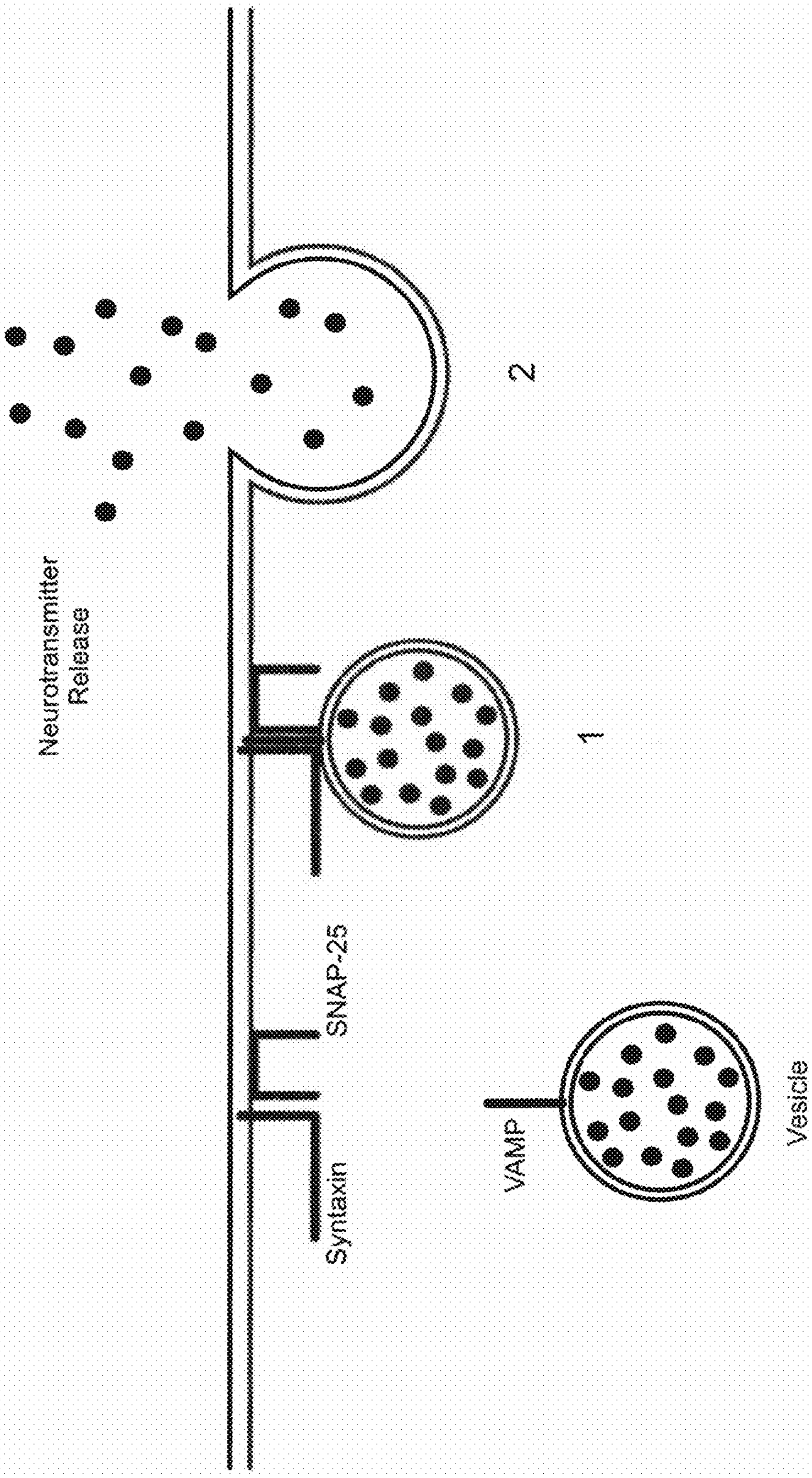
Figure 1B:
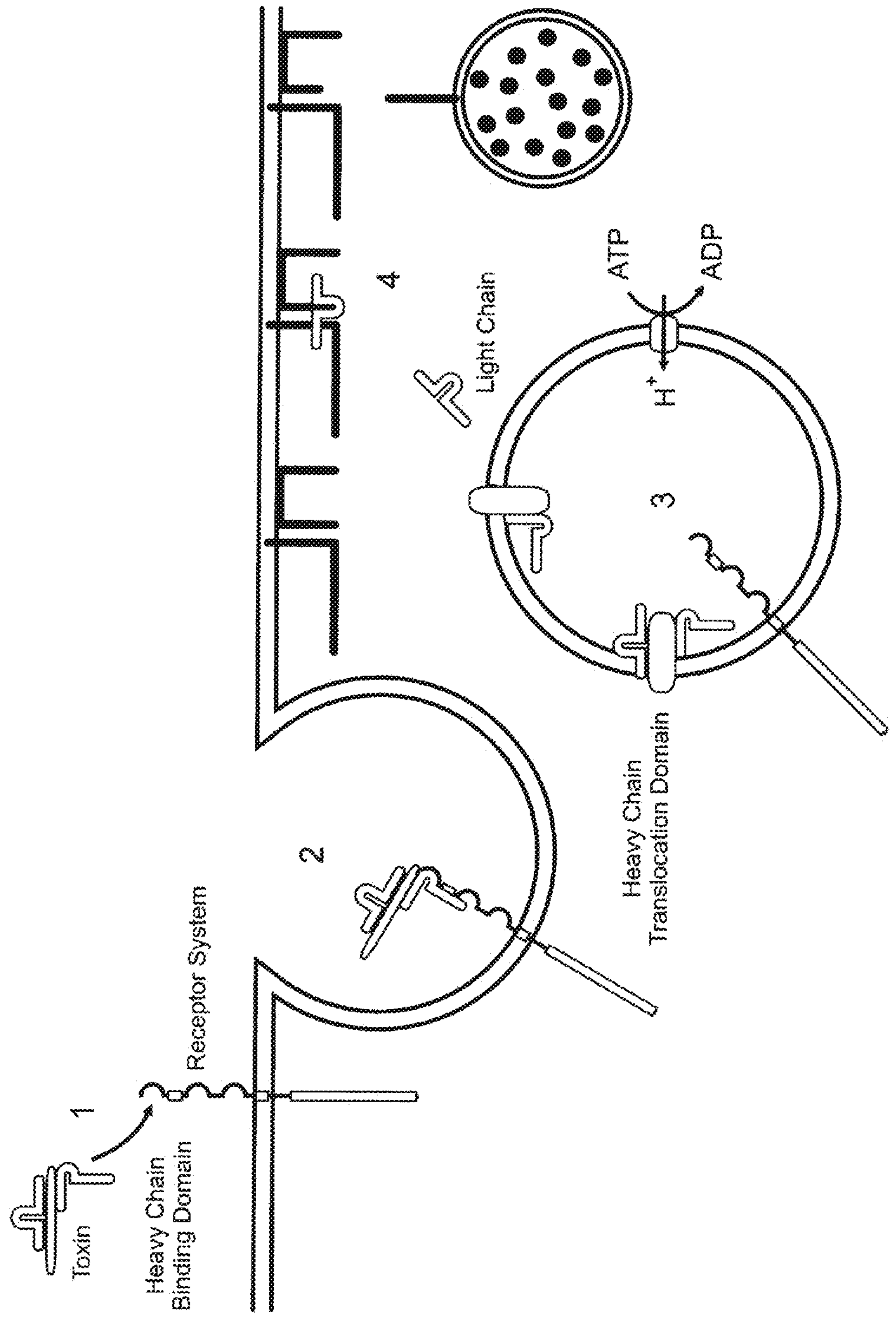
Figure 2:
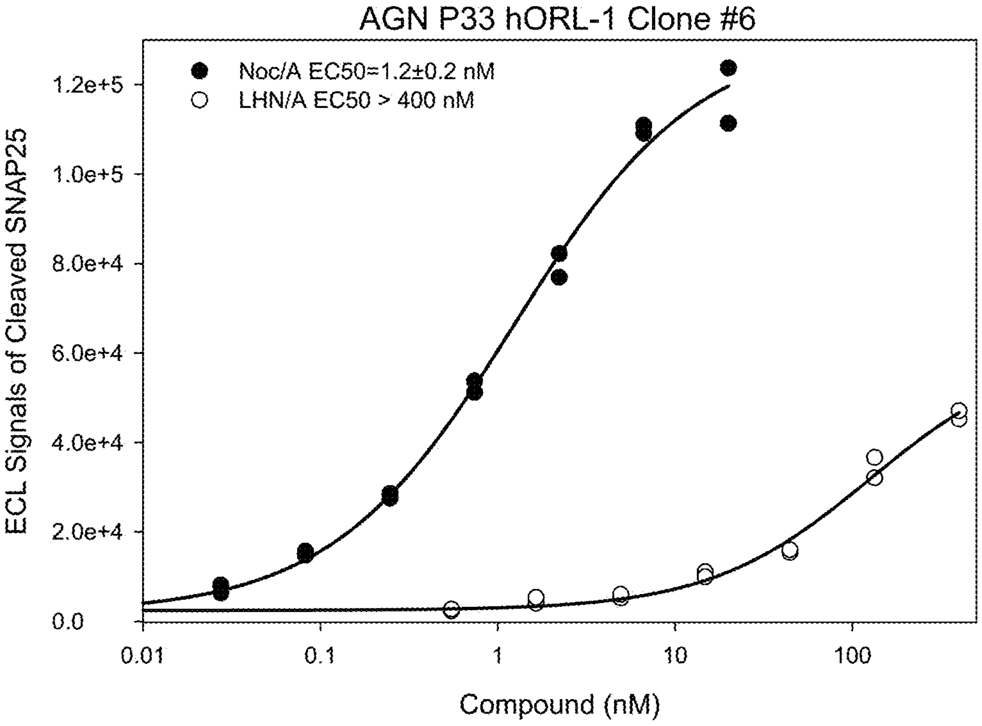
Figure 3:
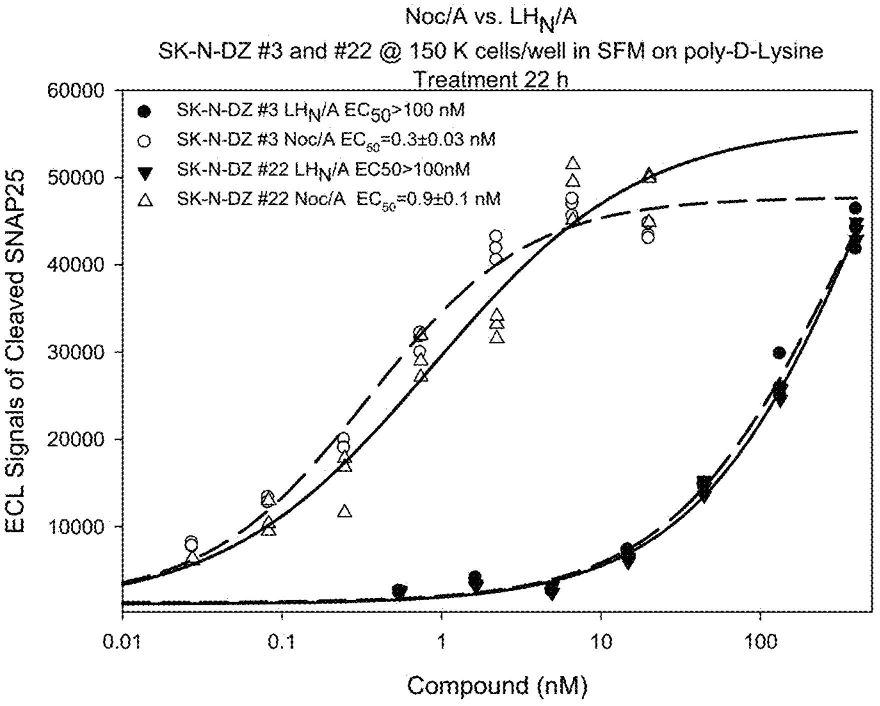
Figure 4:
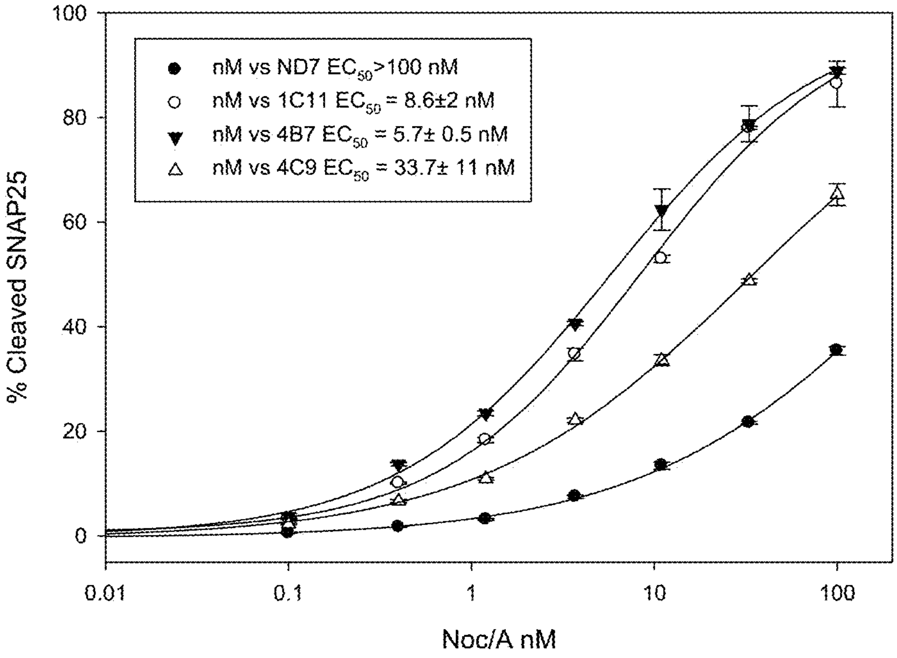
Figure 5:
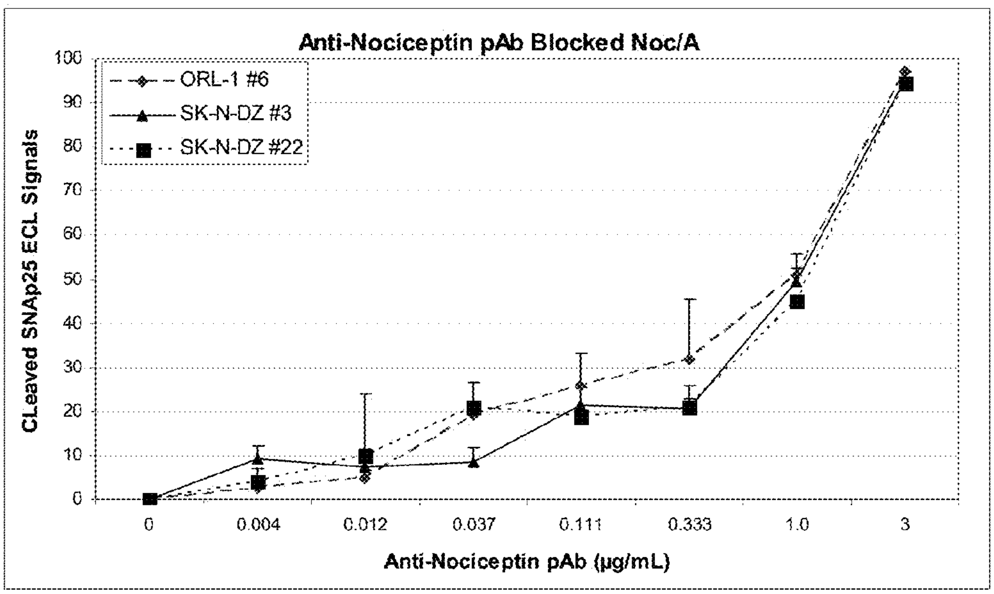
FIG. 5 shows an anti-nociceptin polyclonal antibodies can block re-targeted endopeptidase Noc/A uptake in SK-N-DZ clone #3, clone #22, and AGN P33 ORL-1 clone #6 cell lines. Cells were plated on poly-D-lysine 96-well plates in RPMI SFM+N2+B27+NGF and treated for 22 hours in serum-free media containing with the Anti-nociceptin polyclonal antibodies at different dilutions (0-3 μg/mL) in 1 nM Noc/A.
Figure 6:
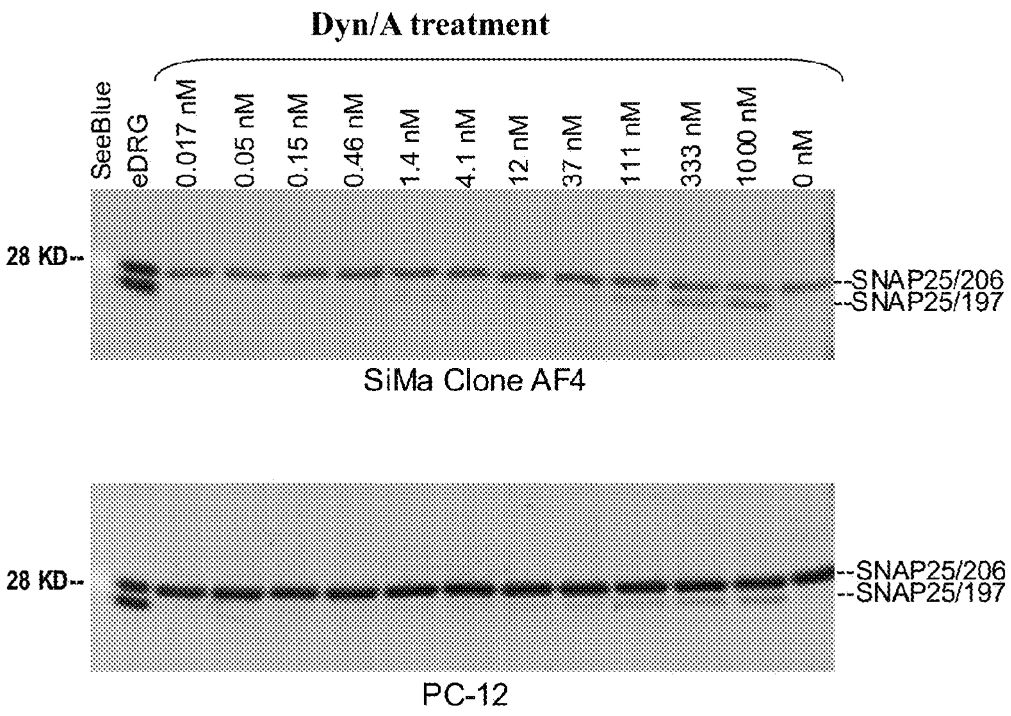
FIG. 6 shows cells from SiMa clone AF4 and the established cell line PC-12 were treated with the re-targeted endopeptidase Dyn/A at concentrations from 0.017 nM to 1 μM as depicted in the Western blot image. Dose-dependent uptake could be observed for both cell lines.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (FIG. 1). The process is initiated when the HC domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate important pH-dependent structural rearrangements that increase hydrophobicity, promote pore formation, and facilitate separation of the heavy and light chains of the toxin. Once separated, the light chain endopeptidase of the toxin is released from the intracellular vesicle into the cytosol where it appears to specifically target core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl terminal region, releasing a nine or twenty six amino acid fragment, respectively, and BoNT/C1 also cleaves SNAP-25 near the carboxyl terminus releasing an eight amino acid fragment. The botulinum serotypes BoNT/B, BoNT/D, BoNT/F and BoNT/G, and tetanus toxin, act on the conserved central portion of VAMP, and release the amino terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82 (5) Biochimie. 427-446 (2000); Kathryn Turton et al., *Botulinum and Tetanus Neurotoxins: Structure, Function and Therapeutic Utility,* 27 (11) Trends Biochem. Sci. 552-558. (2002); Giovanna Lalli et al., *The Journey of Tetanus and Botulinum Neurotoxins in Neurons,* 11 (9) Trends Microbiol. 431-437, (2003).

Re-targeted endopeptidases generally substitute the naturally-occurring di-chain loop protease cleavage site with an exogenous protease cleavage site. See e.g., Dolly, J. O. et al., Activatable Clostridial Toxins, U.S. Pat. No. 7,419,676, which is hereby incorporated by reference. Although re-targeted endopeptidases vary in their overall molecular weight because of the size of the targeting moiety, the activation process and its reliance on cleavage at the exogenous cleavage site to produce a di-chain molecule is essentially the same as that for Clostridial toxins. See e.g., Steward, L. E. et al., Activatable Clostridial Toxins, U.S. Patent Publication 2009/0005313; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Steward, L. E. et al., Modified Clostridial Toxins with Enhanced Translocation Capabilities and Altered Targeting Activity for Clostridial Toxin Target Cells, U.S. Patent Publication 2008/0241881, each of which is hereby incorporated by reference.

Aspects of the present disclosure comprise, in part, an immune response inducing composition for producing α-SNAP-25 antibodies that can selectively bind to a SNAP-25 having a carboxyl-terminus at the $P_1$ residue of the BoNT/A cleavage site scissile bond. As used herein, the term "immune response inducing composition" refers to a composition comprising a SNAP-25 antigen which, when administered to an animal, stimulates an immune response against the SNAP-25 antigen, thereby producing α-SNAP-25 antibodies that can selectively bind to a SNAP-25 having a carboxyl-terminus at the $P_1$ residue of the BoNT/A cleavage site scissile bond. The term "immune response" refers to any response by the immune system of an animal to an immune response inducing composition. Exemplary immune responses include, but are not limited to, cellular as well as local and systemic humoral immunity, such as, e.g., CTL responses, including antigen-specific induction of CD8+ CTLs, helper T-cell responses, including T-cell proliferative responses and cytokine release, and B-cell responses including, e.g., an antibody producing response. The term "inducing an immune response" refers to administration of an immune response inducing composition or a polynucleotide encoding the immune response inducing composition, where an immune response is affected, i.e., stimulated, initiated or induced.

An SNAP-25 immune response inducing composition comprises a SNAP-25 antigen. As used herein, the term "antigen" refers to a molecule that elicits an immune response and includes, without limitation, peptides, polysaccharides and conjugates of lipids, such as, e.g., lipoproteins and glycolipids. As used herein, the term "SNAP-25 antigen" refers to any antigen which has a carboxyl-terminus at the $P_1$ residue of the BoNT/A cleavage site scissile bond that can elicit an immune response. A SNAP-25 antigen used in an immune response inducing composition must be large enough to be substantially unique in sequence, thus reducing the possibility of producing antibodies that are cross reactive against antigens other than SNAP-25. In addition, a SNAP-25 antigen used in an immune response inducing composition must be small enough to only trigger an immune response substantially against a SNAP-25 having a carboxyl-terminus at the $P_1$ residue of the BoNT/A cleavage site scissile bond, thus increasing the possibility of producing α-SNAP-25 antibodies that can distinguish a SNAP-25 having a carboxyl-terminus at the $P_1$ residue of the BoNT/A cleavage site scissile bond from a SNAP-25 lacking a carboxyl-terminus at the $P_1$ residue of the BoNT/A cleavage site scissile bond. Furthermore, it is also very desirable to generate α-SNAP-25 antibodies of a single amino acid sequence in a good yield that are reproducibly selective and which bind with acceptable avidity in order to permit the design of a highly sensitive assay.

The sequence surrounding a BoNT/A cleavage site present in SNAP-25 is denoted as $P_5$-$P_4$-$P_3$-$P_2$-$P_1$-$P_1'$-$P_2'$-$P_3'$-$P_4'$-$P_5'$, with $P_1$-$P_1'$ representing the scissile bond. Upon cleavage by retargeted endopeptidase, the resulting cleavage products produced comprise a fragment including the $P_5$-$P_4$-$P_3$-$P_2$-$P_1$ sequence and a fragment including the $P_1'$-$P_2'$-$P_3'$-$P_4'$-$P_5'$. Thus, as used herein, the term "SNAP-25 having a carboxyl-terminus at the $P_1$ residue of the BoNT/A cleavage site scissile bond" refers to any SNAP-25 having the $P_1$ residue as its carboxyl-terminal amino acid. For example, $Q_{197}$-$R_{198}$ of human SNAP-25 (SEQ ID NO:5) represents the $P_1$-$P_1'$ scissile bond for the BoNT/A cleavage site. As such, "SNAP-25 having a carboxyl-terminus glutamine of the BoNT/A cleavage site scissile bond" would be any SNAP-25 cleavage product having a glutamine at its carboxyl-terminal amino acid where the glutamine represents $Q_{197}$ of the scissile bond. As another example, $K_{204}$-$H_{205}$ of *Torpedo marmorata* SNAP-25 (SEQ ID NO:16) represents the $P_1$-$P_1'$ scissile bond for the BoNT/A cleavage site. As such, "SNAP-25 having a carboxyl-terminus lysine of the BoNT/A cleavage site scissile bond" would be any SNAP-25 cleavage product having a lysine at its carboxyl-terminal amino acid where the lysine represents $K_{204}$ of the scissile bond.

The SNAP-25 antigen having a carboxyl-terminus at the $P_1$ residue of the BoNT/A cleavage site scissile bond from the BoNT/A cleavage site can be modified to enhance the immunogenicity of a SNAP-25 antigen, a hapten, or any other antigenic compound that is immunogenic, non-immunogenic, or weakly immunogenic when not associated with the modification. In an aspect of this embodiment, the carboxyl-terminal $P_1$ residue from the scissile bond of a SNAP-25 antigen can be carboxylated. Carboxylation increases the desired immunogenic properties of a SNAP-25 antigen in two respects. First, because charged amino acids enhance immunogenicity, adding a $COO^-$ group to the carboxyl-terminal residue will increase the overall immunogenicity of a SNAP-25 antigen. Second, because the $P_1$ residue of the BoNT/A cleavage site scissile bond is in a charged state upon cleavage, adding a $COO^-$ group to the carboxyl-terminal residue will better mimic the actual antigen that the α-SNAP-25 antibodies disclosed in the present specification are designed to selectively bind.

In an aspect of this embodiment, the amino-terminal residue from a SNAP-25 antigen can be modified by the addition of an amino acid adapted to attach the SNAP-25 antigen to a carrier protein, such as, e.g., a keyhole limpet hemocyanin (KLH), an ovalbumin (OVA), a thyroglobulin (THY), a bovine serum albumin (BSA), a soybean trypsin inhibitor (STI), or a multiple attachment peptide (MAP). For example, a cysteine residue can be placed at the amino-terminus in order to conjugate the carrier protein KLH.

Thus, an embodiment, a SNAP-25 antigen having a carboxyl-terminus at the $P_1$ residue of the BoNT/A cleavage site scissile bond can be, e.g., at least 5, at least 6, at least 7, at least 8, at least 9, at least 10, at least 11, at least 12, at least 13, at least 14, at least 15, at least 16, at least 17, at least 18, at least 19, at least 20, at least 25, or at least 30 amino acids in length. In another embodiment, a SNAP-25 antigen having a carboxyl-terminus at the $P_1$ residue of the BoNT/A cleavage site scissile bond can be, e.g., at most 5, at most 6, at most 7, at most 8, at most 9, at most 10, at most 11, at most 12, at most 13, at most 14, at most 15, at most 16, at most 17, at most 18, at most 19, at most 20, at most 25, or at most 30 amino acids in length. In still another embodiment, a SNAP-25 antigen having a carboxyl-terminus at the $P_1$ residue of the BoNT/A cleavage site scissile bond can be, e.g., between 7-12 amino acids, between 10-15 amino acids, or between 13-18 amino acids.

In another embodiment, the SNAP-25 antigen having a carboxyl-terminus at the $P_1$ residue of the BoNT/A cleavage site scissile bond comprises SEQ ID NO:33. In aspects of this embodiment, the SNAP-25 antigen having a carboxyl-terminus at the $P_1$ residue of the BoNT/A cleavage site scissile bond comprises SEQ ID NO:32, SEQ ID NO:34, SEQ ID NO:35, SEQ ID NO:36, SEQ ID NO:37, SEQ ID NO:38, or SEQ ID NO:39. In a further embodiment, the SNAP-25 antigen having a carboxyl-terminus at the $P_1$ residue of the BoNT/A cleavage site scissile bond comprises SEQ ID NO:40.

In yet another embodiment, the SNAP-25 antigen having a carboxyl-terminus at the $P_1$ residue of the BoNT/A cleavage site scissile bond comprises SEQ ID NO:41. In aspects of this embodiment, the SNAP-25 antigen having a carboxyl-terminus at the $P_1$ residue of the BoNT/A cleavage site scissile bond comprises SEQ ID NO:42, SEQ ID NO:43, SEQ ID NO:44 SEQ ID NO:45, SEQ ID NO:46. In a further embodiment, the SNAP-25 antigen having a carboxyl-terminus at the $P_1$ residue of the BoNT/A cleavage site scissile bond comprises SEQ ID NO:47.

It is envisioned that any and all SNAP-25 antigens that triggers an immune response that produces α-SNAP-25 antibodies that can selectively bind to a SNAP-25 having a carboxyl-terminus at the $P_1$ residue of the BoNT/A cleavage site scissile bond can be useful as a SNAP-25 antigen. Thus, amino acid sequence variants comprising SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, or SEQ ID NO:46 can be useful as a SNAP-25 antigen to trigger an immune response that produces α-SNAP-25 antibodies that can selectively bind to a SNAP-25 having a carboxyl-terminus at the $P_1$ residue of the BoNT/A cleavage site scissile bond. Thus, in an embodiment, a SNAP-25 antigen can substitute at least 1, at least 2, at least 3, at least 4, or at least 5 amino acid substitutions, deletions or additions to the SNAP-25 antigens comprising SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, or SEQ ID NO:46. In still another embodiment, a SNAP-25 antigen can have at least 70%, at least 75%, at least 80%, at least 85%, at least 90%, or at least 95% amino acid identity to the SNAP-25 antigens comprising SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, or SEQ ID NO:46.

It is envisioned that one or more carriers may be linked to a SNAP-25 antigen in order to enhance the immunogenicity of a SNAP-25 antigen that is immunogenic, non-immunogenic, or weakly immunogenic when not associated with the carrier. Non-limiting examples, include, e.g., a keyhole limpet hemocyanin (KLH), an ovalbumin (OVA), a thyroglobulin (THY), a bovine serum albumin (BSA), a soybean trypsin inhibitor (STI), or a multiple attachment peptide (MAP). As is well known in the art, a non-antigenic or weakly antigenic antigen can be made antigenic by coupling the antigen to a carrier. Various other carrier and methods for coupling an antigen to a carrier are well known in the art. See, e.g., Harlow and Lane, supra, 1998a; Harlow and Lane, supra, 1998b; and David W. Waggoner, Jr. et al., Immunogenicity-enhancing carriers and compositions thereof and methods of using the same, U.S. Patent Publication No. 20040057958 (Mar. 25, 2004). An epitope can also be generated by expressing the epitope as a fusion protein. Methods for expressing polypeptide fusions are well known to those skilled in the art as described, for example, in Ausubel et al., Current Protocols in Molecular Biology (Supplement 47), John Wiley & Sons, New York (1999). As the carboxyl-terminal end of the SNAP-25 antigen must be the $P_1$ residue of the BoNT/A cleavage site scissile bond, a carrier must be linked to the amino end of the SNAP-25 antigen.

It is envisioned that one or more flexible spacers may be linked to a SNAP-25 antigen in order to enhance the immunogenicity of a SNAP-25 antigen that is immunogenic, non-immunogenic, or weakly immunogenic when not associated with the flexible linkers. A flexible spacer increases the overall peptide length of the SNAP-25 antigen and provides flexibility, thereby facilitating the proper presentation of the SNAP-25 antigen to the immune cells. As a non-limiting example, a SNAP-25 immune response inducing composition can comprise a SNAP-25 antigen linked to one or more flexible spacers in tandem to better present SNAP-25 antigen to immune cells, thereby facilitating the immune response.

A flexible space comprising a peptide is at least one amino acid in length and comprises non-charged amino acids with small side-chain R groups, such as, e.g., glycine, alanine, valine, leucine or serine. Thus, in an embodiment a flexible spacer can be, e.g., at least 1, at least 2, at least 3, at least 4, at least 5, at least 6, at least 7, at least 8, at least 9, or at least 10 amino acids in length. In another embodiment, a flexible spacer can be, e.g., at least 1, at most 2, at most 3, at most 4, at most 5, at most 6, at most 7, at most 8, at most 9, or at most 10 amino acids in length. In still another embodiment, a flexible spacer can be, e.g., between 1-3 amino acids, between 2-4 amino acids, between 3-5 amino acids, between 4-6 amino acids, or between 5-7 amino acids. Non-limiting examples of a flexible spacer include, e.g., a G-spacers such as GGG, GGGG (SEQ ID NO:57), and GGGGS (SEQ ID NO:58) or an A-spacers such as AAA, AAAA (SEQ ID NO:59) and AAAAV (SEQ ID NO:60). A flexible spacer is linked in-frame to the SNAP-25 antigen as a fusion protein.

As discussed above, a flexible spacer is used, in part, to increase the overall peptide length of the SNAP-25 antigen. For example, a 5-10 amino acid SNAP-25 antigen can have its overall length increased by linking a 3-5 amino acid flexible space to the amino-end of the SNAP-25 antigen. As another example, a 5-10 amino acid SNAP-25 antigen can have its overall length increased by linking a 4-6 amino acid flexible space to the amino-end of the SNAP-25 antigen. As another example, a 5-10 amino acid SNAP-25 antigen can have its overall length increased by linking a 7-10 amino acid flexible space to the amino-end of the SNAP-25 antigen. As another example, a 7-12 amino acid SNAP-25 antigen can have its overall length increased by linking a 1-3 amino acid flexible space to the amino-end of the SNAP-25 antigen. As another example, a 7-12 amino acid SNAP-25 antigen can have its overall length increased by linking a 4-6 amino acid flexible space to the amino-end of the SNAP-25 antigen. The increased length provided by the flexible spacer allows for the selection of a small sized SNAP-25 antigen, thereby increasing the likelihood that the SNAP-25 antigen will only trigger an immune response substantially against a SNAP-25 having a carboxyl-terminus at the $P_1$ residue of the BoNT/A cleavage site scissile bond, thus increasing the possibility of producing α-SNAP-25 antibodies that can distinguish a SNAP-25 having a carboxyl-terminus at the $P_1$ residue of the BoNT/A cleavage site scissile bond from a SNAP-25 lacking a carboxyl-terminus at the $P_1$ residue of the BoNT/A cleavage site scissile bond.

It is envisioned that a SNAP-25 immune response inducing composition disclosed in the present specification can optionally comprise a SNAP-25 antigen disclosed in the present specification and one or more adjuvants. As used herein, the term "adjuvant" when used in reference to a SNAP-25 immune response inducing composition refers to any substance or mixture of substances that increases or diversifies the immune response to a SNAP-25 antigen. An immune response inducing adjuvant can, for example, serve to reduce the number of immunizations or the amount of antigen required for protective immunization. The use of immune response inducing adjuvants in an immune response inducing composition is well known. The main objective of these adjuvants is to allow an increase in the immune response. Non-limiting adjuvants include, e.g., liposomes, oily phases, including, without limitation, the Freund type of adjuvants, such as, e.g., Freund's complete adjuvant (FCA); Freund's incomplete adjuvant (FIA); sapogenin glycosides, such as, e.g., saponins; carbopol; N-acetylmuramyl-L-alanyl-D-isoglutamine (commonly known as muramyl dipeptide or "MDP"); and lipopolysaccharide (LPS). Such adjuvants are generally used in the form of an emulsion with an aqueous phase, or, more commonly, may consist of water-insoluble inorganic salts. These inorganic salts may consist, for example, of aluminum hydroxide, zinc sulfate, colloidal iron hydroxide, calcium phosphate or calcium chloride. Aluminum hydroxide ($Al(OH)_3$) is a commonly used adjuvant. Currently, the only FDA-approved adjuvant for use in humans is aluminum salts (Alum) which are used to "depot" antigens by precipitation of the antigens. Adjuvants provided above are merely exemplary. In fact, any immune response inducing adjuvant may be used in an immune response inducing composition disclosed in the present specification as long as the adjuvant satisfies the requisite characteristics for inducing an immune response.

A carrier disclosed in the present specification may also act as an adjuvant. Specific adjuvants and methods of making and using are described in, e.g., Gupta et al. Vaccine, 11: 993-306, 1993; Arnon, R. (Ed.) Synthetic Vaccines 1:83-92, CRC Press, Inc., Boca Raton, Fla., 1987; and David W. Waggoner, Jr. et al., Immunogenicity-Enhancing Carriers and Compositions Thereof and Methods of Using the Same, U.S. Patent Publication No. 20040057958 (Mar. 25, 2004). Additional adjuvants include any compound described in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or plasmid DNA containing CpG motifs can also be administered as adjuvants in combination with antigens encapsulated in microparticles. In another example, the adjuvant is an agent that facilitates entry of the antigenic compound into the cytoplasm of a cell such as listeriolysin, streptolysin or a mixture thereof.

Thus, in an embodiment, a SNAP-25 immune response inducing composition comprises a SNAP-25 antigen having a carboxylated carboxyl-terminal glutamine linked to a carrier peptide. In aspects of this embodiment, a SNAP-25 antigen having a carboxylated carboxyl-terminal glutamine comprises SEQ ID NO:32, SEQ ID NO:33, SEQ ID NO:34, SEQ ID NO:35, SEQ ID NO:36, SEQ ID NO:37, SEQ ID NO:38, or SEQ ID NO:39. In another aspect of this embodiment, a SNAP-25 antigen comprises SEQ ID NO:40. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP).

In another embodiment, a SNAP-25 immune response inducing composition comprises a SNAP-25 antigen having a carboxylated carboxyl-terminal lysine linked to a carrier peptide. In aspects of this embodiment, SNAP-25 antigen having a carboxylated carboxyl-terminal lysine comprises SEQ ID NO:41, SEQ ID NO:42, SEQ ID NO:43, SEQ ID NO:44, SEQ ID NO:45, or SEQ ID NO:46. In another aspect of this embodiment, a SNAP-25 antigen comprises SEQ ID NO:47. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP).

In yet another embodiment, a SNAP-25 immune response inducing composition comprises a SNAP-25 antigen having a carboxylated C-terminal glutamine linked to one or more flexible linkers and a carrier peptide wherein the flexible linkers intervene between the SNAP-25 antigen and the carrier peptide. In aspects of this embodiment, SNAP-25 antigen having a carboxylated carboxyl-terminal glutamine comprises SEQ ID NO:32, SEQ ID NO:33, SEQ ID NO:34, SEQ ID NO:35, SEQ ID NO:36, SEQ ID NO:37, SEQ ID NO:38, or SEQ ID NO:39. In another embodiment, a SNAP-25 antigen comprises SEQ ID NO:46. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP). In aspects of this embodiment, the flexible linker is a G-spacer or an A-spacer.

In still another embodiment, a SNAP-25 immune response inducing composition comprises a SNAP-25 antigen having a carboxylated C-terminal lysine linked to a flexible linker and a carrier peptide wherein the flexible linker intervenes between the SNAP-25 antigen and the carrier peptide. In aspects of this embodiment, SNAP-25 antigen having a carboxylated carboxyl-terminal lysine comprises SEQ ID NO:41, SEQ ID NO:42, SEQ ID NO:43, SEQ ID NO:44, SEQ ID NO:45, or SEQ ID NO:46. In another aspect of this embodiment, a SNAP-25 antigen comprises SEQ ID NO:47. In aspects of this embodiment, the carrier peptide is a keyhole limpet hemocyanin (KLH), an ovalbumin (OVA), a thyroglobulin (THY), a bovine serum albumin (BSA), a soybean trypsin inhibitor (STI) or a multiple attachment peptide (MAP). In aspects of this embodiment, the flexible linker is a G-spacer or an A-spacer.

Aspects of the present disclosure comprise, in part, a method for producing α-SNAP-25 antibodies that can selectively bind to a SNAP-25 having a carboxyl-terminus at the $P_1$ residue of the BoNT/A cleavage site scissile bond. An α-SNAP-25 antibody that selectively binds to a SNAP-25 epitope having a carboxyl-terminus at the $P_1$ residue of the BoNT/A cleavage site scissile bond can be produced by a wide variety of methods that are well known in the art. Specific protocols for making and using antibodies as well as detecting, and measuring antibody binding specificity, binding affinity and binding avidity are known in the art. See, e.g., ANTIBODIES: A LABORATORY MANUAL (Edward Harlow & David Lane, eds., Cold Spring Harbor Laboratory Press, $2^{nd}$ ed. 1998a); and USING ANTIBODIES: A LABORATORY MANUAL: PORTABLE PROTOCOL No. I (Edward Harlow & David Lane, Cold Spring Harbor Laboratory Press, 1998b); Molecular Cloning, A Laboratory Manual, 2001; and Current Protocols in Molecular Biology, 2004; David Anderson et al., Therapeutic Polypeptides, Nucleic Acids Encoding Same, and Methods of Use, U.S. Pat. No. 7,034,132 (Apr. 25, 2005); and Beatriz M. Carreno et al., Antibodies Against CTLA4, U.S. Pat. No. 7,034,121 (Apr. 25, 2006).

As a non-limiting example, α-SNAP-25 polyclonal antibodies that selectively bind to a SNAP-25 having a carboxyl-terminus at the $P_1$ residue of the BoNT/A cleavage site scissile bond can be produced by injecting an animal, such as, e.g., a rabbit, a goat, a mouse or another mammal, with one or more injections of an immune response inducing composition disclosed in the present specification. As another non-limiting example, α-SNAP-25 polyclonal antibodies that selectively bind to a SNAP-25 having a carboxyl-terminus at the $P_1$ residue of the BoNT/A cleavage site scissile bond can be produced by injecting an egg, such as, e.g., a chicken egg, with one or more injections of an immune response inducing composition disclosed in the present specification. The antibody titer in the immunized animal can be monitored over time by standard techniques, such as with an enzyme linked immunosorbent assay (ELISA) using immobilized antigen or a cell-based activity assay. If desired, polyclonal antibodies for an α-SNAP-25 antibody that selectively binds to a SNAP-25 epitope having a carboxyl-terminus at the $P_1$ residue of the BoNT/A cleavage site scissile bond can be isolated from the mammal (e.g., from the blood) and further purified by well known techniques, such as protein A affinity chromatography to obtain the IgG fraction, or by affinity purification against the peptide used for producing the antibodies.

As another non-limiting example, α-SNAP-25 monoclonal antibody that selectively binds to a SNAP-25 having a carboxyl-terminus at the $P_1$ residue of the BoNT/A cleavage site scissile bond can be produced using a hybridoma method. See e.g., Chapter 6 *Monoclonal Antibodies*, pp. 196-244, Harlow & Lane, supra, 1998a; and Chapter 7 *Growing Hybridomas*, pp. 245-282, Harlow & Lane, supra, 1998a; and Goding, pp. 59-103, Monoclonal Antibodies: Principles and Practice, Academic Press, (1986). In this method, a host animal, such as, e.g., a mouse, a hamster, or another appropriate host animal, is typically exposed to one or more injections of a SNAP-25 antigen disclosed in the present specification to elicit lymphocytes that produce or are capable of producing α-SNAP-25 antibodies that will specifically bind to a SNAP-25 having a carboxyl-terminus at the $P_1$ residue of the BoNT/A cleavage site scissile bond.

The antibody titer in the immunized animal can be monitored over time by standard techniques, such as with an enzyme linked immunosorbent assay (ELISA) using immobilized antigen or a cell-based activity assay. Alternatively, the lymphocytes can be immunized in vitro using a suitable cell culture line. At an appropriate time after immunization, e.g., when the antibody titers are highest, antibody-producing cells are isolated from the animal. Generally, either peripheral blood lymphocytes are used, if cells of human origin are desired, or spleen cells or lymph node cells are used, if non-human mammalian sources are desired. The isolated antibody-producing cells are fused with an immortal cell line using a suitable fusing agent, such as polyethylene glycol, to form a hybridoma cell. Immortalized cell lines are usually transformed mammalian cells, particularly myeloma cells of rodent, bovine and human origin. Typically, a murine myeloma cell line is fused with splenocytes harvested from an appropriately immunized mouse to produce the hybridoma. Preferred immortal cell lines are mouse myeloma cell lines that are sensitive to culture medium containing hypoxanthine, aminopterin and thymidine (HAT). Any of a number of myeloma cell lines can be used as a fusion partner according to standard techniques, e.g., the P3-NS1/1-Ag4-1, P3-x63-Ag8.653 or Sp2/O-Ag14 myeloma lines. Hybridoma cells resulting from the fusion are then selected using HAT medium, which kills unfused and unproductively fused myeloma cells (unfused splenocytes die after several days in culture because they are not transformed). The culture medium in which the hybridoma cells are grown can then be assayed for the presence of α-SNAP-25 monoclonal antibodies that selectively bind to a SNAP-25 having a carboxyl-terminus at the $P_1$ residue of the BoNT/A cleavage site scissile bond. For example, hybridoma supernatants can be screened using α-SNAP-25 positive media in an immunoprecipitation assay, in vitro binding assay, such as, e.g., a radioimmunoassay (RIA) or an enzyme-linked immunoabsorbent assay (ELISA), or in a cell-based activity assay. Such techniques and assays are known in the art. See e.g., Chapter 11 *Immunoprecipitation*, pp. 421-470, Harlow & Lane, supra, 1998a; Chapter 12 *Immunoblotting*, pp. 471-510, Harlow & Lane, supra, 1998a; Chapter 14 *Immunoassays*, pp. 553-612, Harlow & Lane, supra, 1998a. Additional studies can then be done to determine whether the antibody is also unreactive to a SNAP-25 lacking a carboxyl-terminus at the $P_1$ residue of the BoNT/A cleavage site scissile bond. The binding affinity of an α-SNAP-25 monoclonal antibody can also be determined, e.g., by Scatchard analysis. See, e.g., Peter J. Munson and David Rodbard, *Ligand: A Versatile Computerized Approach For Characterization of Ligand-Binding Systems,* 107 (1) Anal. Biochem. 220-239 (1980). After the desired hybridoma cells are identified, limiting dilution procedures are used to isolate clones originating from a single cell until a clonal cell line expressing the desired monoclonal antibody is obtained. Those antibodies sufficiently selective for a SNAP-25 having a carboxyl-terminus at the $P_1$ residue of the BoNT/A cleavage site scissile bond and bind with sufficiently high avidity are chosen for further characterization and study.

Another alternative for preparing an α-SNAP-25 monoclonal antibody that selectively binds to a SNAP-25 having a carboxyl-terminus at the $P_1$ residue of the BoNT/A cleavage site scissile bond is by screening a recombinant combinatorial immunoglobulin library, such as, e.g., an antibody phage display library, with a SNAP-25 peptide and isolate immunoglobulin library members that bind a SNAP-25 having a carboxyl-terminus at the $P_1$ residue of the BoNT/A cleavage site scissile bond. Kits for generating and screening phage display libraries are commercially available, such as, e.g., the Recombinant Phage Antibody System (Amersham GE Healthcare, Piscataway, N.J.); and the SurfZAP™ Phage Display Kit (Stratagene, La Jolla, Calif.). Additionally, examples of methods and reagents useful in generating and screening antibody display library can be found in, for example, Ladner et al. U.S. Pat. No. 5,223,409; Borrebaeck et al. U.S. Pat. No. 5,712,089; Griffiths et al. U.S. Pat. No. 5,885,793; Griffiths et al. U.S. Pat. No. 5,962,255; McCafferty et al. U.S. Pat. No. 5,969,108; Griffiths et al. U.S. Pat. No. 6,010,884; Jespers et al. U.S. Pat. No. 6,017,732; Borrebaeck et al. U.S. Pat. No. 6,027,930; Johnson et al. U.S. Pat. No. 6,140,471; McCafferty et al. U.S. Pat. No. 6,172,197, each of which is hereby incorporated by reference in its entirety.

Aspects of the present disclosure comprise, in part, collecting a sample containing an α-SNAP-25 antibody or α-SNAP-25 antibody-producing cells. As used herein, the term "sample containing an α-SNAP-25 antibody or α-SNAP-25 antibody-producing cell" refers to any biological matter that contains or potentially contains at least one an α-SNAP-25 antibody that selectively binds to a SNAP-25 epitope having a carboxyl-terminus at the $P_1$ residue of the BoNT/A cleavage site scissile bond. It is envisioned that any and all samples that can contain an α-SNAP-25 antibody that selectively binds to a SNAP-25 epitope having a carboxyl-terminus at the $P_1$ residue of the BoNT/A cleavage site scissile bond can be used in this method, including, without limitation, blood, plasma, serum and lymph fluid. It is also envisioned that any cell capable of producing an α-SNAP-25 antibody that selectively binds to a SNAP-25 epitope having a carboxyl-terminus at the $P_1$ residue of the BoNT/A cleavage site scissile bond can be used in this method, including, without limitation, a CD8 cells, a CTL cell, a helper T-cell and a B-cell. A variety of well known methods can be used for collecting from an individual a sample containing the α-SNAP-25 antibody or α-SNAP-25 antibody-producing cell, see, e.g., Harlow & Lane, supra, 1998a; and Harlow & Lane, supra, 1998b. Similarly, a variety of well known methods can be used for processing a sample to isolate an α-SNAP-25 antibody that selectively binds to a SNAP-25 epitope having a carboxyl-terminus at the $P_1$ residue of the BoNT/A cleavage site scissile bond. A procedure for collecting a sample can be selected based on the type of antibody to be isolated. As a non-limiting example, when isolating an α-SNAP-25 polyclonal antibodies that selectively bind to a SNAP-25 having a carboxyl-terminus at the $P_1$ residue of the BoNT/A cleavage site scissile bond, an appropriate sample can be a blood sample containing such α-SNAP-25 antibodies, whereas when isolating an α-SNAP-25 monoclonal antibodies that selectively bind to a SNAP-25 having a carboxyl-terminus at the $P_1$ residue of the BoNT/A cleavage site scissile bond, an appropriate sample can be an α-SNAP-25 antibody-producing cell such as a spleen cell or hybridoma.

Aspects of the present disclosure comprise, in part, isolating an α-SNAP-25 antibody that selectively binds to a SNAP-25 epitope having a carboxyl-terminus at the $P_1$ residue of the BoNT/A cleavage site scissile bond from the sample. Methods of isolating an such α-SNAP-25 antibodies, such as, e.g., α-SNAP-25 polyclonal antibodies that selectively bind to a SNAP-25 having a carboxyl-terminus at the $P_1$ residue of the BoNT/A cleavage site scissile bond or α-SNAP-25 monoclonal antibodies that selectively bind to a SNAP-25 having a carboxyl-terminus at the $P_1$ residue of the BoNT/A cleavage site scissile bond are well known to those skilled in the art. See, e.g., Harlow and Lane, supra, 1998a; and Harlow and Lane, supra, 1998b. For example, such α-SNAP-25 polyclonal antibodies can be isolated from the sample by well known techniques, such as, e.g., affinity chromatography using protein A or protein G, which provide primarily the IgG fraction of immune serum. Subsequently, or alternatively, a specific SNAP-25 antigen can be immobilized on a column or magnetic beads to purify the α-SNAP-25 polyclonal antibodies that selectively binds to a SNAP-25 having a carboxyl-terminus at the $P_1$ residue of the BoNT/A cleavage site scissile bond by immunoaffinity chromatography. An α-SNAP-25 monoclonal antibody that selectively binds to a SNAP-25 having a carboxyl-terminus at the $P_1$ residue of the BoNT/A cleavage site scissile bond can be isolated from the culture medium or ascites fluid by conventional immunoglobulin purification procedures such as, e.g., protein A-Sepharose, hydroxylapatite chromatography, gel electrophoresis, dialysis, or affinity chromatography.

Thus, in an embodiment, a method of producing a α-SNAP-25 antibody that can selectively bind to a SNAP-25 having a carboxyl-terminus at the $P_1$ residue of the BoNT/A cleavage site scissile bond comprises the steps (a) administering to an animal a SNAP-25 immune response inducing composition comprising a SNAP-25 antigen having a carboxylated C-terminal glutamine linked to a carrier peptide; (b) collecting from the animal a sample containing an α-SNAP-25 antibody or α-SNAP-25 antibody-producing cell; and (c) isolating the α-SNAP-25 antibody component from the sample. In an aspect of this embodiment, the α-SNAP-25 antibody that can selectively bind to a SNAP-25 having a carboxyl-terminus at the $P_1$ residue of the BoNT/A cleavage site scissile bond is a polyclonal antibody. In another aspect of this embodiment, α-SNAP-25 antibody that can selectively bind to a SNAP-25 having a carboxyl-terminus at the $P_1$ residue of the BoNT/A cleavage site scissile bond is a monoclonal antibody. In a further aspect of this embodiment, an α-SNAP-25 monoclonal antibody that can selectively bind to a SNAP-25 having a carboxyl-terminus at the $P_1$ residue of the BoNT/A cleavage site scissile bond produced is an IgG subtype. In other aspects of this embodiment, SNAP-25 immune response inducing composition further comprises an adjuvant, such as, e.g., polyethylene glycol (PEG), monomethoxypolyethylene glycol (mPEG), or polyvinyl alcohol (PVA).

In another embodiment, a method of producing α-SNAP-25 antibodies that can selectively bind to a SNAP-25 having a carboxyl-terminus at the $P_1$ residue of the BoNT/A cleavage site scissile bond comprises the steps (a) administering to an animal a SNAP-25 immune response inducing composition comprising a SNAP-25 peptide having a carboxylated C-terminal glutamine linked to a flexible linker and a carrier peptide wherein the flexible linker intervenes between the SNAP-25 peptide and the carrier peptide; (b) collecting from the animal a sample containing an α-SNAP-25 antibody or α-SNAP-25 antibody-producing cell; and (c) isolating the α-SNAP-25 antibody from the sample. In an aspect of this embodiment, the α-SNAP-25 antibodies that can selectively bind to a SNAP-25 having a carboxyl-terminus at the $P_1$ residue of the BoNT/A cleavage site scissile bond is a polyclonal antibody. In another aspect of this embodiment, α-SNAP-25 antibodies that can selectively bind to a SNAP-25 having a carboxyl-terminus at the $P_1$ residue of the BoNT/A cleavage site scissile bond is a monoclonal antibody. In a further aspect of this embodiment, α-SNAP-25 monoclonal antibody that can selectively bind to a SNAP-25 having a carboxyl-terminus at the $P_1$ residue of the BoNT/A cleavage site scissile bond produced in an IgG subtype. In other aspects of this embodiment, SNAP-25 immune response inducing composition further comprises an adjuvant, such as, e.g., polyethylene glycol (PEG), monomethoxypolyethylene glycol (mPEG), or polyvinyl alcohol (PVA).

Aspects of the present disclosure comprise, in part, an isolated α-SNAP-25 antibody that selectively binds to a SNAP-25 epitope having a carboxyl-terminus at the $P_1$ residue of the BoNT/A cleavage site scissile bond. As used herein, the term "antibody" refers to a molecule generated by an immune system that was made in response to a particular antigen that specifically binds to that antigen, and includes both naturally occurring antibodies and non-naturally occurring antibodies. As used herein, the term "isolated" refers to separating a molecule from its natural environment by the use of human intervention. For example, an antibody can be a polyclonal antibody, a monoclonal antibody, a dimer, a multimer, a multispecific antibody, a humanized antibody, a chimeric antibody, bi-functional antibody, a cell-associated antibody like an Ig receptor, a linear antibody, a diabody, or a minibody, so long as the fragment exhibits the desired biological activity, and single chain derivatives of the same. An antibody can be a full-length immunoglobulin molecule comprising the $V_H$ and $V_L$ domains, as well as a light chain constant domain ($C_L$) and heavy chain constant domains, $C_{H1}$, $C_{H2}$ and $C_{H3}$, or an immunologically active fragment of a full-length immunoglobulin molecule, such as, e.g., a Fab fragment, a $F(ab')_2$ fragment, a Fc fragment, a Fd fragment, a Fv fragment. An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2). For general disclosure on the structure of naturally occurring antibodies, non-naturally occurring antibodies, and antigenic compound-binding fragments thereof, see, e.g., Pluckthun in The Pharmacology of Monoclonal Antibodies, vol. 113, Rosenburg and Moore eds., Springer-Verlag, New York, pp. 269-315 (1994); Borrabeck, *Antibody Engineering,* $2^{nd}$ ed. (Oxford University Press 1995), each of which is hereby incorporated by reference in its entirety.

Naturally-occurring antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The complete antigen-recognition and antigen-binding site is contained within the variable domains of the antibody, i.e., the Fv fragment. This fragment includes a dimer of one heavy chain variable domain ($V_H$) and one light chain variable domain ($V_L$) in tight, non-covalent association. Each domain comprises four framework regions (FR), which largely adopting a β-sheet configuration, connected by three hypervariable regions, which form loops connecting, and in some cases form part of, the β-sheet structure. Each hypervariable region comprises an amino acid sequence corresponding to a complementarity determining region (CDRs). Collectively, it the three-dimensional configuration of the six CDR regions that define an antigen-binding site on the surface of the $V_H$-$V_L$ dimmer that confers antigen-binding specificity. See e.g., Cyrus Chothia, et al., *Conformations of Immunoglobulin Hypervariable Regions*, Nature 342(6252): 877-883 (1989); Elvin A. Kabat, et al *Sequences of Proteins of Immunological Interest,* 5th Ed. Public Health Service, National Institutes of Health, Bethesda, Md. (1991), each of which is incorporated by reference in its entirety. The constant domains of the antibody are not involved directly in binding an antibody to an antigen, but exhibit various effector functions, such as participation of the antibody in antibody dependent cellular cytotoxicity.

A target antigen generally has one or more binding sites, also called epitopes, which are recognized by the CDR-formed antigen-binding site. As used herein, an "epitope" is synonymous with "antigenic determinant" and refers to the site on a target antigen, such as, e.g., a peptide, polysaccharide or lipid-containing molecule, capable of specific binding to an immunoglobulin or T-cell receptor or otherwise interacting with a molecule. Each antibody that specifically binds to a different epitope has a different structure. Thus, one antigen may have more than one corresponding antibody.

Polyclonal antibodies refer to a heterogeneous population of antibody molecules that contain at least two species of antibody capable of binding to a particular antigen. By definition, a polyclonal antibody includes two different antibodies that bind to at least two different epitopes. As used herein, the term "monoclonal antibody" or "monoclonal antibodies" refer to a substantially homogeneous population of antibody molecules that contain only one species of antibody capable of binding a particular antigen i.e., the individual antibodies comprising the population are identical except for possible naturally occurring mutations that may be present in minor amounts. By definition, a monoclonal antibody binds to a single epitope. Monoclonal antibodies are highly specific, being directed against a single antigenic site. Furthermore, in contrast to polyclonal antibodies, each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) Nature 256:495, or may be made by recombinant DNA methods (see for example: U.S. Pat. No. 4,816,567; U.S. Pat. No. 5,807,715). The monoclonal antibodies may also be isolated from phage antibody libraries using the techniques described in Clackson et al (1991) Nature, 352: 624-628; Marks et al (1991) J. Mol. Biol., 222:581-597; for example.

Thus, in an embodiment, an α-SNAP-25 antibody comprises a heavy chain variable domain ($V_H$) and a light chain variable domain ($V_L$) that selectively binds to a SNAP-25 having a carboxyl-terminus at the $P_1$ residue of the BoNT/A cleavage site scissile bond. In an aspect of this embodiment, the heavy chain variable domain ($V_H$) is SEQ ID NO:72, SEQ ID NO:74, SEQ ID NO:76, SEQ ID NO:80, SEQ ID NO:82, or SEQ ID NO:133. In another aspect of this embodiment, the light chain variable domain ($V_L$) is SEQ ID NO:84, SEQ ID NO:86, SEQ ID NO:88, SEQ ID NO:90, or SEQ ID NO:92.

In another embodiment, a nucleic acid sequence encodes an α-SNAP-25 antibody comprising a heavy chain variable domain ($V_H$) and a light chain variable domain ($V_L$) that selectively binds to a SNAP-25 having a carboxyl-terminus at the $P_1$ residue of the BoNT/A cleavage site scissile bond. In an aspect of this embodiment, the heavy chain variable domain ($V_H$) is encoded by the nucleic acid sequence SEQ ID NO:71, SEQ ID NO:73, SEQ ID NO:75, SEQ ID NO:77, SEQ ID NO:79, SEQ ID NO:81, or SEQ ID NO:132. In another aspect of this embodiment, the heavy chain variable domain ($V_H$) is encoded by a nucleic acid sequence that is at least 70% identical to, at least 75% identical to, at least 80% identical to, at least 85% identical to, at least 90% identical to, at least 95% identical, at least 96% identical, at least 97% identical, at least 98% identical, or at least 99% identical to SEQ ID NO:71, SEQ ID NO:73, SEQ ID NO:75, SEQ ID NO:77, SEQ ID NO:79, SEQ ID NO:81, or SEQ ID NO:132. In yet another aspect of this embodiment, the light chain variable domain ($V_L$) is encoded by SEQ ID NO:83, SEQ ID NO:85, SEQ ID NO:87, SEQ ID NO:89, or SEQ ID NO:91. In still another aspect of this embodiment, the light chain variable domain ($V_L$) is encoded by a nucleic acid sequence that is at least 70% identical to, at least 75% identical to, at least 80% identical to, at least 85% identical to, at least 90% identical to, at least 95% identical, at least 96% identical, at least 97% identical, at least 98% identical, or at least 99% identical to SEQ ID NO:83, SEQ ID NO:85, SEQ ID NO:87, SEQ ID NO:89, or SEQ ID NO:91.

In another embodiment, an α-SNAP-25 antibody comprises a heavy chain variable domain ($V_H$) CDR1 region, a CDR2 region, a CDR3 region, or any combination thereof that selectively binds to a SNAP-25 having a carboxyl-terminus at the $P_1$ residue of the BoNT/A cleavage site scissile bond. In an aspect of this embodiment, the heavy chain variable domain ($V_H$) CDR1 region is SEQ ID NO:93, SEQ ID NO:94, SEQ ID NO:95, SEQ ID NO:118, SEQ ID NO:119, or SEQ ID NO:120. In another aspect of this embodiment, the heavy chain variable domain ($V_H$) CDR2 region is SEQ ID NO:96, SEQ ID NO:97, SEQ ID NO:98, SEQ ID NO:99, SEQ ID NO:121, SEQ ID NO:122, or SEQ ID NO:123. In yet another aspect of this embodiment, the heavy chain variable domain ($V_H$) CDR3 region is SEQ ID NO:100, SEQ ID NO:101, SEQ ID NO:102, SEQ ID NO:124, SEQ ID NO:134, or SEQ ID NO:135.

In another embodiment, an α-SNAP-25 antibody comprises a light chain variable domain ($V_L$) CDR1 region, a CDR2 region, a CDR3 region, or any combination thereof that selectively binds to a SNAP-25 having a carboxyl-terminus at the $P_1$ residue of the BoNT/A cleavage site scissile bond. In an aspect of this embodiment, the light chain variable domain ($V_L$) CDR1 region is SEQ ID NO:103, SEQ ID NO:104, SEQ ID NO:105, SEQ ID NO:106, SEQ ID NO:107, SEQ ID NO:125, SEQ ID NO:126, SEQ ID NO:127, SEQ ID NO:128, or SEQ ID NO:129. In another aspect of this embodiment, the light chain variable domain ($V_L$) CDR2 region is SEQ ID NO:108, SEQ ID NO:109, SEQ ID NO:110, SEQ ID NO:111, or SEQ ID NO:112. In yet another aspect of this embodiment, the light chain variable domain ($V_L$) CDR3 region is SEQ ID NO:113, SEQ ID NO:114, SEQ ID NO:115, SEQ ID NO:116, or SEQ ID NO:117.

In yet another embodiment, an α-SNAP-25 antibody specifically binds an epitope comprising a SNAP-25 having a carboxyl-terminus at the $P_1$ residue of the BoNT/A cleavage site scissile bond. In an aspect of this embodiment, the epitope comprises SEQ ID NO:32, SEQ ID NO:33, SEQ ID NO:34, SEQ ID NO:35, SEQ ID NO:36, or SEQ ID NO:37. In an aspect of this embodiment, the epitope comprises SEQ ID NO:39, SEQ ID NO:40, SEQ ID NO:41, SEQ ID NO:42, SEQ ID NO:43, or SEQ ID NO:44.

As discussed above, the sequence surrounding a BoNT/A cleavage site present in SNAP-25 is denoted $P_5$-$P_4$-$P_3$-$P_2$-$P_1$-$P_1$'-$P_2$'-$P_3$'-$P_4$'-$P_5$', with $P_1$-$P_1$' representing the scissile bond. Upon cleavage by BoNT/A, the resulting cleavage products produced comprise a fragment including the $P_5$-$P_4$-$P_3$-$P_2$-$P_1$ sequence and a fragment including the $P_1$'-$P_2$'-$P_3$'-$P_4$'-$P_5$'. As used herein, the term "α-SNAP-25 antibodies that selectively bind to a SNAP-25 having a carboxyl-terminus at the $P_1$ residue of the BoNT/A cleavage site scissile bond" refers to α-SNAP-25 antibodies that selectively bind to any SNAP-25 cleavage product fragment comprising the $P_5$-$P_4$-$P_3$-$P_2$-$P_1$ sequence, but not to any SNAP-25 cleavage product fragment comprising the $P_1$'-$P_2$'-$P_3$'-$P_4$'-$P_5$' sequence or to any SNAP-25 having an intact $P_1$-$P_1$' scissile bond of a BoNT/A cleavage site. As used herein, the term "α-SNAP-$25_{197}$ antibody" refers to an antibody that selectively binds to a SNAP-25 having a carboxyl-terminus $P_1$ residue that corresponds to glutamine 197 of SEQ ID NO:5. As used herein, the term "α-SNAP-$25_{204}$ antibody" refers to an antibody that selectively binds to a SNAP-25 having a carboxyl-terminus $P_1$ residue that corresponds to lysine 204 of SEQ ID NO:16.

As used herein, the term "selectively" refers to having a unique effect or influence or reacting in only one way or with only one thing. As used herein, the term "selectively binds", or "selective binding" when made in reference to an antibody, refers to the discriminatory binding of the antibody to the indicated target epitope such that the antibody does not substantially cross react with non-target epitopes. The minimal size of a peptide epitope, as defined herein, is about five amino acids, and a peptide epitope typically comprises at least 5, at least 6, at least 7, at least 8, at least 9, at least 10, at least 15, or at least 20 amino acids. A peptide epitope may be discontinuous, i.e., it comprises amino acid residues that are not adjacent in the primary structure of the peptide but are brought together into an epitope by way of the secondary, tertiary, or quaternary structure of the peptide. Furthermore, it is also noted that an epitope might comprise a portion of a molecule other than an amino acid sequence, such as, e.g., a carbohydrate moiety, a lipid moiety like lipoproteins or glycolipids, or a chemically-modified amino acid moiety like a phosphorylated amino acid. In aspects of this embodiment, an α-SNAP-25 antibody that selectively binds to a SNAP-25 epitope having a carboxyl-terminus at the $P_1$ residue of the BoNT/A cleavage site scissile bond can selectively bind a SNAP-25 epitope having a carboxyl-terminus at the $P_1$ residue of the BoNT/A cleavage site scissile bond comprising at least 5, at least 6, at least 7, at least 8, at least 9, at least 10, at least 15, or at least 20 amino acids. In other aspects of this embodiment, an α-SNAP-25 antibody that selectively binds to a SNAP-25 epitope having a carboxyl-terminus at the $P_1$ residue of the BoNT/A cleavage site scissile bond can selectively bind a SNAP-25 epitope having a carboxyl-terminus at the $P_1$ residue of the BoNT/A cleavage site scissile bond comprising at most 5, at most 6, at most 7, at most 8, at most 9, at most 10, at most 15, or at most 20 amino acids.

Selective binding includes binding properties such as, e.g., binding affinity, binding specificity, and binding avidity. See David J. King, *Applications and Engineering of Monoclonal Antibodies*, pp. 240 (1998). Binding affinity refers to the length of time the antibody resides at its epitope binding site, and can be viewed as the strength with which an antibody binds its epitope. Binding affinity can be described an antibody's equilibrium dissociation constant (KD), which is defined as the ratio Kd/Ka at equilibrium. Where Ka is the antibody's association rate constant and kd is the antibody's dissociation rate constant. Binding affinity is determined by both the association and the dissociation and alone neither high association or low dissociation can ensure high affinity. The association rate constant (Ka), or on-rate constant (Kon), measures the number of binding events per unit time, or the propensity of the antibody and the antigen to associate reversibly into its antibody-antigen complex. The association rate constant is expressed in $M^{-1}$ $s^{-1}$, and is symbolized as follows: [Ab]×[Ag]×Kon. The larger the association rate constant, the more rapidly the antibody binds to its antigen, or the higher the binding affinity between antibody and antigen. The dissociation rate constant (Kd), or off-rate constant (Koff), measures the number of dissociation events per unit time propensity of an antibody-antigen complex to separate (dissociate) reversibly into its component molecules, namely the antibody and the antigen. The dissociation rate constant is expressed in $s^{-1}$, and is symbolized as follows: [Ab+Ag]×Koff. The smaller the dissociation rate constant, the more tightly bound the antibody is to its antigen, or the higher the binding affinity between antibody and antigen. The equilibrium dissociation constant (KD) measures the rate at which new antibody-antigen complexes formed equals the rate at which antibody-antigen complexes dissociate at equilibrium. The equilibrium dissociation constant is expressed in M, and is defined as Koff/Kon=[Ab]×[Ag]/[Ab+Ag], where [Ab] is the molar concentration of the antibody, [Ag] is the molar concentration of the antigen, and [Ab+Ag] is the molar concentration of the antibody-antigen complex, where all concentrations are of such components when the system is at equilibrium. The smaller the equilibrium dissociation constant, the more tightly bound the antibody is to its antigen, or the higher the binding affinity between antibody and antigen.

Thus, in an embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of, e.g., less than $1\times10^5$ $M^{-1}$ $s^{-1}$, less than $1\times10^6$ $M^{-1}$ $s^{-1}$, less than $1\times10^7$ $M^{-1}$ $s^{-1}$, or less than $1\times10^8$ $M^{-1}$ $s^{-1}$. In another embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of, e.g., more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$. In other aspects, the binding affinity of an α-SNAP-25 antibody that selectively binds to a SNAP-25 epitope having a carboxyl-terminus at the $P_1$ residue of the BoNT/A cleavage site scissile bond can have an association rate constant between $1\times10^5$ $M^{-1}$ $s^{-1}$ to $1\times10^8$ $M^{-1}$ $s^{-1}$, $1\times10^6$ $M^{-1}$ $s^{-1}$ to $1\times10^8$ $M^{-1}$ $s^{-1}$, $1\times10^5$ $M^{-1}$ $s^{-1}$ to $1\times10^7$ $M^{-1}$ $s^{-1}$, or $1\times10^6$ $M^{-1}$ $s^{-1}$ to $1\times10^7$ $M^{-1}$ $s^{-1}$.

In another embodiment, the binding affinity of an α-SNAP-25 antibody that selectively binds to a SNAP-25 epitope having a carboxyl-terminus at the $P_1$ residue of the BoNT/A cleavage site scissile bond can have a disassociation rate constant of less than $1\times10^{-3}$ $s^{-1}$, less than $1\times10^{-4}$ $s^{-1}$, or less than $1\times10^{-5}$ $s^{-1}$. In other aspects of this embodiment, the binding affinity of an α-SNAP-25 antibody that selectively binds to a SNAP-25 epitope having a carboxyl-terminus at the $P_1$ residue of the BoNT/A cleavage site scissile bond can have a disassociation rate constant of, e.g., less than $1.0\times10^{-4}$ $s^{-1}$, less than $2.0\times10^{-4}$ $s^{-1}$, less than $3.0\times10^{-4}$ $s^{-1}$, less than $4.0\times10^{-4}$ $s^{-1}$, less than $5.0\times10^{-4}$ $s^{-1}$, less than $6.0\times10^{-4}$ $s^{-1}$, less than $7.0\times10^{-4}$ $s^{-1}$, less than $8.0\times10^{-4}$ $s^{-1}$, or less than $9.0\times10^{-4}$ $s^{-1}$. In another embodiment, the binding affinity of an α-SNAP-25 antibody that selectively binds to a SNAP-25 epitope having a carboxyl-terminus at the $P_1$ residue of the BoNT/A cleavage site scissile bond can have a disassociation rate constant of, e.g., more than $1\times10^{-3}$ $s^{-1}$, more than $1\times10^{-4}$ $s^{-1}$, or more than $1\times10^{-5}$ $s^{-1}$. In other aspects of this embodiment, the binding affinity of an α-SNAP-25 antibody that selectively binds to a SNAP-25 epitope having a carboxyl-terminus at the $P_1$ residue of the BoNT/A cleavage site scissile bond can have a disassociation rate constant of, e.g., more than $1.0\times10^{-4}$ $s^{-1}$, more than $2.0\times10^{-4}$ $s^{-1}$, more than $3.0\times10^{-4}$ $s^{-1}$, more than $4.0\times10^{-4}$ $s^{-1}$, more than $5.0\times10^{-4}$ $s^{-1}$, more than $6.0\times10^{-4}$ $s^{-1}$, more than $7.0\times10^{-4}$ $s^{-1}$, more than $8.0\times10^{-4}$ $s^{-1}$, or more than $9.0\times10^{-4}$ $s^{-1}$.

In another embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of less than 0.500 nM. In aspects of this embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of more than 0.500 nM. In aspects of this embodiment, the binding affinity of an α-SNAP-25 antibody that selectively binds to a SNAP-25 epitope having a carboxyl-terminus at the $P_1$ residue of the BoNT/A cleavage site scissile bond can have an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

In yet another embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of for the intact SNAP-25 of, e.g., less than $1\times10^{0}$ $M^{-1}$ $s^{-1}$, less than $1\times10^{1}$ $M^{-1}$ $s^{-1}$, less than $1\times10^{2}$ $M^{-1}$ $s^{-1}$, less than $1\times10^{3}$ $M^{-1}$ $s^{-1}$, or less than $1\times10^{4}$ $M^{-1}$ $s^{-1}$. In another embodiment, the binding affinity of an α-SNAP-25 antibody that selectively binds to a SNAP-25 epitope having a carboxyl-terminus at the $P_1$ residue of the BoNT/A cleavage site scissile bond can have an association rate constant of for the intact SNAP-25 of, e.g., at most $1\times10^{0}$ $M^{-1}$ $s^{-1}$, at most $1\times10^{1}$ $M^{-1}$ $s^{-1}$, at most $1\times10^{2}$ $M^{-1}$ $s^{-1}$ at most $1\times10^{3}$ $M^{-1}$ $s^{-1}$, or at most $1\times10^{4}$ $M^{-1}$ $s^{-1}$.

Binding specificity is the ability of an antibody to discriminate between a molecule containing its epitope and a molecule that does not contain that epitope. One way to measure binding specificity is to compare the Kon association rate of the antibody for a molecule containing its epitope relative to the Kon association rate of the antibody for a molecule that does not contain that epitope. For example, comparing the association rate constant (Ka) of an α-SNAP-25 antibody for a SNAP-25 epitope having a carboxyl-terminus at the $P_1$ residue of the BoNT/A cleavage site scissile bond relative to a SNAP-25 not comprising that epitope, such as, e.g., a SNAP-25 epitope lacking a carboxyl-terminus at the $P_1$ residue of the BoNT/A cleavage site scissile bond or a SNAP-25 epitope having an intact $P_1$-$P_1$' scissile bond of a BoNT/A cleavage site. In aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for a SNAP-25 not comprising its epitope(s) of, e.g., less than $1\times10^{0}$ $M^{-1}$ $s^{-1}$, less than $1\times10^{1}$ $M^{-1}$ $s^{-1}$, less than $1\times10^{2}$ $M^{-1}$ $s^{-1}$, less than $1\times10^{3}$ $M^{-1}$ $s^{-1}$ or less than $1\times10^{4}$ $M^{-1}$ $s^{-1}$. In other aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for a SNAP-25 not comprising its epitope(s) of, e.g., at most $1\times10^{0}$ $M^{-1}$ $s^{-1}$, at most $1\times10^{1}$ $M^{-1}$ $s^{-1}$, at most $1\times10^{2}$ $M^{-1}$ $s^{-1}$, at most $1\times10^{3}$ $M^{-1}$ $s^{-1}$ or at most $1\times10^{4}$ $M^{-1}$ $s^{-1}$.

In yet aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for its epitope relative to a SNAP-25 not comprising that epitope of, e.g., at least 2-fold more, at least 3-fold more, at least 4-fold more, at least 5-fold more, at least 6-fold more, at least 7-fold more, at least 8-fold more, or at least 9-fold more. In further aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for its epitope relative to a SNAP-25 not comprising that epitope of, e.g., at least 10-fold more, at least 100-fold more, at least 1,000-fold more or at least 10,000-fold more. In yet other aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for its epitope relative to a SNAP-25 not comprising that epitope of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, an α-SNAP-25 antibody that selectively binds to a SNAP-25 epitope having a carboxyl-terminus at the $P_1$ residue of the BoNT/A cleavage site scissile bond has an association rate constant (Ka) for its epitope relative to a SNAP-25 not comprising that epitope of, e.g., at most 10-fold more, at most 100-fold more, at most 1,000-fold more or at most 10,000-fold more.

The binding specificity of an α-SNAP-25 antibody that selectively binds to a SNAP-25 epitope having a carboxyl-terminus at the $P_1$ residue of the BoNT/A cleavage site scissile bond can also be characterized as a ratio that such an α-SNAP-25 antibody can discriminate its SNAP-25 epitope relative to a SNAP-25 not comprising that epitope, such as, e.g., a SNAP-25 epitope lacking a carboxyl-terminus at the $P_1$ residue of the BoNT/A cleavage site scissile bond or a SNAP-25 epitope having an intact $P_1$-$P_1$' scissile bond of a BoNT/A cleavage site. In aspects of this embodiment, an α-SNAP-25 antibody that selectively binds to a SNAP-25 epitope having a carboxyl-terminus at the $P_1$ residue of the BoNT/A cleavage site scissile bond has a binding specificity ratio for its SNAP-25 epitope relative to a SNAP-25 not comprising that epitope of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In yet other aspects of this embodiment, an α-SNAP-25 antibody that selectively binds to a SNAP-25 epitope having a carboxyl-terminus at the $P_1$ residue of the BoNT/A cleavage site scissile bond has a binding specificity ratio for its SNAP-25 epitope relative to a SNAP-25 lacking a carboxyl-terminus at the $P_1$ residue of the BoNT/A cleavage site scissile bond of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In still other aspects of this embodiment, an α-SNAP-25 antibody that selectively binds to a SNAP-25 epitope having a carboxyl-terminus at the $P_1$ residue of the BoNT/A cleavage site scissile bond has a binding specificity ratio for its SNAP-25 epitope relative to a SNAP-25 having an intake $P_1$-$P_1'$ scissile bond of a BoNT/A cleavage site of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

Binding avidity, also known as functional affinity, refers to the sum total of the functional binding strength between a multivalent antibody and its antigen. Antibody molecules can have more than one binding site (e.g., 2 for IgG, 10 for IgM), and many antigens contain more than one antigenic site. While binding avidity of an antibody depends on the binding affinities of the individual antibody binding sites, binding avidity is greater than the binding affinity as all the antibody-antigen interactions must be broken simultaneously for the antibody to dissociate completely. It is envisioned that an α-SNAP-25 antibody that selectively binds to a SNAP-25 epitope having a carboxyl-terminus at the $P_1$ residue of the BoNT/A cleavage site scissile bond can selectively bind to any and all epitopes for that antibody.

Thus, in an embodiment, an α-SNAP-25 antibody is an α-SNAP-25 antibody that selectively binds to a SNAP-25 epitope having a carboxyl-terminus at the $P_1$ residue of the BoNT/A cleavage site scissile bond. In aspects of this embodiment, an α-SNAP-25 antibody is an α-SNAP-25 antibody that selectively binds to a SNAP-25 epitope having a carboxyl-terminus glutamine or an α-SNAP-25 antibody that selectively binds to a SNAP-25 epitope having a carboxyl-terminus lysine. In other aspects of this embodiment, an α-SNAP-25 antibody is an α-SNAP-25 antibody that selectively binds to a SNAP-25 epitope having a carboxyl-terminus $P_1$ residue that corresponds to glutamine 197 of SEQ ID NO:5 or an α-SNAP-25 antibody that selectively binds to a SNAP-25 epitope having a carboxyl-terminus $P_1$ residue that corresponds to lysine 204 of SEQ ID NO:16. In still other aspects of this embodiment, an α-SNAP-25 antibody is an α-SNAP-25 antibody that selectively binds to a SNAP-25 epitope having a carboxyl-terminal amino acid sequence of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:41, SEQ ID NO:42, SEQ ID NO:43, SEQ ID NO:44, SEQ ID NO:45, or SEQ ID NO:46.

Aspects of the present disclosure comprise, in part, an immuno-based method of detecting retargeted endopeptidase activity. The immuno-based methods disclosed in the present specification can be evaluated by several parameters including, e.g., accuracy, precision, limit of detection (LOD), limits of quantitation (LOQ), range, specificity, selectivity, linearity, ruggedness, and system suitability. The accuracy of a method is the measure of exactness of an analytical method, or the closeness of agreement between the measured value and the value that is accepted as a conventional true value or an accepted reference value. The precision of a method is the degree of agreement among individual test results, when the procedure is applied repeatedly to multiple samplings of a homogeneous sample. As such, precision evaluates 1) within assay variability; 2) within-day variability (repeatability); and 3) between-day variability (intermediate precision); and 4) between-lab variability (reproducibility). Coefficient of variation (CV %) is a quantitative measure of precision expressed relative to the observed or theoretical mean value.

An immuno-based method disclosed in the present specification must be able to detect, over background, the presence of an α-SNAP-25 antibody-antigen complex comprising a SNAP-25 having a carboxyl-terminus at the $P_1$ residue of the BoNT/A cleavage site scissile bond. The limit of detection (LOD) of a method refers to the concentration of analyte which gives rise to a signal that is significantly different from the negative control or blank and represents the lowest concentration of analyte that can be distinguished from background.

Thus, in an embodiment, the immuno-based method disclosed in the present specification can detect the LOD of retargeted endopeptidase at an amount that is significantly different from a negative control or blank. In aspect of this embodiment, the immuno-based method disclosed in the present specification has an LOD of, e.g., 10 ng or less, 9 ng or less, 8 ng or less, 7 ng or less, 6 ng or less, 5 ng or less, 4 ng or less, 3 ng or less, 2 ng or less, 1 ng or less of a retargeted endopeptidase. In still other aspects of this embodiment, the immuno-based method disclosed in the present specification has an LOD of, e.g., 900 pg or less, 800 pg or less, 700 pg or less, 600 pg or less, 500 pg or less, 400 pg or less, 300 pg or less, 200 pg or less, 100 pg or less of a retargeted endopeptidase. In further aspects of this embodiment, the immuno-based method disclosed in the present specification has an LOD of, e.g., 90 pg or less, 80 pg or less, 70 pg or less, 60 pg or less, 50 pg or less, 40 pg or less, 30 pg or less, 20 pg or less, 10 pg or less of a retargeted endopeptidase. In other aspects of this embodiment, the immuno-based method disclosed in the present specification has an LOD of, e.g., 9 pg or less, 8 pg or less, 7 pg or less, 6 pg or less, 5 pg or less, 4 pg or less, 3 pg or less, 2 pg or less, 1 pg or less of a retargeted endopeptidase. In yet other aspects of this embodiment, the immuno-based method disclosed in the present specification has an LOD of, e.g., 0.9 pg or less, 0.8 pg or less, 0.7 pg or less, 0.6 pg or less, 0.5 pg or less, 0.4 pg or less, 0.3 pg or less, 0.2 pg or less, 0.1 pg or less of a retargeted endopeptidase.

In another aspect of this embodiment, the immuno-based method disclosed in the present specification has an LOD of, e.g., 100 nM or less or less, 90 nM or less or less, 80 nM or less or less, 70 nM or less or less, 60 nM or less or less, 50 nM or less or less, 40 nM or less or less, 30 nM or less or less, 20 nM or less or less, 10 nM or less or less, 9 nM or less, 8 nM or less, 7 nM or less, 6 nM or less, 5 nM or less, 4 nM or less, 3 nM or less, 2 nM or less, or 1 nM or less of a retargeted endopeptidase. In other aspects of this embodiment, the immuno-based method disclosed in the present specification has an LOD of, e.g., 900 pM or less, 800 pM or less, 700 pM or less, 600 pM or less, 500 pM or less, 400 pM or less, 300 pM or less, 200 pM or less, or 100 pM or less of a retargeted endopeptidase. In other aspects of this embodiment, the immuno-based method disclosed in the present specification has an LOD of, e.g., 100 pM or less, 90 pM or less, 80 pM or less, 70 pM or less, 60 pM or less, 50 pM or less, 40 pM or less, 30 pM or less, 20 pM or less, or 10 pM or less of a retargeted endopeptidase. In yet other aspects of this embodiment, the immuno-based method disclosed in the present specification has an LOD of, e.g., 10 pM or less of a retargeted endopeptidase, 9 pM or less, 8 pM or less, 7 pM or less, 6 pM or less, 5 pM or less, 4 pM or less, 3 pM or less, 2 pM or less, or 1 pM or less of a retargeted endopeptidase.

The limits of quantitation (LOQ) are the lowest and the highest concentrations of analyte in a sample or specimen that can be measured with an acceptable level of accuracy and precision. The lower limit of quantitation refers to the lowest dose that a detection method can measure consistently from the background. The upper limit of quantitation is the highest dose that a detection method can measure consistently before saturation of the signal occurs. The linear range of the method is the area between the lower and the upper limits of quantitation. The linear range is calculated by subtracting lower limit of quantitation from the upper limit of quantitation. As used herein, the term "signal to noise ratio for the lower asymptote" refers to the signal detected in the method at the lower limit of detection divided by the background signal. As used herein, the term "signal to noise ratio for the upper asymptote" refers to the signal detected in the method at the upper limit of detection divided by the background signal.

Thus, in an embodiment, the immuno-based method disclosed in the present specification can detect the LOQ of retargeted endopeptidase at an amount that is significantly different from a negative control or blank. In aspect of this embodiment, the immuno-based method disclosed in the present specification has an LOQ of, e.g., 10 ng or less, 9 ng or less, 8 ng or less, 7 ng or less, 6 ng or less, 5 ng or less, 4 ng or less, 3 ng or less, 2 ng or less, 1 ng or less of a retargeted endopeptidase. In still other aspects of this embodiment, the immuno-based method disclosed in the present specification has an LOQ of, e.g., 900 pg or less, 800 pg or less, 700 pg or less, 600 pg or less, 500 pg or less, 400 pg or less, 300 pg or less, 200 pg or less, 100 pg or less of a retargeted endopeptidase. In further aspects of this embodiment, the immuno-based method disclosed in the present specification has an LOQ of, e.g., 90 pg or less, 80 pg or less, 70 pg or less, 60 pg or less, 50 pg or less, 40 pg or less, 30 pg or less, 20 pg or less, 10 pg or less of a retargeted endopeptidase. In other aspects of this embodiment, the immuno-based method disclosed in the present specification has an LOQ of, e.g., 9 pg or less, 8 pg or less, 7 pg or less, 6 pg or less, 5 pg or less, 4 pg or less, 3 pg or less, 2 pg or less, 1 pg or less of a retargeted endopeptidase. In yet other aspects of this embodiment, the immuno-based method disclosed in the present specification has an LOQ of, e.g., 0.9 pg or less, 0.8 pg or less, 0.7 pg or less, 0.6 pg or less, 0.5 pg or less, 0.4 pg or less, 0.3 pg or less, 0.2 pg or less, 0.1 pg or less of a retargeted endopeptidase.

In another aspect of this embodiment, the immuno-based method disclosed in the present specification has an LOQ of, e.g., 100 nM or less or less, 90 nM or less or less, 80 nM or less or less, 70 nM or less or less, 60 nM or less or less, 50 nM or less or less, 40 nM or less or less, 30 nM or less or less, 20 nM or less or less, 10 nM or less or less, 9 nM or less, 8 nM or less, 7 nM or less, 6 nM or less, 5 nM or less, 4 nM or less, 3 nM or less, 2 nM or less, or 1 nM or less of a retargeted endopeptidase. In other aspects of this embodiment, the immuno-based method disclosed in the present specification has an LOQ of, e.g., 900 pM or less, 800 pM or less, 700 pM or less, 600 pM or less, 500 pM or less, 400 pM or less, 300 pM or less, 200 pM or less, or 100 pM or less of a retargeted endopeptidase. In other aspects of this embodiment, the immuno-based method disclosed in the present specification has an LOQ of, e.g., 100 pM or less, 90 pM or less, 80 pM or less, 70 pM or less, 60 pM or less, 50 pM or less, 40 pM or less, 30 pM or less, 20 pM or less, or 10 pM or less of a retargeted endopeptidase. In yet other aspects of this embodiment, the immuno-based method disclosed in the present specification has an LOQ of, e.g., 10 pM or less of a retargeted endopeptidase, 9 pM or less, 8 pM or less, 7 pM or less, 6 pM or less, 5 pM or less, 4 pM or less, 3 pM or less, 2 pM or less, or 1 pM or less of a retargeted endopeptidase.

An immuno-based assay useful to practice aspect of the disclosed methods must have a precision of no more than 50%. In aspects of this embodiment, an immuno-based assay has a precision of no more than 50%, no more than 40%, no more than 30%, or no more than 20%. In other aspects of this embodiment, an immuno-based assay has a precision of nor more than 15%, no more than 10%, or no more than 5%. In other aspects of this embodiment, an immuno-based assay has a precision of nor more than 4%, no more than 3%, no more than 2%, or no more than 1%.

An immuno-based assay useful to practice aspect of the disclosed methods must have an accuracy of at least 50%. In aspects of this embodiment, an immuno-based assay has an accuracy of at least 50%, at least 60%, at least 70%, or at least 80%. In other aspects of this embodiment, an immuno-based assay has an accuracy of at least 85%, at least 90%, or at least 95%. In other aspects of this embodiment, an immuno-based assay has an accuracy of at least 96%, at least 97%, at least 98%, or at least 99%.

An immuno-based method disclosed in the present specification must have a signal to noise ratio for the lower asymptote that is statistically significant and a signal to noise ratio for the upper asymptote that is statistically significant. In aspects of this embodiment, an immuno-based method disclosed in the present specification has a signal to noise ratio for the lower asymptote of, e.g., at least 3:1, at least 4:1, at least 5:1, at least 6:1, at least 7:1, at least 8:1, at least 9:1, at least 10:1, at least 15:1 or at least 20:1. In other aspects of this embodiment, an immuno-based method has a signal to noise ratio for the upper asymptote of, e.g., at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1.

The specificity of a method defines the ability of the method to measure the analyte of interest to the exclusion of other relevant components, such as, e.g., partially-active or inactive analyte. The selectivity of a method describes the ability of an analytical method to differentiate various substances in a sample. The linearity of a method is its ability to elicit results that are directly, or by a well defined mathematical transformation, proportional to the concentration of analyte in the sample. Thus in an embodiment, an immuno-based method disclosed in the present specification can distinguish a fully-active retargeted endopeptidase from a partially-active retargeted endopeptidase having, e.g., 70% or less, 60% or less, 50% or less, 40% or less, 30% or less, 20% or less, or 10% or less the activity of a fully-active retargeted endopeptidase.

The ruggedness of the method is the reproducibility of the test results obtained for identical samples under normal (but variable) test conditions. Robustness of a procedure is a measure of its capacity to remain unaffected by small but deliberate variations in the method parameters and provides an indication of its reliability in normal usage. Thus, whereas ruggedness evaluates unavoidable changes, robustness evaluates deliberate changes. Typical parameters evaluated by ruggedness and robustness include the effects of freeze/thaw, incubation times, incubation temperature, longevity of reagent, sample preparation, sample storage, cell passage number, lots of re-targeted endopeptidase, variability between purifications, and variability between nicking reactions. Robustness parameters for cell-based assays include the cell bank (beginning, middle and end of freeze), cell passage level, cell seeding density, cell stock density (how many days in culture), cell age in flask (waiting time to seeding), incubation time, different plates, excessive amounts of serum, and source of reagents. The system suitability of the method is the determination of assay performance, including the performance of reagents and instruments, over time by analysis of a reference standard or reference molecule. System suitability is stressed in FDA guidance referring to the fact that equipment, electronics, assay performance, and samples to be analyzed, constitute an integrated system. System suitability can be evaluated by testing for parallelism, which is when plotting the log dose versus the response, serial dilutions of the reference and serial dilutions of the samples should give rise to parallel curves.

Aspects of the present disclosure comprise, in part, a cell from an established cell line. As used herein, the term "cell" refers to any eukaryotic cell susceptible to retargeted endopeptidase activity by a retargeted endopeptidase or any eukaryotic cell that can uptake a retargeted endopeptidase. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term "established cell line" is synonymous with "immortal cell line," or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a retargeted endopeptidase proteolytically cleaves a SNAP-25 substrate and encompasses the binding of a retargeted endopeptidase to its receptor, the internalization of the endopeptidase/receptor complex, the translocation of the retargeted endopeptidase light chain from an intracellular vesicle into the cytoplasm and the proteolytic cleavage of a SNAP-25. Alternatively, an established cell line can be one whose cells have had introduced from an exogenous source at least one component necessary for the cells to undergo the overall cellular mechanism whereby a retargeted endopeptidase proteolytically cleaves a SNAP-25 substrate and encompasses the binding of a retargeted endopeptidase to its receptor, the internalization of the endopeptidase/receptor complex, the translocation of the retargeted endopeptidase light chain from an intracellular vesicle into the cytoplasm and the proteolytic cleavage of a SNAP-25. Also referred to as a genetically-engineered cell line, cells from such an established cell line may, e.g., express an exogenous retargeted endopeptidase, such as, e.g., an exogenous ORL1, an exogenous DOR, an exogenous KOR, an exogenous MOR, an exogenous Galanin receptor 1, an exogenous Galanin receptor 2, an exogenous Galanin receptor 3, or any combination thereof.

Aspects of the present disclosure comprise, in part, a cell from an established cell line susceptible to retargeted endopeptidase activity. As used herein, the terms "cell(s) susceptible to retargeted endopeptidase activity," "cell(s) susceptible to retargeted endopeptidase activity by a retargeted endopeptidase," or "cell(s) from an established cell line susceptible to retargeted endopeptidase activity by a retargeted endopeptidase" refer to cell(s) that can undergo the overall cellular mechanism whereby a retargeted endopeptidase proteolytically cleaves a SNAP-25 substrate thereby inhibiting exocytosis and encompasses the binding of a retargeted endopeptidase to its receptor, the internalization of the endopeptidase/receptor complex, the translocation of the retargeted endopeptidase activity chain from an intracellular vesicle into the cytoplasm and the proteolytic cleavage of a SNAP-25. By definition, cell(s) susceptible to retargeted endopeptidase activity must express, or be engineered to express, at least one retargeted endopeptidase receptor and at least one SNAP-25 substrate. As used herein, the terms "cell(s) that can uptake retargeted endopeptidase" or "cell(s) comprising an established cell line that can uptake retargeted endopeptidase" refer to cells that can undergo the overall cellular mechanism whereby a retargeted endopeptidase proteolytically cleaves a SNAP-25 substrate thereby inhibiting exocytosis and encompasses the binding of a retargeted endopeptidase to its receptor, the internalization of the endopeptidase/receptor complex, the translocation of the retargeted endopeptidase light chain from an intracellular vesicle into the cytoplasm and the proteolytic cleavage of a SNAP-25. By definition, cell(s) that can uptake retargeted endopeptidase must express, or be engineered to express, at least one retargeted endopeptidase receptor and at least one SNAP-25 substrate.

Thus in an embodiment, cells from an established cell line are susceptible to retargeted endopeptidase activity. In aspects of this embodiment, cells from an established cell line are susceptible to retargeted endopeptidase activity by, e.g., about 100 nM or less or less, about 90 nM or less or less, about 80 nM or less or less, about 70 nM or less or less, about 60 nM or less or less, about 50 nM or less or less, about 40 nM or less or less, about 30 nM or less or less, about 20 nM or less or less, about 10 nM or less or less of a retargeted endopeptidase. In other aspects, cells from an established cell line are susceptible to retargeted endopeptidase activity by, e.g., about 9 nM or less, about 8 nM or less, about 7 nM or less, about 6 nM or less, about 5 nM or less, about 4 nM or less, about 3 nM or less, about 2 nM or less, or about 1 nM or less of a retargeted endopeptidase. In yet other aspects, cells from an established cell line are susceptible to retargeted endopeptidase activity by, e.g., about 0.9 nM or less, about 0.8 nM or less, about 0.7 nM or less, about 0.6 nM or less, about 0.5 nM or less, about 0.4 nM or less, about 0.3 nM or less, about 0.2 nM, or about 0.1 nM or less of a retargeted endopeptidase. As used herein, the term "about" when qualifying a value of a stated item, number, percentage, or term refers to a range of plus or minus ten percent of the value of the stated item, percentage, parameter, or term.

In another embodiment, cells comprising an established cell line can uptake a retargeted endopeptidase. In aspects of this embodiment, cells comprising an established cell line can uptake, e.g., about 100 nM or less or less, about 90 nM or less or less, about 80 nM or less or less, about 70 nM or less or less, about 60 nM or less or less, about 50 nM or less or less, about 40 nM or less or less, about 30 nM or less or less, about 20 nM or less or less, about 10 nM or less or less of a retargeted endopeptidase. In other aspects, cells comprising an established cell line possess the ability to uptake about 9 nM or less, about 8 nM or less, about 7 nM or less, about 6 nM or less, about 5 nM or less, about 4 nM or less, about 3 nM or less, about 2 nM or less, or about 1 nM or less of a retargeted endopeptidase. In yet other aspects, cells comprising an established cell line possess the ability to uptake about 0.9 nM or less, about 0.8 nM or less, about 0.7 nM or less, about 0.6 nM or less, about 0.5 nM or less, about 0.4 nM or less, about 0.3 nM or less, about 0.2 nM or less, or about 0.1 nM or less of a retargeted endopeptidase.

Aspects of the present disclosure comprise, in part, cells from an established cell line that exhibit a selective binding for a retargeted endopeptidase disclosed in the present specification. As used herein, the term "selectively binds", or "selective binding" when made in reference to a retargeted endopeptidase, refers to the discriminatory binding of a retargeted endopeptidase to the indicated target receptor such that the retargeted endopeptidase does not substantially bind to a non-target receptor. The degree to which cells from an established cell line exhibit selectively binding for a retargeted endopeptidase can be measured by the extent these cells exhibit non-selective uptake for a molecule lacking the targeting domain of the retargeted endopeptidase. One way to assess non-selective uptake for a molecule lacking the targeting domain of the retargeted endopeptidase is to measure the non-selective uptake of a $LH_N$ fragment. An $LH_N$ fragment is one that comprises a Clostridial toxin translocation domain and a Clostridial toxin enzymatic domain, but lacks any targeting domain altogether. Non-limiting examples of a $LH_N$ fragments include a $LH_N$/A fragment, a $LH_N$/B fragment, a $LH_N$/C fragment, a $LH_N$/D fragment, a $LH_N$/E fragment, a $LH_N$/F fragment, and a $LH_N$/G fragment. An exemplary $LH_N$/A fragment is SEQ ID NO:146 which is encoded by the polynucleotide molecule SEQ ID NO:147.

Thus, in an embodiment, cells from an established cell line exhibit selective binding for a retargeted endopeptidase. In aspects of this embodiment, cells from an established cell line exhibit selective binding for a retargeted endopeptidase that represents, e.g., at least 75% of the total activity assayed, at least 80% of the total activity assayed, at least 85% of the total activity assayed, at least 90% of the total activity assayed, or at least 95% of the total activity assayed. In other aspects of this embodiment, cells from an established cell line exhibit selective binding for a retargeted endopeptidase that represents, e.g., about 75% to about 100% of the total activity assayed, about 80% to about 100% of the total activity assayed, about 85% to about 100% of the total activity assayed, about 90% to about 100% of the total activity assayed.

In another embodiment, cells from an established cell line exhibit minimal non-selective uptake of a $LH_N$ fragment. In aspects of this embodiment, cells from an established cell line exhibit non-selective uptake of a $LH_N$ fragment that is, e.g., at most 25% of the total uptake measured, at most 20% of the total uptake measured, at most 15% of the total uptake measured, at most 10% of the total uptake measured, or at most 5% of the total uptake measured. In other aspects of this embodiment, cells from an established cell line exhibit non-selective uptake of a $LH_N$ fragment that is, e.g., about 0% to about 25% of the total uptake measured, about 0% to about 20% of the total uptake measured, about 0% to about 15% of the total uptake measured, about 0% to about 10% of the total uptake measured, or about 0% to about 5% of the total uptake measured.

In yet another embodiment, cells from an established cell line exhibit minimal non-selective uptake of a $LH_N$/A fragment. In aspects of this embodiment, cells from an established cell line exhibit non-selective uptake of a $LH_N$/A fragment that is, e.g., at most 25% of the total uptake measured, at most 20% of the total uptake measured, at most 15% of the total uptake measured, at most 10% of the total uptake measured, or at most 5% of the total uptake measured. In other aspects of this embodiment, cells from an established cell line exhibit non-selective uptake of a $LH_N$/A fragment that is, e.g., about 0% to about 25% of the total uptake measured, about 0% to about 20% of the total uptake measured, about 0% to about 15% of the total uptake measured, about 0% to about 10% of the total uptake measured, or about 0% to about 5% of the total uptake measured.

Aspects of the present disclosure comprise, in part, cells from an established cell line that exhibit a sufficient number of receptor binding sites on the plasma membrane to confer sensitive and selective binding for a retargeted endopeptidase. An equilibrium saturation binding assay measures the total and non-specific binding of a ligand at various concentrations. The equilibrium dissociation constant ($K_d$) for the ligand and the maximal number of receptor binding sites, Bmax, can be calculated from the specific binding using non-linear regression analysis. Specific binding is calculated by subtracting the non-specific binding of a ligand from the total binding observed. $K_d$ is the concentration of ligand required to reach half-maximal binding and is measured in terms of molarity. Bmax is the maximal number of binding sites present on the plasma membrane and is measured in terms of pmol/mg, pmol/cell, fmol/cell, or sites/cell.

Thus, in an embodiment, cells from an established cell line exhibit a sufficient number of receptor binding sites on the plasma membrane to confer sensitive and selective binding for a retargeted endopeptidase. In aspects of this embodiment, cells from an established cell line exhibit a Bmax value of, e.g., at least 0.1 fmol/cell, at least 0.2 fmol/cell, at least 0.3 fmol/cell, at least 0.4 fmol/cell, at least 0.5 fmol/cell, at least 0.6 fmol/cell, at least 0.7 fmol/cell, at least 0.8 fmol/cell, at least 0.9 fmol/cell, or at least 1.0 fmol/cell, for the targeting ligand of a retargeted endopeptidase. In other aspects of this embodiment, cells from an established cell line exhibit a Bmax value of, e.g., at least 1 fmol/cell, at least 2 fmol/cell, at least 3 fmol/cell, at least 4 fmol/cell, at least 5 fmol/cell, at least 6 fmol/cell, at least 7 fmol/cell, at least 8 fmol/cell, at least 9 fmol/cell, or at least 10 fmol/cell, for the targeting ligand of a retargeted endopeptidase.

Aspects of the present disclosure comprise, in part, cells from an established clonal cell line susceptible to re-targeted endopeptidase activity that are more stable than cells from the parental cell line from which the clonal cell line was derived. As used herein, the term "stable" refers to cells from an established clonal cell line for a particular passage number that exhibit a relative $EC_{50}$, sensitivity, efficacy, well-defined upper asymptote, and/or a well-defined dose-response curve for re-targeted endopeptidase activity that is similar to the values for relative $EC_{50}$, sensitivity, efficacy, well-defined upper asymptote, and/or a well-defined dose-response curve exhibited by cells from the parental cell line from which the clonal cell line was derived, at the same or similar passage number, where the same assay conditions and the same re-targeted endopeptidase are used in both assays.

Thus in an embodiment, cells from an established clonal cell line are more stable as compared to from the parental cell line from which the clonal cell line was derived. In an aspect of this embodiment, cells from an established clonal cell line are more stable as compared to the parental SK-N-DZ cell line. In another aspect of this embodiment, cells from an established clonal cell line are more stable as compared to the parental SK-N-DZ cell line ATCC CRL-2149. In other aspects of this embodiment, cells from an established clonal cell line are more stable for, e.g., at least 5 more passages, at least 10 more passages, at least 15 more passages, at least 20 more passages, at least 25 more passages, or at least 30 more passages, as compared to from the parental cell line from which the clonal cell line was derived. In yet other aspects of this embodiment, cells from an established clonal cell line are more stable for, e.g., at least 5 more passages, at least 10 more passages, at least 15 more passages, at least 20 more passages, at least 25 more passages, or at least 30 more passages, as compared to from the parental cell line from which the clonal cell line was derived.

Aspects of the present disclosure comprise, in part, cells from an established clonal cell line susceptible to re-targeted endopeptidase activity that are stable over a plurality of cell passages. As used herein, the term "stable" refers to cells from an established clonal cell line for a particular passage number that exhibit a relative $EC_{50}$, sensitivity, efficacy, well-defined upper asymptote, and/or a well-defined dose-response curve for re-targeted endopeptidase activity that is similar to the values for relative $EC_{50}$, sensitivity, efficacy, well-defined upper asymptote, and/or a well-defined dose-response curve exhibited by cells from the same established clonal cell line, but from a prior passage or passages, where the same assay conditions and the same re-targeted endopeptidase are used in both assays.

Cells from an established cell line disclosed in the present specification can exhibit a consistent sensitivity for re-targeted endopeptidase activity over a plurality of cell passages. As used herein, the term "sensitivity for re-targeted endopeptidase activity" refers to the lowest dose that an assay can measure consistently above the signal detected by a non-treatment control or background signal.

Thus, in an embodiment, cells from the established clonal cell line exhibit a sensitivity for re-targeted endopeptidase activity for any given passages that is e.g., 100 nM or less, about 80 nM or less, about 70 nM or less, about 60 nM or less, about 50 nM or less, about 40 nM or less, about 30 nM or less, about 20 nM or less, about 10 nM or less, about 1 nM or less, about 0.9 nM or less, about 0.8 nM or less, about 0.7 nM or less, about 0.6 nM or less, about 0.5 nM or less, about 0.4 nM or less, about 0.3 nM or less, about 0.2 nM or less, or about 0.1 nM or less of a re-targeted endopeptidase. In aspects of this embodiment, cells from the established clonal cell line exhibit a sensitivity for re-targeted endopeptidase activity for any given passages that is, e.g., about 0.01 nM to about 100 nM, about 0.01 nM to about 75 nM, about 0.01 nM to about 50 nM, about 0.01 nM to about 25 nM, about 0.01 nM to about 20 nM, about 0.01 nM to about 15 nM, about 0.01 nM to about 10 nM, about 0.01 nM to about 5 nM, about 0.001 nM to about 100 nM, about 0.001 nM to about 75 nM, about 0.001 nM to about 50 nM, about 0.001 nM to about 25 nM, about 0.001 nM to about 20 nM, about 0.001 nM to about 15 nM, about 0.001 nM to about 10 nM, or about 0.001 nM to about 5 nM of a re-targeted endopeptidase.

In another embodiment, cells from the established clonal cell line exhibit a sensitivity for re-targeted endopeptidase activity that is about 100 nM or less, about 75 nM or less, about 50 nM or less, about 25 nM or less, less about 20 nM or less, about 15 nM or less, about 10 nM or less, or about 1 nM or less for, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from the established clonal cell line exhibit a sensitivity for re-targeted endopeptidase activity that is about 100 nM or less, about 75 nM or less, about 50 nM or less, about 25 nM or less, less about 20 nM or less, about 15 nM or less, about 10 nM or less, or about 1 nM or less for, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a consistent relative efficacy of re-targeted endopeptidase uptake or re-targeted endopeptidase activity over a plurality of cell passages. As used herein, the term "relative efficacy" refers to how well the upper asymptote for the re-targeted endopeptidase activity detected in the current assay run compares to the upper asymptote for the re-targeted endopeptidase activity detected in a reference standard, a reference molecule, or a reference passage number used on that assay. As used herein, the term "signal to noise ratio for the upper asymptote" refers to the signal detected in an assay at the upper limit of detection divided by the signal detected by a non-treatment control or background signal. The upper limit of detection is the highest dose that an assay can measure consistently before saturation of the signal occurs.

Thus, in an embodiment, cells from an established cell line disclosed in the present specification can exhibit a well defined upper asymptote over a plurality of cell passages and maintain a signal to noise ratio that is consistent and adequate for the assay. In aspects of this embodiment, cells from an established cell line disclosed in the present specification must have a well defined signal to noise ratio for the upper asymptote for re-targeted endopeptidase activity of, e.g., at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established cell line disclosed in the present specification must have a well defined signal to noise ratio for the upper asymptote for re-targeted endopeptidase activity of, e.g., at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1, over, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a well defined dose-response curve for re-targeted endopeptidase activity over a plurality of cell passages. As used herein, the term "dose-response curve" refers to the how well the raw data fits the statistical model of choice for that assay. As a non-limiting example, a sigmoidal curve with a four parameter logistics fit is a dose-response curve for an enzymatic activity assay, such as, e.g. a potency assay. As another non-limiting example, a ligand binding with one site saturation fit is a dose-response curve for a ligand/antibody binding assay.

Thus, in an embodiment, cells from an established cell line disclosed in the present specification exhibit a well defined dose-response curve for re-targeted endopeptidase activity over a plurality of cell passages. In aspects of this embodiment, cells from an established cell line disclosed in the present specification exhibit a well defined dose-response curve for re-targeted endopeptidase activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established cell line disclosed in the present specification exhibit a well defined dose-response curve for re-targeted endopeptidase activity over, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a consistent relative $EC_{50}$ value for re-targeted endopeptidase activity over a plurality of cell passages. As used herein, the term "relative $EC_{50}$" or "relative $EC_{50}$ value" refers to an $EC_{50}$ value for re-targeted endopeptidase activity that is normalized against the $EC_{50}$ calculated for a reference standard, a reference molecule, or a reference passage number used on that assay.

Thus, in an embodiment, cells from an established clonal cell line exhibit a consistent relative $EC_{50}$ for re-targeted endopeptidase activity over a plurality of cell passages. In aspects of this embodiment, cells from an established clonal cell line exhibit a consistent relative $EC_{50}$ for re-targeted endopeptidase activity that is, e.g., about ±10%, about ±20%, about ±30%, about ±40%, about ±50%, about ±60%, about ±70%, or about ±75% the relative $EC_{50}$ for re-targeted endopeptidase activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established clonal cell line exhibit a relative $EC_{50}$ for re-targeted endopeptidase activity that is, e.g., about ±10% to about 75%, about ±10% to about 70%, about ±10% to about 60%, about ±10% to about 50%, about ±10% to about 40%, about ±10% to about 30%, or about ±10% to about 20% the relative $EC_{50}$ for re-targeted endopeptidase activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages.

Aspects of the present disclosure comprise, in part, a retargeted endopeptidase. As used herein, the term "retargeted endopeptidase" is synonymous with "Targeted Vesicular Exocytosis Modulator Protein" or "TVEMP." Non-limiting examples of retargeted endopeptidase are disclosed in, e.g., Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; J. Oliver Dolly et al., Activatable Recombinant Neurotoxins, WO 2001/014570; Keith A. Foster et al., Re-targeted Toxin Conjugates, International Patent Publication WO 2005/023309; Lance E. Steward et al., Multivalent Clostridial Toxin Derivatives and Methods of Their Use, U.S. patent application Ser. No. 11/376,696; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Dolly, J. O. et al., Activatable Clostridial Toxins, U.S. patent application Ser. No. 11/829,475; Foster, K. A. et al., Fusion Proteins, International Patent Publication WO 2006/059093; and Foster, K. A. et al., Non-Cytotoxic Protein Conjugates, International Patent Publication WO 2006/059105, each of which is incorporated by reference in its entirety. Non-limiting examples of retargeted endopeptidases include SEQ ID NO:1, SEQ ID NO:2, SEQ ID NO:3, SEQ ID NO:4, SEQ ID NO:130, and SEQ ID NO:131.

Thus in an embodiment, the retargeted endopeptidase activity being detected is from a retargeted endopeptidase. In aspects of this embodiment, the retargeted endopeptidase activity being detected is from a retargeted endopeptidase disclosed in Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; J. Oliver Dolly et al., Activatable Recombinant Neurotoxins, WO 2001/014570; Keith A. Foster et al., Re-targeted Toxin Conjugates, International Patent Publication WO 2005/023309; Lance E. Steward et al., Multivalent Clostridial Toxin Derivatives and Methods of Their Use, U.S. patent application Ser. No. 11/376,696; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Dolly, J. O. et al., Activatable Clostridial Toxins, U.S. patent application Ser. No. 11/829,475; Foster, K. A. et al., Fusion Proteins, International Patent Publication WO 2006/059093; and Foster, K. A. et al., Non-Cytotoxic Protein Conjugates, International Patent Publication WO 2006/059105, each of which is incorporated by reference in its entirety. In aspects of this embodiment, a retargeted endopeptidase is SEQ ID NO:1, SEQ ID NO:2, SEQ ID NO:3, SEQ ID NO:4, SEQ ID NO:130, or SEQ ID NO:131.

In another embodiment, the retargeted endopeptidase activity being detected is from a retargeted endopeptidase having, e.g., at least 70%, at least 75%, at least 80%, at least 85%, at least 90%, or at least 95% amino acid identity with a retargeted endopeptidase disclosed in Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; J. Oliver Dolly et al., Activatable Recombinant Neurotoxins, WO 2001/014570; Keith A. Foster et al., Re-targeted Toxin Conjugates, International Patent Publication WO 2005/023309; Lance E. Steward et al., Multivalent Clostridial Toxin Derivatives and Methods of Their Use, U.S. patent application Ser. No. 11/376,696; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Dolly, J. O. et al., Activatable Clostridial Toxins, U.S. patent application Ser. No. 11/829,475; Foster, K. A. et al., Fusion Proteins, International Patent Publication WO 2006/059093; and Foster, K. A. et al., Non-Cytotoxic Protein Conjugates, International Patent Publication WO 2006/059105, each of which is incorporated by reference in its entirety. In another embodiment, the retargeted endopeptidase activity being detected is from a retargeted endopeptidase having, e.g., at least 70%, at least 75%, at least 80%, at least 85%, at least 90%, or at least 95% amino acid identity with a retargeted endopeptidase of SEQ ID NO:1, SEQ ID NO:2, SEQ ID NO:3, SEQ ID NO:4, SEQ ID NO:130, or SEQ ID NO:131.

In other aspects of this embodiment, the retargeted endopeptidase activity being detected is from a re-targeted endopeptidase having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to a retargeted endopeptidase disclosed in Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; J. Oliver Dolly et al., Activatable Recombinant Neurotoxins, WO 2001/014570; Keith A. Foster et al., Re-targeted Toxin Conjugates, International Patent Publication WO 2005/023309; Lance E. Steward et al., Multivalent Clostridial Toxin Derivatives and Methods of Their Use, U.S. patent application Ser. No. 11/376,696; Steward, L. E. et al., Modified Clostridial Toxins with Enhanced Translocation Capabilities and Altered Targeting Activity For Non-Clostridial Toxin Target Cells, U.S. patent application Ser. No. 11/776,075; Dolly, J. O. et al., Activatable Clostridial Toxins, U.S. patent application Ser. No. 11/829,475; Foster, K. A. et al., Fusion Proteins, International Patent Publication WO 2006/059093; and Foster, K. A. et al., Non-Cytotoxic Protein Conjugates, International Patent Publication WO 2006/059105, each of which is incorporated by reference in its entirety. In other aspects of this embodiment, the retargeted endopeptidase activity being detected is from a retargeted endopeptidase having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to a retargeted endopeptidase of SEQ ID NO:1, SEQ ID NO:2, SEQ ID NO:3, SEQ ID NO:4, SEQ ID NO:130, or SEQ ID NO:131.

In yet other aspects of this embodiment, the retargeted endopeptidase activity being detected is from a non-naturally occurring retargeted endopeptidase variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to a retargeted endopeptidase disclosed in Keith A. Foster et al., Clostridial Toxin Derivatives Able To Modify Peripheral Sensory Afferent Functions, U.S. Pat. No. 5,989,545; Clifford C. Shone et al., Recombinant Toxin Fragments, U.S. Pat. No. 6,461,617; Conrad P. Quinn et al., Methods and Compounds for the Treatment of Mucus Hypersecretion, U.S. Pat. No. 6,632,440; Lance E. Steward et al., Methods And Compositions For The Treatment Of Pancreatitis, U.S. Pat. No. 6,843,998; Stephan Donovan, Clostridial Toxin Derivatives and Methods For Treating Pain, U.S. Patent Publication 2002/0037833; Keith A. Foster et al., Inhibition of Secretion from Non-neural Cells, U.S. Patent Publication 2003/0180289; J. Oliver Dolly et al., Activatable Recombinant Neurotoxins, WO 2001/014570; Keith A. Foster et al., Re-targeted Toxin Conjugates, International Patent Publication WO 2005/023309; Lance E. Steward et al., Multivalent Clostridial Toxin Derivatives and Methods of Their Use, U.S. patent application Ser. No. 11/376,696;

Steward, L. E. et al., Modified Clostridial Toxins with Enhanced Translocation Capabilities and Altered Targeting Activity For Non-Clostridial Toxin Target Cells, U.S. patent application Ser. No. 11/776,075; Dolly, J. O. et al., Activatable Clostridial Toxins, U.S. patent application Ser. No. 11/829,475; Foster, K. A. et al., Fusion Proteins, International Patent Publication WO 2006/059093; and Foster, K. A. et al., Non-Cytotoxic Protein Conjugates, International Patent Publication WO 2006/059105, each of which is incorporated by reference in its entirety. In yet other aspects of this embodiment, the retargeted endopeptidase activity being detected is from a non-naturally occurring retargeted endopeptidase variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to a retargeted endopeptidase of SEQ ID NO:1, SEQ ID NO:2, SEQ ID NO:3, SEQ ID NO:4, SEQ ID NO:130, or SEQ ID NO:131.

In yet another embodiment, the retargeted endopeptidase activity being detected is from an opioid retargeted endopeptidase. Non-limiting examples of opioid re-targeted endopeptidase, or opioid-TVEMPs, are described in, e.g., Keith A. Foster et al., Clostridial Toxin Derivatives Able To Modify Peripheral Sensory Afferent Functions, U.S. Pat. No. 5,989,545; J. Oliver Dolly et al., Activatable Recombinant Neurotoxins, U.S. Pat. No. 7,132,259; Stephan Donovan, Clostridial Toxin Derivatives and Methods For Treating Pain, U.S. Pat. No. 7,244,437; Stephan Donovan, Clostridial Toxin Derivatives and Methods For Treating Pain, U.S. Pat. No. 7,413,742; Stephan Donovan, Clostridial Toxin Derivatives and Methods For Treating Pain, U.S. Pat. No. 7,415,338; Lance E. Steward et al., Multivalent Clostridial Toxin Derivatives and Methods of Their Use, U.S. Pat. No. 7,514,088; Keith A. Foster, Fusion Proteins, U.S. Patent Publication 2008/0064092; Keith A. Foster, Fusion Proteins, U.S. Patent Publication 2009/0035822; Lance E. Steward et al., Multivalent Clostridial Toxin Derivatives and Methods of Their Use, U.S. Patent Publication 2009/0048431; Keith A. Foster, Non-Cytotoxic Protein Conjugates, U.S. Patent Publication 2009/0162341; Keith A. Foster et al., Re-targeted Toxin Conjugates, International Patent Publication WO 2005/023309; and Lance E. Steward, Modified Clostridial Toxins with Enhanced Translocation Capabilities and Altered Targeting Capabilities for Non-Clostridial Toxin Target Cells, International Patent Application WO 2008/008805; each of which is hereby incorporated by reference in its entirety.

In yet another embodiment, the retargeted endopeptidase activity being detected is from a galanin retargeted endopeptidase. Non-limiting examples of galanin re-targeted endopeptidase, or galanin-TVEMPs, are described in, e.g., Steward, L. E. et al., Modified Clostridial Toxins with Enhanced Translocation Capability and Enhanced Targeting Activity, U.S. patent application Ser. No. 11/776,043 (Jul. 11, 2007); Steward, L. E. et al., Modified Clostridial Toxins with Enhanced Translocation Capabilities and Altered Targeting Activity For Clostridial Toxin Target Cells, U.S. patent application Ser. No. 11/776,052 (Jul. 11, 2007); and Steward, L. E. et al., Modified Clostridial Toxins with Enhanced Translocation Capabilities and Altered Targeting Activity For Non-Clostridial Toxin Target Cells, U.S. patent application Ser. No. 11/776,075 (Jul. 11, 2007), each of which is incorporated by reference in its entirety.

Aspects of the present disclosure comprise, in part, a SNAP-25. As used herein, the term "SNAP-25" refers to a naturally-occurring SNAP-25 or a non-naturally occurring SNAP-25 which is preferentially cleaved by a retargeted endopeptidase. As used herein, the term "preferentially cleaved" refers to that the cleavage rate of SNAP-25 by a retargeted endopeptidase is at least one order of magnitude higher than the cleavage rate of any other substrate by a retargeted endopeptidase. In aspects of this embodiment, the cleavage rate of SNAP-25 by a retargeted endopeptidase is at least two orders of magnitude higher, at least three orders of magnitude higher, at least four orders of magnitude higher, or at least five orders of magnitude higher than that the cleavage rate of any other substrate by retargeted endopeptidase.

As used herein, the term "naturally occurring SNAP-25" refers to any SNAP-25 produced by a naturally-occurring process, including, without limitation, SNAP-25 isoforms produced from a post-translational modification, an alternatively-spliced transcript, or a spontaneous mutation, and SNAP-25 subtypes. A naturally occurring SNAP-25 includes, without limitation, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

As used herein, the term "non-naturally occurring SNAP-25" refers to any SNAP-25 whose structure was modified with the aid of human manipulation, including, without limitation, a SNAP-25 produced by genetic engineering using random mutagenesis or rational design and a SNAP-25 produced by in vitro chemical synthesis. Non-limiting examples of non-naturally occurring SNAP-25s are described in, e.g., Steward, L. E. et al., FRET Protease Assays for Clostridial Toxins, U.S. Pat. No. 7,332,567; Fernandez-Salas et al., Lipophilic Dye-based FRET Assays for Clostridial Toxin Activity, U.S. Patent Publication 2008/0160561, each of which is hereby incorporated by reference in its entirety. A non-naturally occurring SNAP-25 may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

Thus in an embodiment, a SNAP-25 is a naturally occurring SNAP-25. In aspects of this embodiment, the SNAP-25 is a SNAP-25 isoform or a SNAP-25 subtype. In aspects of this embodiment, the naturally occurring SNAP-25 is the naturally occurring SNAP-25 of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In other aspects of this embodiment, the SNAP-25 is a naturally occurring SNAP-25 having, e.g., at least 70% amino acid identity, at least 75%, at least 80%, at least 85%, at least 90%, or at least 95% amino acid identity with SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

In another embodiment, a SNAP-25 is a non-naturally occurring SNAP-25. In other aspects of this embodiment, the SNAP-25 is a non-naturally occurring SNAP-25 having, e.g., at least 70%, at least 75%, at least 80%, at least 85%, at least 90%, or at least 95% amino acid identity with SEQ ID NO:1, SEQ ID NO:2, SEQ ID NO:3, or SEQ ID NO:4. In other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In yet other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

A SNAP-25 can be an endogenous SNAP-25 or an exogenous SNAP-25. As used herein, the term "endogenous SNAP-25" refers to a SNAP-25 naturally present in the cell because it is naturally encoded within the cell's genome, such that the cell inherently expresses the SNAP-25 without the need an external source of SNAP-25 or an external source of genetic material encoding a SNAP-25. The expression of an endogenous SNAP-25 may be with or without environmental stimulation such as, e.g., cell differentiation. By definition, an endogenous SNAP-25 can only be a naturally-occurring SNAP-25 or variants thereof. For example, the following established cell lines express an endogenous SNAP-25: BE(2)-M17, Kelly, LA1-55n, N1E-115, N4TG3, N18, Neuro-2a, NG108-15, PC12, SH-SY5Y, SiMa, SK-N-DZ, and SK-N-BE(2)-C.

As used herein, the term "exogenous SNAP-25" refers to a SNAP-25 expressed in a cell through the introduction of an external source of SNAP-25 or an external source of genetic material encoding a SNAP-25 by human manipulation. The expression of an exogenous SNAP-25 may be with or without environmental stimulation such as, e.g., cell differentiation. As a non-limiting example, cells from an established cell line can express an exogenous SNAP-25 by transient or stably transfection of a SNAP-25. As another non-limiting example, cells from an established cell line can express an exogenous SNAP-25 by protein transfection of a SNAP-25. An exogenous SNAP-25 can be a naturally-occurring SNAP-25 or variants thereof, or a non-naturally occurring SNAP-25 or variants thereof.

Thus in an embodiment, cells from an established cell line express an endogenous SNAP-25. In aspects of this embodiment, the endogenous SNAP-25 expressed by cells from an established cell line is a naturally-occurring SNAP-25. In other aspects of this embodiment, the endogenous SNAP-25 expressed by cells from an established cell line is SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In yet aspects of this embodiment, the endogenous SNAP-25 expressed by cells from an established cell line is a naturally occurring SNAP-25, such as, e.g., a SNAP-25 isoform or a SNAP-25 subtype. In other aspects of this embodiment, the endogenous SNAP-25 expressed by cells from an established cell line is a naturally occurring SNAP-25 having, e.g., at least 70% amino acid identity, at least 75%, at least 80%, at least 85%, at least 90%, or at least 95% amino acid identity with SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

In another embodiment, cells from an established cell line are transiently or stably engineered to express an exogenous SNAP-25. In an aspect of this embodiment, cells from an established cell line are transiently or stably engineered to express a naturally-occurring SNAP-25. In other aspects of this embodiment, cells from an established cell line are transiently or stably engineered to express the naturally-occurring SNAP-25 of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In yet other aspects of this embodiment, cells from an established cell line are transiently or stably engineered to express a naturally occurring SNAP-25, such as, e.g., a SNAP-25 isoform or a SNAP-25 subtype. In still other aspects of this embodiment, cells from an established cell line are transiently or stably engineered to express a naturally occurring SNAP-25 having, e.g., at least 70% amino acid identity, at least 75%, at least 80%, at least 85%, at least 90%, or at least 95% amino acid identity with SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

In another aspect of the embodiment, cells from an established cell line are transiently or stably engineered to express a non-naturally occurring SNAP-25. In other aspects of this embodiment, cells from an established cell line are transiently or stably engineered to express a non-naturally occurring SNAP-25 having, e.g., at least 70%, at least 75%, at least 80%, at least 85%, at least 90%, or at least 95% amino acid identity with SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In other aspects of this embodiment, cells from an established cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24. In yet other aspects of this embodiment, cells from an established cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, or SEQ ID NO:24.

Assays that detect the cleavage of a SNAP-25 after exposure to a retargeted endopeptidase can be used to assess whether a cell is expressing an endogenous or exogenous SNAP-25. In these assays, generation of a SNAP-25 cleavage-product would be detected in cells expressing a SNAP-25 after retargeted endopeptidase treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for SNAP-25 cleavage can be useful in identifying cells expressing an endogenous or an exogenous SNAP-25.

As non-limiting examples, Western blot analysis using an antibody that recognize a SNAP-25 cleavage product or both the cleaved and uncleaved forms of SNAP-25 can be used to assay for uptake of retargeted endopeptidase. Examples of α-SNAP-25 antibodies useful for these assays include, without limitation, α-SNAP-25 mouse monoclonal antibody SMI-81 (Sternberger Monoclonals Inc., Lutherville, Md.), mouse α-SNAP-25 monoclonal antibody CI 71.1 (Synaptic Systems, Goettingen, Germany), α-SNAP-25 mouse monoclonal antibody CI 71.2 (Synaptic Systems, Goettingen, Germany), α-SNAP-25 mouse monoclonal antibody SP12 (Abcam, Cambridge, Mass.), α-SNAP-25 rabbit polyclonal antiserum (Synaptic Systems, Goettingen, Germany), α-SNAP-25 rabbit polyclonal antiserum (Abcam, Cambridge, Mass.), and α-SNAP-25 rabbit polyclonal antiserum S9684 (Sigma, St Louis, Mo.).

Aspects of the present disclosure comprise, in part, a retargeted endopeptidase receptor. As used herein, the term "retargeted endopeptidase receptor" refers to either a naturally-occurring retargeted endopeptidase receptor or a non-naturally occurring retargeted endopeptidase receptor which preferentially interacts with a retargeted endopeptidase in a manner that elicits a retargeted endopeptidase activity response. As used herein, the term "preferentially interacts" refers to that the equilibrium dissociation constant (KD) of retargeted endopeptidase for a retargeted endopeptidase receptor is at least one order of magnitude less than that of retargeted endopeptidase for any other receptor at the cell surface. The equilibrium dissociation constant, a specific type of equilibrium constant that measures the propensity of an retargeted endopeptidase-retargeted endopeptidase receptor complex to separate (dissociate) reversibly into its component molecules, namely the retargeted endopeptidase and the retargeted endopeptidase receptor, is defined as KD=Ka/Kd at equilibrium. The association constant (Ka) is defined as Ka=[C]/[L][R] and the disassociation constant (Kd) is defined as Kd=[L][R]/[C], where [L] equals the molar concentration of retargeted endopeptidase, [R] is the molar concentration of a retargeted endopeptidase receptor, and [C] is the molar concentration of the endopeptidase-receptor complex, and where all concentrations are of such components when the system is at equilibrium. The smaller the dissociation constant, the more tightly bound the retargeted endopeptidase is to its receptor, or the higher the binding affinity between retargeted endopeptidase and retargeted endopeptidase receptor. In aspects of this embodiment, the disassociation constant of retargeted endopeptidase for its receptor is at least two orders of magnitude less, at least three orders of magnitude less, at least four orders of magnitude less, or at least five orders of magnitude less than that of retargeted endopeptidase for any other receptor. In other aspects of this embodiment, the binding affinity of a retargeted endopeptidase that preferentially interacts with its receptor can have an equilibrium disassociation constant (KD) of, e.g., of 500 nM or less, 400 nM or less, 300 nM or less, 200 nM, or less 100 nM or less. In other aspects of this embodiment, the binding affinity of a retargeted endopeptidase that preferentially interacts with its receptor can have an equilibrium disassociation constant (KD) of, e.g., of 90 nM or less, 80 nM or less, 70 nM or less, 60 nM, 50 nM or less, 40 nM or less, 30 nM or less, 20 nM, or less 10 nM or less. As used herein, the term "elicits a retargeted endopeptidase activity response" refers to the ability of a retargeted endopeptidase receptor to interact with a retargeted endopeptidase to form a endopeptidase/receptor complex and the subsequent internalization of that complex into the cell cytoplasm.

As used herein, the term "naturally occurring retargeted endopeptidase receptor" refers to any retargeted endopeptidase receptor produced by a naturally-occurring process, including, without limitation, retargeted endopeptidase receptor isoforms produced from a post-translational modification, an alternatively-spliced transcript, or a spontaneous mutation, and retargeted endopeptidase receptor subtypes. A naturally occurring retargeted endopeptidase receptor includes, without limitation, naturally occurring opioid receptors like a opiate-like receptor 1 (ORL1), a δ-opioid receptor (DOR), a κ-opioid receptor (KOR), and a μ-opioid receptor (MOR), such as those described in Christopher Evans et al., Opioid Receptor Genes, U.S. Pat. No. 6,265,563; Christopher Evans et al., Methods of Screening Modulators of Opioid Receptor Activity, U.S. Pat. No. 6,432,652; Christopher Evans et al., Opioid Receptors and Methods of Use, U.S. Pat. No. 7,282,563; and Christopher Evans et al., Delta Opioid Receptor Proteins, U.S. Patent Publication 2008/0219925, each of which is hereby incorporated by reference in its entirety. Other examples of a naturally occurring retargeted endopeptidase receptor includes, without limitation, the galanin receptor 1, the galanin receptor 2, and the galanin receptor 3. Naturally occurring opioid receptors from other vertebrate species are known in the art, such as, e.g., primate, cow, dog, mouse, rat, chicken, and fish, and can be used in aspects of the present specification.

A naturally occurring ORL1 includes, without limitation, SEQ ID NO:25 and SEQ ID NO:26, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:25 or SEQ ID NO:26. A naturally occurring DOR includes, without limitation, SEQ ID NO:27 and SEQ ID NO:28, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:27 or SEQ ID NO:28. A naturally occurring KOR includes, without limitation, SEQ ID NO:29 and SEQ ID NO:30, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:29 or SEQ ID NO:30. A naturally occurring MOR includes, without limitation, SEQ ID NO:31, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:31.

A naturally occurring galanin receptor 1 includes, without limitation, SEQ ID NO:136, SEQ ID NO:137, and SEQ ID NO:138, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:136, SEQ ID NO:137, or SEQ ID NO:138. A naturally occurring galanin receptor 2 includes, without limitation, SEQ ID NO:139, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:139. A naturally occurring galanin receptor 3 includes, without limitation, SEQ ID NO:140, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:140.

As used herein, the term "non-naturally occurring retargeted endopeptidase receptor variant" refers to any retargeted endopeptidase receptor produced with the aid of human manipulation or design, including, without limitation, a retargeted endopeptidase receptor produced by genetic engineering using random mutagenesis or rational design and a retargeted endopeptidase receptor produced by chemical synthesis. Non-limiting examples of non-naturally occurring retargeted endopeptidase receptor variants include, e.g., conservative retargeted endopeptidase receptor variants, non-conservative retargeted endopeptidase receptor variants, retargeted endopeptidase receptor chimeric variants and active retargeted endopeptidase receptor fragments.

As used herein, the term "non-naturally occurring retargeted endopeptidase receptor" refers to any retargeted endopeptidase receptor whose structure was modified with the aid of human manipulation, including, without limitation, a retargeted endopeptidase receptor produced by genetic engineering using random mutagenesis or rational design and a retargeted endopeptidase receptor produced by in vitro chemical synthesis. A non-naturally occurring retargeted endopeptidase receptor may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140.

Thus in an embodiment, a retargeted endopeptidase receptor is a naturally occurring retargeted endopeptidase receptor such as, e.g., ORL1, DOR, KOR, or MOR. In aspects of this embodiment, the retargeted endopeptidase receptor is a retargeted endopeptidase receptor isoform or a retargeted endopeptidase receptor subtype. In aspects of this embodiment, the naturally occurring retargeted endopeptidase receptor is the naturally occurring retargeted endopeptidase receptor of SEQ ID NO:25, SEQ ID NO:26, SEQ ID NO:27, SEQ ID NO:28, SEQ ID NO:29, SEQ ID NO:30, or SEQ ID NO:31. In other aspects of this embodiment, the retargeted endopeptidase receptor is a naturally occurring retargeted endopeptidase receptor having, e.g., at least 70% amino acid identity, at least 75%, at least 80%, at least 85%, at least 90%, or at least 95% amino acid identity with SEQ ID NO:25, SEQ ID NO:26, SEQ ID NO:27, SEQ ID NO:28, SEQ ID NO:29, SEQ ID NO:30, or SEQ ID NO:31.

In another embodiment, a retargeted endopeptidase receptor is a non-naturally occurring retargeted endopeptidase receptor, such as, e.g., a genetically-engineered ORL1, a genetically-engineered DOR, a genetically-engineered KOR, or a genetically-engineered MOR. In other aspects of this embodiment, the retargeted endopeptidase receptor is a non-naturally occurring retargeted endopeptidase receptor having, e.g., at least 70%, at least 75%, at least 80%, at least 85%, at least 90%, or at least 95% amino acid identity with SEQ ID NO:25, SEQ ID NO:26, SEQ ID NO:27, SEQ ID NO:28, SEQ ID NO:29, SEQ ID NO:30, or SEQ ID NO:31. In other aspects of this embodiment, the retargeted endopeptidase receptor is a non-naturally occurring retargeted endopeptidase receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO:25, SEQ ID NO:26, SEQ ID NO:27, SEQ ID NO:28, SEQ ID NO:29, SEQ ID NO:30, or SEQ ID NO:31. In yet other aspects of this embodiment, the retargeted endopeptidase receptor is a non-naturally occurring retargeted endopeptidase receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO:25, SEQ ID NO:26, SEQ ID NO:27, SEQ ID NO:28, SEQ ID NO:29, SEQ ID NO:30, or SEQ ID NO:31.

In another embodiment, a retargeted endopeptidase receptor is a naturally occurring retargeted endopeptidase receptor such as, e.g., galanin receptor 1, galanin receptor 2, or galanin receptor 3. In aspects of this embodiment, the retargeted endopeptidase receptor is a retargeted endopeptidase receptor isoform or a retargeted endopeptidase receptor subtype. In aspects of this embodiment, the naturally occurring retargeted endopeptidase receptor is the naturally occurring retargeted endopeptidase receptor of SEQ ID NO:136, SEQ ID NO:137, SEQ ID NO:138, SEQ ID NO:139, or SEQ ID NO:140. In other aspects of this embodiment, the retargeted endopeptidase receptor is a naturally occurring retargeted endopeptidase receptor having, e.g., at least 70% amino acid identity, at least 75%, at least 80%, at least 85%, at least 90%, or at least 95% amino acid identity with SEQ ID NO:136, SEQ ID NO:137, SEQ ID NO:138, SEQ ID NO:139, or SEQ ID NO:140.

In another embodiment, a retargeted endopeptidase receptor is a non-naturally occurring retargeted endopeptidase receptor, such as, e.g., a genetically-engineered galanin receptor 1, a genetically-engineered galanin receptor 2, or a genetically-engineered galanin receptor 3. In other aspects of this embodiment, the retargeted endopeptidase receptor is a non-naturally occurring retargeted endopeptidase receptor having, e.g., at least 70%, at least 75%, at least 80%, at least 85%, at least 90%, or at least 95% amino acid identity with SEQ ID NO:136, SEQ ID NO:137, SEQ ID NO:138, SEQ ID NO:139, or SEQ ID NO:140. In other aspects of this embodiment, the retargeted endopeptidase receptor is a non-naturally occurring retargeted endopeptidase receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO:136, SEQ ID NO:137, SEQ ID NO:138, SEQ ID NO:139, or SEQ ID NO:140. In yet other aspects of this embodiment, the retargeted endopeptidase receptor is a non-naturally occurring retargeted endopeptidase receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO:136, SEQ ID NO:137, SEQ ID NO:138, SEQ ID NO:139, or SEQ ID NO:140.

A retargeted endopeptidase receptor can be an endogenous retargeted endopeptidase receptor or an exogenous retargeted endopeptidase receptor. As used herein, the term "endogenous retargeted endopeptidase receptor" refers to a retargeted endopeptidase receptor naturally present in the cell because it is naturally encoded within the cell's genome, such that the cell inherently expresses the retargeted endopeptidase receptor without the need an external source of retargeted endopeptidase receptor or an external source of genetic material encoding a retargeted endopeptidase receptor. Expression of an endogenous retargeted endopeptidase receptor may be with or without environmental stimulation such as e.g., cell differentiation or promoter activation. For example, the following established cell lines express at least one endogenous retargeted endopeptidase receptor: AGN P33, Neuro-2a, SiMa, and SK-N-DZ. An endogenous retargeted endopeptidase receptor can only be a naturally-occurring retargeted endopeptidase receptor or naturally-occurring variants thereof.

As used herein, the term "exogenous retargeted endopeptidase receptor" refers to a retargeted endopeptidase receptor expressed in a cell through the introduction of an external source of retargeted endopeptidase receptor or an external source of genetic material encoding a retargeted endopeptidase receptor by human manipulation. The expression of an exogenous retargeted endopeptidase receptor may be with or without environmental stimulation such as, e.g., cell differentiation or promoter activation. As a non-limiting example, cells from an established cell line can express one or more exogenous retargeted endopeptidase receptors by transient or stably transfection of a polynucleotide molecule encoding a retargeted endopeptidase receptor, such as, e.g., an ORL1, a DOR, a KOR, a MOR, a galanin receptor 1, a galanin receptor 2, or a galanin receptor 3. As another non-limiting example, cells from an established cell line can express one or more exogenous retargeted endopeptidase receptors by protein transfection of the retargeted endopeptidase receptors, such as, e.g., an ORL1, a DOR, a KOR, a MOR, a galanin receptor 1, a galanin receptor 2, or a galanin receptor 3. An exogenous retargeted endopeptidase receptor can be a naturally-occurring retargeted endopeptidase receptor or naturally occurring variants thereof, or non-naturally occurring retargeted endopeptidase receptor or non-naturally occurring variants thereof.

Thus in an embodiment, cells from an established cell line express an endogenous retargeted endopeptidase receptor. In aspects of this embodiment, the endogenous retargeted endopeptidase receptor expressed by cells from an established cell line is a naturally-occurring retargeted endopeptidase receptor. In other aspects of this embodiment, the endogenous retargeted endopeptidase receptor expressed by cells from an established cell line is SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140. In yet aspects of this embodiment, the endogenous retargeted endopeptidase receptor expressed by cells from an established cell line is a naturally occurring retargeted endopeptidase receptor, such as, e.g., a retargeted endopeptidase receptor isoform or a retargeted endopeptidase receptor subtype. In other aspects of this embodiment, the endogenous retargeted endopeptidase receptor expressed by cells from an established cell line is a naturally occurring retargeted endopeptidase receptor having, e.g., at least 70% amino acid identity, at least 75%, at least 80%, at least 85%, at least 90%, or at least 95% amino acid identity with SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140.

In another embodiment, cells from an established cell line are transiently or stably engineered to express an exogenous retargeted endopeptidase receptor. In an aspect of this embodiment, cells from an established cell line are transiently or stably engineered to express a naturally-occurring retargeted endopeptidase receptor. In other aspects of this embodiment, cells from an established cell line are transiently or stably engineered to express the naturally-occurring retargeted endopeptidase receptor of SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140. In yet other aspects of this embodiment, cells from an established cell line are transiently or stably engineered to express a naturally occurring retargeted endopeptidase receptor, such as, e.g., a retargeted endopeptidase receptor isoform or a retargeted endopeptidase receptor subtype. In still other aspects of this embodiment, cells from an established cell line are transiently or stably engineered to express a naturally occurring retargeted endopeptidase receptor having, e.g., at least 70% amino acid identity, at least 75%, at least 80%, at least 85%, at least 90%, or at least 95% amino acid identity with SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140.

In another aspect of the embodiment, cells from an established cell line are transiently or stably engineered to express a non-naturally occurring retargeted endopeptidase receptor. In other aspects of this embodiment, cells from an established cell line are transiently or stably engineered to express a non-naturally occurring retargeted endopeptidase receptor having, e.g., at least 70%, at least 75%, at least 80%, at least 85%, at least 90%, or at least 95% amino acid identity with SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140. In other aspects of this embodiment, cells from an established cell line are transiently or stably engineered to express a non-naturally occurring retargeted endopeptidase receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140. In yet other aspects of this embodiment, cells from an established cell line are transiently or stably engineered to express a non-naturally occurring retargeted endopeptidase receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO:25, SEQ ID NO:26, SEQ ID NO:27, SEQ ID NO:28, SEQ ID NO:29, SEQ ID NO:30, SEQ ID NO:31, SEQ ID NO:136, SEQ ID NO:137, SEQ ID NO:138, SEQ ID NO:139, or SEQ ID NO:140.

In another embodiment, cells from an established cell line are transiently or stably engineered to express an exogenous ORL1, an exogenous DOR, an exogenous KOR, an exogenous MOR, or any combination thereof. In aspects of this embodiment, cells from an established cell line are transiently or stably engineered to express a naturally-occurring ORL1, a naturally-occurring DOR, a naturally-occurring KOR, a naturally-occurring MOR, or any combination thereof. In yet other aspects of this embodiment, cells from an established cell line are transiently or stably engineered to express a non-naturally-occurring ORL1, a non-naturally-occurring DOR, a non-naturally-occurring KOR, a non-naturally-occurring MOR, or any combination thereof. In still other aspects of this embodiment, cells from an established cell line are transiently or stably engineered to express either a naturally-occurring ORL1 or a non-naturally-occurring ORL1, a naturally-occurring DOR or a non-naturally-occurring DOR, a naturally-occurring KOR or a non-naturally-occurring KOR, a naturally-occurring MOR or a non-naturally-occurring MOR, or any combination thereof.

In yet another embodiment, cells from an established cell line are transiently or stably engineered to express an exogenous galanin receptor 1, an exogenous galanin receptor 2, an exogenous galanin receptor 3, or any combination thereof. In aspects of this embodiment, cells from an established cell line are transiently or stably engineered to express a naturally-occurring galanin receptor 1, a naturally-occurring galanin receptor 2, a naturally-occurring galanin receptor 3, or any combination thereof. In yet other aspects of this embodiment, cells from an established cell line are transiently or stably engineered to express a non-naturally-occurring galanin receptor 1, a non-naturally-occurring galanin receptor 2, a non-naturally-occurring galanin receptor 3, or any combination thereof. In still other aspects of this embodiment, cells from an established cell line are transiently or stably engineered to express either a naturally-occurring galanin receptor 1 or a non-naturally-occurring galanin receptor 1, a naturally-occurring galanin receptor 2 or a non-naturally-occurring galanin receptor 2, a naturally-occurring galanin receptor 3 or a non-naturally-occurring galanin receptor 3, or any combination thereof.

Cells that express one or more endogenous or exogenous re-targeted endopeptidase receptors can be identified by routine methods including direct and indirect assays for re-targeted endopeptidase uptake. Assays that determine retargeted endopeptidase binding or uptake properties can be used to assess whether a cell is expressing a retargeted endopeptidase receptor. Such assays include, without limitation, cross-linking assays using labeled retargeted endopeptidase, such as, e.g., [125I] retargeted endopeptidase, see, e.g., Noriko Yokosawa et al., *Binding of Clostridium botulinum type C neurotoxin to different neuroblastoma cell lines,* 57 (1) Infect. Immun. 272-277 (1989); Noriko Yokosawa et al., *Binding of botulinum type CI, D and E neurotoxins to neuronal cell lines and synaptosomes,* 29 (2) Toxicon 261-264 (1991); and Tei-ichi Nishiki et al., *Identification of protein receptor for Clostridium botulinum type B neurotoxin in rat brain synaptosomes,* 269 (14) J. Biol. Chem. 10498-10503 (1994). Other non-limiting assays include immunocytochemical assays that detect retargeted endopeptidase binding using labeled or unlabeled antibodies, see, e.g., Atsushi Nishikawa et al., *The receptor* and *transporter for internalization of Clostridium botulinum type C progenitor* toxin *into HT*-29 *cells,* 319 (2) Biochem. Biophys. Res. Commun. 327-333 (2004) and immunoprecipitation assays, see, e.g., Yukako Fujinaga et al., *Molecular characterization of binding subcomponents of Clostridium botulinum type C progenitor toxin for intestinal epithelial cells and erythrocytes,* 150 (Pt 5) Microbiology 1529-1538 (2004), that detect bound re-targeted endopeptidase using labeled or unlabeled antibodies. Antibodies useful for these assays include, without limitation, antibodies selected against retargeted endopeptidase and/or antibodies selected against a retargeted endopeptidase receptor, such as, e.g., ORL1, DOR, KOR, MOR, galanin receptor 1, galanin receptor 2, or galanin receptor 3. If the antibody is labeled, the binding of the molecule can be detected by various means, including Western blot analysis, direct microscopic observation of the cellular location of the antibody, measurement of cell or substrate-bound antibody following a wash step, flow cytometry, electrophoresis or capillary electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine retargeted endopeptidase uptake properties or characteristics can be useful in identifying cells expressing endogenous or exogenous or retargeted endopeptidase receptors.

Assays that monitor the release of a molecule after exposure to a retargeted endopeptidase can also be used to assess whether a cell is expressing one or more endogenous or exogenous retargeted endopeptidase receptors. In these assays, inhibition of the molecule's release would occur in cells expressing a retargeted endopeptidase receptor after retargeted endopeptidase treatment. Well known assays include methods that measure inhibition of radio-labeled catecholamine release from neurons, such as, e.g., [3H] noradrenaline or [3H] dopamine release, see e.g., A Fassio et al., *Evidence for calcium-dependent vesicular transmitter release insensitive to tetanus toxin and botulinum toxin type F,* 90 (3) Neuroscience 893-902 (1999); and Sara Stigliani et al., *The sensitivity of catecholamine release to botulinum toxin C1 and E suggests selective targeting of vesicles set into the readily releasable pool,* 85 (2) J. Neurochem. 409-421 (2003), or measures catecholamine release using a fluorometric procedure, see, e.g., Anton de Paiva et al., *A role for the interchain disulfide or its participating thiols in the internalization of botulinum neurotoxin A revealed by a toxin derivative that binds to ecto-acceptors and inhibits transmitter release intracellularly,* 268 (28) J. Biol. Chem. 20838-20844 (1993); Gary W. Lawrence et al., *Distinct exocytotic responses of intact and permeabilised chromaffin cells after cleavage of the 25-kDa synaptosomal-associated protein (SNAP-25) or synaptobrevin by botulinum toxin A or B,* 236 (3) Eur. J. Biochem. 877-886 (1996); and Patrick Foran et al., *Botulinum neurotoxin C1 cleaves both syntaxin and SNAP-25 in intact and permeabilized chromaffin cells: correlation with its blockade of catecholamine release,* 35 (8) Biochemistry 2630-2636 (1996). Other non-limiting examples include assays that measure inhibition of hormone release from endocrine cells, such as, e.g., anterior pituitary cells or ovarian cells. It is understood that these and similar assays for molecule release can be useful in identifying cells expressing endogenous or exogenous or retargeted endopeptidase receptors.

Assays that detect the cleavage of a SNAP-25 substrate after exposure to a retargeted endopeptidase can also be used to assess whether a cell is expressing one or more endogenous or exogenous retargeted endopeptidase receptors. In these assays, generation of a SNAP-25 cleavage-product, or disappearance of the intact SNAP-25, would be detected in cells expressing a retargeted endopeptidase receptor after a retargeted endopeptidase treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for SNAP-25 cleavage can be useful in identifying cells expressing endogenous or exogenous retargeted endopeptidase receptors.

As non-limiting examples, Western blot analysis using an antibody that recognizes SNAP-25-cleaved product or both the cleaved and uncleaved forms of SNAP-25 can be used to assay for uptake of a retargeted endopeptidase. Examples of α-SNAP-25 antibodies useful for these assays include, without limitation, SMI-81 α-SNAP-25 mouse monoclonal antibody (Sternberger Monoclonals Inc., Lutherville, Md.), CI 71.1 mouse α-SNAP-25 monoclonal antibody (Synaptic Systems, Goettingen, Germany), CI 71.2 α-SNAP-25 mouse monoclonal antibody (Synaptic Systems, Goettingen, Germany), SP12 α-SNAP-25 mouse monoclonal antibody (Abcam, Cambridge, Mass.), α-SNAP-25 rabbit polyclonal antiserum (Synaptic Systems, Goettingen, Germany), α-SNAP-25 rabbit polyclonal antiserum S9684 (Sigma, St. Louis, Mo.), and α-SNAP-25 rabbit polyclonal antiserum (Abcam, Cambridge, Mass.).

Aspects of the present disclosure provide cells that through genetic manipulation or recombinant engineering are made to expresses an exogenous SNAP-25 and/or one or more exogenous retargeted endopeptidase receptors. Cells useful to express an exogenous SNAP-25 and/or one or more exogenous retargeted endopeptidase receptors through genetic manipulation or recombinant engineering include neuronal cells and non-neuronal cells that may or may not express an endogenous SNAP-25 and/or one or more endogenous retargeted endopeptidase receptors. It is further understood that such genetically manipulated or recombinantly engineered cells may express an exogenous SNAP-25 and one or more exogenous retargeted endopeptidase receptors under control of a constitutive, tissue-specific, cell-specific or inducible promoter element, enhancer element or both. It is understood that any cell is useful as long as the cell can be genetically manipulated or recombinantly engineered to expresses an exogenous SNAP-25 and/or one or more exogenous retargeted endopeptidase receptors and is capable of undergoing retargeted endopeptidase activity.

Methods useful for introducing into a cell an exogenous polynucleotide molecule encoding a component necessary for the cells to undergo the overall cellular mechanism whereby a retargeted endopeptidase proteolytically cleaves a SNAP-25 substrate, such as, e.g., a SNAP-25, an ORL1, a DOR, a KOR, or a MOR, include, without limitation, chemical-mediated delivery methods, such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated delivery methods, such as, e.g., biolistic particle delivery, microinjection, protoplast fusion and electroporation; and viral-mediated delivery methods, such as, e.g., retroviral-mediated transfection, see e.g., *Introducing Cloned Genes into Cultured Mammalian Cells, pp.* 16.1-16.62 (Sambrook & Russell, eds., Molecular Cloning A Laboratory Manual, Vol. 3, $3^{rd}$ ed. 2001); Alessia Colosimo et al., *Transfer and Expression of Foreign Genes in Mammalian Cells,* 29 (2) Biotechniques 314-318, 320-322, 324 (2000); Philip Washbourne & A. Kimberley McAllister, *Techniques for Gene Transfer into Neurons,* 12 (5) Curr. Opin. Neurobiol. 566-573 (2002); and Current Protocols in Molecular Biology, John Wiley and Sons, pp 9.16.4-9.16.11 (2000), each of which is incorporated by reference in its entirety. One skilled in the art understands that selection of a specific method to introduce a polynucleotide molecule into a cell will depend, in part, on whether the cell will transiently or stably contain a component necessary for the cells to undergo the overall cellular mechanism whereby a retargeted endopeptidase proteolytically cleaves a SNAP-25 substrate. Non-limiting examples of polynucleotide molecule encoding a component necessary for the cells to undergo the overall cellular mechanism whereby a retargeted endopeptidase proteolytically cleaves a SNAP-25 substrate as follows: ORL1 polynucleotide molecule of SEQ ID NO:61 or SEQ ID NO:62; DOR polynucleotide molecule of SEQ ID NO:63 or SEQ ID NO:64; KOR polynucleotide molecule of SEQ ID NO:65 or SEQ ID NO:66; MOR polynucleotide molecule of SEQ ID NO:67; galanin receptor 1 polynucleotide molecule of SEQ ID NO:141, SEQ ID NO:142, or SEQ ID NO:143, galanin receptor 2 polynucleotide molecule of SEQ ID NO:144, or galanin receptor 3 polynucleotide molecule of SEQ ID NO:145, and SNAP-25 polynucleotide molecule of SEQ ID NO:68, or SEQ ID NO:69.

Chemical-mediated delivery methods are well-known to a person of ordinary skill in the art and are described in, e.g., Martin Jordan & Florian Worm, *Transfection of Adherent and Suspended Cells by Calcium Phosphate,* 33 (2) Methods 136-143 (2004); Chun Zhang et al., *Polyethylenimine Strategies for Plasmid Delivery to Brain-Derived Cells,* 33 (2) Methods 144-150 (2004), each of which is hereby incorporated by reference in its entirety. Such chemical-mediated delivery methods can be prepared by standard procedures and are commercially available, see, e.g., CellPhect Transfection Kit (Amersham Biosciences, Piscataway, N.J.);

Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

Physical-mediated delivery methods are well-known to a person of ordinary skill in the art and are described in, e.g., Jeike E. Biewenga et al., *Plasmid-Mediated Gene Transfer in Neurons using the Biolistics Technique,* 71 (1) J. Neurosci. Methods. 67-75 (1997); John O'Brien & Sarah C. R. Lummis, *Biolistic and Diolistic Transfection: Using the Gene Gun to Deliver DNA and Lipophilic Dyes into Mammalian Cells,* 33 (2) Methods 121-125 (2004); M. Golzio et al., *In Vitro and In Vivo Electric Field-Mediated Permeabilization, Gene Transfer, and Expression,* 33 (2) Methods 126-135 (2004); and Oliver Gresch et al., *New Non-Viral Method for Gene Transfer into Primary Cells,* 33 (2) Methods 151-163 (2004), each of which is hereby incorporated by reference in its entirety.

Viral-mediated delivery methods are well-known to a person of ordinary skill in the art and are described in, e.g., Chooi M. Lai et al., *Adenovirus and Adeno-Associated Virus Vectors,* 21 (12) DNA Cell Biol. 895-913 (2002); Ilya Frolov et al., *Alphavirus-Based Expression Vectors: Strategies and Applications,* 93 (21) Proc. Natl. Acad. Sci. U.S.A. 11371-11377 (1996); Roland Wolkowicz et al., *Lentiviral Vectors for the Delivery of DNA into Mammalian Cells,* 246 Methods Mol. Biol. 391-411 (2004); A. Huser & C. Hofmann, *Baculovirus Vectors: Novel Mammalian Cell Gene-Delivery Vehicles and Their Applications,* 3 (1) Am. J. Pharmacogenomics 53-63 (2003); Tiziana Tonini et al., *Transient Production of Retro viral-and Lentiviral-Based Vectors for the Transduction of Mammalian Cells,* 285 Methods Mol. Biol. 141-148 (2004); Manfred Gossen & Hermann Bujard, Tight Control of Gene Expression in Eukaryotic Cells by Tetracycline-Responsive Promoters, U.S. Pat. No. 5,464,758; Hermann Bujard & Manfred Gossen, Methods for Regulating Gene Expression, U.S. Pat. No. 5,814,618; David S. Hogness, Polynucleotides Encoding Insect Steroid Hormone Receptor Polypeptides and Cells Transformed With Same, U.S. Pat. No. 5,514,578; David S. Hogness, Polynucleotide Encoding Insect Ecdysone Receptor, U.S. Pat. No. 6,245,531; Elisabetta Vegeto et al., Progesterone Receptor Having C. Terminal Hormone Binding Domain Truncations, U.S. Pat. No. 5,364,791; Elisabetta Vegeto et al., Mutated Steroid Hormone Receptors, Methods for Their Use and Molecular Switch for Gene Therapy, U.S. Pat. No. 5,874,534, each of which is hereby incorporated by reference in its entirety. Such viral-mediated delivery methods can be prepared by standard procedures and are commercially available, see, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEasy™ Adenoviral Vector System (Stratagene, Inc., La Jolla, Calif.) and AdEasy™ Adenoviral Vector System Instruction Manual 064004f, Stratagene, Inc. Furthermore, such viral delivery systems can be prepared by standard methods and are commercially available, see, e.g., BD™ Tet-Off and Tet-On Gene Expression Systems (BD Biosciences-Clontech, Palo Alto, Calif.) and BD™ Tet-Off and Tet-On Gene Expression Systems User Manual, PT3001-1, BD Biosciences Clontech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

Thus, in an embodiment, cells from an established cell line susceptible to retargeted endopeptidase activity transiently contain a polynucleotide molecule encoding a component necessary for the cells to undergo the overall cellular mechanism whereby a retargeted endopeptidase proteolytically cleaves a SNAP-25 substrate. In another embodiment, cells from an established cell line susceptible to retargeted endopeptidase activity transiently contain a polynucleotide molecule encoding a plurality of components necessary for the cells to undergo the overall cellular mechanism whereby a retargeted endopeptidase proteolytically cleaves a SNAP-25 substrate. In aspects of this embodiment, cells from an established cell line susceptible to retargeted endopeptidase activity transiently contain a polynucleotide molecule encoding ORL1, DOR, KOR, MOR, or SNAP-25. In aspects of this embodiment, cells from an established cell line susceptible to retargeted endopeptidase activity transiently contain the polynucleotide molecule of SEQ ID NO:61, or SEQ ID NO:62 encoding ORL1. In other aspects of this embodiment, cells from an established cell line susceptible to retargeted endopeptidase activity transiently contain the polynucleotide molecule of SEQ ID NO:63, or SEQ ID NO:64 encoding DOR. In yet other aspects of this embodiment, cells from an established cell line susceptible to retargeted endopeptidase activity transiently contain the polynucleotide molecule of SEQ ID NO:65, or SEQ ID NO:66 encoding KOR. In still other aspects of this embodiment, cells from an established cell line susceptible to retargeted endopeptidase activity transiently contain the polynucleotide molecule of SEQ ID NO:67 encoding MOR.

In other aspects of this embodiment, cells from an established cell line susceptible to retargeted endopeptidase activity transiently contain the polynucleotide molecule of SEQ ID NO:141, SEQ ID NO:142, or SEQ ID NO:143 encoding Galanin receptor 1. In yet other aspects of this embodiment, cells from an established cell line susceptible to retargeted endopeptidase activity transiently contain the polynucleotide molecule of SEQ ID NO:144 encoding Galanin receptor 2. In still other aspects of this embodiment, cells from an established cell line susceptible to retargeted endopeptidase activity transiently contain the polynucleotide molecule of SEQ ID NO:145 encoding Galanin receptor 3. In further aspects of this embodiment, cells from an established cell line susceptible to retargeted endopeptidase activity transiently contain the polynucleotide molecule of SEQ ID NO:68 or SEQ ID NO:69 encoding SNAP-25.

In another embodiment, cells from an established cell line susceptible to retargeted endopeptidase activity stably contain a polynucleotide molecule encoding a component necessary for the cells to undergo the overall cellular mechanism whereby a retargeted endopeptidase proteolytically cleaves a SNAP-25 substrate. In another embodiment, cells from an established cell line susceptible to retargeted endopeptidase activity stably contain a polynucleotide molecule encoding a plurality of components necessary for the cells to undergo the overall cellular mechanism whereby a retargeted endopeptidase proteolytically cleaves a SNAP-25 substrate. In aspects of this embodiment, cells from an established cell line susceptible to retargeted endopeptidase activity stably contain a polynucleotide molecule encoding ORL1, DOR, KOR, MOR, or SNAP-25. In aspects of this embodiment, cells from an established cell line susceptible to retargeted endopeptidase activity stably contain the polynucleotide molecule of SEQ ID NO:61, or SEQ ID NO:62 encoding ORL1. In other aspects of this embodiment, cells from an established cell line susceptible to retargeted endopeptidase activity stably contain the polynucleotide molecule of SEQ ID NO:63, or SEQ ID NO:64 encoding DOR. In yet other aspects of this embodiment, cells from an established cell line susceptible to retargeted endopeptidase activity stably contain the polynucleotide molecule of SEQ ID NO:65, or SEQ ID NO:66 encoding KOR. In still other aspects of this embodiment, cells from an established cell line susceptible to retargeted endopeptidase activity stably contain the polynucleotide molecule of SEQ ID NO:67 encoding MOR.

In other aspects of this embodiment, cells from an established cell line susceptible to retargeted endopeptidase activity stably contain the polynucleotide molecule of SEQ ID NO:141, SEQ ID NO:142, or SEQ ID NO:143 encoding Galanin receptor 1. In yet other aspects of this embodiment, cells from an established cell line susceptible to retargeted endopeptidase activity stably contain the polynucleotide molecule of SEQ ID NO:144 encoding Galanin receptor 2. In yet other aspects of this embodiment, cells from an established cell line susceptible to retargeted endopeptidase activity stably contain the polynucleotide molecule of SEQ ID NO:145 encoding Galanin receptor 3. In further aspects of this embodiment, cells from an established cell line susceptible to retargeted endopeptidase activity stably contain the polynucleotide molecule of SEQ ID NO:68 or SEQ ID NO:69 encoding SNAP-25.

As mentioned above, an exogenous component necessary for the cells to undergo the overall cellular mechanism whereby a retargeted endopeptidase proteolytically cleaves a SNAP-25 substrate, such as, e.g., a SNAP-25, an ORL1, a DOR, a KOR, a MOR, a Galanin receptor 1, a Galanin receptor 2, or a Galanin receptor 3, disclosed in the present specification can be introduced into a cell. Any and all methods useful for introducing such an exogenous component with a delivery agent into a cell population can be useful with the proviso that this method transiently introduces the exogenous component disclosed in the present specification in at least 50% of the cells within a given cell population. Thus, aspects of this embodiment can include a cell population in which, e.g., at least 50%, at least 60%, at least 70%, at least 80%, or at least 90% of the given cell population transiently contains an exogenous component necessary for the cells to undergo the overall cellular mechanism whereby a retargeted endopeptidase proteolytically cleaves a SNAP-25 substrate, such as, e.g., a SNAP-25, an ORL1, a DOR, a KOR, a MOR, a Galanin receptor 1, a Galanin receptor 2, or a Galanin receptor 3, disclosed in the present specification. As used herein, the term "delivery agent" refers to any molecule that enables or enhances internalization of a covalently-linked, non-covalently-linked or in any other manner associated with a polypeptide into a cell. Thus, the term "delivery agent" encompasses, without limitation, proteins, peptides, peptidomimetics, small molecules, polynucleotide molecules, liposomes, lipids, viruses, retroviruses and cells that, without limitation, transport a covalently or non-covalently linked molecule to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

A delivery agent can also be an agent that enables or enhances cellular uptake of a covalently linked component, like SNAP-25, ORL1, DOR, KOR, MOR, Galanin receptor 1, Galanin receptor 2, or Galanin receptor 3, such as, e.g., by chemical conjugation or by genetically produced fusion proteins. Methods that covalently link delivery agents and methods of using such agents are described in, e.g., Steven F. Dowdy, Protein Transduction System and Methods of Use Thereof, International Publication No WO 00/34308; Gerard Chassaing & Alain Prochiantz, Peptides which can be Used as Vectors for the Intracellular Addressing of Active Molecules, U.S. Pat. No. 6,080,724; Alan Frankel et al., Fusion Protein Comprising TAT-derived Transport Moiety, U.S. Pat. No. 5,674,980; Alan Frankel et al., TAT-derived Transport Polypeptide Conjugates, U.S. Pat. No. 5,747,641; Alan Frankel et al., TAT-derived Transport Polypeptides and Fusion Proteins, U.S. Pat. No. 5,804,604; Peter F. J. O'Hare et al., Use of Transport Proteins, U.S. Pat. No. 6,734,167; Yao-Zhong Lin & Jack J. Hawiger, Method for Importing Biologically Active Molecules into Cells, U.S. Pat. No. 5,807,746; Yao-Zhong Lin & Jack J. Hawiger, Method for Importing Biologically Active Molecules into Cells, U.S. Pat. No. 6,043,339; Yao-Zhong Lin et al., Sequence and Method for Genetic Engineering of Proteins with Cell Membrane Translocating Activity, U.S. Pat. No. 6,248,558; Yao-Zhong Lin et al., Sequence and Method for Genetic Engineering of Proteins with Cell Membrane Translocating Activity, U.S. Pat. No. 6,432,680; Jack J. Hawiger et al., Method for Importing Biologically Active Molecules into Cells, U.S. Pat. No. 6,495,518; Yao-Zhong Lin et al., Sequence and Method for Genetic Engineering of Proteins with Cell Membrane Translocating Activity, U.S. Pat. No. 6,780,843; Jonathan B. Rothbard & Paul A Wender, Method and Composition for Enhancing Transport Across Biological Membranes, U.S. Pat. No. 6,306,993; Jonathan B. Rothbard & Paul A Wender, Method and Composition for Enhancing Transport Across Biological Membranes, U.S. Pat. No. 6,495,663; and Pamela B. Davis et al., Fusion Proteins for Protein Delivery, U.S. Pat. No. 6,287,817, each of which is incorporated by reference in its entirety.

A delivery agent can also be an agent that enables or enhances cellular uptake of a non-covalently associated component, like SNAP-25, ORL1, DOR, KOR, MOR, Galanin receptor 1, Galanin receptor 2, or Galanin receptor 3. Methods that function in the absence of covalent linkage and methods of using such agents are described in, e.g., Gilles Divita et al, Peptide-Mediated Transfection Agents and Methods of Use, U.S. Pat. No. 6,841,535; Philip L Feigner and Olivier Zelphati, Intracellular Protein Delivery Compositions and Methods of Use, U.S. Patent Publication No. 2003/0008813; and Michael Karas, Intracellular Delivery of Small Molecules, Proteins and Nucleic Acids, U.S. Patent Publication 2004/0209797, each of which is incorporated by reference in its entirety. Such peptide delivery agents can be prepared and used by standard methods and are commercially available, see, e.g. the CHARIOT™ Reagent (Active Motif, Carlsbad, Calif.); BIO-PORTER® Reagent (Gene Therapy Systems, Inc., San Diego, Calif.), BIO TREK™ Protein Delivery Reagent (Stratagene, La Jolla, Calif.), and PRO-JECT™ Protein Transfection Reagent (Pierce Biotechnology Inc., Rockford, Ill.).

Aspects of the present disclosure comprise, in part, a sample comprising a retargeted endopeptidase. As used herein, the term "sample comprising a retargeted endopeptidase" refers to any biological matter that contains or potentially contains an active retargeted endopeptidase. A variety of samples can be assayed according to a method disclosed in the present specification including, without limitation, purified, partially purified, or unpurified retargeted endopeptidase; recombinant single chain or di-chain retargeted endopeptidase with a naturally or non-naturally occurring sequence; recombinant retargeted endopeptidase with a modified protease specificity; recombinant retargeted endopeptidase with an altered cell specificity; bulk retargeted endopeptidase; a formulated retargeted endopeptidase product; and cells or crude, fractionated or partially purified cell lysates from, e.g., bacteria, yeast, insect, or mammalian sources; blood, plasma or serum; raw, partially cooked, cooked, or processed foods; beverages; animal feed; soil samples; water samples; pond sediments; lotions; cosmetics; and clinical formulations. It is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, and tissue samples obtained from a wound. As non-limiting examples, a method of detecting picomolar amounts of retargeted endopeptidase activity can be useful for determining the presence or activity of a retargeted endopeptidase in a food or beverage sample; to assay a sample from a human or animal, for example, exposed to a retargeted endopeptidase or having one or more symptoms of botulism; to follow activity during production and purification of bulk retargeted endopeptidase; to assay a formulated retargeted endopeptidase product used in pharmaceutical or cosmetics applications; or to assay a subject's blood serum for the presence or absence of neutralizing α-retargeted endopeptidase antibodies.

Thus, in an embodiment, a sample comprising a retargeted endopeptidase is a sample comprising any amount of a retargeted endopeptidase. In aspects of this embodiment, a sample comprising a retargeted endopeptidase comprises about 100 ng or less, about 10 ng or less, about 1 ng or less, about 100 pg or less, about 10 pg or less, or about 1 pg or less of a retargeted endopeptidase. In other aspects of this embodiment, a sample comprising a retargeted endopeptidase comprises about 1 μM or less, about 100 nM or less, about 10 nM or less, about 1 nM or less, about 100 nM or less, about 10 nM or less, about 1 nM or less of a retargeted endopeptidase.

Aspects of the present disclosure comprise, in part, isolating from the treated cell a SNAP-25 component comprising a SNAP-25 having a carboxyl-terminus at the $P_1$ residue of the BoNT/A cleavage site scissile bond. As used herein, the term "SNAP-25 component comprising a SNAP-25 having a carboxyl-terminus at the $P_1$ residue of the BoNT/A cleavage site scissile bond" refers to a cellular component containing the SNAP-25 cleavage product. It is envisioned that any method suitable for enriching or isolating a SNAP-25 component can be useful, including, without limitation, cell lysing protocols, spin-column purification protocols, immunoprecipitation, affinity purification, and protein chromatography.

Aspects of the present disclosure comprise, in part, an α-SNAP-25 antibody linked to a solid phase support. As used herein, the term "solid-phase support" is synonymous with "solid phase" and refers to any matrix that can be used for immobilizing an α-SNAP-25 antibody disclosed in the present specification. Non-limiting examples of solid phase supports include, e.g., a tube; a plate; a column; pins or "dipsticks"; a magnetic particle, a bead or other spherical or fibrous chromatographic media, such as, e.g., agarose, sepharose, silica and plastic; and sheets or membranes, such as, e.g., nitrocellulose and polyvinylidene fluoride (PVDF). The solid phase support can be constructed using a wide variety of materials such as, e.g., glass, carbon, polystyrene, polyvinylchloride, polypropylene, polyethylene, dextran, nylon, diazocellulose, or starch. The solid phase support selected can have a physical property that renders it readily separable from soluble or unbound material and generally allows unbound materials, such as, e.g., excess reagents, reaction by-products, or solvents, to be separated or otherwise removed (by, e.g., washing, filtration, centrifugation, etc.) from solid phase support-bound assay component. Non-limiting examples of how to make and use a solid phase supports are described in, e.g., Molecular Cloning, A Laboratory Manual, supra, (2001); and Current Protocols in Molecular Biology, supra, (2004), each of which is hereby incorporated by reference in its entirety.

Aspects of the present disclosure comprise, in part, detecting the presence of an antibody-antigen complex comprising an α-SNAP-25 antibody that selectively binds to a SNAP-25 epitope having a carboxyl-terminus at the $P_1$ residue of the BoNT/A cleavage site scissile bond and a SNAP-25 cleavage product having a carboxyl-terminus at the $P_1$ residue of the BoNT/A cleavage site scissile bond. It is envisioned that any detection system can be used to practice aspects of this disclosed immuno-based method, with the provision that the signal to noise ratio can distinguish to a statistically significant degree the signal from the antibody-antigen complex from the background signal. Non-limiting examples of immuno-based detection systems include immunoblot analysis, like Western blotting and dot-blotting, immunoprecipitation analysis, enzyme-linked immunosorbent analysis (ELISA), and sandwich ELISA. The detection of the signal can be achieved using autoradiography with imaging or phosphorimaging (AU), chemiluminescence (CL), electrochemiluminescence (ECL), bioluminescence (BL), fluorescence, resonance energy transfer, plane polarization, colorimetric, or flow cytometry (FC). Descriptions of immuno-based detection systems are disclosed in, e.g., Michael M. Rauhut, Chemiluminescence, In Kirk-Othmer Concise Encyclopedia of Chemical Technology (Ed. Grayson, 3rd ed, John Wiley and Sons, 1985); A. W. Knight, *A Review of Recent Trends in Analytical Applications of Electrogenerated Chemiluminescence*, Trends Anal. Chem. 18(1): 47-62 (1999); K. A. Fahnrich, et al., *Recent Applications of Electrogenerated Chemiluminescence in Chemical Analysis*, Talanta 54(4): 531-559 (2001); *Commonly Used Techniques in Molecular Cloning*, pp. A8.1-A8-55 (Sambrook & Russell, eds., Molecular Cloning A Laboratory Manual, Vol. 3, $3^{rd}$ ed. 2001); *Detection Systems*, pp. A9.1-A9-49 (Sambrook & Russell, eds., Molecular Cloning A Laboratory Manual, Vol. 3, $3^{rd}$ ed. 2001); Electrogenerated Chemiluminescence, (Ed. Allen J. Bard, Marcel Dekker, Inc., 2004), each of which is hereby incorporated by reference in its entirety.

A sandwich ELISA (or sandwich immunoassay) is a method based on two antibodies, which bind to different epitopes on the antigen. A capture antibody having a high binding specificity for the antigen of interest, is bound to a solid surface. The antigen is then added followed by addition of a second antibody referred to as the detection antibody. The detection antibody binds the antigen to a different epitope than the capture antibody. The antigen is therefore 'sandwiched' between the two antibodies. The antibody binding affinity for the antigen is usually the main determinant of immunoassay sensitivity. As the antigen concentration increases the amount of detection antibody increases leading to a higher measured response. To quantify the extent of binding different reporter systems can be used, such as, e.g., an enzyme attached to the secondary antibody and a reporter substrate where the enzymatic reaction forms a readout as the detection signal. The signal generated is proportional to the amount of target antigen present in the sample. The reporter substrate used to measure the binding event determines the detection mode. A spectrophotometric plate reader is used for colorimetric detection. Chemiluminescent and electrochemiluminescence substrates have been developed which further amplify the signal and can be read on a luminescent reader. The reporter can also be a fluorescent readout where the enzyme step of the assay is replaced with a fluorophore and the readout is then measured using a fluorescent reader. Reagents and protocols necessary to perform an ECL sandwich ELISA are commercially available, including, without exception, MSD sandwich ELISA-ECL detection platform (Meso Scale Discovery, Gaithersburg, Md.).

Thus, in an embodiment, detecting the presence of an antibody-antigen complex comprising an α-SNAP-25 antibody that selectively binds to a SNAP-25 epitope having a carboxyl-terminus at the $P_1$ residue of the BoNT/A cleavage site scissile bond and a SNAP-25 cleavage product having a carboxyl-terminus at the $P_1$ residue of the BoNT/A cleavage site scissile bond can be performed using an immuno-blot analysis, an immunoprecipitation analysis, an ELISA, or a sandwich ELISA. In aspects of this embodiment, the detection is performed using a AU, CL, ECL, or BL immuno-blot analysis, a AU, CL, ECL, BL, or FC immunoprecipitation analysis, a AU, CL, ECL, BL, or FC ELISA, or a AU, CL, ECL, BL, or FC sandwich ELISA.

Aspects of the present disclosure can be practiced in a singleplex or multiplex fashion. An immuno-based method of detecting retargeted endopeptidase activity practiced in a single-plex fashion is one that only detects the presence of an antibody-antigen complex comprising an α-SNAP-25 antibody and a SNAP-25 cleavage product having a carboxyl-terminus at the $P_1$ residue of the BoNT/A cleavage site scissile bond. An immuno-based method of detecting retargeted endopeptidase activity practiced in a multiplex fashion is one that concurrently detects the presence of two or more antibody-antigen complexes; one of which is the antibody-antigen complex comprising an α-SNAP-25 antibody and a SNAP-25 cleavage product having a carboxyl-terminus at the $P_1$ residue of the BoNT/A cleavage site scissile bond; and the other(s) of which is antibody-antigen complex to a second, third, fourth, etc. different protein. A second protein can be used, e.g., as an internal control to minimize sample to sample variability by normalizing the amount of α-SNAP-25/SNAP-25 antibody-antigen complex detected to the amount of antibody-antigen complex detected for the second protein. As such, the second protein is usually one that is consistently expressed by the cell, such as a house-keeping protein. Non-limiting examples of a useful second protein, include, e.g., a Glyceraldehyde-3-Phosphate Dehydrogenase (GAPDH), Syntaxin, cytokines. Methods of performing an immuno-based assay in a multiplex fashion are described in, e.g., U. B. Nielsen and B. H. Geierstanger, *Multiplexed Sandwich Assays in Microarray Format*, J. Immunol. Methods. 290 (1-2): 107-120 2004); R. Barry and M, Soloviev, *Quantitative Protein Profiling using Antibody Arrays*, Proteomics, 4(12): 3717-3726 (2004); M. M. Ling et al., *Multiplexing Molecular Diagnostics and Immunoassays using Emerging Microarray Technologies*, Expert Rev Mol Diagn. 7(1): 87-98 (2007); S. X. Leng et al., *ELISA and Multiplex Technologies for Cytokine Measurement in Inflammation and Aging Research*, J Gerontol A Biol Sci Med Sci. 63(8): 879-884 (2008), each of which is hereby incorporated by reference in its entirety.

Thus, in one embodiment, an immuno-based method of detecting retargeted endopeptidase activity practiced in a single-plex fashion by only detecting the presence of an antibody-antigen complex comprising an α-SNAP-25 antibody and a SNAP-25 cleavage product having a carboxyl-terminus at the $P_1$ residue of the BoNT/A cleavage site scissile bond. In another embodiment, immuno-based method of detecting retargeted endopeptidase activity practiced in a multiplex fashion by concurrently detecting the presence of an antibody-antigen complex comprising an α-SNAP-25 antibody and a SNAP-25 cleavage product having a carboxyl-terminus at the $P_1$ residue of the BoNT/A cleavage site scissile bond and at least one other antibody-antigen complex to a protein other than SNAP-25, such as, e.g., GAPDH or Syntaxin.

Aspects of the present disclosure provide, in part, a method of determining re-targeted endopeptidase immunoresistance. As used herein, the term "re-targeted endopeptidase immunoresistance" means a mammal that does not fully respond to a re-targeted endopeptidase therapy, or shows a reduced beneficial effect of a re-targeted endopeptidase therapy because the immune response of that mammal, either directly or indirectly, reduces the efficacy of the therapy. A non-limiting example of reduced efficacy would be the presence in a mammal of at least one neutralizing α-re-targeted endopeptidase antibody that binds to a re-targeted endopeptidase in a manner that reduces or prevents the specificity or activity of the re-targeted endopeptidase. As used herein, the term "re-targeted endopeptidase therapy" means a treatment, remedy, cure, healing, rehabilitation or any other means of counteracting something undesirable in a mammal requiring neuromodulation using a re-targeted endopeptidase or administering to a mammal one or more controlled doses of a medication, preparation or mixture of a re-targeted endopeptidase that has medicinal, therapeutic, curative, cosmetic, remedial or any other beneficial effect. Re-targeted endopeptidase therapy encompasses, without limitation, the use of any naturally occurring or modified fragment thereof, in any formulation, combined with any carrier or active ingredient and administered by any route of administration.

Aspects of the present disclosure provide, in part, a test sample obtained from a mammal being tested for the presence or absence of α-re-targeted endopeptidase neutralizing antibodies. As used herein, the term "test sample" refers to any biological matter that contains or potentially contains at least one α-re-targeted endopeptidase antibody. An α-re-targeted endopeptidase antibody can be a neutralizing α-re-targeted endopeptidase antibody or a non-neutralizing α-re-targeted endopeptidase antibody. As used herein, the term "neutralizing α-re-targeted endopeptidase antibodies" means any α-re-targeted endopeptidase antibody that will, under physiological conditions, bind to a region of a re-targeted endopeptidase in such a manner as to reduce or prevent the re-targeted endopeptidase from exerting its effect in a re-targeted endopeptidase therapy. As used herein, the term "non-neutralizing α-re-targeted endopeptidase antibodies" means any α-re-targeted endopeptidase antibody that will, under physiological conditions, bind to a region of a re-targeted endopeptidase, but not prevent the re-targeted endopeptidase from exerting its effect in a re-targeted endopeptidase therapy. It is envisioned that any and all samples that can contain α-re-targeted endopeptidase antibodies can be used in this method, including, without limitation, blood, plasma, serum and lymph fluid. In addition, any and all organisms capable of raising α-re-targeted endopeptidase antibodies against a re-targeted endopeptidase can serve as a source for a sample including, but not limited to, birds and mammals, including mice, rats, goats, sheep, horses, donkeys, cows, primates and humans. Non-limiting examples of specific protocols for blood collection and serum preparation are described in, e.g., Marjorie Schaub Di Lorenzo & Susan King Strasinger, Blood Collection in Healthcare (F. A. Davis Company, 2001); and Diana Garza & Kathleen Becan-McBride, Phlebotomy Handbook: Blood Collection Essentials (Prentice Hall, 6$^{th}$ ed., 2002). These protocols are routine procedures well within the scope of one skilled in the art and from the teaching herein. A test sample can be obtained from an organism prior to exposure to a re-targeted endopeptidase, after a single re-targeted endopeptidase treatment, after multiple re-targeted endopeptidase treatments, before onset of resistance to a re-targeted endopeptidase therapy, or after onset of resistance to a re-targeted endopeptidase therapy.

Aspects of the present disclosure provide, in part, a control sample. As used herein, the term "control sample" means any sample in which the presence or absence of the test sample is known and includes both negative and positive control samples. With respect to neutralizing α-re-targeted endopeptidase antibodies, a negative control sample can be obtained from an individual who had never been exposed to re-targeted endopeptidase and may include, without limitation, a sample from the same individual supplying the test sample, but taken before undergoing a re-targeted endopeptidase therapy; a sample taken from a different individual never been exposed to re-targeted endopeptidase; a pooled sample taken from a plurality of different individuals never been exposed to BoNT/A. With respect to neutralizing α-re-targeted endopeptidase antibodies, a positive control sample can be obtained from an individual manifesting re-targeted endopeptidase immunoresistance and includes, without limitation, individual testing positive in a patient-based testing assays; individual testing positive in an in vivo bioassay; and individual showing hyperimmunity, e.g., a re-targeted endopeptidase vaccinated individual.

It is further foreseen that α-re-targeted endopeptidase antibodies can be purified from a sample. α-Re-targeted endopeptidase antibodies can be purified from a sample, using a variety of procedures including, without limitation, Protein A/G chromatography and affinity chromatography. Non-limiting examples of specific protocols for purifying antibodies from a sample are described in, e.g., Antibodies: A Laboratory Manual (Edward Harlow & David Lane, eds., Cold Spring Harbor Laboratory Press, 2$^{nd}$ ed. 1998); Using Antibodies: A Laboratory Manual: Portable Protocol No. I (Edward Harlow & David Lane, Cold Spring Harbor Laboratory Press, 1998); and Molecular Cloning, A Laboratory Manual, supra, (2001), which are hereby incorporated by reference. In addition, non-limiting examples of antibody purification methods as well as well-characterized reagents, conditions and protocols are readily available from commercial vendors that include, without limitation, Pierce Biotechnology, Inc., Rockford, Ill.; and Zymed Laboratories, Inc., South San Francisco, Calif. These protocols are routine procedures well within the scope of one skilled in the art.

Thus, in an embodiment, a sample comprises blood. In aspect of this embodiment, the sample comprises mouse blood, rat blood, goat blood, sheep blood, horse blood, donkey blood, cow blood, primate blood or human blood. In another embodiment, a sample comprises plasma. In an aspect of this embodiment, a test sample comprises mouse plasma, rat plasma, goat plasma, sheep plasma, horse plasma, donkey plasma, cow plasma, primate plasma or human plasma. In another embodiment, a sample comprises serum. In an aspect of this embodiment, the sample comprises mouse serum, rat serum, goat serum, sheep serum, horse serum, donkey serum, cow serum, primate serum and human serum. In another embodiment, a sample comprises lymph fluid. In aspect of this embodiment, a sample comprises mouse lymph fluid, rat lymph fluid, goat lymph fluid, sheep lymph fluid, horse lymph fluid, donkey lymph fluid, cow lymph fluid, primate lymph fluid or human lymph fluid. In yet another embodiment, a sample is a test sample. In yet another embodiment, a sample is a control sample. In aspects of this embodiment, a control sample is a negative control sample or a positive control sample.

Aspects of the present disclosure provide, in part, comparing the amount of SNAP-25 having a carboxyl-terminus at the $P_1$ residue of the BoNT/A cleavage site scissile bond detected in step (d) to the amount of SNAP-25 having a carboxyl-terminus at the $P_1$ residue of the BoNT/A cleavage site scissile bond detected in step (e). In an embodiment, the amount of SNAP-25 cleavage product in the test sample is higher as compared to the amount of SNAP-25 cleavage product in the control sample. In an aspect of this embodiment, a higher amount of SNAP-25 cleavage product in the test sample as compared to a positive control sample indicates a reduction in or lack of re-targeted endopeptidase immunoresistance in the mammal. In another aspect of this embodiment, an equivalent amount of SNAP-25 cleavage product in the test sample as compared to a negative control sample indicates a reduction in or lack of re-targeted endopeptidase immunoresistance in the mammal. In another embodiment, the amount of SNAP-25 cleavage product in the test sample is lower as compared to the amount of SNAP-25 cleavage product in the control sample. In an aspect of this embodiment, a lower or equivalent amount of SNAP-25 cleavage product in the test sample as compared to a positive control sample indicates an increase in or presence of re-targeted endopeptidase immunoresistance in the mammal. In another aspect of this embodiment, a lower amount of SNAP-25 cleavage product in the test sample as compared to a negative control sample indicates an increase in or presence of re-targeted endopeptidase immunoresistance in the mammal.

It is envisioned that any and all assay conditions suitable for detecting the present of a neutralizing α-re-targeted endopeptidase antibody in a sample are useful in the methods disclosed in the present specification, such as, e.g., linear assay conditions and non-linear assay conditions. In an embodiment, the assay conditions are linear. In an aspect of this embodiment, the assay amount of a re-targeted endopeptidase is in excess. In another aspect of this embodiment, the assay amount of a re-targeted endopeptidase is rate-limiting. In another aspect of this embodiment, the assay amount of a test sample is rate-limiting.

Aspects of the present disclosure can also be described as follows:

1. A method of detecting retargeted endopeptidase activity, the method comprising the steps of: a) treating a cell from an established cell line with a sample comprising a retargeted endopeptidase, wherein the cell from an established cell line is susceptible to retargeted endopeptidase activity by a retargeted endopeptidase; b) isolating from the treated cell a SNAP-25 component comprising a SNAP-25 cleavage product having a carboxyl-terminus at the $P_1$ residue of the BoNT/A cleavage site scissile bond; c) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of retargeted endopeptidase activity.

2. A method of detecting retargeted endopeptidase activity, the method comprising the steps of: a) treating a cell from an established cell line with a sample comprising a retargeted endopeptidase, wherein the cell from an established cell line is susceptible to retargeted endopeptidase activity by a retargeted endopeptidase; b) isolating from the treated cell a SNAP-25 component comprising a SNAP-25 cleavage product having a carboxyl-terminus at the $P_1$ residue of the BoNT/A cleavage site scissile bond; c) contacting the SNAP-25 component with an α-SNAP-25 antibody linked to a solid phase support, wherein the α-SNAP-25 antibody binds an epitope comprising a carboxyl-terminus at the $P_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of retargeted endopeptidase activity.

3. A method of detecting retargeted endopeptidase activity, the method comprising the steps of: a) treating a cell from an established cell line with a sample comprising a retargeted endopeptidase, wherein the cell from an established cell line is susceptible to retargeted endopeptidase activity by a retargeted endopeptidase; b) isolating from the treated cell a SNAP-25 component comprising a SNAP-25 cleavage product having a carboxyl-terminus at the $P_1$ residue of the BoNT/A cleavage site scissile bond; c) fixing the SNAP-25 component to a solid phase support; d) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; and e) detecting the presence of an antibody-antigen complex comprising the α-SNAP-25 antibody and the SNAP-25 cleavage product; wherein detection by the antibody-antigen complex is indicative of retargeted endopeptidase activity.

4. A method of detecting retargeted endopeptidase activity, the method comprising the steps of: a) treating a cell from an established cell line with a sample comprising a retargeted endopeptidase, wherein the cell from an established cell line can uptake retargeted endopeptidase; b) isolating from the treated cell a SNAP-25 component comprising a SNAP-25 cleavage product having a carboxyl-terminus at the $P_1$ residue of the BoNT/A cleavage site scissile bond; c) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of retargeted endopeptidase activity.

5. A method of detecting retargeted endopeptidase activity, the method comprising the steps of: a) treating a cell from an established cell line with a sample comprising a retargeted endopeptidase, wherein the cell from an established cell line can uptake retargeted endopeptidase; b) isolating from the treated cell a SNAP-25 component comprising a SNAP-25 cleavage product having a carboxyl-terminus at the $P_1$ residue of the BoNT/A cleavage site scissile bond; c) contacting the SNAP-25 component with an α-SNAP-25 antibody linked to a solid phase support, wherein the α-SNAP-25 antibody binds an epitope comprising a carboxyl-terminus at the $P_1$ residue of the BoNT/A cleavage site scissile bond from a SNAP-25 cleavage product; and d) detecting the presence of an antibody-antigen complex comprising the α-SNAP-25 antibody and the SNAP-25 cleavage product; wherein detection by the antibody-antigen complex is indicative of retargeted endopeptidase activity.

6. A method of detecting retargeted endopeptidase activity, the method comprising the steps of: a) treating a cell from an established cell line with a sample comprising a retargeted endopeptidase, wherein the cell from an established cell line can uptake retargeted endopeptidase; b) isolating from the treated cell a SNAP-25 component comprising a SNAP-25 cleavage product having a carboxyl-terminus at the $P_1$ residue of the BoNT/A cleavage site scissile bond; c) fixing the SNAP-25 component to a solid phase support; d) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; and e) detecting the presence of an antibody-antigen complex comprising the α-SNAP-25 antibody and the SNAP-25 cleavage product; wherein detection by the antibody-antigen complex is indicative of retargeted endopeptidase activity.

7. A method of determining retargeted endopeptidase immunoresistance in a mammal comprising the steps of: a) adding a retargeted endopeptidase to a test sample obtained from a mammal being tested for the presence or absence of α-retargeted endopeptidase neutralizing antibodies; b) treating a cell from an established cell line with the test sample, wherein the cell from an established cell line is susceptible to retargeted endopeptidase activity; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a retargeted endopeptidase and a serum known not to contain α-retargeted endopeptidase neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-retargeted endopeptidase neutralizing antibodies.

8. A method of determining retargeted endopeptidase immunoresistance in a mammal comprising the steps of: a) adding a retargeted endopeptidase to a test sample obtained from a mammal being tested for the presence or absence of α-retargeted endopeptidase neutralizing antibodies; b) treating a cell from an established cell line with the test sample, wherein the cell from an established cell line is susceptible to retargeted endopeptidase activity; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody linked to a solid phase support, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-retargeted endopeptidase antibody and the SNAP-25 cleavage product; f) repeating steps b-e with a negative control sample instead of a test sample, the negative control sample comprising a re-targeted endopeptidase and a serum known not to contain α-retargeted endopeptidase neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-retargeted endopeptidase neutralizing antibodies.

9. A method of determining retargeted endopeptidase immunoresistance in a mammal comprising the steps of: a) adding a retargeted endopeptidase to a test sample obtained from a mammal being tested for the presence or absence of α-retargeted endopeptidase neutralizing antibodies; b) treating a cell from an established cell line with the test sample, wherein the cell from an established cell line is susceptible to retargeted endopeptidase activity; c) isolating from the treated cells a SNAP-25 component comprising a SNAP-25 cleavage product having a carboxyl-terminus at the $P_1$ residue of the BoNT/A cleavage site scissile bond; d) fixing the SNAP-25 component to a solid phase support; e) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; f) detecting the presence of an antibody-antigen complex comprising the α-SNAP-25 antibody and the SNAP-25 cleavage product; g) repeating steps b-f with a negative control sample instead of a test sample, the negative control sample comprising a re-targeted endopeptidase and a serum known not to contain α-retargeted endopeptidase neutralizing antibodies; and h) comparing the amount of antibody-antigen complex detected in step f to the amount of antibody-antigen complex detected in step g, wherein detection of a lower amount of antibody-antigen complex detected in step f relative to the amount of antibody-antigen complex detected in step g is indicative of the presence of α-retargeted endopeptidase neutralizing antibodies.

10. A method of determining retargeted endopeptidase immunoresistance in a mammal comprising the steps of: a) adding a retargeted endopeptidase to a test sample obtained from a mammal being tested for the presence or absence of α-retargeted endopeptidase neutralizing antibodies; b) treating a cell from an established cell line with the test sample, wherein the cell from an established cell line can uptake retargeted endopeptidase; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a retargeted endopeptidase and a serum known not to contain α-re-targeted endopeptidase neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-retargeted endopeptidase neutralizing antibodies.

11. A method of determining retargeted endopeptidase immunoresistance in a mammal comprising the steps of: a) adding a re-targeted endopeptidase to a test sample obtained from a mammal being tested for the presence or absence of α-re-targeted endopeptidase neutralizing antibodies; b) treating a cell from an established cell line with the test sample, wherein the cell from an established cell line can uptake retargeted endopeptidase; c) isolating from the treated cells a SNAP-25 component comprising a SNAP-25 cleavage product having a carboxyl-terminus at the $P_1$ residue of the BoNT/A cleavage site scissile bond; d) contacting the SNAP-25 component with an α-SNAP-25 antibody linked to a solid phase support, wherein the α-SNAP-25 antibody binds an epitope comprising a carboxyl-terminus at the $P_1$ residue of the BoNT/A cleavage site scissile bond from a SNAP-25 cleavage product; e) detecting the presence of an antibody-antigen complex comprising the α-SNAP-25 antibody and the SNAP-25 cleavage product; f) repeating steps b-e with a negative control sample instead of a test sample, the negative control sample comprising a retargeted endopeptidase and a serum known not to contain α-re-targeted endopeptidase neutralizing antibodies; and g) comparing the amount of antibody-antigen complex detected in step e to the amount of antibody-antigen complex detected in step f, wherein detection of a lower amount of antibody-antigen complex detected in step e relative to the amount of antibody-antigen complex detected in step f is indicative of the presence of α-retargeted endopeptidase neutralizing antibodies.

12. A method of determining retargeted endopeptidase immunoresistance in a mammal comprising the steps of: a) adding a retargeted endopeptidase to a test sample obtained from a mammal being tested for the presence or absence of α-retargeted endopeptidase neutralizing antibodies; b) treating a cell from an established cell line with the test sample, wherein the cell from an established cell line can uptake retargeted endopeptidase; c) isolating from the treated cells a SNAP-25 component comprising a SNAP-25 cleavage product having a carboxyl-terminus at the $P_1$ residue of the BoNT/A cleavage site scissile bond; d) fixing the SNAP-25 component to a solid phase support; e) contacting the SNAP-25 component with an α-SNAP-25 antibody, wherein the α-SNAP-25 antibody binds an epitope comprising a carboxyl-terminus at the $P_1$ residue of the BoNT/A cleavage site scissile bond from a SNAP-25 cleavage product; f) detecting the presence of an antibody-antigen complex comprising the α-SNAP-25 antibody and the SNAP-25 cleavage product; g) repeating steps b-f with a negative control sample instead of a test sample, the negative control sample comprising a retargeted endopeptidase and a serum known not to contain α-retargeted endopeptidase neutralizing antibodies; and h) comparing the amount of antibody-antigen complex detected in step f to the amount of antibody-antigen complex detected in step g, wherein detection of a lower amount of antibody-antigen complex detected in step f relative to the amount of antibody-antigen complex detected in step g is indicative of the presence of α-retargeted endopeptidase neutralizing antibodies.

13. The method of 1-3 and 7-9, wherein the cell is susceptible to retargeted endopeptidase activity by about 500 nM or less, by about 400 nM or less, by about 300 nM or less, by about 200 nM or less, by about 100 nM or less of a retargeted endopeptidase.

14. The method of 4-6 and 10-12, wherein the cell can uptake about 500 nM or less, by about 400 nM or less, by about 300 nM or less, by about 200 nM or less, by about 100 nM or less of retargeted endopeptidase.

15. The method of 1-6, wherein the sample comprises about 100 ng or less, about 10 ng or less, about 1 ng or less, 100 fg or less, 10 fg or less, or 1 fg or less of a retargeted endopeptidase.

16. The method of 1-6, wherein the sample comprises about 100 nM or less, about 10 nM or less, about 1 nM or less, about 100 nM or less, about 10 nM or less, about 1 nM or less, about 0.5 nM or less, or about 0.1 nM or less, of a retargeted endopeptidase.

17. The method of 1-12, wherein the presence of an antibody-antigen complex is detected by an immuno-blot analysis, an immunoprecipitation analysis, an ELISA, or a sandwich ELISA.

18. The method of 1-12, wherein the method has a signal-to-noise ratio for the lower asymptote of at least 3:1, at least 5:1, at least 10:1, at least 20:1, at least 50:1, or at least 100:1.

19. The method of 1-12, wherein the method has a signal-to-noise ratio for the higher asymptote of at least 10:1, at least 20:1, at least 50:1, at least 100:1, at least 200:1, at least 300:1, at least 400:1, at least 500:1, or at least 600:1.

20. The method of 1-12, wherein the method can detect the $EC_{50}$ activity of, e.g., at least 100 ng, at least 50 ng, at least 10 ng, at least 5 ng, at least 100 pg, at least 50 pg, at least 10 pg, at least 5 pg, at least 100 fg, at least 50 fg, at least 10 fg, or at least 5 fg of a retargeted endopeptidase.

21. The method of 1-12, wherein the method can detect the $EC_{50}$ activity of, e.g., at least 10 nM, at least 5 nM, at least 100 nM, at least 50 nM, at least 10 nM, at least 5 nM, at least 1 nM, at least 0.5 nM, or at least 0.1 nM of a retargeted endopeptidase.

22. The method of 1-12, wherein the method has an LOD of, e.g., 10 pg or less, 9 pg or less, 8 pg or less, 7 pg or less, 6 pg or less, 5 pg or less, 4 pg or less, 3 pg or less, 2 pg or less, 1 pg or less of a retargeted endopeptidase.

23. The method of 1-12, wherein the method has an LOD of, e.g., 100 nM or less, 90 nM or less, 80 nM or less, 70 nM or less, 60 nM or less, 50 nM or less, 40 nM or less, 30 nM or less, 20 nM or less, or 10 nM or less of a retargeted endopeptidase.

24. The method of 1-12, wherein the method has an LOQ of, e.g., 10 pg or less, 9 pg or less, 8 pg or less, 7 pg or less, 6 pg or less, 5 pg or less, 4 pg or less, 3 pg or less, 2 pg or less, 1 pg or less of a retargeted endopeptidase.

25. The method of 1-12, wherein the method has an LOQ of, e.g., 100 nM or less, 90 nM or less, 80 nM or less, 70 nM or less, 60 nM or less, 50 nM or less, 40 nM or less, 30 nM or less, 20 nM or less, or 10 nM or less of a retargeted endopeptidase.

26. The method of 1-12, wherein the method can distinguish a fully-active retargeted endopeptidase from a partially-active retargeted endopeptidase having 70% or less, 60% or less, 50% or less, 40% or less, 30% or less, 20% or less, or 10% or less the activity of a fully-active retargeted endopeptidase A.

27. The method of 1-12, wherein the α-SNAP-25 antibody binds an epitope comprising a carboxyl-terminus at the $P_1$ residue from the BoNT/A cleavage site scissile bond from a SNAP-25 cleavage product.

28. The method of 27, wherein the α-SNAP-25 antibody has an association rate constant for an epitope not comprising a carboxyl-terminus glutamine of the BoNT/A cleavage site scissile bond from a SNAP-25 cleavage product of less than $1\times10^1$ $M^{-1}$ $s^{-1}$; and wherein the α-SNAP-25 antibody has an equilibrium disassociation constant for the epitope of less than 0.450 nM.

29. The method of 27, wherein the isolated α-SNAP-25 antibody has a heavy chain variable region comprising the amino acid sequence selected from the group consisting of SEQ ID NO:72, SEQ ID NO:74, SEQ ID NO:76, SEQ ID NO:80, and SEQ ID NO:82; and a light chain variable region comprising the amino acid sequence selected from the group consisting of SEQ ID NO:84, SEQ ID NO:86, SEQ ID NO:88, SEQ ID NO:90, and SEQ ID NO:92.

30. The method of 27, wherein the isolated α-SNAP-25 antibody comprises at least the $V_H$ CDR1 of SEQ ID NO:93, the $V_H$ CDR1 of SEQ ID NO:94, the $V_H$ CDR1 of SEQ ID NO:95, the $V_H$ CDR1 of SEQ ID NO:118, the $V_H$ CDR1 of SEQ ID NO:119, or the $V_H$ CDR1 of SEQ ID NO:120.

32. The method of 27, wherein the isolated α-SNAP-25 antibody comprises at least the $V_H$ CDR2 of SEQ ID NO:96, the $V_H$ CDR2 of SEQ ID NO:97, the $V_H$ CDR2 of SEQ ID NO:98, the $V_H$ CDR2 of SEQ ID NO:99, the $V_H$ CDR2 of SEQ ID NO:121, the $V_H$ CDR2 of SEQ ID NO:122, or the $V_H$ CDR2 of SEQ ID NO:123.

33. The method of 27, wherein the isolated α-SNAP-25 antibody comprises at least the $V_H$ CDR3 of SEQ ID NO:100, the $V_H$ CDR3 of SEQ ID NO:101, the $V_H$ CDR3 of SEQ ID NO:102, or the $V_H$ CDR3 of SEQ ID NO:124.

34. The method of 27, wherein the isolated α-SNAP-25 antibody comprises at least the $V_L$ CDR1 of SEQ ID NO:103, the $V_L$ CDR1 of SEQ ID NO:104, the $V_L$ CDR1 of SEQ ID NO:105, the $V_L$ CDR1 of SEQ ID NO:106, the $V_L$ CDR1 of SEQ ID NO:107, the $V_L$ CDR1 of SEQ ID NO:125, the $V_L$ CDR1 of SEQ ID NO:126, the $V_L$ CDR1 of SEQ ID NO:127, the $V_L$ CDR1 of SEQ ID NO:128, or the $V_L$ CDR1 of SEQ ID NO:129.

35. The method of 27, wherein the isolated α-SNAP-25 antibody comprises at least the $V_L$ CDR2 of SEQ ID NO:108, the $V_L$ CDR2 of SEQ ID NO:109, the $V_L$ CDR2 of SEQ ID NO:110, the $V_L$ CDR2 of SEQ ID NO:111, or the $V_L$ CDR2 of SEQ ID NO:112.

36. The method of 27, wherein the isolated α-SNAP-25 antibody comprises at least the $V_L$ CDR3 of SEQ ID NO:113, the $V_L$ CDR3 of SEQ ID NO:114, the $V_L$ CDR3 of SEQ ID NO:115, the $V_L$ CDR3 of SEQ ID NO:116, or the $V_L$ CDR3 of SEQ ID NO:117.

37. The method of 27, wherein the isolated α-SNAP-25 antibody comprises a heavy chain variable region comprising SEQ ID NO:93, SEQ ID NO:121 and SEQ ID NO:100; and a light chain variable region comprising SEQ ID NO:105, SEQ ID NO:110 and SEQ ID NO:115.

38. The method of 27, wherein the isolated α-SNAP-25 antibody selectively binds the SNAP-25 epitope of SEQ ID NO:32, SEQ ID NO:33, SEQ ID NO:34, SEQ ID NO:35, SEQ ID NO:36, SEQ ID NO:37, SEQ ID NO:147 or SEQ ID NO:148.

39. The method of 27, wherein the isolated α-SNAP-25 antibody selectively binds the SNAP-25 epitope of SEQ ID NO:39, SEQ ID NO:40, SEQ ID NO:41, SEQ ID NO:42, SEQ ID NO:43, or SEQ ID NO:44.

EXAMPLES

Example I

Screening of Candidate Cell Lines for Endogenous Re-Targeted Endopeptidase Receptor Expression The following example illustrates how to identify established cell lines possessing the re-targeted endopeptidase uptake capacity required to develop a cell-based potency assay.

1. Growth of Stock Culture of Candidate Cell Lines.

To grow the cell lines, a suitable density of cells from the cell line being tested were plated in a 162 $cm^2$ tissue culture flask containing 30 mL of a suitable growth medium (see Table 1), and grown in a 37° C. incubator under 5% or 10% carbon dioxide until cells reached the desired density.

TABLE 1

Media Used in Cell Line Screening.

| Cell Line | Serum Growth Media Composition |
|---|---|
| SiMa and SiMa clones | RPMI 1640, 10% fetal bovine serum, 1% Penicillin-Streptomycin, 2 mM L-Glutamine |
| PC12 | RPMI 1640, 5% heat-inactivated fetal bovine serum, 10% equine serum, 2 mM GlutaMAX ™, 10 mM HEPES, 1 mM sodium pyruvate, 1% Penicillin-Streptomycin |
| N18<br>ND8/34<br>NG108-15 | 90% DMEM, 10% heat-inactivated fetal bovine serum, 2 mM Glutamine, 2 mM glucose |
| SK-N-DZ<br>SK-N-F1<br>SK-N-SH | 90% DMEM, 10% heat-inactivated fetal bovine serum, 4 mM Glutamine, 4 mM glucose, 0.1 mM non-essential amino acids, 1.5 g/L $NaHCO_3$ |
| BE(2)-C<br>SK-N-BE(2)<br>SH-SY5Y | EMEM(11090-081, Gibco), Ham's F12 (11765-054, Gibco), 10% heat-inactivated fetal bovine serum, 2 mM Glutamine, 0.1 mM non-essential amino acids, |
| ND3, ND7, ND15 | DMEM media with 2 mM Glutamine (Invitrogen, Cat #. 11885), 10% Fetal Bovine Serum (Invitrogen, Cat #. 16140), and 1x antibiotic/antimycotic |
| Neuro-2a | EMEM, 10% heat-inactivated fetal bovine serum, 2 mM Glutamine, 0.1 mM non-essential amino acids, 1.5 g/L $NaHCO_3$, 1 mM Sodium pyruvate |

2. Screening of Cells Expressing Target Receptor on Cell Surface.

The cell lines were screened for the presence of the desired target receptor using flow cytometry and/or ligand binding assays. Although the examples below used reagents to identify opioid or opioid-like receptor in the plasma membrane, the approaches disclosed below can be used to identify the cognate receptor for any of re-targeted endopeptidase.

a. Identification of Cell Lines Using Flow Cytometry.

To identify cells comprising established cell lines that express target receptors for a retargeted endopeptidase on the cell surface, flow cytometry analysis was conducted. Cells for each candidate cell line were grown as described in Section 1, trypsin-treated, washed in staining buffer comprising 1×PBS, 0.5% BSA, and centrifuged at 1200 rpm for 3 minutes. Pelleted cells were resuspended in staining buffer and about $2.0\times10^6$ cells were transferred to new tubes, two for each receptor tested. To screen for the presence of an opioid or opioid-like receptors, about 2.0-5.0 μL of α-ORL-1 RA14133 (Neuromics, Edina, Minn.), α-DOR rabbit polyclonal antibody RA10101 (Neuromics, Edina, Minn.), α-KOR rabbit polyclonal antibody RA10103 (Neuromics, Edina, Minn.), or α-MOR rabbit polyclonal antibody RA10104 (Neuromics, Edina, Minn.), was added to one tube and the mixture was incubated at 4° C. for 1 hour. The second tube was incubated at 4° C. for 1 hour without any antibodies and served as a negative control. After the antibody incubation, 1.0 mL of staining buffer was added to each tube and centrifuge at 1200 rpm for 3 minutes. The cell pellet was washed once more with 1.0 mL of staining buffer. The cell pellet was resuspend in 200 μL of staining buffer, and 2.0 μL of goat anti-rabbit IgG FITC antibody was added to each tube and incubated at 4° C. for 1 hour in the dark. After incubation with the secondary antibody, 1.0 mL of staining buffer was added to each tube and centrifuge at 1200 rpm for 3 minutes. The cell pellet was washed once more with 1.0 mL of staining buffer and the pellet resuspend in 500 μL of staining buffer. The sample was analyzed using a flow cytometer and the data was displayed as an overlay the anti-receptor antibody staining over the rabbit IgG FITC staining.

The results indicate that. Of the cell lines tested, ORL-1 was expressed on the cell surface of about 50% of the cells comprising SiMa, SiMa P>33, clone H10, ND7, and SK-N-DZ established cell lines; was expressed on the cell surface of between about 25% to about 50% of the cells comprising SH-SY5Y and ND15 established cell lines; and was expressed on the cell surface of less than about 25% of the cells comprising ND3, NDB, N18, and Neuro-2a established cell lines (Table 2). The results also indicate that KOR was expressed on the cell surface of about 50% of the cells comprising SH-SY5Y and ND7 established cell lines; was expressed on the cell surface of between about 25% to about 50% of the cells comprising SiMa clone H10, SiMa P>33, ND15, and Neuro-2a established cell lines; and was expressed on the cell surface of less than about 25% of the cells comprising ND3, ND8, and N18 established cell lines (Table 2). The results also revealed that MOR was expressed on the cell surface of about 50% of the cells comprising ND7, ND15, and SiMa P>33 established cell lines; was expressed on the cell surface of between about 25% to about 50% of the cells comprising SH-SY5Y, SiMa clone H10, ND8, and Neuro-2a established cell lines; and was expressed on the cell surface of less than about 25% of the cells comprising ND3 and N18 established cell lines (Table 2). The α-DOR rabbit polyclonal antibody RA10101 failed to work properly and no useable data was generated.

b. Identification of Cell Lines Using Ligand Binding.

To identify cells comprising established cell lines that express target receptors for a retargeted endopeptidase on the cell surface, ligand binding analysis was conducted. Cells from the candidate cell lines to be tested were seeded on a black-clear bottom 96-well plate for about 4 hours to promote attachment. To screen for the presence of an opioid or opioid-like receptors, media was then aspirated from each well and replaced with 50 μL of ligand solution containing either 0 (untreated control), 0.001 nM, 0.01 nM, 0.1 nM, or 1 nM of FAM-nociceptin (Phoenix Pharmaceuticals, Inc, Burlingame, Calif.); or either 0 (untreated control), 0.001 nM, 0.01 nM, 0.1 nM, or 1 nM of FAM-dynorphin A (Phoenix Pharmaceuticals, Inc, Burlingame, Calif.). Cells were incubated with the ligand solution for 1 hour in the 37° C. incubator under 5% carbon dioxide. The cells were washed to remove unbound ligand by washing the cells three times with 100 μL of 1×PBS. The plate was scanned on the Typhoon (Ex 488 and Em 520 nm), and then read on the M5 Plate Reader (Ex 495 and Em 520 nm) for RFU signals. The results indicate that cells comprising the SiMa clone H10, SH-SY5Y, and SK-N-DZ established cell lines bound nociceptin, whereas cells comprising the SiMa clone H10 also bound Dynorphin (Table 2).

plates containing 1 mL of an appropriate serum growth medium (Table 1). The cells were grown in a 37° C. incubator under 5% carbon dioxide until cells reached the desired density (approximately 18 to 24 hours). To assess the uptake of an opioid re-targeted endopeptidase, the growth media was aspirated from each well and replaced with either 1) fresh growth media containing no opioid re-targeted endopeptidase (untreated cell line) or 2) fresh growth media containing 30 nM for the nociceptin re-targeted endopeptidase (Noc/A) or 100 nM for the dynorphin re-targeted endopeptidase (Dyn/A) (treated cell line). After an overnight incubation, the cells were washed by aspirating the growth media and rinsing each well with 200 μL of 1×PBS. To harvest the cells, the 1×PBS was aspirated, the cells were lysed by adding 50 μL of 2×SDS Loading Buffer, the lysate was transferred to a clean test tube and the sample was heated to 95° C. for 5 minutes.

To detect for the presence of both uncleaved SNAP-25 substrate and cleaved SNAP-25 products, an aliquot from each harvested sample was analyzed by Western blot. In this analysis, a 12 μL aliquot of the harvested sample was separated by MOPS polyacrylamide gel electrophoresis using NuPAGE® Novex 12% Bis-Tris precast polyacrylamide gels (Invitrogen Inc., Carlsbad, Calif.) under denaturing, reducing conditions. Separated peptides were transferred from the gel onto polyvinylidene fluoride (PVDF) membranes (Invitrogen Inc., Carlsbad, Calif.) by Western blotting using a TRANS-BLOT® SD semi-dry electrophoretic transfer cell apparatus (Bio-Rad Laboratories, Hercules, Calif.). PVDF membranes were blocked by incubating at room temperature for 2 hours in a solution containing Tris-Buffered Saline (TBS) (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20® (polyoxyethylene (20) sorbitan mono-

TABLE 2

Cell lines Expressing Target Receptors on Cell Surface

| | Cell Lines Identified | | | | |
|---|---|---|---|---|---|
| | Flow Cytometry | | | Ligand Binding | |
| Target Receptor | More than 50% Expression | 25% to 50% Expression | Less than 50% Expression | Nociceptin | Dynorphin A |
| ORL-1 | AGN P33, SiMa, SiMa clone H10, ND7, SK-N-DZ | SH-SY5Y, ND15 | ND3, ND8, N18, Neuro-2a | SiMa clone H10, SH-SY5Y, SK-N-DZ | — |
| DOR | ND | ND | ND | ND | ND |
| KOR | SH-SY5Y, ND7 | SiMa clone H10, AGN P33, ND15, Neuro-2a | ND3, ND8, N18 | — | SiMa clone H10 |
| MOR | ND7, ND15, AGN P33 | SH-SY5Y, SiMa clone H10, ND8, Neuro-2a | ND3, N18 | ND | ND |

Using a similar approach, cell lines comprising cells having cognate receptors for other re-targeted endopeptidases can be identified by FAM-labeling the targeting domain for these endopeptidases and screening cell lines as described above.

3. Single Dose Screening of Candidate Cell Lines Using Re-Targeted Endopeptidase Molecule.

To determine whether a cell line was able to uptake the appropriate re-targeted endopeptidase molecule, a suitable density of cells from a stock culture of the cell line being tested was plated into the wells of 24-well tissue culture laurate), 2% Bovine Serum Albumin (BSA), 5% nonfat dry milk. Blocked membranes were incubated at 4° C. for overnight in TBS, 0.1% TWEEN-20® (polyoxyethylene (20) sorbitan monolaurate), 2% BSA, and 5% nonfat dry milk containing either 1) a 1:5,000 dilution of an α-SNAP-25 mouse monoclonal antibody as the primary antibody (SMI-81; Sternberger Monoclonals Inc., Lutherville, Md.); or 2) a 1:5,000 dilution of S9684 α-SNAP-25 rabbit polyclonal antiserum as the primary antibody (Sigma, St. Louis, Mo.). Both α-SNAP-25 mouse monoclonal and rabbit polyclonal antibodies can detect both the uncleaved SNAP-25 substrate and the SNAP-25 cleavage product, allowing for the assessment of overall SNAP-25 expression in each cell line and the percent of SNAP-25 cleaved after re-targeted endopeptidase treatment as a parameter to assess the amount of re-targeted endopeptidase uptake. Primary antibody probed blots were washed three times for 15 minutes each time in TBS, TWEEN-20® (polyoxyethylene (20) sorbitan monolaurate). Washed membranes were incubated at room temperature for 2 hours in TBS, 0.1% TWEEN-20® (polyoxyethylene (20) sorbitan monolaurate), 2% BSA, and 5% nonfat dry milk containing either 1) a 1:10,000 dilution of goat polyclonal anti-mouse immunoglobulin G, heavy and light chains (IgG, H+L) antibody conjugated to horseradish peroxidase (Zymed, South San Francisco, Calif.) as a secondary antibody; or 2) a 1:10,000 dilution of goat polyclonal anti-rabbit immunoglobulin G, heavy and light chains (IgG, H+L) antibody conjugated to horseradish peroxidase (Zymed, South San Francisco, Calif.) as a secondary antibody. Secondary antibody-probed blots were washed three times for 15 minutes each time in TBS, 0.1% TWEEN-20® (polyoxyethylene (20) sorbitan monolaurate). Signal detection of the labeled SNAP-25 products were visualized using the ECL Plus™ Western Blot Detection System (GE Healthcare, Amersham Biosciences, Piscataway, N.J.) and the membrane was imaged and the percent of cleaved quantified with a Typhoon 9410 Variable Mode Imager and Imager Analysis software (GE Healthcare, Amersham Biosciences, Piscataway, N.J.). The choice of pixel size (100 to 200 pixels) and PMT voltage settings (350 to 600, normally 400) depended on the individual blot.

Based on the detection of SNAP-25 cleavage product, the following cell lines exhibited uptake of 30 nM Noc/A: BE(2)-C, N18TG2, Neuro-2a, SiMa, SK-N-BE(2)-C, and SK-N-DZ (Table 3); whereas the following cell lines exhibited uptake of 100 nM Dyn/A: N18TG2, Neuro-2a, PC12, and SiMa. Some of these sensitive cell lines were tested with lower doses of compounds and/or with full dose responses.

Using a similar approach, cell lines comprising cells having cognate receptors for other re-targeted endopeptidases can be assessed for retargeted endopeptidase uptake.

Example II

Screening of Candidate Clonal Cell Lines Endogenous Re-Targeted Endopeptidase Receptor Expression 1. Single Dose Re-Targeted Endopeptidase Screening of Candidate Clonal Cell Lines from a Parental SiMa Cell Line.

Companion patent application Zhu Hong et al., Cell Lines Useful in Immuno-Based Botulinum Toxin Serotype A Activity Assays, U.S. Patent Application Ser. No. 61/160,199 discloses clonal cell lines derived from a parental SiMa cell line that were useful in a BoNT/A potency assay, as described in Ester Fernandez-Salas, et al., Immuno-Based Botulinum Toxin Serotype A Activity Assays, U.S. patent application Ser. No. 12/403,531, each of which is hereby incorporated by reference in its entirety. To determine whether these clonal cell lines were able to uptake the appropriate re-targeted endopeptidase, each was screened using an ECL sandwich ELISA assay.

To prepare a lysate treated with a retarget endopeptidase, a suitable density of cells from a stock culture of the cell line being tested was plated into the wells of 96-well tissue culture plates containing 100 μL of an appropriate serum growth medium (Table 1) overnight. The media from the seeded cells was aspirated from each well and replaced with fresh media containing either 30 nM of a Noc/A retargeted endopeptidase or 80 nM of a Dyn/A retargeted endopeptidase. After a 24 hour incubation, the cells were washed by aspirating the growth media and rinsing each well with 200 μL of 1×PBS. To harvest the cells, 1×PBS was aspirated, the cells lysed by adding 30 μL of Lysis Buffer comprising 20 mM Tris-HCl (pH 7.5), 150 mM NaCl, 1 mM EDTA, 1 mM

TABLE 3

Single-Dose Screening of Candidate Cell Lines Using Retargeted Noc/A and Dyn/A

| Cell Line | Description | Source | 30 nM Noc/A Uptake | 100 nM Dyn/A Uptake |
|---|---|---|---|---|
| BE(2)-C | Human neuroblastoma | ATCC CRL-2268 | Yes | NT |
| N18TG2 | Mouse neuroblastoma | DSMZ ACC 103 | Yes | Yes |
| ND3 | Mouse neuroblastoma/primary neonatal rat DRG hybrid | ECACC 92090901 | NDA | NDA |
| ND7/23 | Mouse neuroblastoma/primary rat DRG hybrid | ECACC 92090903 | No | No |
| ND8 | Mouse neuroblastoma/primary neonatal rat DRG hybrid | ECACC 92090904 | NDA | NDA |
| ND15 | Mouse neuroblastoma/primary neonatal rat DRG hybrid | ECACC 92090907 | No | No |
| Neuro-2a | Mouse neuroblastoma | ATCC CCL-131 | Yes | Yes |
| NG108-15 | Mouse neuroblastoma/rat glioma hybrid | ECACC 88112302 | No | NT |
| PC12 | Rat pheochromocytoma | ATCC CRL-1721 | NT | Yes |
| SH-SY5Y | Human neuroblastoma | ATCC CRL-2266 | No | NT |
| SiMa | Human neuroblastoma | DSMZ ACC 164 | Yes | Yes |
| SK-N-BE(2)-C | Human neuroblastoma | ATCC CRL-2271 | Yes | NT |
| SK-N-DZ | Human neuroblastoma | ATCC CRL-2149 | Yes | NT |
| SK-N-F1 | Human neuroblastoma | ATCC CRL-2142 | No | NT |
| SK-N-SH | Human neuroblastoma | ECACC 86012802 | No | NT |

NT: Not tested.

NDA: No detectable amount of SNAP-25 was deteced in this cell line.

EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

To prepare an α-SNAP-$25_{197}$ capture antibody solution, the α-SNAP-$25_{197}$ mouse monoclonal antibody contained in the ascites from hybridoma cell line 2E2A6 (Example XI) was purified using a standard Protein A purification protocol.

To prepare an α-SNAP-25 detection antibody solution, α-SNAP-25 rabbit polyclonal antibody S9684 (Sigma, St. Louis, Mo.) was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding to 30 μL of distilled water reconstituted MSD SULFO-TAG™ stock solution to 200 μL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed. Long term storage of unused aliquots was at −20° C.

To prepare an α-SNAP-25 solid phase support comprising an α-SNAP-$25_{197}$ capture antibody, approximately 5 μL of the appropriate α-SNAP-$25_{197}$ monoclonal antibody solution (20 μg/mL in 1×PBS) is added to each well of a 96-well MSD High Bind plate and the solution is allowed to air dry in a biological safety cabinet for 2-3 hours in order to liquid evaporate the solution. Blocked plates were sealed and stored at 4° C. until needed.

To detect the presence of a cleaved SNAP-25 product by ECL sandwich ELISA, the capture antibody-bound wells were then blocked by adding 150 μL of Blocking Buffer comprising 2% Amersham Blocking Reagent (GE Life Sciences, Piscataway, N.J.) and 10% goat serum (VWR, West Chester, Pa.) at room temperature for 2 hours. The Blocking Buffer was aspirated, 25 μL of a lysate from cells treated with re-targeted endopeptidase was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaurate). After washing, 25 μL of 5 μg/mL α-SNAP-25 detection antibody solution comprising 2% Amersham Blocking Reagent in 1×PBS, 0.1% TWEEN-20® (polyoxyethylene (20) sorbitan monolaurate) was added to each well, sealed, and incubated at room temperature for 1 hour with shaking. After α-SNAP-25 detection antibody incubation, the wells were washed three times with 200 μL 1×PBS, 0.1% TWEEN-20® (polyoxyethylene (20) sorbitan monolaurate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The raw data was collected using the ECL imager.

The results indicate that the parental SiMa cell line as well as clonal cell line H10 showed good uptake of the Noc/A retargeted endopeptidase (Table 4). In addition, these results reveal that many cell lines exhibited uptake of the Dyn/A retargeted endopeptidase (Table 4). Three clonal cell lines (1E11, AF4, and DC4) showed good uptake of the Dyn/A retargeted endopeptidase; eleven clonal cell lines (1E3, 2D2, 2D6, 3D8, 5C10, 5F3, BB10, BFB, CG8, CG10, and DE7) exhibited moderate uptake of the Dyn/A retargeted endopeptidase; and (3B8, 2B9, CE6, YB8, 4C8, 2F5, AC9, CD6, DD10, YF5) showed minimal uptake of the Dyn/A retargeted endopeptidase. Some of these candidate cell lines were tested in a full dose-response assay with the corresponding retargeted endopeptidase.

TABLE 4

Single-Dose Screening of Candidate Clonal Cell Lines Using Retargeted Noc/A and Dyn/A

| Cell Line | 30 nM Noc/A Uptake | 80 nM Dyn/A Uptake |
|---|---|---|
| AGN P33 | +++ | NT |
| A10 | − | NT |
| D11 | − | NT |
| H1 | − | − |
| H10 | +++ | − |
| 1D4 | NT | − |
| 2E4 | NT | − |
| 3D5 | NT | − |
| 3G10 | NT | − |
| 4D3 | NT | − |
| BB3 | NT | − |
| CC11 | NT | − |
| DF5 | NT | − |
| YB7 | NT | − |
| BE3 | NT | − |
| 4B5 | NT | − |
| 2B9 | NT | + |
| 2F5 | NT | + |
| 3B8 | NT | + |
| 4C8 | NT | + |
| AC9 | NT | + |
| CD6 | NT | + |
| CE6 | NT | + |
| DD10 | NT | + |
| YB8 | NT | + |
| YF5 | NT | + |
| 1E3 | NT | ++ |
| 2D2 | NT | ++ |
| 2D6 | NT | ++ |
| 3D8 | NT | ++ |
| 5C10 | NT | ++ |
| 5F3 | NT | ++ |
| BF8 | NT | ++ |
| BB10 | NT | ++ |
| CG8 | NT | ++ |
| CG10 | NT | ++ |
| DE7 | NT | ++ |
| 1E11 | NT | +++ |
| AF4 | NT | +++ |
| DC4 | NT | +++ |

NT: Not Tested
−: no uptake;
+: minimal uptake;
++: moderate uptake;
+++: good uptake 2. Full Dose Response Screening of Candidate Cell Lines.

Established cell lines identified above, were subsequently evaluated using a full dose response of the appropriate re-targeted endopeptidase. Cells from the different cell lines were plated in 96-well plates and exposed to various concentrations of Noc/A (0, 0.14 nM, 0.4 nM, 1.23 nM, 3.7 nM, 11.1 nM, 33.3 nM, and 100 nM) or of Dyn/A (0.017 nM, 0.05 nM, 0.15 nM, 0.45 nM, 1.4 nM, 4.1 nM, 12 nM, 37 nM, 111 nM, 333 nM, and 1000 nM) for 24 hours. Retargeted endopeptidase-containing medium was then removed and replaced with fresh complete medium. Plates were incubated another 24 hours under 5% $CO_2$ at 37° C. to allow for the cleavage of SNAP-25. Cells were lysed in the lysis buffer (Table 5) and plates centrifuged to eliminate debris. The lysates were used either in a Western blot assay or in a sandwich ELISA.

For the Western blot analysis, samples were assayed for the presence of both the intact SNAP-25 and the SNAP-25 cleavage product as described in Example I.

For the sandwich ELISA, ELISA plates coated with 2E2A6 monoclonal antibody were blocked with 150 μL Blocking Buffer at room temperature for 2 hours. After blocking buffer was removed, 25 μL of cell lysate was added to each well and the plates were incubated at 4° C. for 2 hours. Plates were washed three times with PBS-T and 25 μL of SULFO-TAG NHS-Ester labeled detection anti-SNAP25 pAb antibody at 5 μg/mL in 2% blocking reagent in PBS-T was added to the bottom corner of wells. The plates were sealed and shaken at room temperature for 1 hour, followed by three washes with PBS-T. After washes were completed, 150 μL of 1× Read Buffer per well was added and the plate was read in the SI6000 Image reader. To determine the sensitivity of each one of the cell lines tested, and $EC_{50}$ value was calculated for each cell line. The values for the Noc/A retargeted endopeptidase are summarized in Table 5. Full dose response of retargeted endopeptidase Dyn/A were only performed in PC12 and clone AF4. In both cases the assay did not reach an upper asymptote and an $EC_{50}$ could not be calculated. The lower dose that produced a signal for the AF4 clone was 12 nM for both cell lines.

TABLE 5

Full-Dose Screening of Candidate Cell Lines Using Retargeted Noc/A and Dyn/A

| Cell Line | Description | Source | $EC_{50}$ Noc/A Uptake | $EC_{50}$ Dyn/A Uptake |
|---|---|---|---|---|
| AGN P33 | Human neuroblastoma | — | 5-10 nM | NT |
| BE(2)-C | Human neuroblastoma | ATCC CRL-2268 | NT | NT |
| N18TG2 | Mouse neuroblastoma | DSMZ ACC 103 | NT | NT |
| N18 | Mouse Neuroblastoma | ECACC 88112301 | >100 nM | NT |
| ND3 | Mouse neuroblastoma/primary neonatal rat DRG hybrid | ECACC 92090901 | NDA | NT |
| ND7/23 | Mouse neuroblastoma/primary rat DRG hybrid | ECACC 92090903 | >100 nM | NT |
| ND8 | Mouse neuroblastoma/primary neonatal rat DRG hybrid | ECACC 92090904 | NDA | NT |
| ND15 | Mouse neuroblastoma/primary neonatal rat DRG hybrid | ECACC 92090907 | >100 nM | NT |
| Neuro-2a | Mouse neuroblastoma | ATCC CCL-131 | 30 nM | NT |
| NG108-15 | Mouse neuroblastoma/rat glioma hybrid | ECACC 88112302 | NT | NT |
| PC12 | Rat pheochromocytoma | ATCC CRL-1721 | NT | >1000 nM |
| SH-SY5Y | Human neuroblastoma | ATCC CRL-2266 | NT | NT |
| SiMa | Human neuroblastoma | DSMZ ACC 164 | 30 nM | NT |
| SiMa clone AF4 | Human neuroblastoma | — | NT | >300 nM |
| SiMa clone H1 | Human neuroblastoma | — | >100 nM | NT |
| SiMa clone H10 | Human neuroblastoma | — | 20 nM | NT |
| SK-N-BE(2)-C | Human neuroblastoma | ATCC CRL-2271 | NT | NT |
| SK-N-DZ | Human neuroblastoma | ATCC CRL-2149 | 0.5-2 nM | NT |
| SK-N-F1 | Human neuroblastoma | ATCC CRL-2142 | >100 nM | NT |
| SK-N-SH | Human neuroblastoma | ECACC 86012802 | >100 nM | NT |

NT: Not tested.

NDA: No detectable amount of SNAP-25 was deteced in this cell line.

Using a similar approach, clonal cell lines comprising cells having cognate receptors for other re-targeted endopeptidases can be screened and assessed for retargeted endopeptidase uptake.

Example III

Evaluation of Growth Conditions on Retargeted Endopeptidase Uptake in Candidate Cell Lines The following example illustrates how to determine culture conditions, growth and differentiation, for established cell lines that maximize re-targeted endopeptidase uptake.

1. Effects of Cell Differentiation and Trophic Factors on Re-Targeted Endopeptidase Uptake of Candidate Cell Lines.

To determine whether cell differentiation or the present of trophic factors in the growth media improved re-targeted endopeptidase uptake, cell lines exhibiting good uptake of Noc/A were tested with different media compositions. A suitable density of cells from a stock culture of the SiMa P>30 cell line being tested was plated into the wells of 96-well tissue culture plates containing 100 μL of a serum-free medium containing RPMI1640, 1% Penicillin-Streptomycin, 2 mM L-Glutamine, supplemented with B27, and N2, or 100 μL of a serum-free medium containing RPMI1640, 1% Penicillin-Streptomycin, 2 mM L-Glutamine, supplemented with B27, N2, and NGF (Nerve Growth Factor, 100 ng/mL). These cells were incubated in a 37° C. incubator under 5% carbon dioxide until the cells differentiated, as assessed by standard and routine morphological criteria, such as growth arrest and neurite extension (approximately 1 to 2 days). As a control, a suitable density of cells from a stock culture of the cell line being tested was plated into the wells of 96-well tissue culture plates containing 100 μL of an appropriate growth medium (Table 1) without or with NGF (100 ng/mL). These undifferentiated control cells were grown in a 37° C. incubator under 5% carbon dioxide until cells reach the desired density (approximately 18 to 24 hours). The media from both differentiated and undifferentiated control cultures was aspirated from each well and replaced with fresh media containing either 0 (untreated sample) or to various concentrations of Noc/A (0.14, 0.4, 1.23, 3.7, 11.1, 33.3, and 100 nM). After a 24 hours treatment, the cells were washed and incubated for 24 hours in retargeted endopeptidase-free media in order to increase the amount of $SNAP25_{197}$ produced. Cells were then washed and harvested for the ECL sandwich ELISA assay as described in Example II.

Effects of trophic factors were also tested on the SK-N-DZ cell line. SK-N-DZ cells were plated on a poly-D-lysine coated 96-well plate at 25,000 cells per well in eight different SM media (Table 6) for 72 hours. Cells were treated in the same eight media with Noc/A at doses of 0, 0.3 nM, 3 nM, and 30 nM. After a 24 hour treatment, the cells were washed and incubated for 24 hours n retargeted endopeptidase-free media in order to increase the amount of $SNAP25_{197}$ cleavage product produced. Cells were then washed and harvested for the Western blot assay as described in Example I.

Differentiation did not have an effect on Noc/A uptake in the SiMa>P30 cell line while it seemed to improve uptake in the SK-N-DZ cell line. The basal media had a significant effect on Noc/A uptake in the SK-N-DZ cell line with RPMI1640 comprising trophic factors N2 and B27 being the best combination. The presence of NGF in the media did not seem to improve uptake in the two cell lines tested.

TABLE 6

Effects of Trophic Factors and Cell Differentiation on Noc/A Uptake of Candidate Cell Lines.

| Undifferentiated | Differentiated | $EC_{50}$ Noc/A Uptake AGN P33 | $EC_{50}$ Noc/A Uptake SK-N-DZ |
|---|---|---|---|
| DMEM, 10% FBS | — | NT | >30 nM |
| DMEM, 10% FBS, N2, B27 | — | NT | 3 nM |
| DMEM, 10% FBS, N2, B27, NGF | — | NT | 3 nM |
| DMEM, 10% FBS, N2, B27, RA | — | NT | >30 nM |
| RPMI1640, 10% FBS | — | NT | 10 nM |

TABLE 6-continued

Effects of Trophic Factors and Cell Differentiation on Noc/A Uptake of Candidate Cell Lines.

| Undifferentiated | Differentiated | $EC_{50}$ Noc/A Uptake AGN P33 | $EC_{50}$ Noc/A Uptake SK-N-DZ |
|---|---|---|---|
| RPMI1640, 10% FBS, N2, B27 | — | 7.2 nM | 1 nM |
| RPMI1640, 10% FBS, N2, B27, NGF | — | 9.1 nM | 1 nM |
| RPMI1640, 10% FBS, N2, B27, RA | — | NT | 10 nM |
| — | RPMI1640, N2, B27 | 10.2 nM | 1 nM |
| — | RPMI1640, N2, B27, NGF | 9.8 nM | 0.6 nM |

NGF: Nerve Growth Factor;
RA: Retinoic Acid
NT: Not tested

Using a similar approach, the growth and differentiation conditions for clonal cell lines comprising cells having cognate receptors for other re-targeted endopeptidases can be assessed.

Example IV

Development of Established Cell Lines Expressing Exogenous Re-Targeted Endopeptidase Receptors The following example illustrates how to make an established cell line expressing an exogenous receptor for a re-targeted endopeptidase.

1. Transfection of Target Receptor into Cells Comprising a Candidate Cell Line.

The re-targeted endopeptidase Noc/A comprises the nociceptin targeting domain which is the natural ligand of Opioid Receptor Like-1 (ORL-1). To obtain an expression construct comprising an open reading frame for an ORL-1, the expression contract pReceiver-MO2/ORL-1 was obtained from GeneCopoeia (GeneCopoeia, Germantown, Md.).

Alternatively, a polynucleotide molecule based on an ORL-1 amino acid sequence (e.g., the amino acid sequences SEQ ID NO:25 or SEQ ID NO:26) can be synthesized using standard procedures (BlueHeron® Biotechnology, Bothell, Wash.). Oligonucleotides of 20 to 50 bases in length are synthesized using standard phosphoramidite synthesis. These oligonucleotides will be hybridized into double stranded duplexes that are ligated together to assemble the full-length polynucleotide molecule. This polynucleotide molecule will be cloned using standard molecular biology methods into a pUCBHB1 vector at the SmaI site to generate pUCBHB1/ORL-1. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If desired, an expression optimized polynucleotide molecule based on an ORL-1 amino acid sequence (e.g., the amino acid sequences SEQ ID NO:25 or SEQ ID NO:26) can be synthesized in order to improve expression in an *Escherichia coli* strain. The polynucleotide molecule encoding the ORL-1 can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al., *Optimizing Expression of Active Botulinum Toxin Type A*, U.S. Patent Publication 2008/0057575 (Mar. 6, 2008); and Lance E. Steward et al., *Optimizing Expression of Active Botulinum Toxin Type E*, U.S. Patent Publication 2008/0138893 (Jun. 12, 2008). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/ORL-1. The synthesized polynucleotide molecule is verified by DNA sequencing. If so desired, expression optimization to a different organism, such as, e.g., a yeast strain, an insect cell-line or a mammalian cell line, can be done, see, e.g., Steward, U.S. Patent Publication 2008/0057575, supra, (2008); and Steward, U.S. Patent Publication 2008/0138893, supra, (2008). Exemplary polynucleotide molecules encoding an ORL-1 include SEQ ID NO:61 and SEQ ID NO:62.

To construct an expression construct encoding an ORL-1, a pUCBHB1/ORL-1 construct will be digested with restriction endonucleases that 1) excised the polynucleotide molecule encoding the open reading frame of ORL-1; and 2) enabled this polynucleotide molecule to be operably-linked to a pcDNA3 vector (Invitrogen, Inc., Carlsbad, Calif.). This insert will be subcloned using a T4 DNA ligase procedure into a pcDNA3 vector that will be digested with appropriate restriction endonucleases to yield pcDNA3/ORL-1. The ligation mixture will be transformed into electro-competent *E. coli* BL21(DE3) cells (Edge Biosystems, Gaithersburg, Md.) using an electroporation method, and the cells will be plated on 1.5% Luria-Bertani agar plates (pH 7.0) containing 50 μg/mL of ampicillin, and will be placed in a 37° C. incubator for overnight growth. Bacteria containing expression constructs will be identified as ampicillin resistant colonies. Candidate constructs will be isolated using an alkaline lysis plasmid mini-preparation procedure and will be analyzed by restriction endonuclease digest mapping to determine the presence and orientation of the insert. This cloning strategy will yielded a pcDNA3 expression construct comprising the polynucleotide molecule encoding an ORL-1.

The re-targeted endopeptidase Dyn/A comprises the dynorphin targeting domain which is the natural ligand of κ-opioid receptor (KOR). To obtain an expression construct comprising an open reading frame for an ORL-1, the expression contract pReceiver-MO2/KOR-1 was obtained from GeneCopoeia (GeneCopoeia, Germantown, Md.). Alternatively, expression constructs encoding the KOR can be synthesized and subcloned using an approach similar to the one described above to produce the expression construct pcDNA3.1/KOR. Exemplary KOR amino acid sequences include SEQ ID NO:29 and SEQ ID NO:30; exemplary polynucleotide molecules encoding a KOR include SEQ ID NO:65 and SEQ ID NO:66.

Similar cloning strategies can be used to make expression constructs encoding other re-target endopeptidase receptors, such as, e.g., pcDNA3.1/DOR or pcDNA3.1/MOR, pcDNA3.1/Galanin receptor 1, pcDNA3.1/Galanin receptor 2, or pcDNA3.1/Galanin receptor 3. Exemplary DOR amino acid sequences include SEQ ID NO:27 and SEQ ID NO:28; exemplary MOR amino acid sequences include SEQ ID NO:31 exemplary Galanin receptor 1 amino acid sequences include SEQ ID NO:136, SEQ ID NO:137, and SEQ ID NO:138; exemplary Galanin receptor 2 amino acid sequences include SEQ ID NO:139; and exemplary Galanin receptor 3 amino acid sequences include SEQ ID NO:140. Exemplary polynucleotide molecules encoding a DOR include SEQ ID NO:63 and SEQ ID NO:64; exemplary polynucleotide molecules encoding a MOR include SEQ ID NO:67; exemplary polynucleotide molecules encoding a Galanin receptor 1 include SEQ ID NO:141, SEQ ID NO:142, and SEQ ID NO:143; exemplary polynucleotide molecules encoding a Galanin receptor 2 include SEQ ID NO:144; and exemplary polynucleotide molecules encoding a Galanin receptor 3 include SEQ ID NO:145.

To introduce an expression construct encoding a re-targeted endopeptidase receptor, cell lines were transfected with an expression construct encoding a re-targeted endopeptidase receptor. To transfect a cell line with an opioid or opioid-like receptor, cells from a candidate cell line were seeded at a density of $1\times10^7$ cells in a $T_{175}$ Collagen IV coated flask and grown in a 37° C. incubator under 5% carbon dioxide until cells reach the desired density. A 4.2 mL transfection solution is prepared by adding 4 mL of OPTI-MEM Reduced Serum Medium containing 200 μL of LipofectAmine 2000 (Invitrogen, Carlsbad, Calif.) incubated at room temperature for 5 minutes to 4 mL of OPTI-MEM Reduced Serum Medium containing 20 μg of a pReceiver-MO2/ORL-1 or 20 μg of pReceiver-MO2/KOR-1. This transfection was incubated at room temperature for approximately 20 minutes. The media was replaced with 8 mL of fresh serum-free and antibiotic-free media and the transfection solution was added to the cells. The cells were then incubated in a 37° C. incubator under 5% carbon dioxide for approximately 16-18 hours. Transfection media was replaced with fresh growth media and incubate cells in a 37° C. incubator under 5% carbon dioxide. After 24 hours, the growth media were replaced with fresh growth media containing the antibiotic G418 at 1 mg/mL in the culture medium (selection medium) and cells were incubated for 7 days. The selection medium was changed every week for a total of 4 weeks (about 90% cells died and were removed during the weekly media changes).

Candidate cell lines transfected with the ORL-1 receptor included SiMa>P30, ND15, ND7, NG108-T15 and SK-N-DZ cell lines. Candidate cell lines transfected with the KOR-1 receptor included SiMa, SiMa>P30, ND15, ND7, NG108-T15 and SK-N-DZ cell lines. Transfected NG108-T15 cells did not survive selection in G418.

2. Single Dose and Dose Response Screening of Stable Transfected Cell Lines Using Re-Targeted Endopeptidase Molecules.

Cells from the transfected and selected candidate cell lines from the previous section were plated on 96-well poly-D-lysine or Collagen IV coated plates at $1\times10^5$ cells/well in medium RPMI1640 containing N2 and B27 supplements, and NGF (50-100 ng/ml) for 20±4 hours before compound treatment. Then the cells stably transfected with the ORL-1 receptor were treated with re-targeted endopeptidase Noc/A at 30 nM in the same medium for 24±2 hours, except for the SK-N-DZ cell line that was treated at 10 nM. Cells were lysed in 120 μL lysis buffer, and 20 μL of the lysate was mixed with the 2×SDS buffer for the Western Blot assay that was performed as detailed in Example I. All of the cells lines displayed increase uptake of the re-targeted Noc/A compound when transfected with the ORL-1 receptor (Table 7).

TABLE 7

Cell lines stably transfected with ORL-1 tested with re-targeted endopeptidase Noc/A

| Cell line | Description | % Cleaved SNAP25 at 30 nM Non-transfected | Transfected |
|---|---|---|---|
| AGN P33 | Human Neuroblastoma | 20% | 40% |
| SK-N-DZ | Human Neuroblastoma | 25% @ 10 nM | 40% @ 10 nM |
| ND7 | Mouse Neuroblastoma and rat DRG cells hybrid | 10% | 42% |
| ND15 | Mouse Neuroblastoma and rat DRG cells hybrid | 8% | 20% |
| NG108-T15 | Mouse neuroblastoma/rat glioma hybrid | No cells survive | No cells survive |

Cells from the transfected and selected candidate cell lines from the previous section were plated on 96-well poly-D-lysine or Collagen IV coated plates at $1\times10^5$ cells/well in medium RPMI1640 containing 10% FBS and N2 and B27 supplements for 20±4 hours before compound treatment. The cells stably transfected with the KOR-1 receptor were treated with re-targeted endopeptidase Dyn/A at 100 nM in the same medium for 24±2 hours. Cells were lysed in 120 μL lysis buffer, and 20 μL of the lysate was mixed with the 2×SDS buffer for the Western Blot assay that was performed as detailed in Example I. All of the cells lines displayed increase uptake of the re-targeted Dyn/A compound when transfected with the human KOR-1 receptor.

3. Selection of Stably Transfected Clonal Cell Lines Exhibiting High Sensitivity by Serial Dilution The following example illustrates how to identify clonal cells from a stably transfected established cell line that are susceptible to re-targeted endopeptidase action or have re-targeted endopeptidase uptake capacity.

For single cell cloning of the selected cells described above, the limited-dilution cell line cloning method was employed. Cells were trypsinized, counted, diluted to achieve 0.5-1 cell per 100 μL, and plated on selection media in five poly-D-lysine coated 96-well plates at 100 μL per well. Cells were incubated for more than 2 weeks until colonies formed on the bottom of the well. The positive colonies originating from single cells were marked. Pictures of single-cell derived clones were taken using a microscope camera. Cells from wells with single clones were grown for an additional week and transferred into 24 well plates about 4 weeks after cloning started.

For clone selection, the main parameter used to screen for positive clones was the highest amount of SNAP-25 cleavage obtained after Noc/A or Dyn/A treatment measured using the Western Blot analysis with the antibody that recognizes both intact and cleaved SNAP-25. Clones overexpressing ORL-1 were tested with 10 nM and 30 nM re-targeted endopeptidase Noc/A overnight as soon as enough cells became available (Table 8). Clones overexpressing KOR-1 were tested with 100 nM re-targeted endopeptidase Dyn/A overnight (Table 9). In addition, clones overexpressing KOR-1 were tested on the Dynorphin binding assay as described in Example I.

TABLE 8

Single-Dose Screening of Candidate Clonal Cell Lines Stably transfected with ORL-1 Using re-targeted endopeptidase Noc/A

| Cell Line | Clone number | 10 nM Noc/A Uptake | 30 nM Noc/A Uptake | Second screening @ 1 nM (% cleaved) |
|---|---|---|---|---|
| AGN P33 | 1 | + | + | 28% |
| AGN P33 | 2 | ++ | +++ | 50% |
| AGN P33 | 3 | – | + | NT |
| AGN P33 | 4 | ND | ND | NT |
| AGN P33 | 5 | – | + | 31% |
| AGN P33 | 6 | ++ | +++ | 60% |
| AGN P33 | 7 | + | + | 14% |
| AGN P33 | 8 | + | + | NT |
| AGN P33 | 9 | + | + | 38% |
| AGN P33 | 10 | + | ++ | 29% |
| AGN P33 | 11 | + | + | NT |
| AGN P33 | 12 | + | + | 27% |
| ND7 | 1C11 | NT | ++ | NT |
| ND7 | 2F3 | NT | – | NT |
| ND7 | 1D10 | NT | – | NT |
| ND7 | 1F9 | NT | – | NT |
| ND7 | 1G10 | NT | – | NT |
| ND7 | 2D8 | NT | – | NT |
| ND7 | 2E2 | NT | – | NT |
| ND7 | 4B7 | NT | +++ | NT |
| ND7 | 3C11 | NT | – | NT |
| ND7 | 3C3 | NT | + | NT |
| ND7 | 3E8 | NT | – | NT |
| ND7 | 3E11 | NT | – | NT |
| ND7 | 2G3 | NT | – | NT |
| ND7 | 4D5 | NT | + | NT |
| ND7 | 4D8 | NT | + | NT |
| ND7 | 4C8 | NT | – | NT |
| ND7 | 4C9 | NT | +++ | NT |
| ND7 | 4E8 | NT | + | NT |
| ND7 | 2E6 | NT | ++ | NT |
| ND7 | 4F4 | NT | +++ | NT |
| ND7 | 5D6 | NT | – | NT |
| ND7 | 5G3 | NT | – | NT |
| ND7 | 4D5 | NT | ++ | NT |
| ND15 | 1C10 | NT | + | NT |
| ND15 | 1F10 | NT | ++ | NT |
| ND15 | 2D8 | NT | ++ | NT |
| ND15 | 2E11 | NT | – | NT |
| ND15 | 2F4 | NT | ++ | NT |
| ND15 | 2F10 | NT | ++ | NT |
| ND15 | 2F11 | NT | – | NT |
| ND15 | 3C4 | NT | + | NT |
| ND15 | 3C7 | NT | ++ | NT |
| ND15 | 3E8 | NT | +++ | NT |
| ND15 | 4C8 | NT | + | NT |
| ND15 | 4D8 | NT | + | NT |
| SK-N-DZ | #2 | – | – | NT |
| SK-N-DZ | #4 | – | – | NT |
| SK-N-DZ | #5 | +++ | ++ | NT |
| SK-N-DZ | #6 | NT | ++ | NT |
| SK-N-DZ | #7 | + | NT | NT |
| SK-N-DZ | #8 | – | NT | NT |
| SK-N-DZ | #9 | + | NT | NT |
| SK-N-DZ | #10 | – | NT | NT |
| SK-N-DZ | #11 | + | +++ | NT |
| SK-N-DZ | #12 | – | NT | NT |
| SK-N-DZ | #14 | ++ | NT | NT |
| SK-N-DZ | #16 | – | NT | NT |
| SK-N-DZ | #17 | + | +++ | NT |
| SK-N-DZ | #19 | + | +++ | NT |
| SK-N-DZ | #20 | – | NT | NT |
| SK-N-DZ | #23 | NT | ++ | NT |
| SK-N-DZ | #25 | – | NT | NT |
| SK-N-DZ | #26 | – | ++ | NT |
| SK-N-DZ | #27 | + | NT | NT |
| SK-N-DZ | #28 | ++ | + | NT |
| SK-N-DZ | #30 | ++ | NT | NT |
| SK-N-DZ | #31 | – | NT | NT |
| SK-N-DZ | #32 | ++ | ++ | NT |
| SK-N-DZ | #33 | + | NT | NT |
| SK-N-DZ | #34 | +++ | ND | NT |

TABLE 8-continued

Single-Dose Screening of Candidate Clonal Cell Lines Stably transfected with ORL-1 Using re-targeted endopeptidase Noc/A

| Cell Line | Clone number | 10 nM Noc/A Uptake | 30 nM Noc/A Uptake | Second screening @ 1 nM (% cleaved) |
|---|---|---|---|---|
| SK-N-DZ | #35 | + | ++ | NT |
| SK-N-DZ | #36 | − | NT | NT |
| SK-N-DZ | #37 | +++ | ++ | NT |
| SK-N-DZ | #42 | − | NT | NT |
| SK-N-DZ | #43 | + | ++ | NT |

ND: Not Determined;
NT: Not Tested.
−: no uptake;
+: minimal uptake;
++: moderate uptake;
+++: good uptake

TABLE 9

Single-Dose Screening of Candidate Clonal Cell Lines Stably transfected with KOR-1 Using re-targeted endopeptidase Dyn/A

| Cell Line | Clone number | 100 nM Dyn/A Uptake | 100 nM Dyn binding | Selected future testing |
|---|---|---|---|---|
| SiMa | 2 | − | − | No |
| SiMa | 6 | + | + | No |
| SiMa | 8 | + | + | No |
| SiMa | 12 | +++ | ++ | Yes |
| SiMa | 14 | ++ | ++ | No |
| SiMa | 20 | + | ++ | No |
| SiMa | 25 | ++ | ++ | No |
| AGN P33 | 1 | +++ | + | Yes |
| AGN P33 | 3 | ++ | + | No |
| AGN P33 | 5 | ++ | + | Yes |
| AGN P33 | 6 | ++ | + | No |
| AGN P33 | 7 | +++ | + | Yes |
| AGN P33 | 8 | ++ | + | Yes |
| AGN P33 | 9 | +++ | + | Yes |
| AGN P33 | 10 | +++ | + | Yes |
| AGN P33 | 11 | ++ | + | No |
| AGN P33 | 12 | +++ | + | Yes |
| AGN P33 | 14 | + | + | No |
| AGN P33 | 16 | ++ | + | No |
| AGN P33 | 17 | +++ | + | Yes |
| AGN P33 | 21 | + | ++ | No |
| ND7 | A1 | + | + | No |
| ND7 | A2 | − | − | No |
| ND7 | A3 | − | − | No |
| ND7 | A4 | − | − | No |
| ND7 | A5 | − | − | No |
| ND7 | A6 | − | − | No |
| ND7 | A7 | − | − | No |
| ND7 | A8 | − | − | No |
| ND7 | A9 | − | − | No |
| ND7 | A10 | − | − | No |
| ND7 | A11 | − | − | No |
| ND7 | A12 | +++ | +++ | Yes |
| ND7 | B1 | − | − | No |
| ND7 | B2 | − | − | No |
| ND7 | B3 | − | − | No |
| ND7 | B4 | − | − | No |
| ND7 | B5 | + | + | Yes |
| ND7 | B6 | − | − | No |
| ND7 | B7 | − | − | No |
| ND7 | B8 | − | − | No |
| ND7 | B9 | − | − | No |
| ND7 | B10 | − | − | No |
| ND7 | B11 | − | − | No |
| ND7 | B12 | − | − | No |
| ND7 | C1 | − | − | No |
| ND7 | C2 | − | − | No |
| ND7 | C3 | − | − | No |
| ND7 | C4 | − | − | No |

TABLE 9-continued

Single-Dose Screening of Candidate Clonal Cell Lines Stably transfected with KOR-1 Using re-targeted endopeptidase Dyn/A

| Cell Line | Clone number | 100 nM Dyn/A Uptake | 100 nM Dyn binding | Selected future testing |
|---|---|---|---|---|
| ND7 | C5 | − | − | No |
| ND7 | C6 | + | + | No |
| ND7 | C7 | − | − | No |
| ND7 | C8 | − | − | No |
| ND7 | C9 | − | − | No |
| ND7 | C10 | − | − | No |
| ND7 | C11 | − | − | No |
| ND7 | C12 | − | − | No |
| ND7 | D1 | − | − | No |
| ND7 | D2 | − | − | No |
| ND7 | D3 | − | − | No |
| ND7 | D4 | − | − | No |
| ND7 | D5 | − | − | No |
| ND7 | D6 | ++ | ++ | Yes |
| ND7 | D7 | ++ | ++ | Yes |
| ND7 | D8 | − | − | No |
| ND7 | D9 | − | − | No |
| ND7 | D10 | − | − | No |
| ND7 | D11 | − | − | No |
| ND7 | D12 | − | − | No |
| ND7 | E1 | − | − | No |
| ND7 | E2 | − | − | No |
| ND7 | E3 | − | − | No |
| ND7 | E4 | − | − | No |
| ND7 | E5 | − | − | No |
| ND7 | E6 | − | − | No |
| ND7 | E7 | − | − | No |
| ND7 | E8 | − | − | No |
| ND7 | E9 | − | − | No |
| ND7 | E10 | − | − | No |
| ND7 | E11 | − | − | No |
| ND7 | E12 | ++ | ++ | Yes |
| ND7 | F1 | − | − | No |
| ND7 | F2 | − | − | No |
| ND7 | F3 | − | − | No |
| ND7 | F4 | − | − | No |
| ND15 | A1 | − | − | No |
| ND15 | A2 | − | − | No |
| ND15 | A3 | + | − | No |
| ND15 | A4 | + | − | No |
| ND15 | A5 | − | − | No |
| ND15 | A6 | ++ | − | No |
| ND15 | A7 | ++ | − | No |
| ND15 | A8 | ++ | − | No |
| ND15 | A9 | + | − | No |
| ND15 | A10 | + | − | No |
| ND15 | A11 | − | − | No |
| ND15 | A12 | − | − | No |
| ND15 | B1 | − | − | No |
| ND15 | B2 | ++ | − | No |
| ND15 | B3 | − | − | No |
| ND15 | B4 | − | − | No |
| ND15 | B5 | +++ | − | Yes |
| ND15 | B6 | + | − | No |
| ND15 | B7 | − | − | No |
| ND15 | B8 | − | − | No |
| ND15 | B9 | − | − | No |
| ND15 | B10 | − | − | No |
| ND15 | B11 | − | − | No |
| ND15 | B12 | − | − | No |
| ND15 | C1 | − | − | No |
| ND15 | C2 | +++ | + | Yes |
| ND15 | C3 | − | − | No |
| ND15 | C4 | − | − | No |
| ND15 | C5 | + | NT | No |
| ND15 | C6 | +++ | NT | Yes |
| SK-N-DZ | #11 | NT | NT | ND |

ND: Not Determined;
NT: Not Tested.
−: no uptake;
+: minimal uptake;
++: moderate uptake;
+++: good uptake 4. Dose Response Screening of Stably Transfected Clonal Cell Lines Using Re-Targeted Endopeptidase.

Candidate stably transfected clonal cell lines from section 3 showing good uptake of the re-targeted endopeptidase Noc/A were tested in full dose response experiments to determine sensitivity and efficacy towards the re-targeted endopeptidase Noc/A. Cells were plated on 96-well poly-D-lysine or Collagen IV coated plates at $1\times10^5$ cells/well in medium RPMI1640 containing N2 and B27 supplements, and NGF (50-100 ng/mL) for 20±4 hours before compound treatment. Cells from the parental AGN P33 cell line and the ND7 clonal cell lines were treated with 0, 0.14 nM, 0.4 nM, 1.23 nM, 3.7 nM, 11.1 nM, 33.3 nM, and 100 nM of Noc/A in the same medium for 24 hours plus 24 hours incubation in re-targeted endopeptidase free media to allow for cleavage of SNAP-25. Cells from the parental AGN P33 cell line were also treated with 0, 0.03 nM, 0.08 nM, 0.24 nM, 0.74 nM, 2.22 nM, 6.67 nM, and 20 nM of Noc/A in the same medium for 24 hours plus 24 hours incubation in re-targeted endopeptidase free media to allow for cleavage of SNAP-25. Media was removed and cells washed and lysed for the ECL sandwich ELISA assay as detailed in Example II. The data from the AGN P33 parental and the clonal cell lines stably transfected with the ORL-1 receptor is summarized in Table 10. Clones #2 and #6 demonstrated better sensitivity and efficacy towards the re-targeted endopeptidase Noc/A than the parental cell line. Moreover, the increased sensitivity of the new clonal cell lines allowed the use of lower concentrations for the dose-response confirming the new clonal cell lines are more sensitive.

TABLE 10

Summary table of signal-to-noise ratios (S/N) and $EC_{50}$ values of the three most sensitive clones overexpressing ORL-1 in the AGN P33 background cell line.

| | Parental | Clone 2 | Clone 6 | Clone 8 |
|---|---|---|---|---|
| S/N Ratio 0.03 nM/BK | | 41 | 26 | 1.8 |
| S/N Ratio 20 nM/BK | | 259 | 522 | 33.1 |
| S/N Ratio 0.14 nM/BK | | | | |
| S/N Ratio 100 nM/BK | | | | |
| $EC_{50}$ (nM) | 6.8 ± 1.1 | 0.6 ± 0.1 | 0.7 ± 0.07 | 0.3 ± 0.2 |

The data from the ND7 parental and the clonal cell lines stably transfected with the ORL-1 receptor is summarized in Table 11. All the clones tested demonstrated improved sensitivity and efficacy towards the re-targeted endopeptidase Noc/A than the parental cell line ND7. Clones 4B7, 1E6, and 1C11 were the most sensitive with $EC_{50}$ values lower than 10 μM.

TABLE 11

Summary table of signal-to-noise ratios (S/N) and $EC_{50}$ values of the six most sensitive clones overexpressing ORL-1 in the ND7 background cell line.

| | Parental | 1C11 | 4B7 | 4C9 | 4F4 | 1E6 | 3E9 |
|---|---|---|---|---|---|---|---|
| S/N Ratio 0.14 nM/BK | 1.7 | 9.3 | 11.1 | 5.3 | 3.6 | 5.8 | 5.1 |
| S/N Ratio 100 nM/BK | 53 | 217 | 243 | 126 | 169 | 123 | 121 |
| $EC_{50}$ (nM) | >50 | 8.6 ± 2 | 5.7 ± 0.5 | 33 ± 11 | 24 ± 5 | 6.7 ± 1 | >30 nM |

Table 12 summarizes the results obtained with the generation and testing of clonal cell lines overexpressing the ORL-1 receptor in different cell backgrounds.

TABLE 12

Summary of clonal cell lines overexpressing the Human ORL-1 receptor tested with Noc/A

| Background Cell Line | Species | Stable cell lines tested with full dose of Noc/A | $EC_{50}$ (nM) |
|---|---|---|---|
| AGN P33 | Human neuroblastoma | Three | 0.6-2.5 |
| ND7 | Rat neuroblastoma and DRG hybrid | Six | 3.7-8 |
| SK-N-DZ | Human neuroblastoma | None (seven stable clones selected for further studies) | N/A |

Example V

Development of Clonal Cell Lines from a Parental SK-N-DZ Cell Line

The following example illustrates how to identify clonal cells from a parental established cell line that are susceptible to re-targeted endopeptidase inhibition of exocytosis or have re-targeted endopeptidase uptake capacity.

1. Isolation of Clonal Cell Lines.

During characterization of the SK-N-DZ cell line, it was discovered that the cells comprising this established cell line comprised at least five different cellular phenotypes. To determine whether any one of these phenotypically-distinct cell types was responsible for the susceptibility of this cell line to re-targeted endopeptidase inhibition of exocytosis, two different limited-dilution screens were conducted to obtain single colony isolates for each phenotypically-distinct cell type.

A suitable density of cells from a SK-N-DZ stock were grown in DMEM, 10% Fetal Bovine Serum (heat-inactivated), 0.1 mM Non-Essential Amino-Acids, 10 mM HEPES, 1 mM Sodium Pyruvate, 100 U/ml Penicillin, 100 μg/ml Streptomycin, contained in a T175 Collagen IV coated flask. After the second passage, the cells were trypsin-treated to produce a cell suspension and the cell concentration was determined. About $4.0\times10^6$ cells from this cell suspension was transferred into a 50 mL tube and the cells were dissociated into single cells by repeated vigorous expulsion through an 18.5 gauge needle using a 10 mL syringe. Cells from this disassociated single-cell suspension were then diluted to a concentration of $0.2\times10^6$ cells/mL by adding 15 mL of fresh growth medium, and 2.5 μL of this dilution was added to 50 mL of fresh growth medium to obtain a concentration of 10 cells/mL. From this final dilution stock, 100 μL of growth medium was added to each well of a 96-well Collagen IV coated plates and the cells were grown undisturbed in a 37° C. incubator under 5% carbon dioxide for four weeks. Four 96-well plates were setup for analysis. After four weeks, each well was microscopically examined to identify growing single colonies, and for each colony identified 100 μL of fresh growth medium was added to each well and the cells were grown undisturbed in a 37° C. incubator under 5% carbon dioxide for two weeks. After two additional weeks of growth, the growing single colonies were trypsin-treated and transferred to a new 96-well plate for continued growth. Once colonies grew to about 1,000 cells, based on visual inspection, the cells were trypsin-treated and each cell-suspension was transferred into a new well from a 24-well Collagen IV-coated plate. The cells were grown in a 37° C. incubator under 5% carbon dioxide with fresh growth medium being replenished every 2-3 days, if needed. The cells were grown until the culture reached approximately 60% confluence or greater, at which point the cells were trypsin-treated and each cell-suspension was transferred into a 25 $cm^2$ Collagen IV-coated flask, based on the confluence of the cells in the 24-well plate. The cells were grown in a 37° C. incubator under 5% carbon dioxide with fresh growth medium being replenished every 2-3 days, if needed. Once the cells in the flask reached 70-80% confluence, they were frozen and stored in liquid nitrogen until the clonal cell lines were tested to determine their susceptibility to Noc/A inhibition of exocytosis. Of the 384 colony isolates initially setup from both screens, 24 clonal cell lines were selected based on viability and growth criteria and expanded for subsequent screening procedures. Of those, 12 fast growing cell lines were identified.

2. Primary Screen for Re-Targeted Endopeptidase Activity Susceptibility of Cells from a Clonal Cell Line Using a Re-Targeted Endopeptidase.

To determine whether cells from a clonal cell line were susceptible to re-targeted endopeptidase Noc/A activity, a primary screen was conducted using an immuno-based method for determining endopeptidase activity.

Thirteen SK-N-DZ clones (#3, #4, #5, #8, #9, #10, #13, #15, #16, #17, #18, #22, and #23) plus SK-N-DZ parental cells were plated on a 96-well plate (unknown cell number per well) in EMEM, 10% FBS, 1×B27, and 1×N2 and incubated overnight. Cells were treated with 1 nM Noc/A for 24 hours. Cells were lysed with 100 μL of lysis buffer for 20 minutes and centrifuged at 4000 rpm for 20 minutes. Fifty microliters of 2×SDS Sample buffer were added to 50 μL of cell lysate and heated at 95° C. for 5 minutes. Ten microliters of protein sample were loaded per lane on 12% NuPage gels and a Western Blot assay was performed as described in Example I. Evaluation of the total SNAP-25 and the cleaved SNAP-25 demonstrated that clones #3, #8, #15, and #22 were at least as good as parental cells for Noc/A uptake. Full dose response treatment and analysis with the ECL sandwich ELISA assay was conducted after the cells were scale up.

3. Secondary Response Screening of Clonal Cell Lines Using Re-Targeted Endopeptidase Molecule.

To determine whether cells from a clonal cell line were susceptible to re-targeted endopeptidase Noc/A activity, a secondary screen was conducted using an immuno-based method for determining endopeptidase activity.

To further compare these SK-N-DZ cloned cell lines, the ECL sandwich ELISA assay was carried out. Five clones (#3, #9, #15, #16, #22) plus SK-N-DZ parental cells were plated on one 96-well Poly-D-lysine coated plate per cell line at 25,000 cells per well in RPMI 1640, 10% FBS, 1×B27, and 1×N2 media (no NGF) over the weekend. Cells were treated with Noc/A at doses from 0 to 20 nM (0, 0.03, 0.08, 0.24, 0.74, 2.22, 6.67, 20 nM) for 24 hours. The cleaved SNAP-$25_{197}$ was quantified with the ECL ELISA assay as detailed in Example I.

Table 13 shows the $EC_{50}$ values and signal to noise for the five clones and their parental cell line. Three clones named #3, #9, and #15 generated lower $EC_{50}$ values (<1 nM) and clone #16 and #22 generated similar $EC_{50}$ values when compared to the parental cell line (~2 nM). However, the total signals from cleaved SNAP25 were higher in clones #3, #22, and the parental cells. Clones #9, #16, and #15 had lower total signals when compared to the rest of the cell lines.

TABLE 13

Summary table of signal-to-noise ratios (S/N) and $EC_{50}$ values of the five clones obtained from SK-N-DZ cells by limited-dilution cloning.

| | Parental | 3 | 9 | 19 | 16 | 22 |
|---|---|---|---|---|---|---|
| S/N Ratio 0.03 nM/BK | 2 | 3 | 2 | 2 | 2 | 3 |
| S/N Ratio 20 nM/BK | 19 | 27 | 12 | 8 | 14 | 20 |
| $EC_{50}$ (nM) | 2.6 ± 1.5 | 0.8 ± 0.07 | 0.7 ± 0.04 | 0.6 ± 0.1 | 2.2 ± 0.8 | 1.9 ± 0.6 |

Conditions for Noc/A treatment on SK-N-DZ clones were optimized and an assay was run comparing clones #3, #15, and #22, and the parental heterogeneous SK-N-DZ cell line. Table 14 shows the result of the comparison and demonstrated that assay optimization has greatly improved the signal to noise for the assay. Clones #3 and #22 were selected for further assay development as they possess excellent sensitivity and efficacy.

TABLE 14

Summary table of signal-to-noise ratios (S/N) and $EC_{50}$ values of three clones obtained from SK-N-DZ cells using optimized conditions.

| | Parental | 3 | 15 | 22 |
|---|---|---|---|---|
| S/N Ratio 0.03 nM/BK | 15 | 8 | 5 | 10 |
| S/N Ratio 20 nM/BK | 107 | 89 | 33 | 60 |
| $EC_{50}$ (nM) | 0.6 ± 0.2 | 0.9 ± 0.2 | 0.6 ± 0.1 | 0.4 ± 0.09 |

Example VI

Characterization and Comparison of Clonal Cell Lines for Re-Targeted Endopeptidase Uptake The following example illustrates how to characterize and compare clonal cell lines originated either from an established cell line comprising a heterogeneous population or by transfection of the target receptor and subsequent cloning of the cell line.

To evaluate the specificity or selectivity of re-targeted endopeptidase uptake, non-specific uptake assays were performed using of a re-targeted endopeptidase lacking the targeting domain. For opioid re-targeted endopeptidase, cells from the AGN P33 clone #6 cell line (comprising cells stably transformed with an expression construct encoding an ORL-1 receptor) and the SK-N-DZ clonal cell lines #3 and #22 (comprising cells that express endogenous ORL-1 receptor) were seeded at 150,000 cells per well on a 96-well Poly-D-lysine coated plate in RPMI 1640 serum free media containing N2 and B27 supplements, and NGF (50 ng/mL) and incubated for 20±4 hours at 37° C. in a 5% $CO_2$ incubator before compound treatment. Cells were treated with 8-doses of Noc/A ranging from 0-20 nM or 0-40 nM and/or eight doses of $LH_N/A$ ranging from 0 to 400 nM or 0 to 40 nM in the same medium for 22 hours. Media was removed and cells washed, lysed, and centrifuged to eliminate debris in preparation for a sandwich ELISA assay. An ELISA plate coated with 2E2A6 monoclonal antibody was blocked with 150 μL Blocking Buffer at room temperature for 1 hour. After blocking buffer was removed, 30 μL of cell lysate was added to each well and the plate was incubated at 4° C. for 2 hours. Plates were washed three times with PBS-T and 30 μL of SULFO-TAG NHS-Ester labeled detection α-SNAP25 polyclonal antibodies at 5 μg/mL in 2% blocking reagent in PBS-T was added to the bottom corner of wells. The plate was sealed and shaken at room temperature for 1 hour, followed by three washes with PBS-T. After washes were completed, 150 μL of 1× Read Buffer per well was added and the plate was read in the SI6000 Image reader. The results comparing Noc/A uptake relative to the negative control $LH_N$/A are shown in Table 15 and Table 16. These results indicate that there was good separation between Noc/A and $LH_N$/A uptake in both cell lines demonstrating specific uptake of Noc/A.

TABLE 15

Non-specific uptake for SK-N-DZ clone #3. Summary of four independent experiments

| nM | % non-specific uptake | SEM (standard error of the mean) |
|---|---|---|
| 0 | 2 | 0.5 |
| 1 | 6 | 0.5 |
| 2 | 8 | 0.5 |
| 5 | 10 | 1 |
| 15 | 19 | 0.9 |
| 44 | 33 | 1.5 |
| 133 | 65 | 2.4 |
| 400 | 93 | 2.3 |

TABLE 16

Non-specific uptake for hORL-1 #6 cells. Summary of three independent experiments

| nM | % non-specific uptake | SEM (standard error of the mean) |
|---|---|---|
| 0 | 1 | 0.2 |
| 1 | 2 | 0.2 |
| 2 | 3 | 0.6 |
| 5 | 3 | 0.3 |
| 15 | 8 | 1.3 |
| 44 | 12 | 1.9 |
| 133 | 22 | 3.0 |
| 400 | 32 | 3.0 |

Table 17 summarizes the results for the characterization and comparison of the three cell lines. SK-N-DZ clonal cell lines #3 and #22 possess a sensitivity identical to the primary eDRG and an excellent signal-to-noise to develop a robust assay for re-targeted endopeptidase Noc/A. The AGN P33 clonal cell line #6 is also an excellent candidate with low non-specific uptake and adequate sensitivity.

TABLE 17

| Parameter | SK-N-DZ clone 3 | SK-N-DZ clone 22 | AGN P33 clone 6 | eDRG |
|---|---|---|---|---|
| Cell line species | Human Clonal | Human Clonal | Human Clonal | Rat primary |
| Cell Receptor Expression | Human ORL1 endogenous | Human ORL1 endogenous | Human ORL1 transfected | Rat ORL1 endogenous |
| Dynamic Range | 0.03 to 20 nM dose response | 0.03 to 20 nM dose response | 0.04 to 40 nM dose response | 0.17 to 20 nM dose response |
| Sensitivity ($EC_{50}$) | $EC_{50}$ = 0.75 ± 0.1 (N = 10) | $EC_{50}$ = 0.8 ± 0.2 (N = 9) | $EC_{50}$ = 2.4 ± 0.2 (N = 21) | $EC_{50}$ = 0.8 ± 0.15 (N = 6) |
| ULOQ | 20 nM | 20 nM | 20 nM | 10-20 nM |
| S/N ULOQ/ background | 98 ± 15 (N = 10) | 86 ± 17 (N = 9) | 385 ± 32 (N = 19) | ~300 |
| S/N LLOQ/ background | 12 ± 2 (N = 11) | 10 ± 2 (N = 9) | 29 ± 7 (N = 18) | N/A |
| Specificity vs $LH_N$/A | ≥2 logs (N = 4) | ≥2 logs (N = 4) | ≥2 logs (N = 3) | N/A |
| SNAP-25 Expression | Endogenous | Endogenous | Endogenous | Endogenous |
| Competition with Nociceptin Var. | Full competition (n = 4) | Full competition (n = 4) | Partial competition (n = 4) | N/A |
| Inhibition by Ab Anti-nociceptin | Full competition (n = 4) | Full competition (n = 4) | Full competition (n = 4) | N/A |
| Inhibition by Anti-868 Ab | Partial competition (N = 3) | Partial competition (N = 3) | Partial competition (N = 3) | N/A |

To evaluate the sensitivity of re-targeted endopeptidase uptake, ligand saturation binding assays were performed. The interaction of most ligands with their binding sites can be characterized in terms of binding affinity (NIH Assay Guidance). In general, high affinity binding involves a longer residence time for the ligand at its receptor binding site than in the case of low affinity binding. The dissociation constant is commonly used to describe the affinity between a ligand (L) (such as a drug) and a protein (P) i.e. how tightly a ligand binds to a particular protein. An equilibrium saturation binding experiment measures total and nonspecific binding (NSB) at various radioligand concentrations. The equilibrium dissociation constant or affinity for the radioligand, $K_d$, and the maximal number of receptor binding sites, Bmax, can be calculated from specific binding (total−NSB) using non-linear regression analysis. The $K_d$ for the specific binding can be calculated using a one-site binding hyperbola nonlinear regression analysis (i.e. GraphPad Prism) as shown in the equation below, where Bmax is the maximal number of binding sites (pmol/mg, or pmol/cells, or sites/cells), and $K_d$ (nM, pM, etc.) is the concentration of radioligand required to reach half-maximal binding:

$$\text{Bound} = \frac{B_{max} \times [L]}{[L] + K_d}$$

For opioid re-targeted endopeptidase, cells from the AGN P33 clone #6 cell line (comprising cells stably transformed with an expression construct encoding an ORL-1 receptor), the SK-N-DZ parental cell line, and the SK-N-DZ clonal cell lines #3, #15, and #22 (comprising cells that express endogenous ORL-1 receptor) were plated at 200,000 cells per well on a 48-well Poly-D-lysine coated plate in RPMI 1640 serum free media containing 1×N2 and 1×B27 supplements and incubated overnight at 37° C. in a 5% $CO_2$ incubator.

Media was removed and cells and 150 μL of Tris binding buffer was added to wells used to assess total binding and 100 μL of Tris binding buffer was added to well used to assess non-specific binding. About 50 μL of 4× final concentration cold nociceptin (2.5 pM to SK-N-DZ cell lines and 1 μM to AGN P33 clonal cell line #6) was added to the non-specific binding wells, and 50 μL of 4× final concentrations of $^3$H-nociceptin (0 nM, 0.05 nM, 0.1 nM, 0.2 nM, 0.4 nM, 0.8 nM, 1.6 nM, 3.1 nM, 6.3 nM, 12.5 nM, 25 nM, and 50 nM to the SK-N-DZ cell lines and 0, 0.01 nM, 0.02 nM, 0.039 nM, 0.078 nM, 0.156 nM, 0.313 nM, 0.625 nM, 1.25 nM, 2.5 nM, 5.0 nM, and 10 nM to the AGN P33 clonal cell line #6) was added to both the total binding wells and the non-specific binding wells to a final volume of 200 μL. After incubation at 37° C. for 30 minutes, the wells were washed twice in 0.5 mL of cold Washing Buffer. Cells were then denatured in 200 μL 2 N NaOH and transferred to 20 mL scintillation vials containing 5 mL of scintillation fluid. Raw data were used to plot the dose-response graphs and calculate the $K_d$ for each sample. The raw data obtained were transferred to SigmaPlot v10.0 and One Site Saturation fit was used to define the dose-response curves under the equation category of Ligand Binding. Graphical reports were generated and contained the following parameters: $R^2$ (correlation coefficient), Bmax, and $K_d$±SE (Coefficient±standard error). Graphs of total binding, specific binding, and non-specific binding were obtained on the assay performed on the SK-N-DZ clonal cell lines #3, #15, and #22, and AGN P33 clonal cell line #6 cells. SK-N-DZ clonal cell lines #3 and #22 produced a concentration-dependent and saturable binding of $^3$H-nociceptin. Under the same experimental conditions, SK-N-DZ clonal cell line #15 produced a dose-dependent response of $^3$H-nociceptin, but not saturated at the highest dose of 50 nM. Compared to the SK-N-DZ cell lines expressing endogenous ORL-1, cells from the AGN P33 clonal cell line #6 had significantly higher affinity binding to $^3$H-nociceptin (highest dose was 10 nM versus 50 nM in SK-N-DZ) with low non-specificity binding.

The saturation binding curves of SK-N-DZ clonal cell lines #3, #22, #15 and AGN P33 clonal cell line #6 were used to estimate $K_d$ and Bmax values from three independent binding experiments per cell line performed in three different days. The rank order of these four cell lines is: AGN P33 clonal cell line #6 ($K_d$=1.86 nM and Bmax=2.9 fmol/cell)>SK-N-DZ clonal cell line #3 ($K_d$=14 nM and Bmax=0.6 fmol/cell) SK-N-DZ clonal cell line #22 ($K_d$=17 nM and Bmax=0.6 fmol/cell)>>SK-N-DZ clonal cell line #15 ($K_d$>50 nM). To get a saturated dose-response for SK-N-DZ clonal cell line #15, a higher dose range of $^3$H-nociceptin needs to be used. Table 16 summarizes the data regarding the characterization of the specific plasma membrane nociceptin-binding sites in three SK-N-DZ clonal cell lines, #3, #15, and #22, and AGN P33 clonal cell line #6 stable cell lines. The data showed the following: 1) a high affinity site with very low non-specific binding ($K_d$, 1.8 nM, and Bmax 2.9 fmol per cell) in the AGN P33 clonal cell line #6; 2) nociceptin-binding can be performed on SK-N-DZ native cells expressing endogenous receptor; 3) AGN P33 clonal cell line #6 had about 10-fold higher affinity to nociceptin than the SK-N-DZ cell lines; 4) as seen in the cell-based potency assay, SK-N-DZ clonal cell lines #3 and #22 ($K_d$ 14-17 nM, Bmax 0.6 fmol per cell) had more receptor sites per cell than SK-N-DZ clonal cell line #15 (not saturable under the same dose range).

TABLE 18

Summary of $^3$H-nociceptin saturation binding assay for four leading cell lines (n = 3 independent experiments)

| Cell Lines | $K_d$ (nM ± SD) | Bmax (fmol/cell) |
|---|---|---|
| SK-N-DZ #3 | 14 ± 1.6 | 0.59 |
| SK-N-DZ #15 | >50 | ND |
| SK-N-DZ #22 | 16.7 ± 1.1 | 0.58 |
| AGN P33 clonal cell line #6 | 1.86 ± 0.1 | 2.89 |

To evaluate the sensitivity of re-targeted endopeptidase uptake, the amount of re-targeted endopeptidase receptor expressed at the mRNA level was assessed using RT-PCR. The amount of receptor expressed in the cells is an important aspect of the characterization of the cell line being used for testing and it is related to the sensitivity to re-targeted endopeptidases. The amount of expressed re-targeted endopeptidase receptor can also be a tool for screening other potential cell lines and to eliminate cell lines that do not express the target receptor. One method of measuring receptor expression is to quantify the amount of re-targeted endopeptidase receptor mRNA using real time PCR (RT-PCR).

For opioid re-targeted endopeptidase, RNA was isolated from cells of a non-transfected parental SiMa cell line, cells from the AGN P33 clonal cell line #6, cells from the parental SK-N-DZ cell line, and cells from the SK-N-DZ clonal cell lines #3 and #22 grown in either serum free media or media with serum. The mRNA was converted to cDNA and the ORL-1 was amplified and measured real time to determine the relative amount present in each cell line using the following oligonucleotide primers for ORL-1: forward 5'-CACTCGGCTGGTGCTGGTGG-3' (SEQ ID NO:148) and reverse 5'-AATGGCCACGGCAGTCTCGC-3' (SEQ ID NO:149). The DNA is quantified by using SYBR® green which fluoresces relative to the amount of double stranded DNA (PCR product) present in the reaction. Plotting the amount of fluorescence vs. number of cycles gives a logistic curve for each reaction. The faster a reaction reaches the linear phase of the curve the more ORL-1 receptor cDNA there is in the reaction. A control RT reaction where no enzyme is added was be used to determine if there is contamination. Since there is no RT enzyme present in this reaction, no cDNA will be produced. A PCR product cannot be produced using a RNA template, so if a PCR curve appears in the −RT reaction, the only possibility is genomic DNA contamination. In the −RT reactions, no PCR plots appears, confirming there was minimal genomic DNA contamination (data not shown). Table 18 lists the cell lines with their CT value. The CT is the number of PCR cycles it took for that corresponding PCR reaction to produce a signal above a set threshold. The amount of ORL-1 receptor mRNA in a cell line can be compared to another by looking at their corresponding CT values. According to the CT values, cells from the AGN P33 clonal cell line #6 had much more ORL-1 mRNA than cells from the parental SiMa cell line in serum free media (Ave CT: 28.6 vs. 17.3) and in media with serum (Ave CT: 26.1 vs. 16.5). Also, there appears to be minimal difference in mRNA obtained from cells at passage 6 vs. passage 16 in the AGN P33 clonal cell line #6. Also, there are minimal differences in CT values and plots in the parental SK-N-DZ cell line vs. clonal cell line #3 and #22. This conclusion is true in cells grown in media with serum and serum free media and reflects the similarity of these cell lines observed in the cell-based potency assay for Noc/A.

TABLE 19

| Average CT Values for ORL-1 Expression in Cell Lines | | |
|---|---|---|
| Media | Cell line | CT average |
| Serum Free Media | SiMa Parental p26 | 28.6 |
| | SiMa hORL-1 clone #6 p6 | 17.3 |
| | SiMa hORL-1 clone #6 p16 | 17.3 |
| Complete Media | SiMa Parental p26 | 26.1 |
| | SiMa hORL-1 clone #6 p6 | 16.4 |
| | SiMa hORL-1 clone #6 p16 | 16.6 |
| Serum Free Media | SK-N-DZ | 26.3 |
| | SK-N-DZ clone #3 | 25.9 |
| | SK-N-DZ clone #22 | 26.6 |
| Complete Media | SK-N-DZ | 26.2 |
| | SK-N-DZ clone #3 | 25.8 |
| | SK-N-DZ clone #22 | 26.4 |

Example VII

Development of α-SNAP-25 Monoclonal Antibodies that Selectively Bind a SNAP-25 Epitope Having a Free Carboxyl-terminus at the $P_1$ Residue of the BoNT/A Cleavage Site Scissile Bond The following example illustrates how to make α-SNAP-25 monoclonal antibodies that can selectively bind to a SNAP-25 epitope having a carboxyl-terminus at the $P_1$ residue of the BoNT/A cleavage site scissile bond.

1. Generation of α-SNAP-25 Monoclonal Antibodies.

To develop monoclonal α-SNAP-25 antibodies that can selectively bind to a SNAP-25 having a carboxyl-terminus at the $P_1$ residue of the BoNT/A cleavage site scissile bond, the 13-residue peptide CDSNKTRIDEANQ$_{COOH}$ (SEQ ID NO:38) was designed as a SNAP-25 cleavage product antigen. This peptide comprises a flexible linker region and a N-terminal Cysteine residue for conjugation to KLH and amino acids 186-197 of human SNAP-25 (SEQ ID NO:5) with a carboxylated C-terminal glutamine (SEQ ID NO:38). The generation of monoclonal antibodies to well-chosen, unique peptide sequences provides control over epitope specificity, allowing the identification of a particular sub-population of protein among a pool of closely related isoforms. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Six Balb/c mice were immunized with this peptide, and after three immunizations in about eight weeks, the mice were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 μl aliquots and stored at −20° C. until needed.

A similar strategy based on other SNAP-25 antigens disclosed in the present specification is used to develop α-SNAP-25 monoclonal antibodies that can selectively bind to a SNAP-25 having a carboxyl-terminus at the $P_1$ residue of the BoNT/A cleavage site scissile bond. For example, the SNAP-25 antigen of SEQ ID NO:45 can be conjugated to KLH instead of the SNAP-25 antigen of SEQ ID NO:38. As another example, the amino acids 186-197 of human SNAP-25 from the SNAP-25 antigen of SEQ ID NO:38 can be replaced with SEQ ID NO:32, SEQ ID NO:33, SEQ ID NO:34, SEQ ID NO:35, SEQ ID NO:36, SEQ ID NO:39, SEQ ID NO:40, SEQ ID NO:41, SEQ ID NO:42, SEQ ID NO:43, or SEQ ID NO:44.

2. Screening for the Presence of α-SNAP-25 Monoclonal Antibodies.

To determine the presence of an α-SNAP-25 monoclonal antibody that can selectively bind to a SNAP-25 antigen having a carboxyl-terminus at the $P_1$ residue of the BoNT/A cleavage site scissile bond, comparative ELISA and cell-based cleavage assay were performed using the extracted mouse serum. For comparative ELISA, two fusion proteins were constructed: BirA-HisTag®-SNAP-25$_{134-197}$ of SEQ ID NO:48 and the BirA-HisTag®-SNAP-25$_{134-206}$ of SEQ ID NO:49. BirA-HisTag®-SNAP-25$_{134-197}$ comprised a naturally-biotinylated 16 amino acid BirA peptide of SEQ ID NO:50 amino-terminally linked to a SNAP-25 peptide comprising amino acids 134-197 of SEQ ID NO:5. BirA-HisTag®-SNAP-25$_{134-206}$ comprised a naturally-biotinylated 16 amino acid BirA peptide of SEQ ID NO:50 amino-terminally linked to a SNAP-25 peptide comprising amino acids 134-206 of SEQ ID NO:5. These two substrates were suspended in 1×PBS at a concentration of 10 μg/mL BirA-HisTag®-SNAP-25$_{134-197}$ and the BirA-HisTag®-SNAP-25$_{134-206}$. The BirA-HisTag®-SNAP-25$_{134-197}$ and the BirA-HisTag®-SNAP-25$_{134-206}$ were coated onto separate plates by adding approximately 100 μl of the appropriate Substrate Solution and incubating the plates at room temperature for one hour. Washed plates were incubated at 37° C. for one hour in 0.5% BSA in 1×TBS containing a 1:10 to 1:100 dilution of an antibody-containing serum derived from one of the six immunized mice (Mouse 1, Mouse 2, Mouse 3, Mouse 4, Mouse 5, and Mouse 6). Primary antibody probed plates were washed four times for 5 minutes each time in 200 μl TBS, 0.1% TWEEN-20® (polyoxyethylene (20) sorbitan monolaurate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 μl TBS, 0.1% TWEEN-20® (polyoxyethylene (20) sorbitan monolaurate). Chromogenic detection of the labeled SNAP-25 products were visualized by chromogenic detection using ImmunoPure TMB substrate kit (Pierce Biotechnology, Rockford, Ill.). The development of a yellow color in the BirA-HisTag®-SNAP-25$_{134-197}$ coated plates, but not the BirA-HisTag®-SNAP-25$_{134-206}$ coated plates, indicated that the α-SNAP-25 antibody preferentially recognized the SNAP-25$_{197}$ cleavage product. The resulted indicated that of the six mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

These results were confirmed using an ELISA light chain activity assay. A 96-well Reacti-Bind Streptavidin coated plates (Pierce Biotechnology, Rockford, Ill.) were prepared by adding approximately 100 μl of the following Substrate Solution: Rows A-C were coated with 100 μL of BirA-HisTag®-SNAP-25$_{134-197}$ at twelve different concentrations; Rows D-H were coated with 100 μL of BirA-HisTag®-SNAP-25$_{134-296}$ at 10 μg/mL. The plates were washed by aspirating the Substrate Solution and rinsing each well three times with 200 μl TBS, 0.1% TWEEN-20®

(polyoxyethylene (20) sorbitan monolaurate). Dilutions of BoNT/A were pre-reduced at 37° C. for 20 minutes in BoNT/A Incubation Buffer (50 mM HEPES, pH 7.4, 1% fetal bovine serum, 10 μM $ZnCl_2$, 10 mM dithiothreitol) and 100 μl of the pre-reduced BoNT/A was added to the substrate-coated plates and incubated at 37° C. for 90 minutes. BoNT/A treated plates were washed by aspirating the BoNT/A Incubation Buffer and rinsing each plate three times with 200 μl TBS, 0.1% TWEEN-20® (polyoxyethylene (20) sorbitan monolaurate). Washed plates were incubated at 37° C. for one hour in 0.5% BSA in 1×TBS containing a 1:10 to 1:100 dilution of the antibody-containing serum being tested. Primary antibody probed plates were washed four times for 5 minutes each time in 200 μl TBS, 0.1% TWEEN-20® (polyoxyethylene (20) sorbitan monolaurate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 μl TBS, 0.1% TWEEN-20® (polyoxyethylene (20) sorbitan monolaurate). Chromogenic detection of the labeled SNAP-25 products were visualized by chromogenic detection using ImmunoPure TMB substrate kit (Pierce Biotechnology, Rockford, Ill.). The development of a yellow color, which correlated with the presence of the SNAP-$25_{197}$ cleavage product was detected in BoNT/A treated samples, but not untreated controls, using antibody-containing serum derived from all six immunized mice (Mouse 1, Mouse 2, Mouse 3, Mouse 4, Mouse 5, and Mouse 6). Thus, the comparative ELISA analysis indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

For cell-based cleavage assay, a suitable density of PC12 cells were plated into 60 $mm^2$ tissue culture plates containing 3 mL of an appropriate serum medium (Table 1). The cells were grown in a 37° C. incubator under 5% carbon dioxide until cells reached the appropriate density. A 500 μL transfection solution was prepared by adding 250 μL of OPTI-MEM Reduced Serum Medium containing 15 μL of LipofectAmine 2000 (Invitrogen Inc., Carlsbad, Calif.) incubated at room temperature for 5 minutes to 250 μL of OPTI-MEM Reduced Serum Medium containing 10 μg of a pQBI-25/GFP-BoNT/A-LC expression construct (SEQ ID NO:51). The pQBI-25/GFP-BoNT/A-LC expression construct comprises a pQBI-25 expression vector (Qbiogene Inc., Carlsbad, Calif.) whose promoter elements are functionally linked to a polynucleotide encoding the GFP-BoNT/A light chain of SEQ ID NO:52. This transfection mixture was incubated at room temperature for approximately 20 minutes. The media was replaced with fresh unsupplemented media and the 500 μL transfection solution was added to the cells. The cells were then incubated in a 37° C. incubator under 5% carbon dioxide for approximately 6 to 18 hours. The cells were washed and harvested as described in Example II. To detect for the presence of the cleaved SNAP-$25_{197}$ product, an aliquot from each harvested sample was analyzed by Western blot as described in Example II, except that the primary antibody used was a 1:1,000 dilution of the antibody-containing serum and the secondary antibody used was a 1:20,000 of mouse α-IgG Horseradish Peroxidase (Pierce Biotechnology, Rockford, Ill.). A single band corresponding to the SNAP-$25_{197}$ cleavage product was detected in BoNT/A treated samples, but not untreated controls, using antibody-containing serum derived from three mice (Mouse 2, Mouse 3, and Mouse 4). Thus, the cell-based cleavage assay indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

3. Production of Hybridomas.

To make hybridomas producing α-SNAP-25 monoclonal antibodies that can selectively bind to a SNAP-25 antigen having a carboxyl-terminus at the $P_1$ residue of the BoNT/A cleavage site scissile bond, the spleen from Mouse 2 was harvested three days subsequent to a final "booster" immunization and the spleen cells were fused with myeloma cells P3-X63 Ag8.653 using standard hybridoma protocols. These cells were plated into five 96-well plates and hybrids were selected using HAT medium. Within 8-14 days after fusion, the first screening of the approximately 480 parent clones was carried out using comparative ELISA with the BirA-HisTag®-SNAP-$25_{134-197}$ and the BirA-HisTag®-SNAP-$25_{134-206}$ peptides coated in two separate plates. The comparative ELISA provided a quick screen method to identify hybridomas producing antibodies specific for the cleaved SNAP-$25_{197}$. The top 18 clones were subjected to further screening using the cell-based cleavage assay described above and immunostaining of LC/A transfected cells. (Table 20).

TABLE 20

Analysis of Supernatants Containing α-SNAP-25 Monoclonal Antibody

| | Comparative ELISA | | | | Cell-Based Assay | |
|---|---|---|---|---|---|---|
| | OD | OD | | | | |
| Clone | SNAP-$25_{197}$ | SNAP-$25_{206}$ | $Ratio_{197/206}$ | $Ratio_{206/197}$ | SNAP-$25_{197}$ | SNAP-$25_{206}$ |
| 1D3 | 1.805 | 0.225 | 8.02 | 0.13 | +++ | − |
| 1F12 | 0.365 | 0.093 | 3.92 | 0.25 | − | − |
| 1G10 | 0.590 | 0.137 | 4.31 | 0.23 | ++ | − |
| 1H1 | 0.335 | 0.121 | 2.77 | 0.36 | − | − |
| 1H8 | 0.310 | 0.302 | 1.03 | 0.97 | + | − |
| 2C9 | 0.139 | 0.274 | 0.51 | 1.97 | − | − |
| 2E2 | 0.892 | 0.036 | 24.78 | 0.04 | ++ | − |
| 2E4 | 0.228 | 0.069 | 3.30 | 0.30 | + | − |
| 2F11 | 1.095 | 1.781 | 0.61 | 1.63 | − | − |
| 3C1 | 1.268 | 0.053 | 23.92 | 0.04 | ++ | − |
| 3C3 | 0.809 | 0.052 | 15.56 | 0.06 | ++ | − |
| 3E1 | 0.086 | 0.155 | 0.55 | 1.80 | 0 | − |
| 3E8 | 2.048 | 0.053 | 38.64 | 0.03 | +++ | − |
| 3G2 | 0.053 | 0.158 | 0.34 | 2.98 | − | − |
| 4D1 | 0.106 | 0.218 | 0.49 | 2.06 | − | − |
| 4G6 | 0.061 | 0.159 | 0.38 | 2.61 | − | − |
| 5A5 | 0.251 | 0.106 | 2.37 | 0.42 | + | − |
| 5F11 | 0.243 | 0.061 | 3.98 | 0.25 | − | − |

Clones 1D3, 1G10, 2E2, 3C1, 3C3, and 3E8 were further cloned by limiting dilution because the conditioned media produced by these clones comprised α-SNAP-25 antibodies with a preferential binding specificity having a $ratio_{197/206}$ of at least 4:1 for the SNAP-$25_{197}$ cleavage product relative to the SNAP-$25_{206}$ uncleaved substrate and detected the SNAP-$25_{197}$-cleavage product using the cell-based cleavage assay and the immunostaining of PC12 cells transfected with GFP-LC/A. Similarly clones 2C9, 2F11, 3G2, 4D1 and 4G6 were further cloned by limiting dilution because the conditioned media produced by these clones comprised α-SNAP-25 antibodies with a preferential binding specificity having a $ratio_{206/197}$ of at least 1.5:1 for the SNAP-$25_{206}$ uncleaved substrate relative to the SNAP-$25_{197}$ cleavage product and detected the SNAP-$25_{206}$-uncleaved substrate using the cell-based cleavage assay. These single-cell derived clones were screened again using comparative ELISA, cell-based cleavage, and immunostaining to confirm their affinity and specificity, and the antibodies were isotyped using standard procedures. Ascites were produced from clones 1 D3B8 (IgM.k), 1G10A12 (IgG3.k), 2C9B10 (IgG3.k), 2E2A6 (IgG3.k), 2F11B6 (IgM.k), 3C1A5 (IgG2a.k), and 3C3E2 (IgG2a.k). Clone 3E8 stopped producing antibodies during the cloning process and could not be further evaluated.

4. Evaluation of Binding Specificity of α-SNAP-25 Monoclonal Antibodies.

To evaluate binding specificity of an α-SNAP-25 monoclonal antibody that can selectively bind to a SNAP-25 antigen having a carboxyl-terminus at the $P_1$ residue of the BoNT/A cleavage site scissile bond, ascites from clones 1D3B8, 1G10A12, 2C9B10, 2E2A6, 2F11B6, 3C1A5, and 3C3E2 were used to detect SNAP-25 cleavage product using the cell-based activity assay, immunocytochemistry and immunoprecipitation.

For the cell-based activity assay, binding specificity was determined by analyzing the ability of α-SNAP-25 antibody-containing ascites to detect the uncleaved SNAP-$25_{206}$ substrate and the cleaved SNAP-$25_{197}$ product by Western blot analysis. A suitable density of PC12 cells were plated into 60 $mm^2$ tissue culture plates containing 3 mL of an appropriate serum medium, grown in a 37° C. incubator under 5% carbon dioxide until an appropriate cell density was reached, and transfected with the either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed and harvested as described in Example I. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:100 dilution of the α-SNAP-25 monoclonal antibody-containing ascites and the secondary antibody used was a 1:20,000 of α-mouse IgG conjugated to Horseradish Peroxidase (Pierce Biotechnology, Rockford, Ill.). In addition, three commercially available mouse α-SNAP-25 monoclonal antibodies were tested. SMI-81 (Sternberger Monoclonals Inc., Lutherville, Md.), an α-SNAP-25 antibody the manufacturer indicates detects both the uncleaved SNAP-$25_{206}$ substrate and the cleaved SNAP-$25_{197}$ product, was used at a 15,000 dilution according to the manufacturer's recommendations. MC-6050 (Research & Diagnostic Antibodies, Las Vegas, Nev.), an α-SNAP-25 antibody the manufacturer indicates detects both the uncleaved SNAP-$25_{206}$ substrate and the cleaved SNAP-$25_{197}$ product, was used at a 1:100 dilution according to the manufacturer's recommendations. MC-6053 (Research & Diagnostic Antibodies, Las Vegas, Nev.), an α-SNAP-25 antibody the manufacturer indicates detects only the cleaved SNAP-$25_{197}$ product, was used at a 1:100 dilution according to the manufacturer's recommendations.

Table 21 indicates the α-SNAP-25 antibody-containing ascites that detected only the SNAP-$25_{197}$ cleavage product. The cell-based cleavage assay indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the selective recognition of this cleavage product relative to the SNAP-$25_{206}$ uncleaved substrate. Commercial antibody SMI-81 detected the SNAP-$25_{206}$ uncleaved substrate, but only poorly recognized the SNAP-$25_{197}$ cleavage product (Table 21). Surprisingly, commercial antibody MC-6050 only detected the SNAP-$25_{206}$ uncleaved substrate, and failed to recognize the SNAP-$25_{197}$ cleavage product (Table 21). Even more surprisingly, commercial antibody MC-6050 only detected the SNAP-$25_{206}$ uncleaved substrate, and failed to recognize the SNAP-$25_{197}$ cleavage product, even though the manufacturer advertises that this antibody selectively detects the SNAP-$25_{197}$ cleavage product (Table 21). Thus, this analysis indicates that while 1D3B8, 2C9B10, 2E2A6, 3C1A5, and 3C3E2 exhibit suitable selectivity for the SNAP-$25_{197}$ cleavage product, 1G10A12 and 2F11B6 do not. In addition, commercial antibodies SMI-81, MC-6050 and MC-6053 all are unsuitable for the immuno-based methods disclosed in the present application because all failed to selectivity detect the SNAP-$25_{197}$ cleavage product.

For immunocytochemistry analysis, binding specificity was determined by analyzing the ability of α-SNAP-25 antibody-containing ascites to detect the uncleaved SNAP-$25_{206}$ substrate and the cleaved SNAP-$25_{197}$ product by immunostaining. See e.g., Ester Fernandez-Salas et al., *Plasma Membrane Localization Signals in the Light Chain of Botulinum Neurotoxin*, Proc. Natl. Acad. Sci., U.S.A. 101(9): 3208-3213 (2004). A suitable density of PC12 cells were plated, grown, and transfected with either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed in 1×PBS and fixed in 5 mL of PAF at room temperature for 30 minutes. Fixed cells were washed in phosphate buffered saline, incubated in 5 mL of 0.5% Triton® X-100 (polyethylene glycol octylphenol ether) in 1×PBS, washed in 1×PBS, and permeabilized in 5 mL of methanol at −20° C. for six minutes. Permeabilized cells were blocked in 5 mL of 100 mM glycine at room temperature for 30 minutes, washed in 1×PBS, and blocked in 5 mL of 0.5% BSA in 1×PBS at room temperature for 30 minutes. Blocked cells were washed in 1×PBS and incubated at room temperature for two hours in 0.5% BSA in 1×PBS containing a 1:10 dilution of an ascites from a clonal hybridoma cell line being tested. Primary antibody probed cells were washed three times for 5 minutes each time in 1×PBS. Washed cells were incubated at room temperature for 2 hours in 1×PBS containing a 1:200 dilution of goat polyclonal anti-mouse immunoglobulin G, heavy and light chains (IgG, H+L) antibody conjugated to ALEXA® FLUOR 568 (Invitrogen Inc., Carlsbad, Calif.) as a secondary antibody. Secondary antibody-probed cells were washed three times for 5 minutes each time in 1×PBS. Washed cells were prepared for microscopic examination by mounting in VECTASHIELD® Mounting Media (Vector Laboratories, Burlingame, Calif.) and coverslipped. Images of signal detection were obtained with a Leica confocal microscope using appropriate laser settings. Table 21 indicates that the α-SNAP-25 antibody-containing ascites that specifically detected the SNAP-$25_{197}$-cleavage product. The immunocytochemistry analysis indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

For immunoprecipitation analysis, binding specificity was determined by analyzing the ability of Protein A (HiTrap™

Protein A HP Columns, GE Healthcare, Amersham, Piscataway, N.J.), purified α-SNAP-25 monoclonal antibodies to precipitate the uncleaved $SNAP\text{-}25_{206}$ substrate and the cleaved $SNAP\text{-}25_{197}$ product. See e.g., Chapter 8 Storing and Purifying Antibodies, pp. 309-311, Harlow & Lane, supra, 1998a. A suitable density of PC12 cells were plated, grown, and transfected with either a transfection solution containing a pQBI-25/GFP expression construct (control cells; SEQ ID NO:53) or a transfection solution containing the pQBI-25/GFP-BoNT/A-LC expression construct (experimental cells) as described above. The pQBI-25/GFP expression construct comprises an expression vector whose promoter elements are functionally linked to a polynucleotide encoding GFP of SEQ ID NO:54. After an overnight incubation, the cells were washed by aspirating the growth media and rinsing each well with 200 μL 1×PBS. To harvest the cells, the PBS was aspirated, the cells were lysed by adding an Immunoprecipitation Lysis Buffer comprising 50 mM HEPES, 150 mM NaCl, 1.5 mM $MgCl_2$, 1 mM EGDT, 10% glycerol, 1% Triton® X-100 (polyethylene glycol octylphenol ether) and a 1× COMPLETE™ Protease inhibitor cocktail (Roche Applied Biosciences, Indianapolis, Ind.) and incubating at 4° C. for one hour. The lysed cells were centrifuged at 3,000×g at 4° C. for 10 minutes to remove cellular debris and the supernatant transferred to a clean tube and diluted to a protein concentration of approximately 1 mg/mL. Approximately 5 μg of purified monoclonal antibody was added to 0.5 mL of diluted supernatant and incubated at 4° C. for two hours. After primary antibody incubation, approximately 50 μL of immobilized Protein G (Pierce Biotechnology, Rockford, Ill.) was added to the diluted supernatant and incubated at 4° C. for one hour. The incubated supernatant was washed three times for 30 minutes each time by adding 0.5 mL of Immunoprecipitation Lysis Buffer, centrifuging at 300×g at 4° C. for one minute to pellet the immobilized Protein G, and decanting the supernatant. After washing, the pellet was resuspended in 30 μl of 1×SDS Loading Buffer and the sample was heated to 95° C. for 5 minutes. To detect for the presence of both the uncleaved $SNAP\text{-}25_{206}$ substrate and the cleaved $SNAP\text{-}25_{197}$ product, an aliquot from each harvested sample was analyzed by Western blot as described in Example I, except that the primary antibody used was a 1:1,000 dilution of the α-SNAP-25 polyclonal antibody serum (see Example V) and the secondary antibody used was a 1:20,000 of rabbit α-IgG Horseradish Peroxidase (Pierce Biotechnology, Rockford, Ill.). Table 21 indicates the α-SNAP-25 antibody-containing ascites that specifically pulled down the $SNAP\text{-}25_{197}$-cleavage product by immunoprecipitation analysis. The immunoprecipitation analysis indicated that ascites produced from clones 2E2A6 and 3C1A5 synthesize an α-SNAP-25 monoclonal antibody having high binding specificity for the $SNAP\text{-}25_{197}$ cleavage product that allows for the preferential recognition of this cleavage product relative to the $SNAP\text{-}25_{206}$ uncleaved substrate.

TABLE 21

Analysis of Clone Ascites Containing α-SNAP-25 Monoclonal Antibody

| | Cell-Based Assay | | Immunocytochemistry | | Immunoprecipitation | |
|---|---|---|---|---|---|---|
| Clone | $SNAP\text{-}25_{197}$ | $SNAP\text{-}25_{206}$ | $SNAP\text{-}25_{197}$ | $SNAP\text{-}25_{206}$ | $SNAP\text{-}25_{197}$ | $SNAP\text{-}25_{206}$ |
| 1D3B8 | ++ | − | ++ | − | Not Tested | Not Tested |
| 1G10A12 | ++ | ++ | Not Tested | Not Tested | Not Tested | Not Tested |
| 2C9B10 | ++ | − | ++ | − | Not Tested | Not Tested |
| 2E2A6 | ++ | − | ++ | − | ++ | − |
| 2F11B6 | + | + | + | + | Not Tested | Not Tested |
| 3C1A5 | ++ | − | ++ | − | ++ | − |
| 3C3E2 | + | − | Not Tested | Not Tested | Not Tested | Not Tested |
| MC-6050 | − | + | Not Tested | Not Tested | Not Tested | Not Tested |
| MC-6053 | − | + | Not Tested | Not Tested | Not Tested | Not Tested |
| SMI-81 | −/+ | ++ | Not Tested | Not Tested | Not Tested | Not Tested |

5. Evaluation of Binding Affinity of α-SNAP-25 Monoclonal Antibodies

To determine the binding affinity of an α-SNAP-25 monoclonal antibody showing high binding specificity for either the $SNAP\text{-}25_{197}$ cleavage product or the $SNAP\text{-}25_{206}$ uncleaved substrate, binding affinity assays were performed on a BIAcore® 3000 instrument using carboxymethyl dextran (CM5) sensor chips (BIAcore, Inc., Piscataway, N.J.). Runs were conducted at 25° C. with HBS-EP buffer comprising 10 mM HEPES (pH 7.4), 150 mM sodium chloride, 3 mM EDTA, 0.005% (v/v) surfactant P20 at a flow rate of 10 μL/min. SNAP-25 peptides comprising amino acids 134-197 of SEQ ID NO:5 ($SNAP\text{-}25_{134\text{-}197}$) or amino acids 134-206 of SEQ ID NO:5 ($SNAP\text{-}25_{134\text{-}206}$) were covalently attached to the surface of the CM5 sensor chips using standard amine coupling. Briefly, the CM5 chips were activated by a 7 minute injection of a mixture of 0.2 M 1-ethyl-3-(3-dimethylaminopropyl) carbodiimide and 0.05 M N-hydroxysuccinimide; the SNAP-25 peptides were then injected in 10 mM sodium acetate (pH 4.0) for 20 min at a flow rate of 10 μL/min; and unreacted succinimide esters were blocked by a 7-min injection of 1 M ethanolamine hydrochloride, pH 8.5. The immobilized amount of $SNAP\text{-}25_{134\text{-}197}$ or $SNAP\text{-}25_{134\text{-}206}$ on the chip was reflected by a 100-150 increase in response units (about 0.10-0.15 $ng/mm^2$). Antibody samples comprising either ascites or purified monoclonal antibodies produced from clones 1D3B8, 2C9B10, 2E2A6, 3C1A5, and 3C3E2, as well as, commercially available α-SNAP-25 antibodies were passed over the surface of the CM5 chips allowing an association time of 10 min and a dissociation time of 20 min. The surfaces were regenerated between runs by a 1 minute injection of 10 mM glycine-HCl (pH 2.5) at a flow rate of 15 μL/min. Sensorgram curves were fitted to a 1:1 kinetic binding model with the BIAevaluation 3.0 software.

The results indicate that both 2E2A6 and 3C1A5 were highly specific for cleaved $SNAP\text{-}25_{197}$ product over SNAP-25 uncleaved substrate (Table 22). When compared to the binding affinities of MC-6050 and MC-6053, 1D3B6 had an approximately 10-fold higher equilibrium disassociation constant for the SNAP-25 cleavage product relative to these commercial antibodies (Table 22). Interestingly, 2E2A6 had only a slightly lower equilibrium disassociation constant for the SNAP-25 cleavage product relative to these commercial antibodies (0.405 nM versus 0.497 and 0.508)(Table 22). As neither of these commercial α-SNAP-25 antibodies selectively recognized the SNAP-25 cleavage product (Table 21), an equilibrium disassociation constant lower than about 0.5 nM appears, in part, critical to achieve such selectivity. Similarly, when compared to the binding affinities of MC-6050 and MC-6053, 2E2A6 had an about at least one-fold slower off rate/dissociation constant ($6.74\times10^{-5}$ versus $8.82\times10^{-4}$ $s^{-1}$ and $1.18\times10^{-3}$ $s^{-1}$) (Table 22). This further suggests that an off rate/dissociation constant lower than about $8.82\times10^{-4}$ appears, in part, critical to achieve selective binding for the SNAP-25 cleavage product. This result is consistent with 1 D3B8, which had an off rate/dissociation constant of $5.78\times10^{-5}$ $s^{-1}$ (Table 22).

TABLE 22

Analysis of Binding Affinity α-SNAP-25 Monoclonal Antibodies

| SPR | 1D3B8 | | 2E2A6 | |
|---|---|---|---|---|
| Parameter | SNAP-$25_{197}$ | SNAP-$25_{206}$[a] | SNAP-$25_{197}$ | SNAP-$25_{206}$[b] |
| Ka ($M^{-1}$ $s^{-1}$) | $1.06 \times 10^6$ | — | $1.70 \times 10^6$ ($1.66 \times 10^5$) | — (—) |
| Kd ($s^{-1}$) | $5.78 \times 10^{-5}$ | — | $1.53 \times 10^{-4}$ ($6.74 \times 10^{-5}$) | — (—) |
| KD (nM) | 0.050 | — | 0.090 (0.405) | — (—) |
| **SPR** | **3C1A5** | | **2C9B10** | |
| Parameter | SNAP-$25_{197}$ | SNAP-$25_{206}$[c] | SNAP-$25_{197}$ | SNAP-$25_{206}$[d] |
| Ka ($M^{-1}$ $s^{-1}$) | $2.17 \times 10^5$ | — | $1.15 \times 10^4$ | — |
| Kd ($s^{-1}$) | $2.88 \times 10^{-4}$ | — | $3.11 \times 10^{-4}$ | — |
| KD (nM) | 1.33 | — | 27.1 | — |
| **SPR** | **MC-6050** | | **MC-6053** | |
| Parameter | SNAP-$25_{197}$ | SNAP-$25_{206}$ | SNAP-$25_{197}$ | SNAP-$25_{206}$ |
| Ka ($M^{-1}$ $s^{-1}$) | $1.78 \times 10^6$ | $3.06 \times 10^2$ | $2.32 \times 10^6$ | $1.06 \times 10^2$ |
| Kd ($s^{-1}$) | $8.82 \times 10^{-4}$ | $6.07 \times 10^{-3}$ | $1.18 \times 10^{-3}$ | $2.56 \times 10^{-5}$ |
| KD (nM) | 0.497 | 19,800 | 0.508 | 240 |

[a]No binding was observed when up to 125 nM of α-SNAP-25 monoclonal antibody 1D3B8 was passed over the surface of the CM5 sensor chip after a 10 minute association time.
[b]No binding was observed when up to 10 μM of α-SNAP-25 monoclonal antibody 2E2A6 was passed over the surface of the CM5 sensor chip after a 10 minute association time.
[c]No binding was observed when up to 100 nM of α-SNAP-25 monoclonal antibody 3C1A5 was passed over the surface of the CM5 sensor chip after a 10 minute association time.
[d]No binding was observed when up to 100 nM of α-SNAP-25 monoclonal antibody 2C9B10 was passed over the surface of the CM5 sensor chip after a 10 minute association time.

To compare the six different antibodies, the on-rate (ka) and off-rate (kd) for each was normalized using a program from the BIA evaluation 4.1 software. For comparison of the on-rates, the data were first individually trimmed by deleting the re-generation portion and the injection spikes, and then normalized to a 0 to 100 scale. For comparison of the off-rate, the data were normalized to the injection stop/top point. This analysis showed that 2C9B10 had a much slower on-rate than the other antibodies (FIG. 7A), and that MC-6053 has a much faster off-rate (dissociation) that the other antibodies (FIG. 7B). The fast off-rate of MC-6053 indicates that this antibody will not perform well in the methods disclosed in the present specification because this antibody will have difficulty staying bound to the substrate antigen during the washing steps.

6. Sequencing of the Epitope from Isolated α-SNAP-25 Monoclonal Antibodies.

To determine the epitope of an isolated α-SNAP-25 monoclonal antibody that can selectively bind to a SNAP-25 antigen having a carboxyl-terminus at the $P_1$ residue of the BoNT/A cleavage site scissile bond, the polynucleotide molecule encoding the variable heavy ($V_H$) and variable light ($V_L$) chains of the α-SNAP-25 monoclonal antibody produced by hybridomas 1D3B8, 2C9B10, 2E2A6, 3C1A5 and 3C3E2 were sequenced. mRNA was extracted and purified from each hybridoma using standard protocols and reversed transcribed into cDNA using either an oligo dT anti-sense primer or a gene-specific (murine IgG1 CH and kappa CL) anti-sense primer. Specific murine and human constant domain primers were used to amplify the cDNA by PCR after cDNA production to determine the isotype of the antibody. Degenerate $V_H$ and $V_L$ primers were used to amplify the variable domains from the cDNA. For 5'RACE, a homopolymeric dCTP tail was added to the 3' end of the cDNA. The heavy and light chains were then amplified with an oligo dG sense primer and a gene specific (CH/KC) anti-sense primer. PCR products included the sequence of the signal peptide, variable domains and constant domains up to the anti-sense primer. The PCR products were gel purified to remove small fragments, and cloned into a blunt or TA vector for sequencing. Five independent clones for each chain were sequenced and alignments of $V_H$ and $V_L$ chains and consensus sequences were determined. Methods used to determine the $V_H$ and $V_L$ amino acid sequences are described in, e.g., Roger A. Sabbadini, et al., Novel Bioactive Lipid Derivatives and Methods of Making and Using Same, U.S. Patent Publication 2007/0281320; and Peter Amersdorfer, et al., *Molecular Characterization of Murine Humoral Immune Response to Botulinum Neurotoxin Type A Binding Domain as Assessed by Using Phage Antibody Libraries,* 65 (9) Infect. Immun. 3743-3752, each of which is hereby incorporated by reference in its entirety. In addition, commercial services are available to sequence the variable heavy ($V_H$) and variable light ($V_L$) chains of an antibody and identify the CDR regions, see, e.g., Fusion Antibodies Ltd., Northern Ireland. In one case, for the 3C1A5 $V_L$ region, the amino acid sequence was also determined by separating the affinity purified antibody by high resolution 2DE electrophoresis and then subjecting the protein to peptide fragmentation fingerprinting analysis using high resolution nanoLC-MSMS after proteolytic digestion.

The polynucleotide sequence comprising the $V_H$ and $V_L$ chains of the α-SNAP-25 monoclonal antibody produced by the hybridomas disclosed in the present specification is as follows: 1D3B8 $V_H$ (SEQ ID NO:71), 2C9B10 $V_H$ (SEQ ID NO:73), 2E2A6 $V_H$ (SEQ ID NO:75), 3C1A5 $V_H$ (SEQ ID NO:77), 3C3E2 $V_H$ variant 1 (SEQ ID NO:79), 3C3E2 $V_H$ variant 2 (SEQ ID NO:81), 3C3E2 $V_H$ variant 3 (SEQ ID NO:132), 1D3B8 $V_L$ (SEQ ID NO:83), 2C9B10 $V_L$ (SEQ ID NO:85), 2E2A6 $V_L$ (SEQ ID NO:87), 3C1A5 $V_L$ (SEQ ID NO:89), and 3C3E2 $V_L$ (SEQ ID NO:91). The amino acid sequence comprising the $V_H$ and $V_L$ chains of the α-SNAP-25 monoclonal antibody produced by the hybridomas disclosed in the present specification is as follows: 1D3B8 $V_H$ (SEQ ID NO:72), 2C9B10 $V_H$ (SEQ ID NO:74), 2E2A6 $V_H$ (SEQ ID NO:76), 3C1A5 $V_H$ (SEQ ID NO:78), 3C3E2 $V_H$ variant 1 (SEQ ID NO:80), 3C3E2 $V_H$ variant 2 (SEQ ID NO:82); 3C3E2 $V_H$ variant 2 (SEQ ID NO:133), 1 D3B8 $V_L$ (SEQ ID NO:84), 2C9B10 $V_L$ (SEQ ID NO:86), 2E2A6 $V_L$ (SEQ ID NO:88), 3C1A5 $V_L$ (SEQ ID NO:90), and 3C3E2 $V_L$ (SEQ ID NO:92). The amino acid sequences comprising the $V_H$ and $V_L$ CDR domains of the α-SNAP-25 monoclonal antibody produced by the hybridomas 1D3B8, 2C9B10, 2E2A6, 3C1A5, and 3C3E2 are given in Table 23.

TABLE 23

CDR Sequences of $V_H$ and $V_L$ domains from α-SNAP-25 Monoclonal Antibodies

| CDR | Sequence | Identified In | SEQ ID NO: |
|---|---|---|---|
| $V_H$ CDR 1 | TFTDHSIH | 2E2A6<br>2C9B10<br>3C1A5 | 93 |
| $V_H$ CDR 1 | TFTNYVIH | 3C3E2 | 94 |
| $V_H$ CDR 1 | IFTDHALH | 1D3B8 | 95 |
| $V_H$ CDR 2 | YIFPGNGNIEYNDKFKG | 2E2A6 | 96 |
| $V_H$ CDR 2 | YLFPGNGNFEYNEKFKG | 2C9B10<br>3C1A5 | 97 |
| $V_H$ CDR 2 | YINPYNDGSKYNEKFKG | 3C3E2 | 98 |
| $V_H$ CDR 2 | YIFPGNGNIEYNEKFKG | 1D3B8 | 99 |
| $V_H$ CDR 3 | KRMGY | 2E2A6<br>3C1A5 | 100 |
| $V_H$ CDR 3 | KKMDY | 2C9B10<br>1D3B8 | 101 |
| $V_H$ CDR 3 | ARMDY | 3C3E2var1 | 102 |
| $V_H$ CDR 3 | ARMGY | 3C3E2var2 | 134 |
| $V_H$ CDR 3 | ARHLANTYYYFDY | 3C3E2var3 | 135 |
| $V_L$ CDR 1 | RSSQSIVHSNGNTYLE | 1D3B8 | 103 |
| $V_L$ CDR 1 | RTTENIYSYFV | 2C9B10 | 104 |
| $V_L$ CDR 1 | KSSQSLLYTNGKTYLT | 2E2A6 | 105 |
| $V_L$ CDR 1 | KSSQSLLNTNGKTYLT | 3C1A5 | 106 |
| $V_L$ CDR 1 | RASQNIGNYLH | 3C3E2 | 107 |
| $V_L$ CDR 2 | KVSNRFS | 1D3B8 | 108 |
| $V_L$ CDR 2 | NAKSLAE | 2C9B10 | 109 |
| $V_L$ CDR 2 | LVSELDS | 2E2A6 | 110 |
| $V_L$ CDR 2 | LVSKLDS | 3C1A5 | 111 |
| $V_L$ CDR 2 | YASQSIS | 3C3E2 | 112 |
| $V_L$ CDR 3 | FQGSHVPPT | 1D3B8 | 113 |
| $V_L$ CDR 3 | QHHYGTPYT | 2C9B10 | 114 |
| $V_L$ CDR 3 | LQSAHFPFT | 2E2A6 | 115 |
| $V_L$ CDR 3 | LQSSHFPFT | 3C1A5 | 116 |
| $V_L$ CDR 3 | QQSDTWPLT | 3C3E2 | 117 |

Non-limiting examples of amino acid sequences comprising $V_H$ CDR domain variants of the α-SNAP-25 monoclonal antibody produced by the hybridomas disclosed in the present specification include $V_H$ CDR1 variant SEQ ID NO:118 for 1D3B8; $V_H$ CDR1 variant SEQ ID NO:119 for 2C9B10, 2E2A6 and 3C1A5 $V_H$; $V_H$ CDR1 variant SEQ ID NO:120 for 3C1A5 $V_H$ and 3C3E2 variant 3; $V_H$ CDR2 variant SEQ ID NO:121 for 1D3B8 and 2E2A6; $V_H$ CDR2 variant SEQ ID NO:122 for 2C9B10 and 3C1A5 $V_H$; $V_H$ CDR2 variant SEQ ID NO:123 for 3C1A5 $V_H$ and 3C3E2 variant 3; $V_H$ CDR3 variant MDY for 1D3B8 and 2C9B10; $V_H$ CDR3 variant MGY for 2E2A6 and 3C1A5 $V_H$; and $V_H$ CDR3 variant SEQ ID NO:124 for 3C1A5 $V_H$ and 3C3E2 variant 3. Non-limiting examples of amino acid sequences comprising $V_L$ CDR domain variants of the α-SNAP-25 monoclonal antibody produced by the hybridomas disclosed in the present specification include $V_L$ CDR1 variant SEQ ID NO:125 for 1D3B8; $V_L$ CDR1 variant SEQ ID NO:126 for 2C9B10; $V_L$ CDR1 variant SEQ ID NO:127 for 2E2A6; $V_L$ CDR1 variant SEQ ID NO:128 for 3C1A5; $V_L$ CDR1 variant SEQ ID NO:129 for 3C3E2; $V_L$ CDR2 variant KVS for 1D3B8; $V_L$ CDR2 variant NAK for 2C9B10; $V_L$ CDR2 variant LVS for 2E2A6; $V_L$ CDR2 variant YAT for 3C1A5; and $V_L$ CDR2 variant YAS for 3C3E2.

Example VIII

Development of α-SNAP-25 Polyclonal Antibodies that Selectively Bind a SNAP-25 Epitope Having a Free Carboxyl-Terminus at the $P_1$ Residue of the BoNT/A Cleavage Site Scissile Bond The following example illustrates how to make α-SNAP-25 polyclonal antibodies that can selectively bind to a SNAP-25 epitope having a carboxyl-terminus at the $P_1$ residue of the BoNT/A cleavage site scissile bond.

To develop α-SNAP-25 polyclonal antibodies that can selectively bind to a SNAP-25 having a carboxyl-terminus at the $P_1$ residue of the BoNT/A cleavage site scissile bond, the 10-residue peptide CGGGRIDEANQ (SEQ ID NO:46) was designed as a SNAP-25 cleavage product antigen. This peptide comprising a N-terminal Cysteine residue for conjugation to KLH, a G-spacer flexible spacer (GGG) linked to amino acids 191-197 of human SNAP-25 (SEQ ID NO:5) and has a carboxylated C-terminal glutamine. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Before the animals were immunized, naïve rabbits were first screened against cell lysates from candidate cell lines in a Western blot in order to identify animals that had no immunoreactivity to the proteins present in the cell lysates. Two pre-screened rabbits were immunized with this peptide, and after three immunizations in about eight weeks, the rabbits were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 μL aliquots and stored at −20° C. until needed.

A similar strategy based on other SNAP-25 antigens disclosed in the present specification is used to develop α-SNAP-25 polyclonal antibodies that can selectively bind to a SNAP-25 having a carboxyl-terminus at the $P_1$ residue of the BoNT/A cleavage site scissile bond. For example, the SNAP-25 antigen of SEQ ID NO:47 can be conjugated to KLH instead of the SNAP-25 antigen of SEQ ID NO:46. As another example, the amino acids 191-197 of human SNAP-25 from the SNAP-25 antigen of SEQ ID NO:38 can be replaced with SEQ ID NO:33, SEQ ID NO:34, SEQ ID NO:35, SEQ ID NO:36, SEQ ID NO:37, SEQ ID NO:39, SEQ ID NO:40, SEQ ID NO:41, SEQ ID NO:42, SEQ ID NO:43, or SEQ ID NO:44.

2. Screening for the Presence of α-SNAP-25 Polyclonal Antibodies.

To determine the presence of α-SNAP-25 polyclonal antibodies that can selectively bind to a SNAP-25 antigen having a carboxyl-terminus at the $P_1$ residue of the BoNT/A cleavage site scissile bond, comparative ELISA and cell-based cleavage assays were performed using the extracted rabbit serum as described in Example III. The serum from both rabbits contained α-SNAP-25 polyclonal antibodies that can selectively bind to a SNAP-25 antigen having a carboxyl-terminus at the $P_1$ residue of the BoNT/A cleavage site scissile bond. The α-SNAP-25 rabbit polyclonal antibodies were designated as NTP 22 and NTP 23.

3. Purification of α-SNAP-25 Polyclonal Antibodies.

To purify α-SNAP-25 polyclonal antibodies that can selectively bind to a SNAP-25 antigen having a carboxyl-terminus at the $P_1$ residue of the BoNT/A cleavage site scissile bond, NTP 22 and NTP 23 antibodies from rabbit serum were purified using affinity columns containing the SNAP-25 antigen of SEQ ID NO:46.

4. Evaluation of Binding Specificity of α-SNAP-25 Polyclonal Antibodies.

To evaluate binding specificity of an α-SNAP-25 polyclonal antibody that can selectively bind to a SNAP-25 antigen having a carboxyl-terminus at the $P_1$ residue of the BoNT/A cleavage site scissile bond, purified NTP 22 and NTP 23 α-SNAP-25 polyclonal antibodies were used to detect cleavage product using the cell-based activity assay, immunocytochemistry and immunoprecipitation as described in Example III. The cell-based cleavage assay, immunocytochemistry analysis and immunoprecipitation analysis all indicated that NTP 22 and NTP 23 α-SNAP-25 polyclonal antibodies did not cross-react with uncleaved SNAP-25. Thus both NTP 22 and NTP 23 have high binding specificity for the SNAP-$25_{197}$ cleavage product that allows for the preferential recognition of this cleavage product relative to the SNAP-$25_{206}$ uncleaved substrate. Affinity for the antigens can be determined using SPR in the BiAcore as described in Example III.

Example IX

Component and Condition Preparation for a Sandwich ELISA

The following example illustrates how to identify and prepare the components and conditions necessary to perform a sandwich ELISA useful for conducting immuno-based methods of detecting retargeted endopeptidase activity by detecting a SNAP-25 cleavage product using an α-SNAP-25 monoclonal antibody specific for a SNAP-25 having a carboxyl-terminus at the $P_1$ residue of the BoNT/A cleavage site scissile bond.

1. Preparation of Cell Lysates from Cells Treated with Re-Targeted Endopeptidase.

To obtain a re-targeted endopeptidase treated cell lysate for analysis, a suitable density of cells from a stock culture of Neuro-2a was seeded into a T175 flask containing 50 mL of a serum-free medium containing Minimum Essential Medium, 2 mM GlutaMAX™ I with Earle's salts, 1×B27 supplement, 1×N2 supplement, 0.1 mM Non-Essential Amino Acids, 10 mM HEPES. These cells were incubated in a 37° C. incubator under 5% carbon dioxide until the cells differentiated, as assessed by standard and routine morphological criteria, such as growth arrest and neurite extension (approximately 2 to 3 days). As a control, a suitable density of cells from a stock culture of Neuro-2a was seeded into a T175 flask containing 50 mL of an appropriate growth medium (Table 1). These undifferentiated control cells were grown in a 37° C. incubator under 5% carbon dioxide until 50% confluence was reached (approximately 18 hours). The media from both differentiated and undifferentiated control cultures was aspirated from each well and replaced with fresh media containing either 0 (untreated sample) or 10 nM of a re-targeted endopeptidase. After an overnight incubation, the cells were washed and the cells harvested by lysing in freshly prepared Triton X-100 Lysis Buffer (50 mM HEPES, 150 mM NaCl, 1.5 mM $MgCl_2$, 1 mM EGTA, 1% Triton X-100) at 4° C. for 30 minutes with constant agitation. Lysed cells were centrifuged at 4000 rpm for 20 min at 4° C. to eliminate debris using a bench-top centrifuge. The protein concentrations of cell lysates were measured by Bradford assay.

2. Preparation and Identification of Sandwich ELISA Components.

To identify an appropriate capture antibody-detection antibody pair an ECL sandwich ELISA analysis was conducted on twenty-six different combinations of capture and detection antibody pairs comprising eleven different α-SNAP-25 capture antibodies and seven different α-SNAP-25 detection antibodies (Table 12). The α-SNAP-25 antibodies used were 2E2A6 and 3C1A5 α-SNAP-25 mouse monoclonal antibodies disclosed in the present specification, SMI-81, MC-6050, and MC-6053 α-SNAP-25 mouse monoclonal antibodies disclosed in the present specification, NTP 23 α-SNAP-25 rabbit polyclonal antibodies disclosed in the present specification, S9684 α-SNAP-25 rabbit polyclonal antibodies (Sigma, St. Louis, Mo.), H-50 α-SNAP-25 rabbit polyclonal antibodies (Santa Cruz Biotechnology, Inc., Santa Cruz, Calif.), C-18 α-SNAP-25 goat polyclonal antibodies (Santa Cruz Biotechnology, Inc., Santa Cruz, Calif.), N-19 α-SNAP-25 goat polyclonal antibodies (Santa Cruz Biotechnology, Inc., Santa Cruz, Calif.), and SP12 α-SNAP-25 mouse polyclonal antibodies (Santa Cruz Biotechnology, Inc., Santa Cruz, Calif.).

To prepare the capture antibody solution, the α-SNAP-25 monoclonal antibodies contained in the ascites from hybridoma cell lines 2E2A6 and 3C1A5 as well as the α-SNAP-25 MC-6050 and MC-6053 monoclonal antibodies were purified using a standard Protein A purification protocol. All other α-SNAP-25 antibodies were purchased as purified antibodies.

To prepare the detection antibody solution, the appropriate α-SNAP-25 antibody was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 μL of distilled water reconstituted MSD SULFO-TAG™ stock solution to 200 μL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed.

To prepare the solid phase support comprising the capture antibody that is specific for a SNAP-25 cleavage product, approximately 5 μL of the appropriate α-SNAP-25 monoclonal antibody solution (20 μg/mL in 1×PBS) is added to each well of a 96-well MSD High Bind plate and the solution is allowed to air dry in a biological safety cabinet for 2-3 hours in order to liquid evaporate the solution. The capture antibody-bound wells were then blocked by adding 150 μL of Blocking Buffer comprising 2% Amersham Blocking Reagent (GE Life Sciences, Piscataway, N.J.) and 10% goat serum (VWR, West Chester, Pa.) at room temperature for 2 hours. Blocked plates were sealed and stored at 4° C. until needed.

To detect the presence of a cleaved SNAP-25 cleavage product by ECL sandwich ELISA analysis, the Blocking Buffer from stored plates was aspirated from the wells, 25 μL of a lysate from cells treated with re-targeted endopeptidase, as described above, was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaurate). After washing, 25 μl of 5 μg/mL detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature at room temperature for 1 hour with shaking. After detection antibody incubation, the wells were washed three times with 200 μL 1×PBS, 0.1% TWEEN-20® (polyoxyethylene (20) sorbitan monolaurate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). A ratio was calculated by dividing the signal obtained at the 10 nM dose for each antibody-pair by the signal obtained at the 0 nM dose for each antibody-pair (Table 24). These results indicated that among the twenty-six different combinations of antibody pairs tested, only three antibody pairs had signal-to-noise ratios above 10:1 for the higher dose tested: Pair No. 1 (2E2A6 mouse mAb and S9684 rabbit pAb), Pair No. 4 (3C1A5 mouse mAb and S9684 rabbit pAb), and Pair No. 18 (S9684 rabbit pAb and 2E2A6 mouse mAb). Antibody Pair 1 was chosen for further assay development.

TABLE 24

Screening of α-SNAP-25 Antibody Combinations

| Antibody Pair No. | Capture Antibody | Detection Antibody | Detection SNAP-25 cleavage product | Detection SNAP-25 uncleaved substrate | Signal/Noise Ratio (10 nM/0 nM) |
|---|---|---|---|---|---|
| 1 | 2E2A6 mouse mAb | S9684 rabbit pAb | Yes | No | 26.6:1 |
| 2 | 2E2A6 mouse mAb | N-19 goat pAb | Yes | No | 7.3:1 |
| 3 | 2E2A6 mouse mAb | H-50 rabbit pAb | Yes | No | 0.9:1 |
| 4 | 3C1A5 mouse mAb | S9684 rabbit pAb | Yes | No | 12.1:1 |
| 5 | 3C1A5 mouse mAb | N-19 goat pAb | Yes | No | 1.9:1 |
| 6 | 3C1A5 mouse mAb | H-50 rabbit pAb | Yes | No | 0.9:1 |
| 7 | C-18 goat pAb | S9684 rabbit pAb | No | No | 0.8:1 |
| 8 | C-18 goat pAb | N-19 goat pAb | No | No | 0.9:1 |
| 9 | C-18 goat pAb | H-50 rabbit pAb | No | No | 0.9:1 |
| 10 | H-50 rabbit pAb | 2E2A6 mouse mAb | Yes | No | 0.9:1 |
| 11 | H-50 rabbit pAb | C-18 goat pAb | No | No | 1.0:1 |
| 12 | N-19 goat pAb | 2E2A6 mouse mAb | Yes | No | 0.9:1 |
| 13 | N-19 goat pAb | C-18 goat pAb | No | No | 1.1:1 |
| 14 | NTP 23 rabbit pAb | N-19 goat pAb | Yes | No | 1.2:1 |
| 15 | NTP 23 rabbit pAb | C-18 goat pAb | No | No | 1.1:1 |
| 16 | NTP 23 rabbit pAb | SP12 mouse pAb | Yes | No | 1.3:1 |
| 17 | NTP 23 rabbit pAb | H-50 rabbit pAb | Yes | No | 1.1:1 |
| 18 | S9684 rabbit pAb | 2E2A6 mouse mAb | Yes | No | 21.3:1 |
| 19 | S9684 rabbit pAb | C-18 goat pAb | No | No | 0.7:1 |
| 20 | S9684 rabbit pAb | SMI-81mouse mAb | Yes | Yes | 1.2:1 |
| 21 | SMI-81 mouse mAb | S9684 rabbit pAb | Yes | Yes | 1.1:1 |
| 22 | SMI-81 mouse mAb | N-19 goat pAb | Yes | Yes | 1.0:1 |
| 23 | SMI-81 mouse mAb | C-18 goat pAb | No | No | 0.8:1 |
| 24 | SP12 mouse pAb | C-18 goat pAb | No | No | 1.0:1 |
| 25 | MC-6050 mouse mAb | S9684 rabbit pAb | Yes | Yes | 5.0:1 |
| 26 | MC-6053 mouse mAb | S9684 rabbit pAb | Yes | Yes | 7.1:1 |

Example X

Immuno-Based Method of Detecting Re-Targeted Endopeptidase Having a BoNT/A Light Chain Enzymatic Activity Using ECL Sandwich ELISA The following example illustrates immuno-based methods of detecting retargeted endopeptidase activity by detecting a SNAP-25 cleavage product using an α-SNAP-25 monoclonal antibody specific for a SNAP-25 cleavage product having a carboxyl-terminus at the $P_1$ residue of the BoNT/A cleavage site scissile bond by ECL sandwich ELISA.

To prepare a lysate from cells treated with a re-targeted endopeptidase having BoNT/A light chain enzymatic activity, a suitable density of cells from an established cell line was plated into the wells of 96-well tissue culture plates containing 100 μL of the appropriate media. These cells were incubated in a 37° C. incubator under 5% carbon dioxide for about 24 hours. The media from the cells was aspirated from each well and replaced with fresh media containing either 0 (untreated sample) or one of the doses determined from a dose-response experiment for that re-targeted endopeptidase. After 24 hours incubation, the cells were washed and harvested.

To prepare the α-SNAP-25 capture antibody solution, the α-SNAP-25 monoclonal antibody contained in the ascites from hybridoma cell line 2E2A6 was purified using a standard Protein A purification protocol To prepare the α-SNAP-25 detection antibody solution, α-SNAP-25 rabbit polyclonal antibody S9684 (Sigma, St. Louis, Mo.) was conjugated to Ruthenium(II)-tris-bipyridine-(4-methylsulfonate) NHS ester labeling reagent (Meso Scale Discovery, Gaithersburg, Md.) according to the manufacturer's instructions (Meso Scale Discovery, Gaithersburg, Md.). The conjugation reaction, purification of labeled α-SNAP-25 antibody, concentration determination and storage were as described in Example VI.

To prepare the solid phase support comprising the capture antibody that is specific for a SNAP-25 cleaved product, approximately 5 μL of α-SNAP-25 monoclonal antibody 2E2A6 solution (20 μg/mL in 1×PBS) was added to each well of a 96-well MSD High Bind plate and the solution is allowed to air dry in a biological safety cabinet for 2-3 hours in order to liquid evaporate the solution. The capture antibody-bound wells were then blocked and used directly to detect retargeted endopeptidase activity.

To detect the presence of a cleaved SNAP-25 product by ECL sandwich ELISA analysis, the Blocking Buffer from stored plates was aspirated from the wells, 25 μL of a lysate from cells treated with re-targeted endopeptidase was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaurate). After washing, 25 μL of 5 μg/mL detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature at room temperature for 1 hour with shaking. After detection antibody incubation, the wells were washed three times with 200 μL 1×PBS, 0.1% TWEEN-20® (polyoxyethylene (20) sorbitan monolaurate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The collected data was analyzed and the $EC_{50}$ calculated as described in Example VI. For opioid re-targeted endopeptidases, these results indicated that on average 1.0 nM of Noc/A at the $EC_{50}$ was detected (a range of about 0.3 nM to about 2.0 nM) with a signal-to-noise ratio for the lower asymptote of about 15:1 to about 20:1 and a signal-to-noise ratio for the upper asymptote of about 180:1 to about 300:1.

Example XI

Immuno-Based Method of Detecting Re-Targeted Endopeptidase Activity Using CL Sandwich ELISA The following example illustrates immuno-based methods of detecting retargeted endopeptidase activity by detecting a SNAP-25 cleavage product using an α-SNAP-25 monoclonal antibody specific for a SNAP-25 having a carboxyl-terminus at the $P_1$ residue of the BoNT/A cleavage site scissile bond by CL sandwich ELISA.

Lysate from cells treated with a re-targeted endopeptidase and the α-SNAP-25 capture antibody solution will be prepared as described in Example VII.

To prepare the α-SNAP-25 detection antibody solution, α-SNAP-25 polyclonal antibody S9684 (Sigma, St. Louis, Mo.) will be conjugated to Horseradish peroxidase (HRP) according to the manufacturer's instructions (Pierce Biotechnology, Inc., Rockford, Ill.). The conjugation reaction will be performed by adding to 500 μL of 1 mg/mL α-SNAP-25 polyclonal antibodies to a vial containing lyophilized activated peroxidase, mixing the components, and then adding 10 μL of sodium cyanoborohydride. This reaction mixture will be incubated at room temperature for 1 hour in a fume hood. After quenching the reaction, the labeled antibodies will be purified using a standard spin column protocol and the protein concentration will be determined using a standard colorimetric protein assay. The absorbance of the α-SNAP-25 polyclonal antibody/HRP conjugate will be measured at 455 nm using a spectrophotometer to determine the concentration in moles per liter. The α-SNAP-25 detection antibody solution will be stored at 4° C. until needed.

To prepare the solid phase support comprising the α-SNAP-25 capture antibody that is specific for the SNAP-25 cleaved product, approximately 100 μL of α-SNAP-25 monoclonal antibody 2E2A6 solution (1 mg/mL in 1×PBS) will be added to each well of a 96-well Greiner white plate and the plates will be incubated at 4° C. overnight, and then any excess antibody solution will be discarded. The capture antibody-bound wells will then be blocked by adding 150 μL of Blocking Buffer comprising 2% Amersham Blocking Reagent (GE Life Sciences, Piscataway, N.J.) and 10% goat serum (VWR, West Chester, Pa.) at room temperature for 1 hour. The blocking buffer will be discarded and the plates will be blotted dry on paper towels by inverting and tapping. The capture antibody-bound wells will then be blocked and will be used directly to detect retargeted endopeptidase activity.

To detect the presence of a cleaved SNAP-25 product by CL sandwich ELISA analysis, 50 μL of a lysate from cells treated with retargeted-endopeptidase will be added to each well, the plate will be sealed, and the sealed plate will be incubated on a shaker rotating at 500 rpm at 4° C. for 2-4 hours to overnight. Plate wells will be washed three times by aspirating the cell lysate and rinsing each well three times with 200 μl 1×PBS, 0.05% TWEEN-20® (polyoxyethylene (20) sorbitan monolaurate). After washing, 100 μL of 1 mg/mL α-SNAP-25 polyclonal antibody/HRP detection antibody solution comprising 2% Amersham Blocking Reagent in 1×PBS, 0.1% TWEEN-20® (polyoxyethylene (20) sorbitan monolaurate) will be added to each well, the plate will be sealed, and the sealed plate will be incubated on a shaker rotating at 650 rpm at room temperature for 1 hour. After detection antibody incubation, the wells will be washed three times with 200 μl 1×PBS, 0.05% TWEEN-20® (polyoxyethylene (20) sorbitan monolaurate). After washing 100 μl of SuperSignal ELISA Pico 1:1 mixture (Pierce Biotechnology, Inc., Rockford, Ill.) will be added to each well and the plates will be read using a luminometer (Molecular Devices, Sunnyvale, Calif.) at 395 nm. The collected data will be analyzed and the $EC_{50}$ will be calculated as described in Example VI.

Example XII

Immuno-Based Method of Detecting Re-Targeted Endopeptidase Activity Using Multiplex ECL Sandwich ELISA The following example illustrates multiplex immuno-based methods of detecting retargeted endopeptidase activity by detecting a SNAP-25 cleavage product using an α-SNAP-25 monoclonal antibody specific for a SNAP-25 cleavage product and a second antibody pair for a different protein.

A re-targeted endopeptidase potency assay can be performed using a multiplex ECL sandwich ELISA. Such an assay is described in companion patent application Ester Fernandez-Salas, et al., Immuno-Based Botulinum Toxin Serotype A Activity Assays, U.S. patent application Ser. No. 12/403,531, which is hereby incorporated by reference in its entirety, and can be used using the cell lines and re-targeted endopeptidases and the corresponding cell lines disclosed in the present specification.

Example XIII

Immuno-Based Method of Detecting Re-Targeted Endopeptidase Activity Using Multiplex EC Sandwich ELISA The following example illustrates multiplex immuno-based methods of detecting retargeted endopeptidase activity by detecting a SNAP-25 cleavage product using an α-SNAP-25 monoclonal antibody specific for a SNAP-25 cleavage product and a second antibody pair for a different protein.

A re-targeted endopeptidase potency assay can be performed using a multiplex EC sandwich ELISA. Such an assay is described in companion patent application Ester Fernandez-Salas, et al., Immuno-Based Botulinum Toxin Serotype A Activity Assays, U.S. patent application Ser. No. 12/403,531, which is hereby incorporated by reference in its entirety, and can be used using the cell lines and re-targeted endopeptidases and the corresponding cell lines disclosed in the present specification.

Example XIV

Immuno-Based Method to Detect Nanomolar Amounts of Retargeted Endopeptidases The following example illustrates how to perform immuno-based methods of detecting Nanomolar amounts of retargeted endopeptidase activity.

1. Immuno-Based Method of Detecting Retargeted Endopeptidases Using ECL Sandwich ELISA.

To prepare a lysate from cells treated with a retargeted endopeptidase, approximately 50,000 to 150,000 cells from an established cell line suitable for the assay were plated into the wells of 96-well tissue culture poly-D-lysine plates containing 100 μL of the appropriate media (see Examples I and II). These cells were incubated in a 37° C. incubator under 5% carbon dioxide for 24 hours. The media from the cells was aspirated from each well and replaced with fresh media containing either 0 (untreated sample) and the appropriate dose response as described for each retargeted endopeptidase in this application. After a 24 hour incubation, the cells were washed and harvested or incubated for an additional two days without retargeted endopeptidase before harvesting. To harvest the cells, the medium was aspirated, washed with 1×PBS, and lysed by adding 30 μL of Lysis Buffer comprising 50 mM HEPES, 150 mM NaCl, 1.5 mM $MgCl_2$, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

The α-SNAP-25 capture antibody solution, the α-SNAP-25 detection antibody solution, and the solid phase support comprising the capture antibody that is specific for a SNAP-25 cleaved product were prepared as described in Example VII.

To detect the presence of a cleaved SNAP-25 product by ECL sandwich ELISA analysis, the Blocking Buffer from stored plates was aspirated, 25-30 μL of a lysate from cells treated with retargeted endopeptidase was added to each well and the plates were incubated at 4° C. for either 2 hours or 24 hours. Plate wells were washed three times by aspirating the cell lysate and rinsing each well three times with 200 μL 1×PBS, 0.1% TWEEN-20® (polyoxyethylene (20) sorbitan monolaurate). After washing, 25 μL of 5 μg/mL α-SNAP-25 detection antibody solution comprising 2% Amersham Blocking Reagent in 1×PBS, 0.1% TWEEN-20® (polyoxyethylene (20) sorbitan monolaurate) was added to each well, the plate was sealed, and the sealed plate was incubated at room temperature for 1 hour with shaking. After α-SNAP-25 detection antibody incubation, the wells were washed three times with 200 μL 1×PBS, 0.1% TWEEN-20® (polyoxyethylene (20) sorbitan monolaurate). After washing, the plates were processed, collected data was analyzed, and the $EC_{50}$ calculated as described in Example VI. These results indicated that on average 1.0 nM of Noc/A at the $EC_{50}$ was detected when using SK-N-DZ clonal cell line #3 cells (a range of about 0.3 nM to about 2.0 nM) with a signal-to-noise ratio for the upper asymptote of about 20:1 to about 300:1. Moreover, on average 3.7 nM of Noc/A at the $EC_{50}$ was detected when using AGN P33 clonal cell line #6 cells (a range of about 2.0 nM to about 5.5 nM) with a signal-to-noise ratio for the upper asymptote of about 20:1 to about 500:1. For the SK12 cells that are specific for the retargeted endopeptidase containing a dynorphin A ligand, on average 8.4 nM of Dyn/A at the $EC_{50}$ was detected when using SK12 cells (a range of about 4.5 nM to about 10.0 nM) with a signal-to-noise ratio for the upper asymptote of about 10:1 to about 20:1. Additionally, on average 8.8 nM of TVEMP-galanin at the $EC_{50}$ was detected when using Neuro-2a clonal cell line #7 cells (a range of about 5.0 nM to about 15.5 nM) with a signal-to-noise ratio for the upper asymptote of about 20:1 to about 200:1. This method can also be performed in a multiplex fashion as described in Example IX.

2. Immuno-Based Method of Detecting Retargeted Endopeptidases Using CL Sandwich ELISA.

Lysate from cells treated with a retargeted endopeptidase and the α-SNAP-25 capture antibody solution will be prepared as described in Example VII. The α-SNAP-25 detection antibody solution and solid phase support comprising the capture antibody that is specific for a SNAP-25 cleaved product will be prepared as described in Example VIII.

To detect the presence of a cleaved SNAP-25 product by CL sandwich ELISA analysis, 100 μL of a lysate from cells treated with a retargeted endopeptidase will be added to each well, the plate will sealed, and the sealed plate will be incubated on a shaker rotating at 500 rpm at 4° C. for either 2 hours or 24 hours. Plate wells will be washed three times by aspirating the cell lysate and rinsing each well three times with 200 μL 1×PBS, 0.05% TWEEN-20® (polyoxyethylene (20) sorbitan monolaurate). After washing, 100 μL of 1 mg/mL α-SNAP-25 polyclonal antibody/HRP detection antibody solution comprising 2% Amersham Blocking Reagent in 1×PBS, 0.1% TWEEN-20® (polyoxyethylene (20) sorbitan monolaurate) will be added to each well, the plate will be sealed, and the sealed plate will be incubated on a shaker rotating at 650 rpm at room temperature for 1 hour. After detection antibody incubation, the wells will be washed three times with 200 μL 1×PBS, 0.05% TWEEN-20® (polyoxyethylene (20) sorbitan monolaurate). After washing 100 μL of SuperSignal ELISA Pico 1:1 mixture (Pierce Biotechnology, Inc., Rockford, Ill.) will be added to each well and the plates will be read using a luminometer (Molecular Devices, Sunnyvale, Calif.) at 395 nm. The collected data will be analyzed and the $EC_{50}$ will be calculated as described in Example VI. This method can also be performed in a multiplex fashion as described in Example IX.

Example XV

Immuno-Based Method to Detect Neutralizing α-Retargeted-Endopeptidase Antibodies The following example illustrates how to perform an immuno-based method that can detect the presence of neutralizing α-Noc/A antibodies.

Noc/A, is currently being evaluated for treating painful conditions, some of them chronic. With repeated long-term treatment of Noc/A, a patient may develop neutralizing α-Noc/A antibodies to the retargeted endopeptidase leading to immunoresistance. Neutralizing α-Noc/A antibodies will inhibit retargeted endopeptidase activity by stopping the retargeted endopeptidase's uptake into neuronal and other target cells by binding to the targeting ligand and/or the translocation domain ($H_N$) of the retargeted endopeptidase. There is not established assay to determine the presence of the neutralizing α-Noc/A antibodies in patient's blood. It would be more cost and time efficient if a cell-based assay could be developed to detect neutralizing antibodies in patients treated with retargeted endopeptidases.

To detect the presence or absence of neutralizing α-Noc/A antibodies, the immuno-based methods of determining retargeted endopeptidase activity disclosed in the present specification can be used. One way is to determine the amount of SNAP-25 cleavage product present after treatment with various concentrations of Noc/A using a Western blot detection method, the other way was to use an ECL sandwich ELISA detection method.

To prepare a sample comprising neutralizing α-Noc/A antibodies, serum was isolated from blood of a monkey immunized with Noc/A and the antibodies were affinity purified. Rabbits were also immunized with the nociceptin variant peptide, the targeting ligand present in the Noc/A molecule, their serum collected, and the antibodies affinity purified (anti-nociceptin polyclonal antibodies).

To prepare a lysate from cells treated with a sample comprising Noc/A, SK-N-DZ clonal cell line #3 cells and AGN P33 clonal cell line #6 cells were seeded in poly-D-lysine 96-well plates for 16-18 hours. Anti-nociceptin pAb at 0-3 μg/mL was diluted in RPMI SFM (with N2, B27, and NGF supplements) containing 1 nM of Noc/A and the mix was pre-incubated at room temperature for 1 hour. Then the solutions were added to the cells and incubated for 24 h before performing the ECL ELISA assay. This anti-nociceptin variant antibody totally blocked 1 nM Noc/A uptake at 1 μg/mL (>90% inhibition) on both cell lines. Anti-Noc/A monkey polyclonal antibody was also assayed these cell lines. Cells were plated in a 96-well poly-D-lysine plate at 100,000 cells per well for 24 hours in RPMI growth media supplemented with N2, B27, and NGF. Anti-Noc/A polyclonal antibodies at 0-20 μg/mL was diluted in media containing 1 nM Noc/A and the mix was pre-incubated at room temperature for 1 h. Then the mix was added to the cells and incubated for 24 h before performing the ECL ELISA assay. Up to 60% inhibition was seen at the higher concentrations of 6-20 μg/mL of anti-Noc/A pAb on the SK-N-DZ cell line and about 30% on the AGN P33 clonal cell line #6 cell line. This may due to the fact that the anti-Noc/A polyclonal antibodies is not specific to the binding site and contains other antibodies that bind other parts of the molecule producing only partial blocking at the concentrations tested. Higher concentrations maybe needed to achieve complete blocking.

To detect the presence of a cleaved SNAP-25 product by Western blot analysis, the media will aspirated from each well, the cells suspended in 50 μL of SDS-PAGE loading buffer, and then heated to 95° C. for 5 minutes. An aliquot from each harvested sample will be analyzed by Western blot as described in Example I, except that harvested samples will be separated by SDS-PAGE using 12% 26-well Criterion gels (Bio-Rad Laboratories, Hercules, Calif.), and the rabbit polyclonal α-SNAP-$25_{197}$ antibody serum will be used as the primary antibody (see Example V). The results will reveal the lowest concentration of retargeted endopeptidase that will produce a detectable band of SNAP-25 cleavage product in the Western blot.

To detect the presence of a cleaved SNAP-25 product by ECL Sandwich ELISA, the media was removed from each well and the cells were lysed as described in Example VI. The α-SNAP-25 capture antibody solution, the α-SNAP-25 detection antibody solution, and the α-SNAP-25 solid phase support were prepared as described in Example VIII. Supernatants were transferred to the α-SNAP-25 solid phase support and an ECL sandwich ELISA assay was performed as detailed in Example VI. The collected data was analyzed and the $EC_{50}$ calculated as described in Example VI, except that the $EC_{50}$ is the serum dilution needed to inhibit the activity of the retargeted endopeptidase to ½ its maximum and the ratio of maximal signal ($Signal_{Max}$) to minimum signal ($Signal_{Min}$) was obtained by dividing the SNAP-25 cleavage product signal obtained with the highest dilution of antibody by the signal obtained with the lowest antibody dilution.

The results indicate that the presence of neutralizing α-Noc/A antibodies in monkey serum and the presence of α-nociceptin variant antibodies from rabbit could be detected. The activity of the Noc/A molecule incubated in affinity purified antibodies from the immunized animal decreased as the antibody dilution decreased. The same assay will be performed with the Dyn/A and the TVEMP-galanin compounds utilizing the cell lines specific for each compound to be tested.

Example XV

Development of a Cell-Based Assay for a Galanin Re-Targeted Endopeptidase

The following example illustrates how to identify established cell lines possessing the re-targeted endopeptidase uptake capacity required to develop a cell-based potency assay.

1. Growth of Stock Culture of Candidate Cell Lines.

To grow the cell lines, a suitable density of cells from the cell line being tested were plated in a 162 $cm^2$ tissue culture flask containing 30 mL of a suitable growth medium (see Table 25), and grown in a 37° C. incubator under 5% or 10% carbon dioxide until cells reached the desired density.

TABLE 25

| Summary table of all cell lines and their respective media. | | |
|---|---|---|
| Cell type; description; source | Complete Media (CM) All from Invitrogen (unless otherwise specified) | Serum Free media (SFM) All from Invitrogen, (unless otherwise specified) |
| SiMa (Human neuroblastoma cell line, DSMZ# ACC 164, Braunschweig, Germany) SiMa H1 (cloned cell line from SiMa cells) | RPMI 1640 (90%) Fetal Bovine Serum (FBS, 10%) NEAA (0.1 mM), HEPES (10 mM), Sodium Pyruvate (1 mM) Penicillin (100 U per ml) Streptomycin (100 μg per ml), | RPMI 1640 (90%) NEAA (0.1 mM), HEPES (10 mM), Sodium Pyruvate (1 mM) Penicillin (100 U per ml) Streptomycin (100 μg per ml) N2 supplement (1x) B27 supplement (1x) |
| Neuro-2a (Mouse neuroblastoma: (ATCC#CCI131, Manassas, VA,) | Earle's MEM (90%) Fetal Bovine Serum 10%) NEAA (0.1 mM), HEPES (10 mM), Sodium Pyruvate (1 mM), Penicillin (100 U per ml), Streptomycin (100 μg per ml) | EMEM (90%) NEAA (0.1 mM), HEPES (10 mM), Sodium Pyruvate (1 mM), Penicillin (100 U per ml), Streptomycin (100 μg per ml) |
| PC-12 Rat Pheochromocytoma (ATCC # CRL-1721) | RPMI 1640 (90%) Dialyzed FBS (5%) Horse serum (10%) HEPES (10 mM) Sodium Pyruvate (1 mM) D-glucose (0.5%, Sigma) Penicillin (100 U per ml); Streptomycin (100 μg per ml) N2 supplement (1x) | Differentiation media: RPMI 1640 (90%) HEPES (10 mM) Sodium Pyruvate (1 mM) D-glucose (0.5%, Sigma) Penicillin (100 U per ml); Streptomycin (100 μg per ml) N2 supplement (1x) Bovine serum albumin (0.2% w/v) NGF (50 ng per ml, Promega) |
| P19 Mouse embryonic carcinoma (ATCC #CRL-1825) | Alpha MEM (90%) Bovine Calf Serum (7.5%) FBS (2.5%) Penicillin (100 U per ml); Streptomycin (100 μg per ml) | Alpha MEM (90%) FBS (2.5%) Penicillin (100 U per ml); Streptomycin (100 μg per ml) |

NEAA: Non-Essential Amino Acids,
MEM: Minimum Essential Media.
DMEM: Dulbecco's MEM.
EMEM—Earle's MEM.
Please note PC-12 cells were differentiated in differentiation media and not SFM.

2. Screening of Commercial Cell Lines for Sensitivity to Galanin TVEMP-Galanin Compounds Commercial cell lines were screened for their sensitivity to TVEMP-galanin compounds as measured by the cleavage of SNAP25 after treatment with the corresponding compounds. Various TVEMP-galanin compounds were used for screening and testing. PC-12, Neuro-2a, SiMa, and P19 cells were plated in serum free media for three days or in CM for one day. These differentiated and naïve cells were treated for 18 hours with TVEMP-galanin Batch A at concentrations of 0 and 75 nM. TVEMP-galanin Batch A showed activity in both PC-12 and Neuro-2a cells as seen by the increased presence of cleaved SNAP25, and Neuro-2a cells in the differentiated condition are more sensitive to TVEMP compounds with galanin ligand, than the naïve cells. The rank order in activity of the cells shows PC-12 have the most activity, followed by Neuro-2a and finally SiMa cells. It was necessary to determine if the uptake was specific for these galanin-retargeted compounds and therefore it was important to test the cells with other compounds that do not contain the galanin ligand. Noc/A is a retargeted compound which contains a nociceptin variant ligand, and $LH_N/A$ (a negative control) a compound that lacks the binding domain. The uptake of $LH_N/A$ is non-specific and should have significantly lower activity than the TVEMP-galanin compound if the cell line possess specific uptake for the retargeted compound. The Noc/A compound has been shown previously to have specific uptake in the SiMa cells and will be used as a baseline to test the cell lines. A favorable cell line should have low uptake of the $LH_N/A$ and the Noc/A compound and high uptake of the TVEMP-galanin compound. Table 26 displays the results from this experiment.

TABLE 26

Screening of PC-12, Neuro-2a, and SiMa cells at different conditions using TVEMP-galanin.

| | | TVEMP-galanin Batch A | TVEMP-galanin Batch B | $LH_N/A$ | Noc/A |
|---|---|---|---|---|---|
| | Conc. (mg/mL) | 0.168 | 0.175 | 1.63 | 1.00 |
| $EC_{50}$ | PC-12, naïve | 73.4 ± 10.7 | 105.6 ± 16.0 | >200 | 72.9 ± 26.9 |
| Values | SiMa, naïve | 138.6 ± 43.9 | 133.8 ± 24.2 | >300 | 48.3 ± 18.1 |
| (nM) | Neuro-2a, naïve | 122.4 ± 15.7 | 116 ± 17.5 | >200 | >150 |
| | SiMa, Dif O/N | >400 | >150 | >400 | 16.1 ± 11.9 |

TABLE 26-continued

Screening of PC-12, Neuro-2a, and SiMa cells at different conditions using TVEMP-galanin.

| | TVEMP-galanin Batch A | TVEMP-galanin Batch B | $LH_N/A$ | Noc/A |
|---|---|---|---|---|
| Neuro-2a Dif 4 d | | 34.5 ± 7.5 | 39.7 ± 5.6 | 105.9 ± 44.3 |
| SiMa, Dif 4 d | 101.8 ± 20.5 | 65.3 ± 7.8 | >150 | 88.7 ± 23.3 |

TVEMP-galanin Batches A and B, and $LH_N/A$ and Noc/A controls testing on various cell lines and growth/differentiation conditions. Summary chart showing details of each compound tested plus $EC_{50}$ values.

The results show that TVEMP-galanin Batch A and TVEMP-galanin Batch B had plots or $EC_{50}$ values that were either similar to, or only 1-2 fold more active than the negative controls in the cell lines tested. This data implies that the native cells are not sensitive enough and that these cells will have to be transfected with the plasmids encoding galanin receptor proteins GalR1 or GalR2 receptors.

3. Stable Transfection of PC-12, Neuro-2a, and SiMa Cells with GalR.

One day before transfection, cells were seeded at densities of $0.5\times10^6$ cells/well in either a 6-well Collagen IV coated plate (Cat#354554: BD Biosciences) (SiMa, PC-12) or a 6 well Costar plate (Cat#3516: Corning) (Neuro-2a). Transfections were performed by diluting 12 µl of Lipofectamine™ 2000 (Cat #52758, Invitrogen) in 250 µl Opti-MEM® I Reduced Serum Medium (Cat#3195, Invitrogen) followed by incubation at room temperature for 5 min. Four micrograms of GalR plasmid DNA was mixed with 0.4 µg pAdVantage™ vector (1 mg per ml, Cat#E1711, Promega) in 250 µl Opti-MEM® I Reduced Serum Media for 5 minutes. After 5 minutes of incubation, the diluted Lipofectamine™ 2000 and the diluted plasmids DNA were mixed and incubated for an additional 20 min at room temperature, for complex formation. In the meantime, the cells were washed with OPTI-MEM® and 0.5 ml OPTI-MEM® was added to each well. After the 20 minute incubation, 0.5 ml containing the complexes of diluted Lipofectamine™ 2000 and diluted plasmids DNA was carefully added to the wells containing cells in 0.5 ml OPTI-MEM®. The plate was incubated at 37° C. for 5 hours, after which 1 ml of complete media was added. The next day, the medium was replaced with growth media for 48 hours. On day 4, after cells were recovered from the transfection, the growth media was replaced with fresh growth media containing Geneticin® (Cat #10131: Invitrogen) at 0.5 mg per ml (1:100 dilution) and incubated for an additional 3 days. On day 7 post transfection, the cells were transferred to a 75 cm Collagen IV flask (Cat#35423: BD Biosciences) containing growth medium and geneticin (0.5 mg per ml, 1:100 dilution). On this transfer, approximately 90% of the cells were dead and were removed during the media change. Growth media containing geneticin (0.5 mg per ml, 1:100 dilution) was changed every two days till day 21.

For the selection of stable cells able to take up galanin TVEMP compounds, the parameters were to screen for clones that produced the highest percentage of SNAP25 cleavage with TVEMP-galanin treatment in the ECL Sandwich ELISA using monoclonal 2E2A6 coated plates for capture and polyclonal SNAP25 (Sigma Cat # S9684) sulfotagged antibody for detection. The $EC_{50}$ values in Table 27 show that TVEMP-galanin Batch D exhibits at least 10-fold greater uptake than the negative control in the SiMa and Neuro-2a cells transfected with GalR1 and GalR2, and only 2-4 fold greater uptake in transfected PC-12 cells. Since the PC-12 transfected cells seem to have lower sensitivity and specificity than the SiMa and Neuro-2a cells they will not be cloned. Also, since the galanin 1-16 mer ligand in the TVEMP-Galanin compounds binds to GALR1 receptor with more affinity than the GALR2, only cells transfected with GALR1 will be cloned. The figure also shows that TVEMP-galanin Batches C and D exhibit 9-10 fold greater uptake than both $LH_N/A$ and the retargeted nociceptin compound TVEMP-nociceptin in the Neuro-2a GalR1.

TABLE 27

Test of stably transfected but non-clonal populations of SiMa, Neuro-2a, and PC12 transfected with GalR1 or GalR2 receptors

| | | TVEMP-galanin C | TVEMP-galanin D | $LH_N/A$ | TVEMP-nociceptin |
|---|---|---|---|---|---|
| | Conc. (mg/mL) | 1.260 | 0.303 | 1.46 | 1.00 |
| $EC_{50}$ Values (nM) | SiMa GalR1 | | 36.2 ± 8.6 | >300 | |
| | SiMa GalR2 | | 26.6 ± 6.7 | >300 | |
| | PC-12 GalR1 | | 64.1 ± 19.5 | 202.7 | |
| | PC-12 GalR2 | | >150 | >300 | |
| | Neuro-2a GalR1 | 32.2 ± 3.3 | 40.8 ± 6.0 | >300 | >300 |
| | Neuro-2a GalR2 | 35.2 ± 3.1 | 46.0 ± 6.1 | >300 | >300 |

The non-clonal selected populations are not a good population of cells to use on a regular basis because they contain a mix of cells expressing different levels of receptor and these populations can change over time. To obtain stable cell lines derived from single cells, a dilutional cloning approach was initiated. On day 21, the transfected cells were trypsinized, needle-dissociated and counted. The remaining transfected cell lines were frozen for future use. The cells were serially diluted to 10 cells per ml in growth media containing geneticin (0.5 mg per ml, 1:100 dilution). Either 2×96-well Collagen IV coated plates (SiMa, PC-12) or 2×96-well Costar plates (Neuro-2a) were plated at 100 µl per well to achieve 1 cell per well density. The plates were returned to the incubator and left untouched for two weeks for colony formation. After two weeks (day 35), the wells were carefully checked for the presence of single colonies formed on the bottom of the well (the entire well was carefully checked for multiple colonies). When a well was identified with a single cluster of cells, that entire well was carefully scrutinized to make sure that one and only one cluster of cells was present. A picture of that single cluster was taken. If there were any queries about additional clusters, the well was not selected. On day 36, the clones that were selected were detached with TrypLE and 0.5 ml of complete media containing geneticin (0.5 mg per ml, 1:100 dilution) was added to stop the trypsin reaction. This entire volume was transferred to 6-well plates and further diluted with 3.0 ml additional complete media containing geneticin (0.5 mg per ml, 1:100 dilution). The clones were allowed to grow to 90% confluence, then trypsinized again and transferred to 75 cm Collagen IV or Costar flasks with 10.0 ml complete media containing geneticin (0.5 mg per ml, 1:100 dilution). Once the cells were 90% confluent again, the cells were used to either fill three cryovials for frozen storage or used for screening in the ELISA assay for galanin retargeted compounds.

The reference compound TVEMP-galanin Batch C was used to test these clones using two operators performing independent tests. The SiMa GalR1 clones grew slowly and were not available for testing at this time. Fortunately, the Neuro-2a clones grew faster, and soon sufficient quantities of 8 of the 12 clones were available for testing. These Neuro-2a GalR1 clonal cells were tested with a full dose range of TVEMP-galanin compounds (0-300 nM) and the results of nine of these clones is shown below. The remaining four clones grew very slowly and were not tested. The selected but non-clonal parental cells were plated along with the clones to use as a benchmark. Table 28 shows the activity of each of the eight clones together with the selected non-clonal Neuro-2a GalR1 cells, when tested with TVEMP-galanin compound. Out of the eight clones tested, only clones #4, 7 and 12 showed good uptake of the TVEMP-galanin compound with acceptable $EC_{50}$ values. Neuro-2a GalR1clones #1, 3 and 10 did not take up the TVEMP-galanin compound, while clones #5, 11 and 13 together with the non-clonal population generated very high $EC_{50}$ values and no further testing was done with these cells.

TABLE 28

Results of screening Neuro-2a GalR1 single-cell derived clones with the TVEMP-galanin Batch C.

| | | EC50 ± Std. error (nM) | |
|---|---|---|---|
| Plate | Cell type | Operator 1 | Operator 2 |
| 1 | N2A Non-clonal | 82.1 ± 9.6 | 92.0 ± 10.8 |
| 1 | N2A GALR1 Clone #1 | >300 | >300 |
| 1 | N2A GALR1 Clone #3 | >300 | >300 |
| 1 | N2A GALR1 Clone #4 | 39.7 ± 3.4 | 39.4 ± 6.6 |
| 2 | N2A Non-clonal | 211.2 ± 167.7 | 116.0 ± 26.8 |
| 2 | N2A GALR1 Clone #5 | 202.6 ± 82.9 | 113.0 ± 18.1 |
| 2 | N2A GALR1 Clone #7 | 23.1 ± 3.3 | 15.5 ± 1.8 |
| 2 | N2A GALR1 Clone #10 | >300 | >300 |
| 3 | N2A GALR1 Clone #7 | 20.3 ± 1.6 | 38.0 ± 6.3 |
| 3 | N2A GALR1 Clone #11 | 270.0 ± 243 | 247.0 ± 101 |
| 3 | N2A GALR1 Clone #12 | 43.2 ± 5.2 | 57.5 ± 14.3 |
| 3 | N2A GALR1 Clone #13 | 144.1 ± 143 | 184.7 ± 15.6 |

4. Characterization of GalR1 Expression in the Clonal Cell Lines

The screening of the clones showed that only clones #4, 7, and 12 are more sensitive than the non-clonal cells. Messenger RNA (mRNA) was extracted from these 3 clones as well as the non-transfected parental and stably transfected non-clonal Neuro-2a cells for characterization by RT-PCR using the RT-PCR conditions described in Example V and the primers described in Table 29.

TABLE 29

Specific GALR1 and GALR2 primers

| Name | Sequence | SEQ ID NO: |
|---|---|---|
| GALR1 fwd | 5" CCCCATCATGTCATCCACCT 3' | 150 |
| GALR1 rev | 5' ATGGGGTTCACCGAGGAGTT 3' | 151 |
| GALR2 fwd | 5' CATCGTGGCGGTGCTTTT 3' | 152 |
| GALR2 rev | 5' AGCGGGAAGCGACCAAAC 3' | 153 |

The results in Table 30 show that the transfected non-clonal cells and clones have much greater amounts of GALR1 mRNA than the parental cells. In the TVEMP-Galanin cell screening, Clone #7 was shown to be the most sensitive to TVEMP-galanin. Clone #7 also is shown to have the highest amount of GALR1 mRNA according to Table 30. The CT values for Neuro-2a GalR1 clone 7 (Neuro-2a #7) was the lowest, followed by clone 4 and then clone 12. The non-clonals tested at this time provided a CT close to clone 12, however, these cells contain a constantly changing population of cells containing varying concentrations of GalR1 receptor, and therefore were not considered a good population for future work. Of the three clones with low $EC_{50}$'s, Neuro-2a clone GalR1 clone #12 (Neuro-2a #12) grew the fastest, followed by Neuro-2a clone #7 and lastly Neuro-2a clone #4. In addition to its slow growth rate, Neuro-2a clone #4 was not tested further because the sensitivity of Neuro-2a clone #7 was much better than for clone #4.

TABLE 30

Large differences in GALR1 mRNA in Neuro-2a transfected clonal cells vs. transfected non-clonal and parental cells.

| Cell line | Parental | Non-Clonal | Clone 4 | Clone 7 | Clone 12 |
|---|---|---|---|---|---|
| Ave CT | 32.0 | 21.7 | 20.8 | 19.3 | 21.6 |
| fold mRNA change | 1.0 | 1269.5 | 2418.7 | 6793.8 | 1332.6 |

5. Comparison of the Sensitivity and Specificity of Neuro-2a Clones #7 and #12 with TVEMP-Galanin Compounds The two clones were tested side-by-side in an attempt to identify the most sensitive and selective of the two, so that data could be confidently collected from the best performing clone. Table 31 shows the results of these two clones when treated with TVEMP-galanin Batch C and $LH_N/A$ for sensitivity and selectivity respectively. Both clones exhibit high Signal-to-Noise ratios. Neuro-2a Clone #7 has an $EC_{50}$ of 5.5 nM while the $EC_{50}$ for Neuro-2a clone #12 is 68.4 nM. The Neuro-2a clone #12 has to be tested with a dose range of 0-300 nM, while the Neuro-2a Clone #7 can be tested with a dose range of 0-30 nM to elicit a plateau at the highest concentration used. Both clones show good separation between the $LH_N/A$ and TVEMP-galanin Batch C, Neuro-2a Clone #12 shows some non-specific uptake at the high concentrations, while Neuro-2a Clone #7 does not. As seen in the tabulated results, the range for testing with Neuro-2a #7 cells is 10-fold lower than that for Neuro-2a #12 cells resulting in a 10-fold less compound being used for Neuro-2a #7 than Neuro-2a #12. Neuro-2a #7 is 8-fold more selective than Neuro-2a clone #12 when $LH_N/A$ was used as a comparison. The Signal-to-Noise ratio is over 100 for both clones, however a ratio of 10 would be sufficient to develop a cell based potency assay. The $EC_{50}$ for the Neuro-2a #7 clone is 5.5 nM about 12-fold lower than that for Neuro-2a #12, whose $EC_{50}$ is 68.4 nM. The lower dose-range for testing, the 24-fold selectivity over $LH_N/A$, the high signal-to-noise ratio, the excellent sensitivity resulting in low $EC_{50}$, and the low amount of protein required for each test, all imply that Neuro-2a Clone #7 would be the clone to go forward with the cell-based potency assay for use in determining potency ratios for TVEMP-galanin compounds.

TABLE 31

| Comparison of characteristics of Neuro-2a clone #7 and #12. | | |
|---|---|---|
| | Neuro-2a #7 | Neuro-2a #12 |
| Range | 0-30 nM | 0-300 nM |
| Selectivity | 24-fold | 3-fold |
| Signal-to-Noise ratio | 190 | 547 |
| Percent of max $LH_N/A$ signal over max TVEMP-Gal signal | 4.3% | 37.6% |
| $EC_{50}$ | 5.5 nM | 68.4 nM |
| Protein required | ~1 μg | ~10 μg |

Neuro-2a # 7 and #12 were treated with TVEMP-galanin Batch C and $LH_N/A$ for 16 hours in CM. Activity was detected using ECL-ELISA.

Example XVI

Generation of Clonal Cell Lines Overexpressing the KOR-1 Receptor for Dynorphin a Retargeted Endopeptidase Uptake The following example illustrates how to characterize and compare several clonal cell lines originated from an established cell line transfected with the target receptor and subsequent cloning of the cell line. This specific example refers to the identification and characterization of clonal cell lines transfected with hKOR-1 that were first described in Example III, Table 9.

Four of the AGN P33-KOR clones (clones number 8, 9, 10, and 12 Table 9 in Example III) were selected and tested with Dyn/A with a full dose response of 0-150 nM. At the same time, two SiMa-KOR clones (clones number 12, and 16 from Table 9 in Example III) selected and tested with Dyn/A with a full dose response of 0-150 nM. In this experiment, AGN P33-KOR clones 8, 9, and 12 produced very low uptake and were therefore discarded; AGN P33-KOR clone 10 displayed good uptake and an $EC_{50}$ of 30.3 nM was obtained. The two SiMa-KOR clones tested displayed good uptake and an $EC_{50}$ of 26.6 nM was obtained for clone 16 and an $EC_{50}$ of 11.8 nM was obtained for clone 12. These three clones were then tested for sensitivity and selectivity by comparing the uptake of the target Dyn/A compound against the negative control $LH_N/A$ that lacks a targeting ligand and the Noc/A control. The comparison of the three clones and the parental SiMa cells utilizing a full dose response of 0-150 nM is summarized in Table 32.

TABLE 32

| Cell Line | $EC_{50}$ Dyn/A (nM) | $EC_{50}$ LHN/A (nM) | $EC_{50}$ Noc/A (nM) |
|---|---|---|---|
| SiMa Parental | >100 | >100 | 5.4 |
| AGN P33-KOR clone 10 | 9.7 | >150 | 9.4 |
| SiMa-KOR clone 16 | 10.6 | >100 | 1.6 |
| SiMa-KOR clone 12 | 4.65 | >150 | 19.7 |

There was a marked increase in Dyn/A uptake in the KOR-1 transfected clones treated with Dyn/A while the parental SiMa cells showed minimal uptake of the compound (uptake was similar to the negative control $LH_N/A$). There is some Noc/A in all the cell lines including parental SiMa cells. This is not surprising as uptake of Noc/A in SiMa cells was observed during the assay development for this retargeted compound. Moreover, Noc/A uptake is best in the AGN P33 cell line that was specifically derived for this retargeted endopeptidase. The difference between Noc/A uptake and Dyn/A compound uptake is greater in the clonal SiMa-KOR clone 12 (SK12) cells. In all the graphs, activity of the negative control, LHN/A, is minimal, showing that in the absence of the binding domain there is no specific uptake in these cell lines and the lowest was in the SK12 cells showing that the uptake of the Dyn/A compound is highly specific. From these results, the SK12 clone was selected for future optimization and characterization.

Optimization studies were performed with the SK12 cells in order to develop a robust, specific and sensitive assay. Several parameters were assayed including plating media and plating densities, treatment media, and treatment time. A summary of the data obtained during the optimization is provided in Table 33.

TABLE 33

| Medium used | | Treatment | Cells/well | | | | |
|---|---|---|---|---|---|---|---|
| plating | treating | time | 25000 | 50000 | 75000 | 100000 | 150000 |
| complete | complete | 6 hr + o/n | 51.3 | 76 | 13.4 | 9.2 | n/a |
| complete | complete | 16 hr | 21.3 | 19.0 | 4.96 | 4.64 | n/a |
| complete | complete | 16 hr | n/a | n/a | n/a | 2.1 | 15.3 |
| serum free | serum free | 16 hr | n/a | n/a | n/a | 9.0 | 12.1 |
| complete | serum free | 16 hr | n/a | 10.3 | 5.4 | 8.97 | 8.38 |
| complete | complete | 16 hr | n/a | 7.7 | 4.86 | 13.72 | 11.26 |
| serum free | serum free | 16 hr | n/a | 11.2 | 8.5 | 8.4 | 9.2 |

Table B shows that cells plated at 100,000 cells per well in CM and treated with compounds in CM showed more variability in $EC_{50}$ values from one experiment to the next (4.6; 1.2 and 13.72 nM) while cells plated at 100,000 cells per well in SFM and treated with compounds diluted in SFM provided the best curves and consistent $EC_{50}$ values (9.0 and 8.4 nM). In future, cells would be plated at 100,000 cells per well in SFM and treated with compounds in SFM too.

SK12 plated on PDL plates at 100,000 cells per well in SFM for 24 hours, followed by treatment in SFM for 16 hours yielded the lowest $EC_{50}$ value of 8.4+/−1.1 nM and a Signal-to Noise ratio of 12. Both these values would be acceptable for future use of this cell in CBPA.

Characterization of SK12 Cells with the Saturation Binding Assay

The saturation Binding assay utilized here was described in detail in Example V. Saturation binding studies were performed using the KOR-1 antagonist $^3H$-diprenorphine to evaluate binding. The total, specific, and non-specific binding were measured in several experiments. A saturation binding curve of $^3H$-diprenorphine with the receptor was generated from two independent experiments. It appears that about 25% binding is non-specific and 75% specific binding of the molecule to the receptor. The affinity of the molecule to the receptor is adequate at 6.5 nM. The Bmax indicates that there are 23 fmol KOR-1 receptors per cell on the SK12 cells.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

SEQUENCE LISTING

```
<160> NUMBER OF SEQ ID NOS: 153

<210> SEQ ID NO 1
<211> LENGTH: 903
<212> TYPE: PRT
<213> ORGANISM: Artificial Sequence
<220> FEATURE:
<223> OTHER INFORMATION: Retargeted endopeptidase

<400> SEQUENCE: 1

Met Gly Ser Met Glu Phe Val Asn Lys Gln Phe Asn Tyr Lys Asp Pro
 1               5                  10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
```

```
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Ile Ile Thr Ser Lys Thr Lys Ser Asp Asp Asp Asp
        435                 440                 445

Lys Phe Gly Gly Phe Thr Gly Ala Arg Lys Ser Ala Arg Lys Arg Lys
    450                 455                 460
```

-continued

Asn Gln Ala Leu Ala Gly Gly Gly Gly Ser Gly Gly Gly Gly Ser Gly
465 470 475 480

Gly Gly Gly Ser Ala Leu Val Leu Gln Cys Ile Lys Val Asn Asn Trp
485 490 495

Asp Leu Phe Phe Ser Pro Ser Glu Asp Asn Phe Thr Asn Asp Leu Asn
500 505 510

Lys Gly Glu Glu Ile Thr Ser Asp Thr Asn Ile Glu Ala Ala Glu Glu
515 520 525

Asn Ile Ser Leu Asp Leu Ile Gln Gln Tyr Tyr Leu Thr Phe Asn Phe
530 535 540

Asp Asn Glu Pro Glu Asn Ile Ser Ile Glu Asn Leu Ser Ser Asp Ile
545 550 555 560

Ile Gly Gln Leu Glu Leu Met Pro Asn Ile Glu Arg Phe Pro Asn Gly
565 570 575

Lys Lys Tyr Glu Leu Asp Lys Tyr Thr Met Phe His Tyr Leu Arg Ala
580 585 590

Gln Glu Phe Glu His Gly Lys Ser Arg Ile Ala Leu Thr Asn Ser Val
595 600 605

Asn Glu Ala Leu Leu Asn Pro Ser Arg Val Tyr Thr Phe Phe Ser Ser
610 615 620

Asp Tyr Val Lys Lys Val Asn Lys Ala Thr Glu Ala Ala Met Phe Leu
625 630 635 640

Gly Trp Val Glu Gln Leu Val Tyr Asp Phe Thr Asp Glu Thr Ser Glu
645 650 655

Val Ser Thr Thr Asp Lys Ile Ala Asp Ile Thr Ile Ile Ile Pro Tyr
660 665 670

Ile Gly Pro Ala Leu Asn Ile Gly Asn Met Leu Tyr Lys Asp Asp Phe
675 680 685

Val Gly Ala Leu Ile Phe Ser Gly Ala Val Ile Leu Leu Glu Phe Ile
690 695 700

Pro Glu Ile Ala Ile Pro Val Leu Gly Thr Phe Ala Leu Val Ser Tyr
705 710 715 720

Ile Ala Asn Lys Val Leu Thr Val Gln Thr Ile Asp Asn Ala Leu Ser
725 730 735

Lys Arg Asn Glu Lys Trp Asp Glu Val Tyr Lys Tyr Ile Val Thr Asn
740 745 750

Trp Leu Ala Lys Val Asn Thr Gln Ile Asp Leu Ile Arg Lys Lys Met
755 760 765

Lys Glu Ala Leu Glu Asn Gln Ala Glu Ala Thr Lys Ala Ile Ile Asn
770 775 780

Tyr Gln Tyr Asn Gln Tyr Thr Glu Glu Glu Lys Asn Asn Ile Asn Phe
785 790 795 800

Asn Ile Asp Asp Leu Ser Ser Lys Leu Asn Glu Ser Ile Asn Lys Ala
805 810 815

Met Ile Asn Ile Asn Lys Phe Leu Asn Gln Cys Ser Val Ser Tyr Leu
820 825 830

Met Asn Ser Met Ile Pro Tyr Gly Val Lys Arg Leu Glu Asp Phe Asp
835 840 845

Ala Ser Leu Lys Asp Ala Leu Leu Lys Tyr Ile Tyr Asp Asn Arg Gly
850 855 860

Thr Leu Ile Gly Gln Val Asp Arg Leu Lys Asp Lys Val Asn Asn Thr
865 870 875 880

-continued

```
Leu Ser Thr Asp Ile Pro Phe Gln Leu Ser Lys Tyr Val Asp Asn Gln
                885                 890                 895

Arg Leu Leu Ser Thr Leu Asp
            900


<210> SEQ ID NO 2
<211> LENGTH: 908
<212> TYPE: PRT
<213> ORGANISM: Artificial Sequence
<220> FEATURE:
<223> OTHER INFORMATION: Retargeted endopeptidase

<400> SEQUENCE: 2

Met Gly Ser Met Glu Phe Val Asn Lys Gln Phe Asn Tyr Lys Asp Pro
 1               5                  10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335
```

```
Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Ile Ile Thr Ser Lys Thr Lys Ser Asp Asp Asp Asp
        435                 440                 445

Lys Tyr Gly Gly Phe Leu Arg Arg Ile Arg Pro Lys Leu Lys Trp Asp
    450                 455                 460

Asn Gln Ala Leu Ala Gly Gly Gly Gly Ser Gly Gly Gly Gly Ser Gly
465                 470                 475                 480

Gly Gly Gly Ser Ala Leu Val Leu Gln Cys Ile Lys Val Asn Asn Trp
                485                 490                 495

Asp Leu Phe Phe Ser Pro Ser Glu Asp Asn Phe Thr Asn Asp Leu Asn
            500                 505                 510

Lys Gly Glu Glu Ile Thr Ser Asp Thr Asn Ile Glu Ala Ala Glu Glu
        515                 520                 525

Asn Ile Ser Leu Asp Leu Ile Gln Gln Tyr Tyr Leu Thr Phe Asn Phe
    530                 535                 540

Asp Asn Glu Pro Glu Asn Ile Ser Ile Glu Asn Leu Ser Ser Asp Ile
545                 550                 555                 560

Ile Gly Gln Leu Glu Leu Met Pro Asn Ile Glu Arg Phe Pro Asn Gly
                565                 570                 575

Lys Lys Tyr Glu Leu Asp Lys Tyr Thr Met Phe His Tyr Leu Arg Ala
            580                 585                 590

Gln Glu Phe Glu His Gly Lys Ser Arg Ile Ala Leu Thr Asn Ser Val
        595                 600                 605

Asn Glu Ala Leu Leu Asn Pro Ser Arg Val Tyr Thr Phe Phe Ser Ser
    610                 615                 620

Asp Tyr Val Lys Lys Val Asn Lys Ala Thr Glu Ala Ala Met Phe Leu
625                 630                 635                 640

Gly Trp Val Glu Gln Leu Val Tyr Asp Phe Thr Asp Glu Thr Ser Glu
                645                 650                 655

Val Ser Thr Thr Asp Lys Ile Ala Asp Ile Thr Ile Ile Ile Pro Tyr
            660                 665                 670

Ile Gly Pro Ala Leu Asn Ile Gly Asn Met Leu Tyr Lys Asp Asp Phe
        675                 680                 685

Val Gly Ala Leu Ile Phe Ser Gly Ala Val Ile Leu Leu Glu Phe Ile
    690                 695                 700

Pro Glu Ile Ala Ile Pro Val Leu Gly Thr Phe Ala Leu Val Ser Tyr
705                 710                 715                 720

Ile Ala Asn Lys Val Leu Thr Val Gln Thr Ile Asp Asn Ala Leu Ser
                725                 730                 735

Lys Arg Asn Glu Lys Trp Asp Glu Val Tyr Lys Tyr Ile Val Thr Asn
            740                 745                 750

Trp Leu Ala Lys Val Asn Thr Gln Ile Asp Leu Ile Arg Lys Lys Met
```

-continued 755 760 765

Lys Glu Ala Leu Glu Asn Gln Ala Glu Ala Thr Lys Ala Ile Ile Asn
770 775 780

Tyr Gln Tyr Asn Gln Tyr Thr Glu Glu Glu Lys Asn Asn Ile Asn Phe
785 790 795 800

Asn Ile Asp Asp Leu Ser Ser Lys Leu Asn Glu Ser Ile Asn Lys Ala
805 810 815

Met Ile Asn Ile Asn Lys Phe Leu Asn Gln Cys Ser Val Ser Tyr Leu
820 825 830

Met Asn Ser Met Ile Pro Tyr Gly Val Lys Arg Leu Glu Asp Phe Asp
835 840 845

Ala Ser Leu Lys Asp Ala Leu Leu Lys Tyr Ile Tyr Asp Asn Arg Gly
850 855 860

Thr Leu Ile Gly Gln Val Asp Arg Leu Lys Asp Lys Val Asn Asn Thr
865 870 875 880

Leu Ser Thr Asp Ile Pro Phe Gln Leu Ser Lys Tyr Val Asp Asn Gln
885 890 895

Arg Leu Leu Ser Thr Leu Glu Ala Leu Ala Ser Gly
900 905

<210> SEQ ID NO 3
<211> LENGTH: 906
<212> TYPE: PRT
<213> ORGANISM: Artificial Sequence
<220> FEATURE:
<223> OTHER INFORMATION: Retargeted endopeptidase

<400> SEQUENCE: 3

Ile Ser Glu Phe Gly Ser Met Glu Phe Val Asn Lys Gln Phe Asn Tyr
1 5 10 15

Lys Asp Pro Val Asn Gly Val Asp Ile Ala Tyr Ile Lys Ile Pro Asn
20 25 30

Ala Gly Gln Met Gln Pro Val Lys Ala Phe Lys Ile His Asn Lys Ile
35 40 45

Trp Val Ile Pro Glu Arg Asp Thr Phe Thr Asn Pro Glu Glu Gly Asp
50 55 60

Leu Asn Pro Pro Pro Glu Ala Lys Gln Val Pro Val Ser Tyr Tyr Asp
65 70 75 80

Ser Thr Tyr Leu Ser Thr Asp Asn Glu Lys Asp Asn Tyr Leu Lys Gly
85 90 95

Val Thr Lys Leu Phe Glu Arg Ile Tyr Ser Thr Asp Leu Gly Arg Met
100 105 110

Leu Leu Thr Ser Ile Val Arg Gly Ile Pro Phe Trp Gly Gly Ser Thr
115 120 125

Ile Asp Thr Glu Leu Lys Val Ile Asp Thr Asn Cys Ile Asn Val Ile
130 135 140

Gln Pro Asp Gly Ser Tyr Arg Ser Glu Glu Leu Asn Leu Val Ile Ile
145 150 155 160

Gly Pro Ser Ala Asp Ile Ile Gln Phe Glu Cys Lys Ser Phe Gly His
165 170 175

Glu Val Leu Asn Leu Thr Arg Asn Gly Tyr Gly Ser Thr Gln Tyr Ile
180 185 190

Arg Phe Ser Pro Asp Phe Thr Phe Gly Phe Glu Glu Ser Leu Glu Val
195 200 205

Asp Thr Asn Pro Leu Leu Gly Ala Gly Lys Phe Ala Thr Asp Pro Ala

-continued

```
    210                 215                 220

Val Thr Leu Ala His Glu Leu Ile His Ala Gly His Arg Leu Tyr Gly
225                 230                 235                 240

Ile Ala Ile Asn Pro Asn Arg Val Phe Lys Val Asn Thr Asn Ala Tyr
                245                 250                 255

Tyr Glu Met Ser Gly Leu Glu Val Ser Phe Glu Glu Leu Arg Thr Phe
            260                 265                 270

Gly Gly His Asp Ala Lys Phe Ile Asp Ser Leu Gln Glu Asn Glu Phe
        275                 280                 285

Arg Leu Tyr Tyr Tyr Asn Lys Phe Lys Asp Ile Ala Ser Thr Leu Asn
    290                 295                 300

Lys Ala Lys Ser Ile Val Gly Thr Thr Ala Ser Leu Gln Tyr Met Lys
305                 310                 315                 320

Asn Val Phe Lys Glu Lys Tyr Leu Leu Ser Glu Asp Thr Ser Gly Lys
                325                 330                 335

Phe Ser Val Asp Lys Leu Lys Phe Asp Lys Leu Tyr Lys Met Leu Thr
            340                 345                 350

Glu Ile Tyr Thr Glu Asp Asn Phe Val Lys Phe Phe Lys Val Leu Asn
        355                 360                 365

Arg Lys Thr Tyr Leu Asn Phe Asp Lys Ala Val Phe Lys Ile Asn Ile
    370                 375                 380

Val Pro Lys Val Asn Tyr Thr Ile Tyr Asp Gly Phe Asn Leu Arg Asn
385                 390                 395                 400

Thr Asn Leu Ala Ala Asn Phe Asn Gly Gln Asn Thr Glu Ile Asn Asn
                405                 410                 415

Met Asn Phe Thr Lys Leu Lys Asn Phe Thr Gly Leu Phe Glu Phe Tyr
            420                 425                 430

Lys Leu Leu Cys Val Asp Gly Ile Ile Thr Ser Lys Thr Lys Ser Leu
        435                 440                 445

Ile Glu Gly Arg Asn Lys Ala Leu Asn Asp Leu Cys Ile Lys Val Asn
    450                 455                 460

Asn Trp Asp Leu Phe Phe Ser Pro Ser Glu Asp Asn Phe Thr Asn Asp
465                 470                 475                 480

Leu Asn Lys Gly Glu Glu Ile Thr Ser Asp Thr Asn Ile Glu Ala Ala
                485                 490                 495

Glu Glu Asn Ile Ser Leu Asp Leu Ile Gln Gln Tyr Tyr Leu Thr Phe
            500                 505                 510

Asn Phe Asp Asn Glu Pro Glu Asn Ile Ser Ile Glu Asn Leu Ser Ser
        515                 520                 525

Asp Ile Ile Gly Gln Leu Glu Leu Met Pro Asn Ile Glu Arg Phe Pro
    530                 535                 540

Asn Gly Lys Lys Tyr Glu Leu Asp Lys Tyr Thr Met Phe His Tyr Leu
545                 550                 555                 560

Arg Ala Gln Glu Phe Glu His Gly Lys Ser Arg Ile Ala Leu Thr Asn
                565                 570                 575

Ser Val Asn Glu Ala Leu Leu Asn Pro Ser Arg Val Tyr Thr Phe Phe
            580                 585                 590

Ser Ser Asp Tyr Val Lys Lys Val Asn Lys Ala Thr Glu Ala Ala Met
        595                 600                 605

Phe Leu Gly Trp Val Glu Gln Leu Val Tyr Asp Phe Thr Asp Glu Thr
    610                 615                 620

Ser Glu Val Ser Thr Thr Asp Lys Ile Ala Asp Ile Thr Ile Ile Ile
625                 630                 635                 640
```

```
Pro Tyr Ile Gly Pro Ala Leu Asn Ile Gly Asn Met Leu Tyr Lys Asp
                645                 650                 655

Asp Phe Val Gly Ala Leu Ile Phe Ser Gly Ala Val Ile Leu Leu Glu
            660                 665                 670

Phe Ile Pro Glu Ile Ala Ile Pro Val Leu Gly Thr Phe Ala Leu Val
        675                 680                 685

Ser Tyr Ile Ala Asn Lys Val Leu Thr Val Gln Thr Ile Asp Asn Ala
    690                 695                 700

Leu Ser Lys Arg Asn Glu Lys Trp Asp Glu Val Tyr Lys Tyr Ile Val
705                 710                 715                 720

Thr Asn Trp Leu Ala Lys Val Asn Thr Gln Ile Asp Leu Ile Arg Lys
                725                 730                 735

Lys Met Lys Glu Ala Leu Glu Asn Gln Ala Glu Ala Thr Lys Ala Ile
            740                 745                 750

Ile Asn Tyr Gln Tyr Asn Gln Tyr Thr Glu Glu Glu Lys Asn Asn Ile
        755                 760                 765

Asn Phe Asn Ile Asp Asp Leu Ser Ser Lys Leu Asn Glu Ser Ile Asn
    770                 775                 780

Lys Ala Met Ile Asn Ile Asn Lys Phe Leu Asn Gln Cys Ser Val Ser
785                 790                 795                 800

Tyr Leu Met Asn Ser Met Ile Pro Tyr Gly Val Lys Arg Leu Glu Asp
                805                 810                 815

Phe Asp Ala Ser Leu Lys Asp Ala Leu Leu Lys Tyr Ile Tyr Asp Asn
            820                 825                 830

Arg Gly Thr Leu Ile Gly Gln Val Asp Arg Leu Lys Asp Lys Val Asn
        835                 840                 845

Asn Thr Leu Ser Thr Asp Ile Pro Phe Gln Leu Ser Lys Tyr Val Asp
    850                 855                 860

Asn Gln Arg Leu Leu Ser Thr Leu Glu Gly Gly Gly Gly Ser Gly Gly
865                 870                 875                 880

Gly Gly Ser Gly Gly Gly Gly Ser Ala Leu Val Val Gly Arg Pro Glu
                885                 890                 895

Trp Trp Met Asp Tyr Gln Lys Arg Tyr Gly
            900                 905


<210> SEQ ID NO 4
<211> LENGTH: 919
<212> TYPE: PRT
<213> ORGANISM: Artificial Sequence
<220> FEATURE:
<223> OTHER INFORMATION: Retargeted endopeptidase

<400> SEQUENCE: 4

Met Glu Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95
```

```
Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Asp
            420                 425                 430

Gly Ile Ile Thr Ser Lys Thr Lys Ser Asp Asp Asp Asp Lys Tyr Gly
        435                 440                 445

Gly Phe Met Thr Ser Glu Lys Ser Gln Thr Pro Leu Val Thr Leu Phe
    450                 455                 460

Lys Asn Ala Ile Ile Lys Asn Ala Tyr Lys Lys Gly Glu Ala Leu Ala
465                 470                 475                 480

Gly Gly Gly Gly Ser Gly Gly Gly Gly Ser Gly Gly Gly Gly Ser Ala
                485                 490                 495

Leu Val Leu Gln Cys Ile Lys Val Asn Asn Trp Asp Leu Phe Phe Ser
            500                 505                 510
```

```
Pro Ser Glu Asp Asn Phe Thr Asn Asp Leu Asn Lys Gly Glu Glu Ile
        515                 520                 525

Thr Ser Asp Thr Asn Ile Glu Ala Ala Glu Glu Asn Ile Ser Leu Asp
    530                 535                 540

Leu Ile Gln Gln Tyr Tyr Leu Thr Phe Asn Phe Asp Asn Glu Pro Glu
545                 550                 555                 560

Asn Ile Ser Ile Glu Asn Leu Ser Ser Asp Ile Ile Gly Gln Leu Glu
                565                 570                 575

Leu Met Pro Asn Ile Glu Arg Phe Pro Asn Gly Lys Lys Tyr Glu Leu
            580                 585                 590

Asp Lys Tyr Thr Met Phe His Tyr Leu Arg Ala Gln Glu Phe Glu His
        595                 600                 605

Gly Lys Ser Arg Ile Ala Leu Thr Asn Ser Val Asn Glu Ala Leu Leu
    610                 615                 620

Asn Pro Ser Arg Val Tyr Thr Phe Phe Ser Ser Asp Tyr Val Lys Lys
625                 630                 635                 640

Val Asn Lys Ala Thr Glu Ala Ala Met Phe Leu Gly Trp Val Glu Gln
                645                 650                 655

Leu Val Tyr Asp Phe Thr Asp Glu Thr Ser Glu Val Ser Thr Thr Asp
            660                 665                 670

Lys Ile Ala Asp Ile Thr Ile Ile Ile Pro Tyr Ile Gly Pro Ala Leu
        675                 680                 685

Asn Ile Gly Asn Met Leu Tyr Lys Asp Asp Phe Val Gly Ala Leu Ile
    690                 695                 700

Phe Ser Gly Ala Val Ile Leu Leu Glu Phe Ile Pro Glu Ile Ala Ile
705                 710                 715                 720

Pro Val Leu Gly Thr Phe Ala Leu Val Ser Tyr Ile Ala Asn Lys Val
                725                 730                 735

Leu Thr Val Gln Thr Ile Asp Asn Ala Leu Ser Lys Arg Asn Glu Lys
            740                 745                 750

Trp Asp Glu Val Tyr Lys Tyr Ile Val Thr Asn Trp Leu Ala Lys Val
        755                 760                 765

Asn Thr Gln Ile Asp Leu Ile Arg Lys Lys Met Lys Glu Ala Leu Glu
    770                 775                 780

Asn Gln Ala Glu Ala Thr Lys Ala Ile Ile Asn Tyr Gln Tyr Asn Gln
785                 790                 795                 800

Tyr Thr Glu Glu Glu Lys Asn Asn Ile Asn Phe Asn Ile Asp Asp Leu
                805                 810                 815

Ser Ser Lys Leu Asn Glu Ser Ile Asn Lys Ala Met Ile Asn Ile Asn
            820                 825                 830

Lys Phe Leu Asn Gln Cys Ser Val Ser Tyr Leu Met Asn Ser Met Ile
        835                 840                 845

Pro Tyr Gly Val Lys Arg Leu Glu Asp Phe Asp Ala Ser Leu Lys Asp
    850                 855                 860

Ala Leu Leu Lys Tyr Ile Tyr Asp Asn Arg Gly Thr Leu Ile Gly Gln
865                 870                 875                 880

Val Asp Arg Leu Lys Asp Lys Val Asn Asn Thr Leu Ser Thr Asp Ile
                885                 890                 895

Pro Phe Gln Leu Ser Lys Tyr Val Asp Asn Gln Arg Leu Leu Ser Thr
            900                 905                 910

Leu Glu Ala Leu Ala Ser Gly
        915
```

```
<210> SEQ ID NO 5
<211> LENGTH: 206
<212> TYPE: PRT
<213> ORGANISM: Homo sapiens

<400> SEQUENCE: 5

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 6
<211> LENGTH: 206
<212> TYPE: PRT
<213> ORGANISM: Homo sapiens

<400> SEQUENCE: 6

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
```

```
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 7
<211> LENGTH: 206
<212> TYPE: PRT
<213> ORGANISM: Macaca mulatta

<400> SEQUENCE: 7

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 8
<211> LENGTH: 206
<212> TYPE: PRT
<213> ORGANISM: Rattus norvegicus

<400> SEQUENCE: 8

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
```

```
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 9
<211> LENGTH: 206
<212> TYPE: PRT
<213> ORGANISM: Rattus norvegicus

<400> SEQUENCE: 9

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 10
<211> LENGTH: 206
```

<212> TYPE: PRT
<213> ORGANISM: Mus musculus

<400> SEQUENCE: 10

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 11
<211> LENGTH: 206
<212> TYPE: PRT
<213> ORGANISM: Gallus gallus

<400> SEQUENCE: 11

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140
```

```
Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 12
<211> LENGTH: 204
<212> TYPE: PRT
<213> ORGANISM: Carassius auratus

<400> SEQUENCE: 12

Met Ala Glu Asp Ala Asp Met Arg Asn Glu Leu Ser Asp Met Gln Gln
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200


<210> SEQ ID NO 13
<211> LENGTH: 203
<212> TYPE: PRT
<213> ORGANISM: Carassius auratus

<400> SEQUENCE: 13

Met Ala Asp Glu Ala Asp Met Arg Asn Glu Leu Thr Asp Met Gln Ala
 1               5                  10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60
```

-continued

Asp Gln Ile Asn Lys Asp Met Lys Glu Ala Glu Lys Asn Leu Thr Asp
65 70 75 80

Leu Gly Asn Leu Cys Gly Leu Cys Pro Cys Pro Cys Asn Lys Leu Lys
85 90 95

Gly Gly Gly Gln Ser Trp Gly Asn Asn Gln Asp Gly Val Val Ser Ser
100 105 110

Gln Pro Ala Arg Val Val Asp Glu Arg Glu Gln Met Ala Ile Ser Gly
115 120 125

Gly Phe Ile Arg Arg Val Thr Asn Asp Ala Arg Glu Asn Glu Met Asp
130 135 140

Glu Asn Leu Glu Gln Val Gly Ser Ile Ile Gly Asn Leu Arg His Met
145 150 155 160

Ala Leu Asp Met Gly Asn Glu Ile Asp Thr Gln Asn Arg Gln Ile Asp
165 170 175

Arg Ile Met Asp Met Ala Asp Ser Asn Lys Thr Arg Ile Asp Glu Ala
180 185 190

Asn Gln Arg Ala Thr Lys Met Leu Gly Ser Gly
195 200

<210> SEQ ID NO 14
<211> LENGTH: 204
<212> TYPE: PRT
<213> ORGANISM: Danio rerio

<400> SEQUENCE: 14

Met Ala Glu Asp Ser Asp Met Arg Asn Glu Leu Ala Asp Met Gln Gln
1 5 10 15

Arg Ala Asp Gln Leu Ala Asp Glu Ser Leu Glu Ser Thr Arg Arg Met
20 25 30

Leu Gln Leu Val Glu Glu Ser Lys Asp Ala Gly Ile Arg Thr Leu Val
35 40 45

Met Leu Asp Glu Gln Gly Glu Gln Leu Glu Arg Ile Glu Glu Gly Met
50 55 60

Asp Gln Ile Asn Lys Asp Met Lys Asp Ala Glu Lys Asn Leu Asn Asp
65 70 75 80

Leu Gly Lys Phe Cys Gly Leu Cys Ser Cys Pro Cys Asn Lys Met Lys
85 90 95

Ser Gly Ala Ser Lys Ala Trp Gly Asn Asn Gln Asp Gly Val Val Ala
100 105 110

Ser Gln Pro Ala Arg Val Val Asp Glu Arg Glu Gln Met Ala Ile Ser
115 120 125

Gly Gly Phe Ile Arg Arg Val Thr Asp Asp Ala Arg Glu Asn Glu Met
130 135 140

Asp Glu Asn Leu Glu Gln Val Gly Gly Ile Ile Gly Asn Leu Arg His
145 150 155 160

Met Ala Leu Asp Met Gly Asn Glu Ile Asp Thr Gln Asn Arg Gln Ile
165 170 175

Asp Arg Ile Met Glu Lys Ala Asp Ser Asn Lys Thr Arg Ile Asp Glu
180 185 190

Ala Asn Gln Arg Ala Thr Lys Met Leu Gly Ser Gly
195 200

<210> SEQ ID NO 15
<211> LENGTH: 203
<212> TYPE: PRT
<213> ORGANISM: Danio rerio

<400> SEQUENCE: 15

Met Ala Asp Glu Ser Asp Met Arg Asn Glu Leu Asn Asp Met Gln Ala
1 5 10 15

Arg Ala Asp Gln Leu Gly Asp Glu Ser Leu Glu Ser Thr Arg Arg Met
20 25 30

Leu Gln Leu Val Glu Glu Ser Lys Asp Ala Gly Ile Arg Thr Leu Val
35 40 45

Met Leu Asp Glu Gln Gly Glu Gln Leu Glu Arg Ile Glu Glu Gly Met
50 55 60

Asp Gln Ile Asn Lys Asp Met Lys Glu Ala Glu Lys Asn Leu Thr Asp
65 70 75 80

Leu Gly Asn Leu Cys Gly Leu Cys Pro Cys Pro Cys Asn Lys Leu Lys
85 90 95

Gly Gly Gly Gln Ser Trp Gly Asn Asn Gln Asp Gly Val Val Ser Ser
100 105 110

Gln Pro Ala Arg Val Val Asp Glu Arg Glu Gln Met Ala Ile Ser Gly
115 120 125

Gly Phe Ile Arg Arg Val Thr Asn Asp Ala Arg Glu Asn Glu Met Asp
130 135 140

Glu Asn Leu Glu Gln Val Gly Ser Ile Ile Gly Asn Leu Arg His Met
145 150 155 160

Ala Leu Asp Met Gly Asn Glu Ile Asp Thr Gln Asn Arg Gln Ile Asp
165 170 175

Arg Ile Met Asp Met Ala Asp Ser Asn Lys Thr Arg Ile Asp Glu Ala
180 185 190

Asn Gln Arg Ala Thr Lys Met Leu Gly Ser Gly
195 200

<210> SEQ ID NO 16
<211> LENGTH: 210
<212> TYPE: PRT
<213> ORGANISM: Torpedo marmorata

<400> SEQUENCE: 16

Met Glu Asn Ser Val Glu Asn Ser Met Asp Pro Arg Ser Glu Gln Glu
1 5 10 15

Glu Met Gln Arg Cys Ala Asp Gln Ile Thr Asp Glu Ser Leu Glu Ser
20 25 30

Thr Arg Arg Met Leu Gln Leu Val Glu Glu Ser Lys Asp Ala Gly Ile
35 40 45

Arg Thr Leu Val Met Leu Asp Glu Gln Gly Glu Gln Leu Glu Arg Ile
50 55 60

Glu Glu Gly Met Asp Gln Ile Asn Lys Asp Met Lys Glu Ala Glu Lys
65 70 75 80

Asn Leu Ser Asp Leu Gly Lys Cys Cys Gly Leu Cys Ser Cys Pro Cys
85 90 95

Asn Lys Leu Lys Asn Phe Glu Ala Gly Gly Ala Tyr Lys Lys Val Trp
100 105 110

Gly Asn Asn Gln Asp Gly Val Val Ala Ser Gln Pro Ala Arg Val Met
115 120 125

Asp Asp Arg Glu Gln Met Ala Met Ser Gly Gly Tyr Ile Arg Arg Ile
130 135 140

Thr Asp Asp Ala Arg Glu Asn Glu Met Glu Glu Asn Leu Asp Gln Val
145 150 155 160

```
Gly Ser Ile Ile Gly Asn Leu Arg His Met Ala Leu Asp Met Ser Asn
                165                 170                 175

Glu Ile Gly Ser Gln Asn Ala Gln Ile Asp Arg Ile Val Val Lys Gly
            180                 185                 190

Asp Met Asn Lys Ala Arg Ile Asp Glu Ala Asn Lys His Ala Thr Lys
        195                 200                 205

Met Leu
    210


<210> SEQ ID NO 17
<211> LENGTH: 206
<212> TYPE: PRT
<213> ORGANISM: Xenopus laevis

<400> SEQUENCE: 17

Met Ala Asp Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Gly Ala Tyr Asn Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205


<210> SEQ ID NO 18
<211> LENGTH: 206
<212> TYPE: PRT
<213> ORGANISM: Xenopus laevis

<400> SEQUENCE: 18

Met Ala Asp Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60
```

```
Glu Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
    130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205


<210> SEQ ID NO 19
<211> LENGTH: 212
<212> TYPE: PRT
<213> ORGANISM: Strongylocentrotus purpuratus

<400> SEQUENCE: 19

Met Glu Asp Gln Asn Asp Met Asn Met Arg Ser Glu Leu Glu Glu Ile
 1               5                  10                  15

Gln Met Gln Ser Asn Met Gln Thr Asp Glu Ser Leu Glu Ser Thr Arg
            20                  25                  30

Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
    50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210
```

-continued

```
<210> SEQ ID NO 20
<211> LENGTH: 212
<212> TYPE: PRT
<213> ORGANISM: Drosophila melanogaster

<400> SEQUENCE: 20

Met Pro Ala Asp Pro Ser Glu Glu Val Ala Pro Gln Val Pro Lys Thr
 1               5                  10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210


<210> SEQ ID NO 21
<211> LENGTH: 212
<212> TYPE: PRT
<213> ORGANISM: Hirudo medicinalis

<400> SEQUENCE: 21

Met Ala Lys Asp Ile Lys Pro Lys Pro Ala Asn Gly Arg Asp Ser Pro
 1               5                  10                  15

Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80

Asp Ala Glu Lys Asn Leu Glu Gly Met Glu Lys Cys Cys Gly Leu Cys
                85                  90                  95

Ile Leu Pro Trp Lys Arg Thr Lys Asn Phe Asp Lys Gly Ala Glu Trp
            100                 105                 110

Asn Lys Gly Asp Glu Gly Lys Val Asn Thr Asp Gly Pro Arg Leu Val
```

```
        115                 120                 125

Val Gly Asp Gly Asn Met Gly Pro Ser Gly Gly Phe Ile Thr Lys Ile
    130                 135                 140

Thr Asn Asp Ala Arg Glu Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210


<210> SEQ ID NO 22
<211> LENGTH: 212
<212> TYPE: PRT
<213> ORGANISM: Loligo pealei

<400> SEQUENCE: 22

Met Ser Ala Asn Gly Glu Val Glu Val Pro Lys Thr Glu Leu Glu Glu
 1               5                  10                  15

Ile Gln Gln Gln Cys Asn Gln Val Thr Asp Asp Ser Leu Glu Ser Thr
            20                  25                  30

Arg Arg Met Leu Asn Met Cys Glu Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110

Lys Asp Asp Asp Gly Pro Thr Asn Thr Asn Gly Pro Arg Val Thr Val
        115                 120                 125

Gly Asp Gln Asn Gly Met Gly Pro Ser Ser Gly Tyr Val Thr Arg Ile
    130                 135                 140

Thr Asn Asp Ala Arg Glu Asp Asp Met Glu Asn Asn Met Lys Glu Val
145                 150                 155                 160

Ser Ser Met Ile Gly Asn Leu Arg Asn Met Ala Ile Asp Met Gly Asn
                165                 170                 175

Glu Ile Gly Ser Gln Asn Arg Gln Val Asp Arg Ile Gln Gln Lys Ala
            180                 185                 190

Glu Ser Asn Glu Ser Arg Ile Asp Glu Ala Asn Lys Lys Ala Thr Lys
        195                 200                 205

Leu Leu Lys Asn
    210


<210> SEQ ID NO 23
<211> LENGTH: 220
<212> TYPE: PRT
<213> ORGANISM: Lymnaea stagnalis

<400> SEQUENCE: 23

Met Thr Thr Asn Gly Glu Ile Leu Pro Val Gly Glu Glu Glu Glu Glu
```

-continued

```
 1               5                   10                  15

Glu Leu Gly Glu Asp Ala Leu Leu Arg Lys Gln Ile Asp Cys Asn Thr
            20                  25                  30

Asn Glu Ser Leu Glu Ser Thr Arg Arg Met Leu Ser Leu Cys Glu Glu
        35                  40                  45

Ser Lys Glu Ala Gly Ile Lys Thr Leu Val Met Leu Asp Glu Gln Gly
    50                  55                  60

Glu Gln Leu Asp Arg Ile Glu Glu Gly Met Gly Gln Ile Asn Gln Asp
65                  70                  75                  80

Met Arg Asp Ala Glu Lys Asn Leu Glu Gly Leu Glu Lys Cys Cys Gly
                85                  90                  95

Leu Cys Val Leu Pro Trp Lys Arg Ser Lys Asn Phe Glu Lys Gly Ser
            100                 105                 110

Asp Tyr Asn Lys Thr Trp Lys Ala Ser Glu Asp Gly Lys Ile Asn Thr
        115                 120                 125

Asn Gly Pro Arg Leu Val Val Asp Gln Gly Asn Gly Ser Gly Pro Thr
    130                 135                 140

Gly Gly Tyr Ile Thr Arg Ile Thr Asn Asp Ala Arg Glu Asp Glu Met
145                 150                 155                 160

Glu Gln Asn Ile Gly Glu Val Ala Gly Met Val Ser Asn Leu Arg Asn
                165                 170                 175

Met Ala Val Asp Met Gly Asn Glu Ile Glu Ser Gln Asn Lys Gln Leu
            180                 185                 190

Asp Arg Ile Asn Gln Lys Gly Gly Ser Leu Asn Val Arg Val Asp Glu
        195                 200                 205

Ala Asn Lys Arg Ala Asn Arg Ile Leu Arg Lys Gln
    210                 215                 220


<210> SEQ ID NO 24
<211> LENGTH: 207
<212> TYPE: PRT
<213> ORGANISM: Caenorhabditis elegans

<400> SEQUENCE: 24

Met Ser Gly Asp Asp Asp Ile Pro Glu Gly Leu Glu Ala Ile Asn Leu
 1               5                   10                  15

Lys Met Asn Ala Thr Thr Asp Asp Ser Leu Glu Ser Thr Arg Arg Met
            20                  25                  30

Leu Ala Leu Cys Glu Glu Ser Lys Glu Ala Gly Ile Lys Thr Leu Val
        35                  40                  45

Met Leu Asp Asp Gln Gly Glu Gln Leu Glu Arg Cys Glu Gly Ala Leu
    50                  55                  60

Asp Thr Ile Asn Gln Asp Met Lys Glu Ala Glu Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
        115                 120                 125

Met Gly Pro Gln Gly Gly Tyr Ile Thr Lys Ile Thr Asn Asp Ala Arg
    130                 135                 140

Glu Asp Glu Met Asp Glu Asn Val Gln Gln Val Ser Thr Met Val Gly
145                 150                 155                 160
```

```
Asn Leu Arg Asn Met Ala Ile Asp Met Ser Thr Glu Val Ser Asn Gln
            165                 170                 175

Asn Arg Gln Leu Asp Arg Ile His Asp Lys Ala Gln Ser Asn Glu Val
        180                 185                 190

Arg Val Glu Ser Ala Asn Lys Arg Ala Lys Asn Leu Ile Thr Lys
        195                 200                 205


<210> SEQ ID NO 25
<211> LENGTH: 370
<212> TYPE: PRT
<213> ORGANISM: Homo sapiens

<400> SEQUENCE: 25

Met Glu Pro Leu Phe Pro Ala Pro Phe Trp Glu Val Ile Tyr Gly Ser
1               5                   10                  15

His Leu Gln Gly Asn Leu Ser Leu Leu Ser Pro Asn His Ser Leu Leu
            20                  25                  30

Pro Pro His Leu Leu Leu Asn Ala Ser His Gly Ala Phe Leu Pro Leu
        35                  40                  45

Gly Leu Lys Val Thr Ile Val Gly Leu Tyr Leu Ala Val Cys Val Gly
    50                  55                  60

Gly Leu Leu Gly Asn Cys Leu Val Met Tyr Val Ile Leu Arg His Thr
65                  70                  75                  80

Lys Met Lys Thr Ala Thr Asn Ile Tyr Ile Phe Asn Leu Ala Leu Ala
                85                  90                  95

Asp Thr Leu Val Leu Leu Thr Leu Pro Phe Gln Gly Thr Asp Ile Leu
            100                 105                 110

Leu Gly Phe Trp Pro Phe Gly Asn Ala Leu Cys Lys Thr Val Ile Ala
        115                 120                 125

Ile Asp Tyr Tyr Asn Met Phe Thr Ser Thr Phe Thr Leu Thr Ala Met
    130                 135                 140

Ser Val Asp Arg Tyr Val Ala Ile Cys His Pro Ile Arg Ala Leu Asp
145                 150                 155                 160

Val Arg Thr Ser Ser Lys Ala Gln Ala Val Asn Val Ala Ile Trp Ala
                165                 170                 175

Leu Ala Ser Val Val Gly Val Pro Val Ala Ile Met Gly Ser Ala Gln
            180                 185                 190

Val Glu Asp Glu Glu Ile Glu Cys Leu Val Glu Ile Pro Thr Pro Gln
        195                 200                 205

Asp Tyr Trp Gly Pro Val Phe Ala Ile Cys Ile Phe Leu Phe Ser Phe
    210                 215                 220

Ile Val Pro Val Leu Val Ile Ser Val Cys Tyr Ser Leu Met Ile Arg
225                 230                 235                 240

Arg Leu Arg Gly Val Arg Leu Leu Ser Gly Ser Arg Glu Lys Asp Arg
                245                 250                 255

Asn Leu Arg Arg Ile Thr Arg Leu Val Leu Val Val Val Ala Val Phe
            260                 265                 270

Val Gly Cys Trp Thr Pro Val Gln Val Phe Val Leu Ala Gln Gly Leu
        275                 280                 285

Gly Val Gln Pro Ser Ser Glu Thr Ala Val Ala Ile Leu Arg Phe Cys
    290                 295                 300

Thr Ala Leu Gly Tyr Val Asn Ser Cys Leu Asn Pro Ile Leu Tyr Ala
305                 310                 315                 320

Phe Leu Asp Glu Asn Phe Lys Ala Cys Phe Arg Lys Phe Cys Cys Ala
                325                 330                 335
```

```
Ser Ala Leu Arg Arg Asp Val Gln Val Ser Asp Arg Val Arg Ser Ile
            340                 345                 350

Ala Lys Asp Val Ala Leu Ala Cys Lys Thr Ser Glu Thr Val Pro Arg
        355                 360                 365

Pro Ala
    370


<210> SEQ ID NO 26
<211> LENGTH: 365
<212> TYPE: PRT
<213> ORGANISM: Homo sapiens

<400> SEQUENCE: 26

Met Glu Pro Leu Phe Pro Ala Pro Phe Trp Glu Val Ile Tyr Gly Ser
 1               5                  10                  15

His Leu Gln Gly Asn Leu Ser Leu Leu Ser Pro Asn His Ser Leu Leu
            20                  25                  30

Pro Pro His Leu Leu Leu Asn Ala Ser His Gly Ala Phe Leu Pro Leu
        35                  40                  45

Gly Leu Lys Val Thr Ile Val Gly Leu Tyr Leu Ala Val Cys Val Gly
    50                  55                  60

Gly Leu Leu Gly Asn Cys Leu Val Met His Thr Lys Met Lys Thr Ala
65                  70                  75                  80

Thr Asn Ile Tyr Ile Phe Asn Leu Ala Leu Ala Asp Thr Leu Val Leu
                85                  90                  95

Leu Thr Leu Pro Phe Gln Gly Thr Asp Ile Leu Leu Gly Phe Trp Pro
            100                 105                 110

Phe Gly Asn Ala Leu Cys Lys Thr Val Ile Ala Ile Asp Tyr Tyr Asn
        115                 120                 125

Met Phe Thr Ser Thr Phe Thr Leu Thr Ala Met Ser Val Asp Arg Tyr
    130                 135                 140

Val Ala Ile Cys His Pro Ile Arg Ala Leu Asp Val Arg Thr Ser Ser
145                 150                 155                 160

Lys Ala Gln Ala Val Asn Val Ala Ile Trp Ala Leu Ala Ser Val Val
                165                 170                 175

Gly Val Pro Val Ala Ile Met Gly Ser Ala Gln Val Glu Asp Glu Glu
            180                 185                 190

Ile Glu Cys Leu Val Glu Ile Pro Thr Pro Gln Asp Tyr Trp Gly Pro
        195                 200                 205

Val Phe Ala Ile Cys Ile Phe Leu Phe Ser Phe Ile Val Pro Val Leu
    210                 215                 220

Val Ile Ser Val Cys Tyr Ser Leu Met Ile Arg Arg Leu Arg Gly Val
225                 230                 235                 240

Arg Leu Leu Ser Gly Ser Arg Glu Lys Asp Arg Asn Leu Arg Arg Ile
                245                 250                 255

Thr Arg Leu Val Leu Val Val Val Ala Val Phe Val Gly Cys Trp Thr
            260                 265                 270

Pro Val Gln Val Phe Val Leu Ala Gln Gly Leu Gly Val Gln Pro Ser
        275                 280                 285

Ser Glu Thr Ala Val Ala Ile Leu Arg Phe Cys Thr Ala Leu Gly Tyr
    290                 295                 300

Val Asn Ser Cys Leu Asn Pro Ile Leu Tyr Ala Phe Leu Asp Glu Asn
305                 310                 315                 320

Phe Lys Ala Cys Phe Arg Lys Phe Cys Cys Ala Ser Ala Leu Arg Arg
```

325 330 335

Asp Val Gln Val Ser Asp Arg Val Arg Ser Ile Ala Lys Asp Val Ala
340 345 350

Leu Ala Cys Lys Thr Ser Glu Thr Val Pro Arg Pro Ala
355 360 365

<210> SEQ ID NO 27
<211> LENGTH: 372
<212> TYPE: PRT
<213> ORGANISM: Homo sapiens

<400> SEQUENCE: 27

Met Glu Pro Ala Pro Ser Ala Gly Ala Glu Leu Gln Pro Pro Leu Phe
1 5 10 15

Ala Asn Ala Ser Asp Ala Tyr Pro Ser Ala Cys Pro Ser Ala Gly Ala
20 25 30

Asn Ala Ser Gly Pro Pro Gly Ala Arg Ser Ala Ser Ser Leu Ala Leu
35 40 45

Ala Ile Ala Ile Thr Ala Leu Tyr Ser Ala Val Cys Ala Val Gly Leu
50 55 60

Leu Gly Asn Val Leu Val Met Phe Gly Ile Val Arg Tyr Thr Lys Met
65 70 75 80

Lys Thr Ala Thr Asn Ile Tyr Ile Phe Asn Leu Ala Leu Ala Asp Ala
85 90 95

Leu Ala Thr Ser Thr Leu Pro Phe Gln Ser Ala Lys Tyr Leu Met Glu
100 105 110

Thr Trp Pro Phe Gly Glu Leu Leu Cys Lys Ala Val Leu Ser Ile Asp
115 120 125

Tyr Tyr Asn Met Phe Thr Ser Ile Phe Thr Leu Thr Met Met Ser Val
130 135 140

Asp Arg Tyr Ile Ala Val Cys His Pro Val Lys Ala Leu Asp Phe Arg
145 150 155 160

Thr Pro Ala Lys Ala Lys Leu Ile Asn Ile Cys Ile Trp Val Leu Ala
165 170 175

Ser Gly Val Gly Val Pro Ile Met Val Met Ala Val Thr Arg Pro Arg
180 185 190

Asp Gly Ala Val Val Cys Met Leu Gln Phe Pro Ser Pro Ser Trp Tyr
195 200 205

Trp Asp Thr Val Thr Lys Ile Cys Val Phe Leu Phe Ala Phe Val Val
210 215 220

Pro Ile Leu Ile Ile Thr Val Cys Tyr Gly Leu Met Leu Leu Arg Leu
225 230 235 240

Arg Ser Val Arg Leu Leu Ser Gly Ser Lys Glu Lys Asp Arg Ser Leu
245 250 255

Arg Arg Ile Thr Arg Met Val Leu Val Val Val Gly Ala Phe Val Val
260 265 270

Cys Trp Ala Pro Ile His Ile Phe Val Ile Val Trp Thr Leu Val Asp
275 280 285

Ile Asp Arg Arg Asp Pro Leu Val Val Ala Ala Leu His Leu Cys Ile
290 295 300

Ala Leu Gly Tyr Ala Asn Ser Ser Leu Asn Pro Val Leu Tyr Ala Phe
305 310 315 320

Leu Asp Glu Asn Phe Lys Arg Cys Phe Arg Gln Leu Cys Arg Lys Pro
325 330 335

Cys Gly Arg Pro Asp Pro Ser Ser Phe Ser Arg Ala Arg Glu Ala Thr
340 345 350

Ala Arg Glu Arg Val Thr Ala Cys Thr Pro Ser Asp Gly Pro Gly Gly
355 360 365

Gly Ala Ala Ala
370

<210> SEQ ID NO 28
<211> LENGTH: 372
<212> TYPE: PRT
<213> ORGANISM: Homo sapiens

<400> SEQUENCE: 28

Met Glu Pro Ala Pro Ser Ala Gly Ala Glu Leu Gln Pro Pro Leu Phe
1 5 10 15

Ala Asn Ala Ser Asp Ala Tyr Pro Ser Ala Phe Pro Ser Ala Gly Ala
20 25 30

Asn Ala Ser Gly Pro Pro Gly Ala Arg Ser Ala Ser Ser Leu Ala Leu
35 40 45

Ala Ile Ala Ile Thr Ala Leu Tyr Ser Ala Val Cys Ala Val Gly Leu
50 55 60

Leu Gly Asn Val Leu Val Met Phe Gly Ile Val Arg Tyr Thr Lys Met
65 70 75 80

Lys Thr Ala Thr Asn Ile Tyr Ile Phe Asn Leu Ala Leu Ala Asp Ala
85 90 95

Leu Ala Thr Ser Thr Leu Pro Phe Gln Ser Ala Lys Tyr Leu Met Glu
100 105 110

Thr Trp Pro Phe Gly Glu Leu Leu Cys Lys Ala Val Leu Ser Ile Asp
115 120 125

Tyr Tyr Asn Met Phe Thr Ser Ile Phe Thr Leu Thr Met Met Ser Val
130 135 140

Asp Arg Tyr Ile Ala Val Cys His Pro Val Lys Ala Leu Asp Phe Arg
145 150 155 160

Thr Pro Ala Lys Ala Lys Leu Ile Asn Ile Cys Ile Trp Val Leu Ala
165 170 175

Ser Gly Val Gly Val Pro Ile Met Val Met Ala Val Thr Arg Pro Arg
180 185 190

Asp Gly Ala Val Val Cys Met Leu Gln Phe Pro Ser Pro Ser Trp Tyr
195 200 205

Trp Asp Thr Val Thr Lys Ile Cys Val Phe Leu Phe Ala Phe Val Val
210 215 220

Pro Ile Leu Ile Ile Thr Val Cys Tyr Gly Leu Met Leu Leu Arg Leu
225 230 235 240

Arg Ser Val Arg Leu Leu Ser Gly Ser Lys Glu Lys Asp Arg Ser Leu
245 250 255

Arg Arg Ile Thr Arg Met Val Leu Val Val Val Gly Ala Phe Val Val
260 265 270

Cys Trp Ala Pro Ile His Ile Phe Val Ile Val Trp Thr Leu Val Asp
275 280 285

Ile Asp Arg Arg Asp Pro Leu Val Val Ala Ala Leu His Leu Cys Ile
290 295 300

Ala Leu Gly Tyr Ala Asn Ser Ser Leu Asn Pro Val Leu Tyr Ala Phe
305 310 315 320

Leu Asp Glu Asn Phe Lys Arg Cys Phe Arg Gln Leu Cys Arg Lys Pro
325 330 335

Cys Gly Arg Pro Asp Pro Ser Ser Phe Ser Arg Ala Arg Glu Ala Thr
340 345 350

Ala Arg Glu Arg Val Thr Ala Cys Thr Pro Ser Asp Gly Pro Gly Gly
355 360 365

Gly Ala Ala Ala
370

<210> SEQ ID NO 29
<211> LENGTH: 380
<212> TYPE: PRT
<213> ORGANISM: Homo sapiens

<400> SEQUENCE: 29

Met Asp Ser Pro Ile Gln Ile Phe Arg Gly Glu Pro Gly Pro Thr Cys
1 5 10 15

Ala Pro Ser Ala Cys Leu Pro Pro Asn Ser Ser Ala Trp Phe Pro Gly
20 25 30

Trp Ala Glu Pro Asp Ser Asn Gly Ser Ala Gly Ser Glu Asp Ala Gln
35 40 45

Leu Glu Pro Ala His Ile Ser Pro Ala Ile Pro Val Ile Ile Thr Ala
50 55 60

Val Tyr Ser Val Val Phe Val Val Gly Leu Val Gly Asn Ser Leu Val
65 70 75 80

Met Phe Val Ile Ile Arg Tyr Thr Lys Met Lys Thr Ala Thr Asn Ile
85 90 95

Tyr Ile Phe Asn Leu Ala Leu Ala Asp Ala Leu Val Thr Thr Thr Met
100 105 110

Pro Phe Gln Ser Thr Val Tyr Leu Met Asn Ser Trp Pro Phe Gly Asp
115 120 125

Val Leu Cys Lys Ile Val Ile Ser Ile Asp Tyr Tyr Asn Met Phe Thr
130 135 140

Ser Ile Phe Thr Leu Thr Met Met Ser Val Asp Arg Tyr Ile Ala Val
145 150 155 160

Cys His Pro Val Lys Ala Leu Asp Phe Arg Thr Pro Leu Lys Ala Lys
165 170 175

Ile Ile Asn Ile Cys Ile Trp Leu Leu Ser Ser Ser Val Gly Ile Ser
180 185 190

Ala Ile Val Leu Gly Gly Thr Lys Val Arg Glu Asp Val Asp Val Ile
195 200 205

Glu Cys Ser Leu Gln Phe Pro Asp Asp Asp Tyr Ser Trp Trp Asp Leu
210 215 220

Phe Met Lys Ile Cys Val Phe Ile Phe Ala Phe Val Ile Pro Val Leu
225 230 235 240

Ile Ile Ile Val Cys Tyr Thr Leu Met Ile Leu Arg Leu Lys Ser Val
245 250 255

Arg Leu Leu Ser Gly Ser Arg Glu Lys Asp Arg Asn Leu Arg Arg Ile
260 265 270

Thr Arg Leu Val Leu Val Val Val Ala Val Phe Val Val Cys Trp Thr
275 280 285

Pro Ile His Ile Phe Ile Leu Val Glu Ala Leu Gly Ser Thr Ser His
290 295 300

Ser Thr Ala Ala Leu Ser Ser Tyr Tyr Phe Cys Ile Ala Leu Gly Tyr
305 310 315 320

Thr Asn Ser Ser Leu Asn Pro Ile Leu Tyr Ala Phe Leu Asp Glu Asn

```
                325                 330                 335

Phe Lys Arg Cys Phe Arg Asp Phe Cys Phe Pro Leu Lys Met Arg Met
            340                 345                 350

Glu Arg Gln Ser Thr Ser Arg Val Arg Asn Thr Val Gln Asp Pro Ala
        355                 360                 365

Tyr Leu Arg Asp Ile Asp Gly Met Asn Lys Pro Val
    370                 375                 380


<210> SEQ ID NO 30
<211> LENGTH: 380
<212> TYPE: PRT
<213> ORGANISM: Homo sapiens

<400> SEQUENCE: 30

Met Glu Ser Pro Ile Gln Ile Phe Arg Gly Glu Pro Gly Pro Thr Cys
 1               5                  10                  15

Ala Pro Ser Ala Cys Leu Pro Pro Asn Ser Ser Ala Trp Phe Pro Gly
            20                  25                  30

Trp Ala Glu Pro Asp Ser Asn Gly Ser Ala Gly Ser Glu Asp Ala Gln
        35                  40                  45

Leu Glu Pro Ala His Ile Ser Pro Ala Ile Pro Val Ile Ile Thr Ala
    50                  55                  60

Val Tyr Ser Val Val Phe Val Val Gly Leu Val Gly Asn Ser Leu Val
65                  70                  75                  80

Met Phe Val Ile Ile Arg Tyr Thr Lys Met Lys Thr Ala Thr Asn Ile
                85                  90                  95

Tyr Ile Phe Asn Leu Ala Leu Ala Asp Ala Leu Val Thr Thr Thr Met
            100                 105                 110

Pro Phe Gln Ser Thr Val Tyr Leu Met Asn Ser Trp Pro Phe Gly Asp
        115                 120                 125

Val Leu Cys Lys Ile Val Ile Ser Ile Asp Tyr Tyr Asn Met Phe Thr
    130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ser Ser Ser Val Gly Ile Ser
            180                 185                 190

Ala Ile Val Leu Gly Gly Thr Lys Val Arg Glu Asp Val Asp Val Ile
        195                 200                 205

Glu Cys Ser Leu Gln Phe Pro Asp Asp Asp Tyr Ser Trp Trp Asp Leu
    210                 215                 220

Phe Met Lys Ile Cys Val Phe Ile Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
            260                 265                 270

Thr Arg Leu Val Leu Val Val Val Ala Val Phe Val Val Cys Trp Thr
        275                 280                 285

Pro Ile His Ile Phe Ile Leu Val Glu Ala Leu Gly Ser Thr Ser His
    290                 295                 300

Ser Thr Ala Ala Leu Ser Ser Tyr Tyr Phe Cys Ile Ala Leu Gly Tyr
305                 310                 315                 320
```

```
Thr Asn Ser Ser Leu Asn Pro Ile Leu Tyr Ala Phe Leu Asp Glu Asn
                325                 330                 335

Phe Lys Arg Cys Phe Arg Asp Phe Cys Phe Pro Leu Lys Met Arg Met
            340                 345                 350

Glu Arg Gln Ser Thr Ser Arg Val Arg Asn Thr Val Gln Asp Pro Ala
        355                 360                 365

Tyr Leu Arg Asp Ile Asp Gly Met Asn Lys Pro Val
    370                 375                 380


<210> SEQ ID NO 31
<211> LENGTH: 493
<212> TYPE: PRT
<213> ORGANISM: Homo sapiens

<400> SEQUENCE: 31

Met Cys Leu His Arg Arg Val Pro Ser Glu Glu Thr Tyr Ser Leu Asp
 1               5                  10                  15

Arg Phe Ala Gln Asn Pro Pro Leu Phe Pro Pro Pro Ser Leu Pro Ala
            20                  25                  30

Ser Glu Ser Arg Met Ala His Ala Pro Leu Leu Gln Arg Cys Gly Ala
        35                  40                  45

Ala Arg Thr Gly Phe Cys Lys Lys Gln Gln Glu Leu Trp Gln Arg Arg
    50                  55                  60

Lys Glu Ala Ala Glu Ala Leu Gly Thr Arg Lys Val Ser Val Leu Leu
65                  70                  75                  80

Ala Thr Ser His Ser Gly Ala Arg Pro Ala Val Ser Thr Met Asp Ser
                85                  90                  95

Ser Ala Ala Pro Thr Asn Ala Ser Asn Cys Thr Asp Ala Leu Ala Tyr
            100                 105                 110

Ser Ser Cys Ser Pro Ala Pro Ser Pro Gly Ser Trp Val Asn Leu Ser
        115                 120                 125

His Leu Asp Gly Asn Leu Ser Asp Pro Cys Gly Pro Asn Arg Thr Asp
    130                 135                 140

Leu Gly Gly Arg Asp Ser Leu Cys Pro Pro Thr Gly Ser Pro Ser Met
145                 150                 155                 160

Ile Thr Ala Ile Thr Ile Met Ala Leu Tyr Ser Ile Val Cys Val Val
                165                 170                 175

Gly Leu Phe Gly Asn Phe Leu Val Met Tyr Val Ile Val Arg Tyr Thr
            180                 185                 190

Lys Met Lys Thr Ala Thr Asn Ile Tyr Ile Phe Asn Leu Ala Leu Ala
        195                 200                 205

Asp Ala Leu Ala Thr Ser Thr Leu Pro Phe Gln Ser Val Asn Tyr Leu
    210                 215                 220

Met Gly Thr Trp Pro Phe Gly Thr Ile Leu Cys Lys Ile Val Ile Ser
225                 230                 235                 240

Ile Asp Tyr Tyr Asn Met Phe Thr Ser Ile Phe Thr Leu Cys Thr Met
                245                 250                 255

Ser Val Asp Arg Tyr Ile Ala Val Cys His Pro Val Lys Ala Leu Asp
            260                 265                 270

Phe Arg Thr Pro Arg Asn Ala Lys Ile Ile Asn Val Cys Asn Trp Ile
        275                 280                 285

Leu Ser Ser Ala Ile Gly Leu Pro Val Met Phe Met Ala Thr Thr Lys
    290                 295                 300

Tyr Arg Gln Gly Ser Ile Asp Cys Thr Leu Thr Phe Ser His Pro Thr
305                 310                 315                 320
```

```
Trp Tyr Trp Glu Asn Leu Leu Lys Ile Cys Val Phe Ile Phe Ala Phe
                325                 330                 335

Ile Met Pro Val Leu Ile Ile Thr Val Cys Tyr Gly Leu Met Ile Leu
            340                 345                 350

Arg Leu Lys Ser Val Arg Met Leu Ser Gly Ser Lys Glu Lys Asp Arg
        355                 360                 365

Asn Leu Arg Arg Ile Thr Arg Met Val Leu Val Val Val Ala Val Phe
    370                 375                 380

Ile Val Cys Trp Thr Pro Ile His Ile Tyr Val Ile Ile Lys Ala Leu
385                 390                 395                 400

Val Thr Ile Pro Glu Thr Thr Phe Gln Thr Val Ser Trp His Phe Cys
                405                 410                 415

Ile Ala Leu Gly Tyr Thr Asn Ser Cys Leu Asn Pro Val Leu Tyr Ala
            420                 425                 430

Phe Leu Asp Glu Asn Phe Lys Arg Cys Phe Arg Glu Phe Cys Ile Pro
        435                 440                 445

Thr Ser Ser Asn Ile Glu Gln Gln Asn Ser Thr Arg Ile Arg Gln Asn
    450                 455                 460

Thr Arg Asp His Pro Ser Thr Ala Asn Thr Val Asp Arg Thr Asn His
465                 470                 475                 480

Gln Leu Glu Asn Leu Glu Ala Glu Thr Ala Pro Leu Pro
                485                 490


<210> SEQ ID NO 32
<211> LENGTH: 5
<212> TYPE: PRT
<213> ORGANISM: Artificial Sequence
<220> FEATURE:
<223> OTHER INFORMATION: SNAP-25 antigen having a free carboxyl-terminus
      at the P1

<400> SEQUENCE: 32

Asp Glu Ala Asn Gln
1               5


<210> SEQ ID NO 33
<211> LENGTH: 6
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A cleavage site

<400> SEQUENCE: 33

Ile Asp Glu Ala Asn Gln
1               5


<210> SEQ ID NO 34
<211> LENGTH: 7
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A cleavage site

<400> SEQUENCE: 34

Arg Ile Asp Glu Ala Asn Gln
1               5


<210> SEQ ID NO 35
<211> LENGTH: 8
```

<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 35

Thr Arg Ile Asp Glu Ala Asn Gln
1 5

<210> SEQ ID NO 36
<211> LENGTH: 9
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 36

Lys Thr Arg Ile Asp Glu Ala Asn Gln
1 5

<210> SEQ ID NO 37
<211> LENGTH: 10
<212> TYPE: PRT
<213> ORGANISM: Artificial Sequence
<220> FEATURE:
<223> OTHER INFORMATION: SNAP-25 antigen having a free carboxyl-terminus at the P1

<400> SEQUENCE: 37

Asn Lys Thr Arg Ile Asp Glu Ala Asn Gln
1 5 10

<210> SEQ ID NO 38
<211> LENGTH: 11
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 38

Ser Asn Lys Thr Arg Ile Asp Glu Ala Asn Gln
1 5 10

<210> SEQ ID NO 39
<211> LENGTH: 12
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 39

Asp Ser Asn Lys Thr Arg Ile Asp Glu Ala Asn Gln
1 5 10

<210> SEQ ID NO 40
<211> LENGTH: 13
<212> TYPE: PRT
<213> ORGANISM: Artificial Sequence
<220> FEATURE:
<223> OTHER INFORMATION: SNAP-25 antigen having a free carboxylated carboxyl-terminus at the P1 residue of the scissile bond of the BoNT/A cleavage site
<220> FEATURE:
<221> NAME/KEY: SITE
<222> LOCATION: (13)...(13)

```
<223> OTHER INFORMATION: carboxylated glutamine

<400> SEQUENCE: 40

Cys Asp Ser Asn Lys Thr Arg Ile Asp Glu Ala Asn Gln
 1               5                   10


<210> SEQ ID NO 41
<211> LENGTH: 7
<212> TYPE: PRT
<213> ORGANISM: Artificial Sequence
<220> FEATURE:
<223> OTHER INFORMATION: SNAP-25 antigen having a free carboxyl-terminus
      at the P1

<400> SEQUENCE: 41

Arg Ile Asp Glu Ala Asn Lys
 1               5


<210> SEQ ID NO 42
<211> LENGTH: 8
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A cleavage site

<400> SEQUENCE: 42

Ala Arg Ile Asp Glu Ala Asn Lys
 1               5


<210> SEQ ID NO 43
<211> LENGTH: 9
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A cleavage site

<400> SEQUENCE: 43

Lys Ala Arg Ile Asp Glu Ala Asn Lys
 1               5


<210> SEQ ID NO 44
<211> LENGTH: 10
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A cleavage site

<400> SEQUENCE: 44

Asn Lys Ala Arg Ile Asp Glu Ala Asn Lys
 1               5                   10


<210> SEQ ID NO 45
<211> LENGTH: 11
<212> TYPE: PRT
<213> ORGANISM: Artificial Sequence
<220> FEATURE:
<223> OTHER INFORMATION: SNAP-25 antigen having a free carboxyl-terminus
      at the P1 residue of the scissile bond of the BoNT/A cleavage site

<400> SEQUENCE: 45

Met Asn Lys Ala Arg Ile Asp Glu Ala Asn Lys
 1               5                   10


<210> SEQ ID NO 46
```

<211> LENGTH: 12
<212> TYPE: PRT
<213> ORGANISM: Artificial Sequence
<220> FEATURE:
<223> OTHER INFORMATION: SNAP-25 antigen having a free carboxyl-terminus at the P1 residue of the scissile bond of the BoNT/A cleavage site

<400> SEQUENCE: 46

Asp Met Asn Lys Ala Arg Ile Asp Glu Ala Asn Lys
1 5 10

<210> SEQ ID NO 47
<211> LENGTH: 13
<212> TYPE: PRT
<213> ORGANISM: Artificial Sequence
<220> FEATURE:
<223> OTHER INFORMATION: SNAP-25 antigen having a free carboxylated carboxyl-terminus at the P1 residue of the scissile bond of the BoNT/A cleavage site
<220> FEATURE:
<221> NAME/KEY: SITE
<222> LOCATION: (13)...(13)
<223> OTHER INFORMATION: Carboxylated lysine

<400> SEQUENCE: 47

Cys Asp Met Asn Lys Ala Arg Ile Asp Glu Ala Asn Lys
1 5 10

<210> SEQ ID NO 48
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 48

Cys Gly Gly Gly Arg Ile Asp Glu Ala Asn Gln
1 5 10

<210> SEQ ID NO 49
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 49

Cys Gly Gly Gly Arg Ile Asp Glu Ala Asn Lys
1 5 10

<210> SEQ ID NO 50
<211> LENGTH: 88
<212> TYPE: PRT
<213> ORGANISM: Artificial Sequence
<220> FEATURE:
<223> OTHER INFORMATION: BirA-HisTag?-SNAP-25-134-197

<400> SEQUENCE: 50

Met Gly Gly Gly Leu Asn Asp Ile Phe Glu Ala Gln Lys Ile Glu Trp
1 5 10 15

His His His His His His His His Ile Arg Arg Val Thr Asn Asp Ala
20 25 30

Arg Glu Asn Glu Met Asp Glu Asn Leu Glu Gln Val Ser Gly Ile Ile
35 40 45

Gly Asn Leu Arg His Met Ala Leu Asp Met Gly Asn Glu Ile Asp Thr
50 55 60

```
Gln Asn Arg Gln Ile Asp Arg Ile Met Glu Lys Ala Asp Ser Asn Lys
65                  70                  75                  80

Thr Arg Ile Asp Glu Ala Asn Gln
                85


<210> SEQ ID NO 51
<211> LENGTH: 97
<212> TYPE: PRT
<213> ORGANISM: Artificial Sequence
<220> FEATURE:
<223> OTHER INFORMATION: BirA-HisTag?-SNAP-25-134-206

<400> SEQUENCE: 51

Met Gly Gly Gly Leu Asn Asp Ile Phe Glu Ala Gln Lys Ile Glu Trp
 1               5                  10                  15

His His His His His His His His Ile Arg Arg Val Thr Asn Asp Ala
            20                  25                  30

Arg Glu Asn Glu Met Asp Glu Asn Leu Glu Gln Val Ser Gly Ile Ile
        35                  40                  45

Gly Asn Leu Arg His Met Ala Leu Asp Met Gly Asn Glu Ile Asp Thr
    50                  55                  60

Gln Asn Arg Gln Ile Asp Arg Ile Met Glu Lys Ala Asp Ser Asn Lys
65                  70                  75                  80

Thr Arg Ile Asp Glu Ala Asn Gln Arg Ala Thr Lys Met Leu Gly Ser
                85                  90                  95

Gly


<210> SEQ ID NO 52
<211> LENGTH: 16
<212> TYPE: PRT
<213> ORGANISM: Artificial Sequence
<220> FEATURE:
<223> OTHER INFORMATION: BirA peptide

<400> SEQUENCE: 52

Gly Gly Gly Leu Asn Asp Ile Phe Glu Ala Gln Lys Ile Glu Trp His
 1               5                  10                  15


<210> SEQ ID NO 53
<211> LENGTH: 7570
<212> TYPE: DNA
<213> ORGANISM: Artificial Sequence
<220> FEATURE:
<223> OTHER INFORMATION: pQBI-25/GFP-BoNT/A-LC expression construct.

<400> SEQUENCE: 53

gacggatcgg gagatctccc gatcccctat ggtcgactct cagtacaatc tgctctgatg      60

ccgcatagtt aagccagtat ctgctccctg cttgtgtgtt ggaggtcgct gagtagtgcg     120

cgagcaaaat ttaagctaca acaaggcaag gcttgaccga caattgcatg aagaatctgc     180

ttagggttag gcgttttgcg ctgcttcgcc tcgaggcctg gccattgcat acgttgtatc     240

catatcataa tatgtacatt tatattggct catgtccaac attaccgcca tgttgacatt     300

gattattgac tagttattaa tagtaatcaa ttacggggtc attagttcat agcccatata     360

tggagttccg cgttacataa cttacggtaa atggcccgcc tggctgaccg cccaacgacc     420

cccgcccatt gacgtcaata atgacgtatg ttcccatagt aacgccaata gggactttcc     480

attgacgtca atgggtggag tatttacggt aaactgccca cttggcagta catcaagtgt     540

atcatatgcc aagtacgccc cctattgacg tcaatgacgg taaatggccc gcctggcatt     600
```

-continued atgcccagta catgacctta tgggactttc ctacttggca gtacatctac gtattagtca 660
tcgctattac catggtgatg cggttttggc agtacatcaa tgggcgtgga tagcggtttg 720
actcacgggg atttccaagt ctccacccca ttgacgtcaa tgggagtttg ttttggcacc 780
aaaatcaacg ggactttcca aaatgtcgta acaactccgc cccattgacg caaatgggcg 840
gtaggcgtgt acggtgggag gtctatataa gcagagctcg tttagtgaac cgtcagatcg 900
cctggagacg ccatccacgc tgttttgacc tccatagaag acaccgggac cgatccagcc 960
tccgcgggcc accatggagg gcccggttac cggtaccgga tccagatatc tgggcggccg 1020
ctcagcaagc ttcgcgaatt cgggaggcgg aggtggagct agcaaaggag aagaactctt 1080
cactggagtt gtcccaattc ttgttgaatt agatggtgat gttaacggcc acaagttctc 1140
tgtcagtgga gagggtgaag gtgatgcaac atacggaaaa cttaccctga agttcatctg 1200
cactactggc aaactgcctg ttccatggcc aacactagtc actactctgt gctatggtgt 1260
tcaatgcttt tcaagatacc cggatcatat gaaacggcat gactttttca agagtgccat 1320
gcccgaaggt tatgtacagg aaaggaccat cttcttcaaa gatgacggca actacaagac 1380
acgtgctgaa gtcaagtttg aaggtgatac ccttgttaat agaatcgagt taaaaggtat 1440
tgacttcaag gaagatggca acattctggg acacaaattg gaatacaact ataactcaca 1500
caatgtatac atcatggcag acaaacaaaa gaatggaatc aaagtgaact tcaagacccg 1560
ccacaacatt gaagatggaa gcgttcaact agcagaccat tatcaacaaa atactccaat 1620
tggcgatggc cctgtccttt taccagacaa ccattacctg tccacacaat ctgccctttc 1680
gaaagatccc aacgaaaaga gagaccacat ggtccttctt gagtttgtaa cagctgctgg 1740
gattacacat ggcatggatg aactgtacaa catcgatgga ggcggaggtg gacctttttgt 1800
taataaacaa tttaattata aagatcctgt aaatggtgtt gatattgctt atataaaaat 1860
tccaaatgca ggacaaatgc aaccagtaaa agcttttaaa attcataata aaatatgggt 1920
tattccagaa agagatacat ttacaaatcc tgaagaagga gatttaaatc caccaccaga 1980
agcaaaacaa gttccagttt catattatga ttcaacatat ttaagtacag ataatgaaaa 2040
agataattat ttaaagggag ttacaaaatt atttgagaga atttattcaa ctgatcttgg 2100
aagaatgttg ttaacatcaa tagtaagggg aataccattt tggggtggaa gtacaataga 2160
tacagaatta aaagttattg atactaattg tattaatgtg atacaaccag atggtagtta 2220
tagatcagaa gaacttaatc tagtaataat aggaccctca gctgatatta tacagtttga 2280
atgtaaaagc tttggacatg aagttttgaa tcttacgcga aatggttatg gctctactca 2340
atacattaga tttagcccag attttacatt tggttttgag gagtcacttg aagttgatac 2400
aaatcctctt ttaggtgcag gcaaatttgc tacagatcca gcagtaacat tagcacatga 2460
acttatacat gctggacata gattatatgg aatagcaatt aatccaaata gggtttttaa 2520
agtaaatact aatgcctatt atgaaatgag tgggttagaa gtaagctttg aggaacttag 2580
aacatttggg ggacatgatg caaagtttat agatagttta caggaaaacg aatttcgtct 2640
atattattat aataagttta aagatatagc aagtacactt aataaagcta aatcaatagt 2700
aggtactact gcttcattac agtatatgaa aaatgttttt aaagagaaat atctcctatc 2760
tgaagataca tctggaaaat tttcggtaga taaattaaaa tttgataagt tatacaaaat 2820
gttaacagag atttacacag aggataattt tgttaagttt tttaaagtac ttaacagaaa 2880
aacatatttg aattttgata aagccgtatt taagataaat atagtaccta aggtaaatta 2940
cacaatatat gatggattta atttaagaaa tacaaattta gcagcaaact ttaatggtca 3000

-continued aaatacagaa attaataata tgaattttac taaactaaaa aattttactg gattgtttga 3060
attttataag ttgctatgtg taagagggat aatcacttcg aaatgaacgc gttggcccta 3120
ttctatagtg tcacctaaat gctagagctc gctgatcagc ctcgactgtg ccttctagtt 3180
gccagccatc tgttgtttgc ccctcccccg tgccttcctt gaccctggaa ggtgccactc 3240
ccactgtcct ttcctaataa aatgaggaaa ttgcatcgca ttgtctgagt aggtgtcatt 3300
ctattctggg gggtggggtg gggcaggaca gcaaggggga ggattgggaa gacaatagca 3360
ggcatgctgg ggatgcggtg ggctctatgg cttctgaggc ggaaagaacc agctggggct 3420
ctagggggta tccccacgcg ccctgtagcg gcgcattaag cgcggcgggt gtggtggtta 3480
cgcgcagcgt gaccgctaca cttgccagcg ccctagcgcc cgctcctttc gctttcttcc 3540
cttcctttct cgccacgttc gccggctttc cccgtcaagc tctaaatcgg ggcatccctt 3600
tagggttccg atttagtgct ttacggcacc tcgaccccaa aaaacttgat tagggtgatg 3660
gttcacgtag tgggccatcg ccctgataga cggtttttcg ccctttgacg ttggagtcca 3720
cgttctttaa tagtggactc ttgttccaaa ctggaacaac actcaaccct atctcggtct 3780
attcttttga tttataaggg attttgggga tttcggccta ttggttaaaa aatgagctga 3840
tttaacaaaa atttaacgcg aattaattct gtggaatgtg tgtcagttag ggtgtggaaa 3900
gtccccaggc tccccaggca ggcagaagta tgcaaagcat gcatctcaat tagtcagcaa 3960
ccaggtgtgg aaagtcccca ggctccccag caggcagaag tatgcaaagc atgcatctca 4020
attagtcagc aaccatagtc ccgcccctaa ctccgcccat cccgccccta actccgccca 4080
gttccgccca ttctccgccc catggctgac taattttttt tatttatgca gaggccgagg 4140
ccgcctctgc ctctgagcta ttccagaagt agtgaggagg cttttttgga ggcctaggct 4200
tttgcaaaaa gctcccggga gcttgtatat ccattttcgg atctgatcaa gagacaggat 4260
gaggatcgtt tcgcatgatt gaacaagatg gattgcacgc aggttctccg gccgcttggg 4320
tggagaggct attcggctat gactgggcac aacagacaat cggctgctct gatgccgccg 4380
tgttccggct gtcagcgcag gggcgcccgg ttctttttgt caagaccgac ctgtccggtg 4440
ccctgaatga actgcaggac gaggcagcgc ggctatcgtg gctggccacg acgggcgttc 4500
cttgcgcagc tgtgctcgac gttgtcactg aagcgggaag ggactggctg ctattgggcg 4560
aagtgccggg gcaggatctc ctgtcatctc accttgctcc tgccgagaaa gtatccatca 4620
tggctgatgc aatgcggcgg ctgcatacgc ttgatccggc tacctgccca ttcgaccacc 4680
aagcgaaaca tcgcatcgag cgagcacgta ctcggatgga agccggtctt gtcgatcagg 4740
atgatctgga cgaagagcat caggggctcg cgccagccga actgttcgcc aggctcaagg 4800
cgcgcatgcc cgacggcgag gatctcgtcg tgacccatgg cgatgcctgc ttgccgaata 4860
tcatggtgga aaatggccgc ttttctggat tcatcgactg tggccggctg ggtgtggcgg 4920
accgctatca ggacatagcg ttggctaccc gtgatattgc tgaagagctt ggcggcgaat 4980
gggctgaccg cttcctcgtg ctttacggta tcgccgctcc cgattcgcag cgcatcgcct 5040
tctatcgcct tcttgacgag ttcttctgag cgggactctg gggttcgaaa tgaccgacca 5100
agcgacgccc aacctgccat cacgagattt cgattccacc gccgccttct atgaaaggtt 5160
gggcttcgga atcgttttcc gggacgccgg ctggatgatc ctccagcgcg gggatctcat 5220
gctggagttc ttcgcccacc ccaacttgtt tattgcagct tataatggtt acaaataaag 5280
caatagcatc acaaatttca caaataaagc atttttttca ctgcattcta gttgtggttt 5340

-continued gtccaaactc atcaatgtat cttatcatgt ctgtataccg tcgacctcta gctagagctt 5400
ggcgtaatca tggtcatagc tgtttcctgt gtgaaattgt tatccgctca caattccaca 5460
caacatacga gccggaagca taaagtgtaa agcctggggt gcctaatgag tgagctaact 5520
cacattaatt gcgttgcgct cactgcccgc tttccagtcg ggaaacctgt cgtgccagct 5580
gcattaatga atcggccaac gcgcggggag aggcggtttg cgtattgggc gctcttccgc 5640
ttcctcgctc actgactcgc tgcgctcggt cgttcggctg cggcgagcgg tatcagctca 5700
ctcaaaggcg gtaatacggt tatccacaga atcaggggat aacgcaggaa agaacatgtg 5760
agcaaaaggc cagcaaaagg ccaggaaccg taaaaaggcc gcgttgctgg cgtttttcca 5820
taggctccgc ccccctgacg agcatcacaa aaatcgacgc tcaagtcaga ggtggcgaaa 5880
cccgacagga ctataaagat accaggcgtt tccccctgga agctccctcg tgcgctctcc 5940
tgttccgacc ctgccgctta ccggatacct gtccgccttt ctcccttcgg gaagcgtggc 6000
gctttctcaa tgctcacgct gtaggtatct cagttcggtg taggtcgttc gctccaagct 6060
gggctgtgtg cacgaacccc ccgttcagcc cgaccgctgc gccttatccg gtaactatcg 6120
tcttgagtcc aacccggtaa gacacgactt atcgccactg gcagcagcca ctggtaacag 6180
gattagcaga gcgaggtatg taggcggtgc tacagagttc ttgaagtggt ggcctaacta 6240
cggctacact agaaggacag tatttggtat ctgcgctctg ctgaagccag ttaccttcgg 6300
aaaaagagtt ggtagctctt gatccggcaa acaaaccacc gctggtagcg gtggtttttt 6360
tgtttgcaag cagcagatta cgcgcagaaa aaaaggatct caagaagatc ctttgatctt 6420
ttctacgggg tctgacgctc agtggaacga aaactcacgt taagggattt tggtcatgag 6480
attatcaaaa aggatcttca cctagatcct tttaaattaa aaatgaagtt ttaaatcaat 6540
ctaaagtata tatgagtaaa cttggtctga cagttaccaa tgcttaatca gtgaggcacc 6600
tatctcagcg atctgtctat ttcgttcatc catagttgcc tgactccccg tcgtgtagat 6660
aactacgata cgggagggct taccatctgg ccccagtgct gcaatgatac cgcgagaccc 6720
acgctcaccg gctccagatt tatcagcaat aaaccagcca gccggaaggg ccgagcgcag 6780
aagtggtcct gcaactttat ccgcctccat ccagtctatt aattgttgcc gggaagctag 6840
agtaagtagt tcgccagtta atagtttgcg caacgttgtt gccattgcta caggcatcgt 6900
ggtgtcacgc tcgtcgtttg gtatggcttc attcagctcc ggttcccaac gatcaaggcg 6960
agttacatga tcccccatgt tgtgcaaaaa agcggttagc tccttcggtc ctccgatcgt 7020
tgtcagaagt aagttggccg cagtgttatc actcatggtt atggcagcac tgcataattc 7080
tcttactgtc atgccatccg taagatgctt ttctgtgact ggtgagtact caaccaagtc 7140
attctgagaa tagtgtatgc ggcgaccgag ttgctcttgc ccggcgtcaa tacgggataa 7200
taccgcgcca catagcagaa ctttaaaagt gctcatcatt ggaaaacgtt cttcggggcg 7260
aaaactctca aggatcttac cgctgttgag atccagttcg atgtaaccca ctcgtgcacc 7320
caactgatct tcagcatctt ttactttcac cagcgtttct gggtgagcaa aaacaggaag 7380
gcaaaatgcc gcaaaaaagg gaataagggc gacacggaaa tgttgaatac tcatactctt 7440
cctttttcaa tattattgaa gcatttatca gggttattgt ctcatgagcg gatacatatt 7500
tgaatgtatt tagaaaaata aacaaatagg ggttccgcgc acatttcccc gaaaagtgcc 7560
acctgacgtc 7570

<210> SEQ ID NO 54
<211> LENGTH: 682

```
<212> TYPE: PRT
<213> ORGANISM: Artificial Sequence
<220> FEATURE:
<223> OTHER INFORMATION: GFP-BoNT/A light chain amino acid sequence.

<400> SEQUENCE: 54

Ala Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Cys Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly Pro Phe Val Asn Lys Gln Phe Asn Tyr Lys Asp
                245                 250                 255

Pro Val Asn Gly Val Asp Ile Ala Tyr Ile Lys Ile Pro Asn Ala Gly
            260                 265                 270

Gln Met Gln Pro Val Lys Ala Phe Lys Ile His Asn Lys Ile Trp Val
        275                 280                 285

Ile Pro Glu Arg Asp Thr Phe Thr Asn Pro Glu Glu Gly Asp Leu Asn
    290                 295                 300

Pro Pro Pro Glu Ala Lys Gln Val Pro Val Ser Tyr Tyr Asp Ser Thr
305                 310                 315                 320

Tyr Leu Ser Thr Asp Asn Glu Lys Asp Asn Tyr Leu Lys Gly Val Thr
                325                 330                 335

Lys Leu Phe Glu Arg Ile Tyr Ser Thr Asp Leu Gly Arg Met Leu Leu
            340                 345                 350

Thr Ser Ile Val Arg Gly Ile Pro Phe Trp Gly Gly Ser Thr Ile Asp
        355                 360                 365

Thr Glu Leu Lys Val Ile Asp Thr Asn Cys Ile Asn Val Ile Gln Pro
    370                 375                 380
```

```
Asp Gly Ser Tyr Arg Ser Glu Glu Leu Asn Leu Val Ile Ile Gly Pro
385                 390                 395                 400

Ser Ala Asp Ile Ile Gln Phe Glu Cys Lys Ser Phe Gly His Glu Val
                405                 410                 415

Leu Asn Leu Thr Arg Asn Gly Tyr Gly Ser Thr Gln Tyr Ile Arg Phe
            420                 425                 430

Ser Pro Asp Phe Thr Phe Gly Phe Glu Glu Ser Leu Glu Val Asp Thr
        435                 440                 445

Asn Pro Leu Leu Gly Ala Gly Lys Phe Ala Thr Asp Pro Ala Val Thr
    450                 455                 460

Leu Ala His Glu Leu Ile His Ala Gly His Arg Leu Tyr Gly Ile Ala
465                 470                 475                 480

Ile Asn Pro Asn Arg Val Phe Lys Val Asn Thr Asn Ala Tyr Tyr Glu
                485                 490                 495

Met Ser Gly Leu Glu Val Ser Phe Glu Glu Leu Arg Thr Phe Gly Gly
            500                 505                 510

His Asp Ala Lys Phe Ile Asp Ser Leu Gln Glu Asn Glu Phe Arg Leu
        515                 520                 525

Tyr Tyr Tyr Asn Lys Phe Lys Asp Ile Ala Ser Thr Leu Asn Lys Ala
    530                 535                 540

Lys Ser Ile Val Gly Thr Thr Ala Ser Leu Gln Tyr Met Lys Asn Val
545                 550                 555                 560

Phe Lys Glu Lys Tyr Leu Leu Ser Glu Asp Thr Ser Gly Lys Phe Ser
                565                 570                 575

Val Asp Lys Leu Lys Phe Asp Lys Leu Tyr Lys Met Leu Thr Glu Ile
            580                 585                 590

Tyr Thr Glu Asp Asn Phe Val Lys Phe Phe Lys Val Leu Asn Arg Lys
        595                 600                 605

Thr Tyr Leu Asn Phe Asp Lys Ala Val Phe Lys Ile Asn Ile Val Pro
    610                 615                 620

Lys Val Asn Tyr Thr Ile Tyr Asp Gly Phe Asn Leu Arg Asn Thr Asn
625                 630                 635                 640

Leu Ala Ala Asn Phe Asn Gly Gln Asn Thr Glu Ile Asn Asn Met Asn
                645                 650                 655

Phe Thr Lys Leu Lys Asn Phe Thr Gly Leu Phe Glu Phe Tyr Lys Leu
            660                 665                 670

Leu Cys Val Arg Gly Ile Ile Thr Ser Lys
        675                 680
```

```
<210> SEQ ID NO 55
<211> LENGTH: 6259
<212> TYPE: DNA
<213> ORGANISM: Artificial Sequence
<220> FEATURE:
<223> OTHER INFORMATION: pQBI-25/GFP expression construct.

<400> SEQUENCE: 55

gacggatcgg gagatctccc gatcccctat ggtcgactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcc tcgaggcctg gccattgcat acgttgtatc    240

catatcataa tatgtacatt tatattggct catgtccaac attaccgcca tgttgacatt    300

gattattgac tagttattaa tagtaatcaa ttacggggtc attagttcat agcccatata    360
```

-continued

```
tggagttccg cgttacataa cttacggtaa atggcccgcc tggctgaccg cccaacgacc    420
cccgcccatt gacgtcaata atgacgtatg ttcccatagt aacgccaata gggactttcc    480
attgacgtca atgggtggag tatttacggt aaactgccca cttggcagta catcaagtgt    540
atcatatgcc aagtacgccc cctattgacg tcaatgacgg taaatggccc gcctggcatt    600
atgcccagta catgacctta tgggactttc ctacttggca gtacatctac gtattagtca    660
tcgctattac catggtgatg cggttttggc agtacatcaa tgggcgtgga tagcggtttg    720
actcacgggg atttccaagt ctccacccca ttgacgtcaa tgggagtttg ttttggcacc    780
aaaatcaacg ggactttcca aaatgtcgta acaactccgc cccattgacg caaatgggcg    840
gtaggcgtgt acggtgggag gtctatataa gcagagctcg tttagtgaac cgtcagatcg    900
cctggagacg ccatccacgc tgttttgacc tccatagaag acaccgggac cgatccagcc    960
tccgcgggcc accatggagg gcccggttac cggtaccgga tccagatatc tgggcggccg   1020
ctcagcaagc ttcgcgaatt cgggaggcgg aggtggagct agcaaaggag aagaactctt   1080
cactggagtt gtcccaattc ttgttgaatt agatggtgat gttaacggcc acaagttctc   1140
tgtcagtgga gagggtgaag gtgatgcaac atacggaaaa cttaccctga agttcatctg   1200
cactactggc aaactgcctg ttccatggcc aacactagtc actactctgt gctatggtgt   1260
tcaatgcttt tcaagatacc cggatcatat gaaacggcat gactttttca agagtgccat   1320
gcccgaaggt tatgtacagg aaaggaccat cttcttcaaa gatgacggca actacaagac   1380
acgtgctgaa gtcaagtttg aaggtgatac ccttgttaat agaatcgagt taaaaggtat   1440
tgacttcaag gaagatggca acattctggg acacaaattg gaatacaact ataactcaca   1500
caatgtatac atcatggcag acaaacaaaa gaatggaatc aaagtgaact tcaagacccg   1560
ccacaacatt gaagatggaa gcgttcaact agcagaccat tatcaacaaa atactccaat   1620
tggcgatggc cctgtccttt taccagacaa ccattacctg tccacacaat ctgccctttc   1680
gaaagatccc aacgaaaaga gagaccacat ggtccttctt gagtttgtaa cagctgctgg   1740
gattacacat ggcatggatg aactgtacaa catcgatgga ggcggaggtg gatgaacgcg   1800
ttggccctat tctatagtgt cacctaaatg ctagagctcg ctgatcagcc tcgactgtgc   1860
cttctagttg ccagccatct gttgtttgcc cctcccccgt gccttccttg accctggaag   1920
gtgccactcc cactgtcctt tcctaataaa atgaggaaat tgcatcgcat tgtctgagta   1980
ggtgtcattc tattctgggg ggtggggtgg ggcaggacag caagggggag gattgggaag   2040
acaatagcag gcatgctggg gatgcggtgg gctctatggc ttctgaggcg gaaagaacca   2100
gctggggctc tagggggtat ccccacgcgc cctgtagcgg cgcattaagc gcggcgggtg   2160
tggtggttac gcgcagcgtg accgctacac ttgccagcgc cctagcgccc gctcctttcg   2220
ctttcttccc ttcctttctc gccacgttcg ccggctttcc ccgtcaagct ctaaatcggg   2280
gcatcccttt agggttccga tttagtgctt tacggcacct cgaccccaaa aaacttgatt   2340
agggtgatgg ttcacgtagt gggccatcgc cctgatagac ggtttttcgc cctttgacgt   2400
tggagtccac gttctttaat agtggactct tgttccaaac tggaacaaca ctcaacccta   2460
tctcggtcta ttcttttgat ttataaggga ttttggggat ttcggcctat tggttaaaaa   2520
atgagctgat ttaacaaaaa tttaacgcga attaattctg tggaatgtgt gtcagttagg   2580
gtgtggaaag tccccaggct ccccaggcag gcagaagtat gcaaagcatg catctcaatt   2640
agtcagcaac caggtgtgga aagtccccag gctccccagc aggcagaagt atgcaaagca   2700
tgcatctcaa ttagtcagca accatagtcc cgcccctaac tccgcccatc ccgcccctaa   2760
```

-continued ctccgcccag ttccgcccat tctccgcccc atggctgact aattttttt atttatgcag 2820 aggccgaggc cgcctctgcc tctgagctat tccagaagta gtgaggaggc tttttggag 2880 gcctaggctt ttgcaaaaag ctcccgggag cttgtatatc cattttcgga tctgatcaag 2940
agacaggatg aggatcgttt cgcatgattg aacaagatgg attgcacgca ggttctccgg 3000
ccgcttgggt ggagaggcta ttcggctatg actgggcaca acagacaatc ggctgctctg 3060
atgccgccgt gttccggctg tcagcgcagg ggcgcccggt tctttttgtc aagaccgacc 3120
tgtccggtgc cctgaatgaa ctgcaggacg aggcagcgcg gctatcgtgg ctggccacga 3180
cgggcgttcc ttgcgcagct gtgctcgacg ttgtcactga agcgggaagg gactggctgc 3240
tattgggcga agtgccgggg caggatctcc tgtcatctca ccttgctcct gccgagaaag 3300
tatccatcat ggctgatgca atgcggcggc tgcatacgct tgatccggct acctgcccat 3360
tcgaccacca agcgaaacat cgcatcgagc gagcacgtac tcggatggaa gccggtcttg 3420
tcgatcagga tgatctggac gaagagcatc aggggctcgc gccagccgaa ctgttcgcca 3480
ggctcaaggc gcgcatgccc gacggcgagg atctcgtcgt gacccatggc gatgcctgct 3540
tgccgaatat catggtggaa aatggccgct tttctggatt catcgactgt ggccggctgg 3600
gtgtggcgga ccgctatcag gacatagcgt tggctacccg tgatattgct gaagagcttg 3660
gcggcgaatg ggctgaccgc ttcctcgtgc tttacggtat cgccgctccc gattcgcagc 3720
gcatcgcctt ctatcgcctt cttgacgagt tcttctgagc gggactctgg ggttcgaaat 3780
gaccgaccaa gcgacgccca acctgccatc acgagatttc gattccaccg ccgccttcta 3840
tgaaaggttg ggcttcggaa tcgttttccg ggacgccggc tggatgatcc tccagcgcgg 3900
ggatctcatg ctggagttct tcgcccaccc caacttgttt attgcagctt ataatggtta 3960
caaataaagc aatagcatca caaatttcac aaataaagca tttttttcac tgcattctag 4020
ttgtggtttg tccaaactca tcaatgtatc ttatcatgtc tgtataccgt cgacctctag 4080
ctagagcttg gcgtaatcat ggtcatagct gtttcctgtg tgaaattgtt atccgctcac 4140
aattccacac aacatacgag ccggaagcat aaagtgtaaa gcctggggtg cctaatgagt 4200
gagctaactc acattaattg cgttgcgctc actgcccgct ttccagtcgg gaaacctgtc 4260
gtgccagctg cattaatgaa tcggccaacg cgcggggaga ggcggtttgc gtattgggcg 4320
ctcttccgct tcctcgctca ctgactcgct gcgctcggtc gttcggctgc ggcgagcggt 4380
atcagctcac tcaaaggcgg taatacggtt atccacagaa tcaggggata acgcaggaaa 4440
gaacatgtga gcaaaaggcc agcaaaaggc caggaaccgt aaaaaggccg cgttgctggc 4500
gtttttccat aggctccgcc cccctgacga gcatcacaaa aatcgacgct caagtcagag 4560
gtggcgaaac ccgacaggac tataaagata ccaggcgttt ccccctggaa gctccctcgt 4620
gcgctctcct gttccgaccc tgccgcttac cggatacctg tccgcctttc tcccttcggg 4680
aagcgtggcg ctttctcaat gctcacgctg taggtatctc agttcggtgt aggtcgttcg 4740
ctccaagctg ggctgtgtgc acgaaccccc cgttcagccc gaccgctgcg ccttatccgg 4800
taactatcgt cttgagtcca acccggtaag acacgactta tcgccactgg cagcagccac 4860
tggtaacagg attagcagag cgaggtatgt aggcggtgct acagagttct tgaagtggtg 4920
gcctaactac ggctacacta gaaggacagt atttggtatc tgcgctctgc tgaagccagt 4980
taccttcgga aaaagagttg gtagctcttg atccggcaaa caaaccaccg ctggtagcgg 5040
tggttttttt gtttgcaagc agcagattac gcgcagaaaa aaaggatctc aagaagatcc 5100

-continued

```
tttgatcttt tctacggggt ctgacgctca gtggaacgaa aactcacgtt aagggatttt   5160

ggtcatgaga ttatcaaaaa ggatcttcac ctagatcctt ttaaattaaa aatgaagttt   5220

taaatcaatc taaagtatat atgagtaaac ttggtctgac agttaccaat gcttaatcag   5280

tgaggcacct atctcagcga tctgtctatt tcgttcatcc atagttgcct gactccccgt   5340

cgtgtagata actacgatac gggagggctt accatctggc cccagtgctg caatgatacc   5400

gcgagaccca cgctcaccgg ctccagattt atcagcaata aaccagccag ccggaagggc   5460

cgagcgcaga agtggtcctg caactttatc cgcctccatc cagtctatta attgttgccg   5520

ggaagctaga gtaagtagtt cgccagttaa tagtttgcgc aacgttgttg ccattgctac   5580

aggcatcgtg gtgtcacgct cgtcgtttgg tatggcttca ttcagctccg gttcccaacg   5640

atcaaggcga gttacatgat cccccatgtt gtgcaaaaaa gcggttagct ccttcggtcc   5700

tccgatcgtt gtcagaagta agttggccgc agtgttatca ctcatggtta tggcagcact   5760

gcataattct cttactgtca tgccatccgt aagatgcttt tctgtgactg gtgagtactc   5820

aaccaagtca ttctgagaat agtgtatgcg gcgaccgagt tgctcttgcc cggcgtcaat   5880

acgggataat accgcgccac atagcagaac tttaaaagtg ctcatcattg gaaaacgttc   5940

ttcggggcga aaactctcaa ggatcttacc gctgttgaga tccagttcga tgtaacccac   6000

tcgtgcaccc aactgatctt cagcatcttt tactttcacc agcgtttctg ggtgagcaaa   6060

aacaggaagg caaaatgccg caaaaaaggg aataagggcg acacggaaat gttgaatact   6120

catactcttc ctttttcaat attattgaag catttatcag ggttattgtc tcatgagcgg   6180

atacatattt gaatgtattt agaaaaataa acaaataggg gttccgcgca catttccccg   6240

aaaagtgcca cctgacgtc                                                6259
```

<210> SEQ ID NO 56
<211> LENGTH: 245
<212> TYPE: PRT
<213> ORGANISM: Artificial Sequence
<220> FEATURE:
<223> OTHER INFORMATION: GFP amino acid sequence.

<400> SEQUENCE: 56

```
Ala Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Cys Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160
```

```
Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly
                245


<210> SEQ ID NO 57
<211> LENGTH: 4
<212> TYPE: PRT
<213> ORGANISM: Artificial Sequence
<220> FEATURE:
<223> OTHER INFORMATION: G-spacer flexible spacer

<400> SEQUENCE: 57

Gly Gly Gly Gly
 1


<210> SEQ ID NO 58
<211> LENGTH: 5
<212> TYPE: PRT
<213> ORGANISM: Artificial Sequence
<220> FEATURE:
<223> OTHER INFORMATION: G-spacer flexible spacer

<400> SEQUENCE: 58

Gly Gly Gly Gly Ser
 1               5


<210> SEQ ID NO 59
<211> LENGTH: 4
<212> TYPE: PRT
<213> ORGANISM: Artificial Sequence
<220> FEATURE:
<223> OTHER INFORMATION: A-spacer flexible spacer

<400> SEQUENCE: 59

Ala Ala Ala Ala
 1


<210> SEQ ID NO 60
<211> LENGTH: 5
<212> TYPE: PRT
<213> ORGANISM: Artificial Sequence
<220> FEATURE:
<223> OTHER INFORMATION: A-spacer flexible spacer

<400> SEQUENCE: 60

Ala Ala Ala Ala Val
 1               5


<210> SEQ ID NO 61
<211> LENGTH: 3359
<212> TYPE: DNA
<213> ORGANISM: Homo sapiens

<400> SEQUENCE: 61
```

-continued

```
gtcgaggtgc tcatagtgga gccctggctc ccgggcggac ggagccgcac ggtagtagat     60
gggggtgtgg ccgtggcccc cgactctgct cggcggggcc gttcctgctt tgccatccgt    120
gtgggacttc cacgacagtg gaggcacgag agctgggccc catatgctgc ttgcccagct    180
tgggaaagag gaggctgctg caaaggaccg atcggcggct tcgggctgcc ggctcactcg    240
gctgctgcgt ctggtctggc gtctgctgag aagatcctct tctaccctgc tctgcacctg    300
tgctcgactg ccagccggct gagggcgggg gtctccacgg tggtcccagc tcccaaggag    360
gttgcagaag taccgtacag agtggatttg cagggcagtg gcatggagcc cctcttcccc    420
gcgccgttct gggaggttat ctacggcagc caccttcagg gcaacctgtc cctcctgagc    480
cccaaccaca gtctgctgcc cccgcatctg ctgctcaatg ccagccacgg cgccttcctg    540
cccctcgggc tcaaggtcac catcgtgggg ctctacctgg ccgtgtgtgt cggagggctc    600
ctggggaact gccttgtcat gtacgtcatc ctcaggcaca ccaaaatgaa gacagccacc    660
aatatttaca tctttaacct ggccctggcc gacactctgg tcctgctgac gctgcccttc    720
cagggcacgg acatcctcct gggcttctgg ccgtttggga atgcgctgtg caagacagtc    780
attgccattg actactacaa catgttcacc agcaccttca ccctaactgc catgagtgtg    840
gatcgctatg tagccatctg ccaccccatc cgtgccctcg acgtccgcac gtccagcaaa    900
gcccaggctg tcaatgtggc catctgggcc ctggcctctg ttgtcggtgt tcccgttgcc    960
atcatgggct cggcacaggt cgaggatgaa gagatcgagt gcctggtgga gatccctacc   1020
cctcaggatt actggggccc ggtgtttgcc atctgcatct tcctcttctc cttcatcgtc   1080
cccgtgctcg tcatctctgt ctgctacagc ctcatgatcc ggcggctccg tggagtccgc   1140
ctgctctcgg gctcccgaga gaaggaccgg aacctgcggc gcatcactcg gctggtgctg   1200
gtggtagtgg ctgtgttcgt gggctgctgg acgcctgtcc aggtcttcgt gctggcccaa   1260
gggctggggg ttcagccgag cagcgagact gccgtggcca ttctgcgctt ctgcacggcc   1320
ctgggctacg tcaacagctg cctcaacccc atcctctacg ccttcctgga tgagaacttc   1380
aaggcctgct tccgcaagtt ctgctgtgca tctgccctgc gccgggacgt gcaggtgtct   1440
gaccgcgtgc gcagcattgc caaggacgtg gccctggcct gcaagacctc tgagacggta   1500
ccgcggcccg catgactagg cgtggacctg cccatggtgc ctgtcagccc gcagagccca   1560
tctacgccca acacagagct cacacaggtc actgctctct aggcggacac accctgggcc   1620
ctgagcatcc agagcctggg atgggctttt ccctgtgggc cagggatgct cggtcccaga   1680
ggaggaccta gtgacatcat gggacaggtc aaagcattag ggccacctcc atggccccag   1740
acagactaaa gctgccctcc tggtgcaggg ccgaggggac acaaggacct acctggaagc   1800
agctgacatg ctggtggacg gccgtgactg gagcccgtgc cctccctcc ccgtgcttca    1860
tgtgactctt ggcctctctg ctgctgcgtt ggcagaaccc tgggtgggca ggcacccgga   1920
ggaggagcag cagctgtgtc atcctgtgcc ccccatgtgc tgtgtgctgt ttgcatggca   1980
gggctccagc tgccttcagc cctgtgacgt ctcctcaggg cagctggaca ggcttggcac   2040
tgcccgggaa gtgcagcagg cagcttttct ttggggtggg acttgccctg agcttggagc   2100
tgccacctgg aggacttgcc tgttccgact ccacctgtgc agccggggcc accccaggag   2160
aaagtgtcca ggtgggggct ggcagtccct ggctgcagac cccgagctgg ccctgggcca   2220
gccgcacctc tgaaggtttt ctgtgtgctg cacggtgcag gcctcatccc tgactgcagc   2280
ttgactctgg gcccaacccc catttccctt caggagacca gcgagaggcc ctggcccatt   2340
ccctccagcg gtgcaatgaa ctatcatgct gtggaccgtc aacccagccc tgcttctcag   2400
```

tgtggggcag gtgtctcagg acgaaggcgc cgcgtgacca catgggcagc tctgttcaca 2460
aagtggaggc ctcgttttcc tggtcttgac tgctctgttt gggtgggaga agattctctg 2520
ggggtcccca catcctccca aggctcccct cacagcctct cctttgcttg aagccagagg 2580
tcagtggccg tgctgtgttg cgggggaagc tgtgtggaag gagaagctgg tggccacagc 2640
agagtcctgc tctggggacg cctgcttcat ttacaagcct caagatggct ctgtgtaggg 2700
cctgagcttg ctgcccaacg ggaggatggc ttcacagcag agccagcatg aggggtgggg 2760
cctggcaggg cttgcttgag ccaaactgca aaggctgtgg tggctgtgag gacactgcgg 2820
gggttggggg gggggcgtct gtacctcagg ggatgccccg ctgtggtcac ccagagaatc 2880
acccttcctg gtctacagat ggaagctgca ggttggtgac tttgcaaatg cacttcctac 2940
agatgaacta ttaaaagacc tgcaacattg aaaaaactca ttttttccac caaaaccttg 3000
gccaggtaac ctaccttagg cacctgcaaa gaacaggaag tgatggctgt ctcgcaacag 3060
agcctgggct gctcctcctg ctctggggag tctaggccgt ggggactgtt ctggggaggc 3120
tcatgctgtc tccatgacgt ctgtggcagg agtccctgag gacgggagct gcctagctac 3180
agttttcttg ccaaggcgag gtgttttgtg aatctgtgct gatgtaatgt gcaccttcac 3240
gtatttatgc atgtggcaag cgttacttcc tgtgcacgta gccagccctg ggtctgtctc 3300
tggggtaatg aaaaaggacc ctaataaaca cctgctcact ggctgggtat tcttcgtaa 3359

<210> SEQ ID NO 62
<211> LENGTH: 1134
<212> TYPE: DNA
<213> ORGANISM: Homo sapiens

<400> SEQUENCE: 62
ttgcagggca gtggcatgga gcccctcttc cccgcgccgt tctgggaggt tatctacggc 60
agccaccttc agggcaacct gtccctcctg agccccaacc acagtctgct gcccccgcat 120
ctgctgctca atgccagcca cggcgccttc ctgcccctcg ggctcaaggt caccatcgtg 180
gggctctacc tggccgtgtg tgtcggaggg ctcctgggga actgccttgt catgcacacc 240
aaaatgaaga cagccaccaa tatttacatc tttaacctgg ccctggccga cactctggtc 300
ctgctgacgc tgcccttcca gggcacggac atcctcctgg gcttctggcc gtttgggaat 360
gcgctgtgca agacagtcat tgccattgac tactacaaca tgttcaccag caccttcacc 420
ctaactgcca tgagtgtgga tcgctatgta gccatctgcc accccatccg tgccctcgac 480
gtccgcacgt ccagcaaagc ccaggctgtc aatgtggcca tctgggccct ggcctctgtt 540
gtcggtgttc ccgttgccat catgggctcg gcacaggtcg aggatgaaga gatcgagtgc 600
ctggtggaga tccctacccc tcaggattac tggggcccgg tgtttgccat ctgcatcttc 660
ctcttctcct tcatcgtccc cgtgctcgtc atctctgtct gctacagcct catgatccgg 720
cggctccgtg gagtccgcct gctctcgggc tcccgagaga aggaccggaa cctgcggcgc 780
atcactcggc tggtgctggt ggtagtggct gtgttcgtgg gctgctggac gcctgtccag 840
gtcttcgtgc tggcccaagg gctgggggtt cagccgagca gcgagactgc cgtggccatt 900
ctgcgcttct gcacggccct gggctacgtc aacagctgcc tcaaccccat cctctacgcc 960
ttcctggatg agaacttcaa ggcctgcttc cgcaagttct gctgtgcatc tgccctgcgc 1020
cgggacgtgc aggtgtctga ccgcgtgcgc agcattgcca aggacgtggc cctggcctgc 1080
aagacctctg agacggtacc gcggcccgca tgactaggcg tggacctgcc catg 1134

<210> SEQ ID NO 63
<211> LENGTH: 1774
<212> TYPE: DNA
<213> ORGANISM: Homo sapiens

<400> SEQUENCE: 63
ccgaggagcc tgcggctgct cctggctcac agcgctccgg gcgaggagag cgggcggacg 60
ccgggggctg ggccggtgcg ggcggcgagg caggcggacg aggcgcagag acagcggggc 120
ggccggggcg cggcagccgg cggcgtcggg gccgcggcct ctgccttgcc gctcccctcg 180
cgtcggatcc ccgcgcccag ggcgcacggt ggagagggac gcggcggagc cggccggcag 240
ccatggaacc ggcccccctcc gccggcgccg agctgcagcc cccgctcttc gccaacgcct 300
cggacgccta ccctagcgcc tgccccagcg ctggcgccaa tgcgtcgggg ccgccaggcg 360
cgcggagcgc ctcgtccctc gccctggcaa tcgccatcac cgcgctctac tcggccgtgt 420
gcgccgtggg gctgctgggc aacgtgcttg tcatgttcgg catcgtccgg tacactaaga 480
tgaagacggc caccaacatc tacatcttca acctggcctt agccgatgcg ctggccacca 540
gcacgctgcc tttccagagt gccaagtacc tgatggagac gtggcccttc ggcgagctgc 600
tctgcaaggc tgtgctctcc atcgactact acaatatgtt caccagcatc ttcacgctca 660
ccatgatgag tgttgaccgc tacatcgctg tctgccaccc tgtcaaggcc ctggacttcc 720
gcacgcctgc caaggccaag ctgatcaaca tctgtatctg ggtcctggcc tcaggcgttg 780
gcgtgcccat catggtcatg gctgtgaccc gtccccggga cggggcagtg gtgtgcatgc 840
tccagttccc cagccccagc tggtactggg acacggtgac caagatctgc gtgttcctct 900
tcgccttcgt ggtgcccatc ctcatcatca ccgtgtgcta tggcctcatg ctgctgcgcc 960
tgcgcagtgt gcgcctgctg tcgggctcca aggagaagga ccgcagcctg cggcgcatca 1020
cgcgcatggt gctggtggtt gtgggcgcct tcgtggtgtg ttgggcgccc atccacatct 1080
tcgtcatcgt ctggacgctg gtggacatcg accggcgcga cccgctggtg gtggctgcgc 1140
tgcacctgtg catcgcgctg ggctacgcca atagcagcct caaccccgtg ctctacgctt 1200
tcctcgacga gaacttcaag cgctgcttcc gccagctctg ccgcaagccc tgcggccgcc 1260
cagaccccag cagcttcagc cgcgcccgcg aagccacggc ccgcgagcgt gtcaccgcct 1320
gcaccccgtc cgatggtccc ggcggtggcg ctgccgcctg accaggccat ccggccccca 1380
gagcgcccct ccctagtgac ccggaggcca catgagtccc agtgggaggc gcgagccatg 1440
atgtggagtg gggcagtaga aggtcggagg cttgggaccg ccagatgggg cctctgtttc 1500
ggagacggga ccgggccgct agatgggcat ggggtgggcc tctggtttgg ggcgaggcag 1560
aggacagatc aatggcgcag tgcctctggt ctgggtgccc cgtccacggc tctaggtggg 1620
gcgggaaagc cagtgactcc aggagaggag cgggacctgt ggctctacaa ctgagtcctt 1680
aaacagggca tctccaggaa ggcggggctt caaccttgag acagcttcgg tttctaactt 1740
ggagccggac tttcggagtt gggggtccgg gccc 1774

<210> SEQ ID NO 64
<211> LENGTH: 1773
<212> TYPE: DNA
<213> ORGANISM: Homo sapiens

<400> SEQUENCE: 64
ccgaggagcc tgcgctgctc ctggctcaca gcgctccggg cgaggagagc gggcggaccg 60
gggggctggg ccggtgcggg cggcgaggca ggcggacgag gcgcagagac agcggggcgg 120
ccggggcgcg gcacgcggcg ggtcggggcc ggcctctgcc ttgccgctcc cctcgcgtcg 180
gatccccgcg cccaggcagc cggtggagag ggacgcggcg gacgccggca gccatggaac 240
cggccccctc cgccggcgcc gagctgcagc ccccgctctt cgccaacgcc tcggacgcct 300
accctagcgc cttccccagc gctggcgcca atgcgtcggg gccgccaggc gcgcggagcg 360
cctcgtccct cgccctggca atcgccatca ccgcgctcta ctcggccgtg tgcgccgtgg 420
ggctgctggg caacgtgctt gtcatgttcg gcatcgtccg gtacactaag atgaagacgg 480
ccaccaacat ctacatcttc aacctggcct tagccgatgc gctggccacc agcacgctgc 540
ctttccagag tgccaagtac ctgatggaga cgtggccctt cggcgagctg ctctgcaagg 600
ctgtgctctc catcgactac tacaatatgt tcaccagcat cttcacgctc accatgatga 660
gtgttgaccg ctacatcgct gtctgccacc ctgtcaaggc cctggacttc cgcacgcctg 720
ccaaggccaa gctgatcaac atctgtatct gggtcctggc ctcaggcgtt ggcgtgccca 780
tcatggtcat ggctgtgacc cgtccccggg acggggcagt ggtgtgcatg ctccagttcc 840
ccagccccag ctggtactgg gacacggtga ccaagatctg cgtgttcctc ttcgccttcg 900
tggtgcccat cctcatcatc accgtgtgct atggcctcat gctgctgcgc ctgcgcagtg 960
tgcgcctgct gtcgggctcc aaggagaagg accgcagcct gcggcgcatc acgcgcatgg 1020
tgctggtggt tgtgggcgcc ttcgtggtgt gttgggcgcc catccacatc ttcgtcatcg 1080
tctggacgct ggtggacatc gaccggcgcg acccgctggt ggtggctgcg ctgcacctgt 1140
gcatcgcgct gggctacgcc aatagcagcc tcaaccccgt gctctacgct ttcctcgacg 1200
agaacttcaa gcgctgcttc cgccagctct gccgcaagcc ctgcggccgc ccagacccca 1260
gcagcttcag ccgcgcccgc gaagccacgg cccgcgagcg tgtcaccgcc tgcaccccgt 1320
ccgatggtcc cggcggtggc gctgccgcct gaccaggcca tccggccccc agacgcccct 1380
ccctagttgt acccggaggc cacatgagtc ccagtgggag gcgcgagcca tgatgtggag 1440
tggggccagt agataggtcg gagggctttg ggaccgccag atggggcctc tgtttcggag 1500
acgggaccgg gccgctagat gggcatgggg tgggcctctg gtttggggcg aggcagagga 1560
cagatcaatg gcgcagtgcc tctggtctgg gtgcccccgt ccacggctct aggtggggcg 1620
ggaaagccag tgactccagg agaggagcgg gacctgtggc tctacaactg agtccttaaa 1680
cagggcatct ccaggaaggc ggggcttcaa ccttgagaca gcttcggttt ctaacttgga 1740
gccggacttt cggagttggg gggtccgggg ccc 1773

<210> SEQ ID NO 65
<211> LENGTH: 1154
<212> TYPE: DNA
<213> ORGANISM: Homo sapiens

<400> SEQUENCE: 65
atggactccc cgatccagat cttccgcggg gagccgggcc ctacctgcgc cccgagcgcc 60
tgcctgcccc ccaacagcag cgcctggttt cccggctggg ccgagcccga cagcaacggc 120
agcgccggct cggaggacgc gcagctggag cccgcgcaca tctccccggc catcccggtc 180
atcatcacgg cggtctactc cgtagtgttc gtcgtgggct tggtgggcaa ctcgctggtc 240
atgttcgtga tcatccgata cacaaagatg aagacagcaa ccaacattta catatttaac 300
ctggctttgg cagatgcttt agttactaca accatgccct ttcagagtac ggtctacttg 360
atgaattcct ggccttttgg ggatgtgctg tgcaagatag taatttccat tgattactac 420

```
aacatgttca ccagcatctt caccttgacc atgatgagcg tggaccgcta cattgccgtg    480

tgccaccccg tgaaggcttt ggacttccgc acacccttga aggcaaagat catcaatatc    540

tgcatctggc tgctgtcgtc atctgttggc atctctgcaa tagtccttgg aggcaccaaa    600

gtcagggaag acgtcgatgt cattgagtgc tccttgcagt tcccagatga tgactactcc    660

tggtgggacc tcttcatgaa gatctgcgtc ttcatctttg ccttcgtgat ccctgtcctc    720

atcatcatcg tctgctacac cctgatgatc ctgcgtctca agagcgtccg gctccttttct    780

ggctcccgag agaaagatcg caacctgcgt aggatcacca gactggtcct ggtggtggtg    840

gcagtcttcg tcgtctgctg gactcccatt cacatattca tcctggtgga ggctctgggg    900

agcacctccc acagcacagc tgctctctcc agctattact tctgcatcgc cttaggctat    960

accaacagta gcctgaatcc cattctctac gcctttcttg atgaaaactt caagcggtgt   1020

ttccgggact tctgctttcc actgaagatg aggatggagc ggcagagcac tagcagagtc   1080

cgaaatacag ttcaggatcc tgcttacctg agggacatcg atgggatgaa taaaccagta   1140

tgactagtcg tgga                                                     1154
```

```
<210> SEQ ID NO 66
<211> LENGTH: 1143
<212> TYPE: DNA
<213> ORGANISM: Homo sapiens

<400> SEQUENCE: 66

atggaatccc cgattcagat cttccgcggg gagccgggcc ctacctgcgc cccgagcgcc     60

tgcctgcccc ccaacagcag cgcctggttt cccggctggg ccgagcccga cagcaacggc    120

agcgccggct cggaggacgc gcagctggag cccgcgcaca tctccccggc catcccggtc    180

atcatcacgg cggtctactc cgtagtgttc gtcgtgggct tggtgggcaa ctcgctggtc    240

atgttcgtga tcatccgata cacaaagatg aagacagcaa ccaacattta catatttaac    300

ctggctttgg cagatgcttt agttactaca accatgccct ttcagagtac ggtctacttg    360

atgaattcct ggccttttgg ggatgtgctg tgcaagatag taatttccat tgattactac    420

aacatgttca ccagcatctt caccttgacc atgatgagcg tggaccgcta cattgccgtg    480

tgccaccccg tgaaggcttt ggacttccgc acacccttga aggcaaagat catcaatatc    540

tgcatctggc tgctgtcgtc atctgttggc atctctgcaa tagtccttgg aggcaccaaa    600

gtcagggaag acgtcgatgt cattgagtgc tccttgcagt tcccagatga tgactactcc    660

tggtgggacc tcttcatgaa gatctgcgtc ttcatctttg ccttcgtgat ccctgtcctc    720

atcatcatcg tctgctacac cctgatgatc ctgcgtctca agagcgtccg gctccttttct    780

ggctcccgag agaaagatcg caacctgcgt aggatcacca gactggtcct ggtggtggtg    840

gcagtcttcg tcgtctgctg gactcccatt cacatattca tcctggtgga ggctctgggg    900

agcacctccc acagcacagc tgctctctcc agctattact tctgcatcgc cttaggctat    960

accaacagta gcctgaatcc cattctctac gcctttcttg atgaaaactt caagcggtgt   1020

ttccgggact tctgctttcc actgaagatg aggatggagc ggcagagcac tagcagagtc   1080

cgaaatacag ttcaggatcc tgcttacctg agggacatcg atgggatgaa taaaccagta   1140

tga                                                                 1143
```

```
<210> SEQ ID NO 67
<211> LENGTH: 2738
<212> TYPE: DNA
<213> ORGANISM: Homo sapiens
```

<400> SEQUENCE: 67
cctgtaaaga aaatgatgag ggctaaatcc atcagcacca aagctgggaa gccctccagg 60
ttcatttgga agaaaatact cctctgagct caaaggaagt gtgatctgtc acaatattgt 120
atgcctgcac taagtttgca tcctgaaaac tcactggaag ataggaaagc aagcatgaaa 180
aagcagccgg gtcagacagg cttctggatt cagtgtgtgg acatgacttt gcctgcatga 240
attgcccctt tctcctacaa acaagagaat tcggtcaagt ggatgtggca gaactgggct 300
gctctgagat gatagaaaag ggctcctgct tttcctgtaa ttgcagcccc ttgttcttgt 360
ggttgctaca tgcaataaat gtaattctat gagaaggacc agcccttaca tcccatcaaa 420
atgtttcctg gaaacctgga gcacagaact ctgatatcct ctcacactgt ggcaggagaa 480
gcagcacaag gcacaatgct gaaatagcat ggtccaggat gtgtttgcac agaagagtgc 540
ccagtgaaga gacctactcc ttggatcgct ttgcgcaaaa tccacccctt ttccctcctc 600
cctcccttcc agcctccgaa tcccgcatgg cccacgctcc cctcctgcag cggtgcgggg 660
cagccaggac tggtttctgt aagaaacagc aggagctgtg gcagcggcga aaggaagcgg 720
ctgaggcgct tggaacccga aaagtctcgg tgctcctggc tacctcgcac agcggtgccc 780
gcccggccgt cagtaccatg gacagcagcg ctgcccccac gaacgccagc aattgcactg 840
atgccttggc gtactcaagt tgctccccag cacccagccc cggttcctgg gtcaacttgt 900
cccacttaga tggcaacctg tccgacccat gcggtccgaa ccgcaccgac ctgggcggga 960
gagacagcct gtgccctccg accggcagtc cctccatgat cacggccatc acgatcatgg 1020
ccctctactc catcgtgtgc gtggtggggc tcttcggaaa cttcctggtc atgtatgtga 1080
ttgtcagata caccaagatg aagactgcca ccaacatcta cattttcaac cttgctctgg 1140
cagatgcctt agccaccagt accctgccct tccagagtgt gaattaccta atgggaacat 1200
ggccatttgg aaccatcctt tgcaagatag tgatctccat agattactat aacatgttca 1260
ccagcatatt caccctctgc accatgagtg ttgatcgata cattgcagtc tgccaccctg 1320
tcaaggcctt agatttccgt actccccgaa atgccaaaat tatcaatgtc tgcaactgga 1380
tcctctcttc agccattggt cttcctgtaa tgttcatggc tacaacaaaa tacaggcaag 1440
gttccataga ttgtacacta acattctctc atccaacctg gtactgggaa aacctgctga 1500
agatctgtgt tttcatcttc gccttcatta tgccagtgct catcattacc gtgtgctatg 1560
gactgatgat cttgcgcctc aagagtgtcc gcatgctctc tggctccaaa gaaaaggaca 1620
ggaatcttcg aaggatcacc aggatggtgc tggtggtggt ggctgtgttc atcgtctgct 1680
ggactcccat tcacatttac gtcatcatta aagccttggt tacaatccca gaaactacgt 1740
tccagactgt ttcttggcac ttctgcattg ctctaggtta cacaaacagc tgcctcaacc 1800
cagtccttta tgcatttctg gatgaaaact tcaaacgatg cttcagagag ttctgtatcc 1860
caacctcttc caacattgag caacaaaact ccactcgaat tcgtcagaac actagagacc 1920
acccctccac ggccaataca gtggatagaa ctaatcatca gctagaaaat ctggaagcag 1980
aaactgctcc gttgccctaa cagggtctca tgccattccg accttcacca agcttagaag 2040
ccaccatgta tgtggaagca ggttgcttca agaatgtgta ggaggctcta attctctagg 2100
aaagtgcctg cttttaggtc atccaacctc tttcctctct ggccactctg ctctgcacat 2160
tagagggaca gccaaaagta agtggagcat ttggaaggaa aggaatatac cacaccgagg 2220
agtccagttt gtgcaagaca cccagtggaa ccaaaaccca tcgtggtatg tgaattgaag 2280

```
tcatcataaa aggtgaccct tctgtctgta agattttatt ttcaagcaaa tatttatgac   2340

ctcaacaaag aagaaccatc ttttgttaag ttcaccgtag taacacataa agtaaatgct   2400

acctctgatc aaagcacctt gaatggaagg tccgagtctt tttagtgttt tgcaagggaa   2460

tgaatccatt attctatttt agacttttaa cttcacctta aaattagcat ctggctaagg   2520

catcattttc acctccattt cttggttttg tattgtttaa aaaaataaca tctctttcat   2580

ctagctccat aattgcaagg gaagagatta gcatgaaagg taatctgaaa cacagtcatg   2640

tgtcagctgt agaaaggttg attctcatgc actgcaaata cttccaaaga gtcatcatgg   2700

gggattttc attcttaggc tttcagtggt ttgttcct                           2738


<210> SEQ ID NO 68
<211> LENGTH: 2053
<212> TYPE: DNA
<213> ORGANISM: Homo sapiens

<400> SEQUENCE: 68

catctttgat gagggcagag ctcacgttgc attgaagacg aaacctcggg gaggtcaggc     60

gctgtctttc cttccctccc tgctcggcgg ctccaccaca gttgcaacct gcagaggccc    120

ggagaacaca accctcccga gaagcccagg tccagagcca aacccgtcac tgaccccccca    180

gcccaggcgc ccagccactc cccaccgcta ccatggccga agacgcagac atgcgcaatg    240

agctggagga gatgcagcga agggctgacc agttggctga tgagtcgctg gaaagcaccc    300

gtcgtatgct gcaactggtt gaagagagta aagatgctgg tatcaggact ttggttatgt    360

tggatgaaca aggagaacaa ctcgatcgtg tcgaagaagg catgaaccat atcaaccaag    420

acatgaagga ggctgagaaa aatttaaaag atttagggaa atgctgtggc cttttcatat    480

gtccttgtaa caagcttaaa tcaagtgatg cttacaaaaa agcctggggc aataatcagg    540

acggagtggt ggccagccag cctgctcgtg tagtggacga acgggagcag atggccatca    600

gtggcggctt catccgcagg gtaacaaatg atgcccgaga aaatgaaatg gatgaaaacc    660

tagagcaggt gagcggcatc atcgggaacc tccgtcacat ggccctggat atgggcaatg    720

agatcgatac acagaatcgc cagatcgaca ggatcatgga gaaggctgat tccaacaaaa    780

ccagaattga tgaggccaac caacgtgcaa caaagatgct gggaagtggt taagtgtgcc    840

cacccgtgtt ctcctccaaa tgctgtcggg caagatagct ccttcatgct tttctcatgg    900

tattatctag taggtctgca cacataacac acatcagtcc acccccattg tgaatgttgt    960

cctgtgtcat ctgtcagctt cccaacaata ctttgtgtct tttgttctct cttggtctct   1020

ttctttccaa aggttgtaca tagtggtcat ttggtggctc taactccttg atgtcttgag   1080

tttcattttt catttctctt cctcggtggc atttgctgaa taacaacaat ttaggaatgc   1140

tcaatgtgct gttgattctt tcaatccaca gtattgttct tgtaaaactg tgacattcca   1200

cagagttact gccacggtcc tttgagtgtc aggctctgaa tctctcaaaa tgtgccgtct   1260

ttggttcctc atggctgtta tctgtcttta tgatttcatg attagacaat gtggaattac   1320

ataacaggca ttgcactaaa agtgatgtga tttatgcatt tatgcatgag aactaaatag   1380

atttttagat tcctacttaa acaaaaactt tccatgacag tagcatactg atgagacaac   1440

acacacacac acaaaacaac agcaacaaca acagaacaac aacaaagcat gctcagtatt   1500

gagacactgt caagattaag ttataccagc aaaagtgcag tagtgtcact tttttcctgt   1560

caatatatag agacttctaa atcataatca tcctttttta aaaaaaagaa ttttaaaaaa   1620

gatggatttg acacactcac catttaatca tttccagcaa aatatatgtt tggctgaaat   1680
```

-continued tatgtcaaat ggatgtaata tagggtttgt ttgctgcttt tgatggctac gttttggaga 1740
gagcaatctt gctgtgaaac agtgtggatg taaattttat aaggctgact cttactaacc 1800
accatttccc ctgtggtttg ttatcagtac aattctttgt tgcttaatct agagctatgc 1860
acaccaaatt gctgagatgt ttagtagctg ataaagaaac cttttaaaaa aataatataa 1920
atgaatgaaa tataaactgt gagataaata tcattatagc atgtaatatt aaattcctcc 1980
tgtctcctct gtcagtttgt gaagtgattg acattttgta gctagtttaa aattattaaa 2040
aattatagac tcc 2053

<210> SEQ ID NO 69
<211> LENGTH: 2053
<212> TYPE: DNA
<213> ORGANISM: Homo sapiens

<400> SEQUENCE: 69
catctttgat gagggcagag ctcacgttgc attgaagacg aaacctcggg gaggtcaggc 60
gctgtctttc cttccctccc tgctcggcgg ctccaccaca gttgcaacct gcagaggccc 120
ggagaacaca accctcccga gaagcccagg tccagagcca aacccgtcac tgaccccccca 180 gcccaggcgc ccagccactc cccaccgcta ccatggccga agacgcagac atgcgcaatg 240
agctggagga gatgcagcga agggctgacc agttggctga tgagtcgctg gaaagcaccc 300
gtcgtatgct gcaactggtt gaagagagta aagatgctgg tatcaggact ttggttatgt 360
tggatgaaca aggagaacaa ctggaacgca ttgaggaagg gatggaccaa atcaataagg 420
acatgaaaga agcagaaaag aatttgacgg acctaggaaa attctgcggg ctttgtgtgt 480
gtccctgtaa caagcttaaa tcaagtgatg cttacaaaaa agcctggggc aataatcagg 540
acggagtggt ggccagccag cctgctcgtg tagtggacga acgggagcag atggccatca 600
gtggcggctt catccgcagg gtaacaaatg atgcccgaga aaatgaaatg gatgaaaacc 660
tagagcaggt gagcggcatc atcgggaacc tccgtcacat ggccctggat atgggcaatg 720
agatcgatac acagaatcgc cagatcgaca ggatcatgga gaaggctgat tccaacaaaa 780
ccagaattga tgaggccaac caacgtgcaa caaagatgct gggaagtggt taagtgtgcc 840
cacccgtgtt ctcctccaaa tgctgtcggg caagatagct ccttcatgct tttctcatgg 900
tattatctag taggtctgca cacataacac acatcagtcc acccccattg tgaatgttgt 960
cctgtgtcat ctgtcagctt cccaacaata ctttgtgtct tttgttctct cttggtctct 1020
ttctttccaa aggttgtaca tagtggtcat ttggtggctc taactccttg atgtcttgag 1080
tttcattttt cattttctct cctcggtggc atttgctgaa taacaacaat ttaggaatgc 1140
tcaatgtgct gttgattctt tcaatccaca gtattgttct tgtaaaactg tgacattcca 1200
cagagttact gccacggtcc tttgagtgtc aggctctgaa tctctcaaaa tgtgccgtct 1260
ttggttcctc atggctgtta tctgtcttta tgatttcatg attagacaat gtggaattac 1320
ataacaggca ttgcactaaa agtgatgtga tttatgcatt tatgcatgag aactaaatag 1380
atttttagat tcctacttaa acaaaaactt tccatgacag tagcatactg atgagacaac 1440
acacacacac acaaaacaac agcaacaaca acagaacaac aacaaagcat gctcagtatt 1500
gagacactgt caagattaag ttataccagc aaaagtgcag tagtgtcact tttttcctgt 1560
caatatatag agacttctaa atcataatca tcctttttta aaaaaaagaa ttttaaaaaa 1620
gatggatttg acacactcac catttaatca tttccagcaa aatatatgtt tggctgaaat 1680

```
tatgtcaaat ggatgtaata tagggtttgt ttgctgcttt tgatggctac gttttggaga   1740

gagcaatctt gctgtgaaac agtgtggatg taaattttat aaggctgact cttactaacc   1800

accatttccc ctgtggtttg ttatcagtac aattctttgt tgcttaatct agagctatgc   1860

acaccaaatt gctgagatgt ttagtagctg ataaagaaac cttttaaaaa aataatataa   1920

atgaatgaaa tataaactgt gagataaata tcattatagc atgtaatatt aaattcctcc   1980

tgtctcctct gtcagtttgt gaagtgattg acattttgta gctagtttaa aattattaaa   2040

aattatagac tcc                                                      2053
```

<210> SEQ ID NO 70
<211> LENGTH: 266
<212> TYPE: PRT
<213> ORGANISM: Homo sapiens

<400> SEQUENCE: 70

```
Met Val Ser Trp Gly Arg Phe Ile Cys Leu Val Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Gly Glu Ser Ala Ser Pro Arg
                245                 250                 255

Val Ala Ala Ala Tyr Gln Pro Ile Leu Ala
            260                 265
```

<210> SEQ ID NO 71
<211> LENGTH: 336
<212> TYPE: DNA
<213> ORGANISM: Mus musculus

<400> SEQUENCE: 71
caggtgaagc tgcaggagtc tggcgctgag ttggtgaaac ctggggcttc agtgaagata 60
tcctgcaagg cttctggcta catcttcact gaccatgctc ttcactgggt gaggcagaag 120
cctgaacagg gcctggaatg gattgggtat atttttcccg gaaatggtaa tattgagtac 180
aatgagaagt tcaagggcaa ggccacactg actgcagaca aatcctccag tactgcctac 240
atgcagctca acagcctgac atctggagat tctgcaatgt atttctgtaa aaagatggac 300
tactggggcc aagggaccac ggtcaccgtc tcctca 336

<210> SEQ ID NO 72
<211> LENGTH: 112
<212> TYPE: PRT
<213> ORGANISM: Mus musculus

<400> SEQUENCE: 72

Gln Val Lys Leu Gln Glu Ser Gly Ala Glu Leu Val Lys Pro Gly Ala
1 5 10 15

Ser Val Lys Ile Ser Cys Lys Ala Ser Gly Tyr Ile Phe Thr Asp His
20 25 30

Ala Leu His Trp Val Arg Gln Lys Pro Glu Gln Gly Leu Glu Trp Ile
35 40 45

Gly Tyr Ile Phe Pro Gly Asn Gly Asn Ile Glu Tyr Asn Glu Lys Phe
50 55 60

Lys Gly Lys Ala Thr Leu Thr Ala Asp Lys Ser Ser Ser Thr Ala Tyr
65 70 75 80

Met Gln Leu Asn Ser Leu Thr Ser Gly Asp Ser Ala Met Tyr Phe Cys
85 90 95

Lys Lys Met Asp Tyr Trp Gly Gln Gly Thr Thr Val Thr Val Ser Ser
100 105 110

<210> SEQ ID NO 73
<211> LENGTH: 336
<212> TYPE: DNA
<213> ORGANISM: Mus musculus

<400> SEQUENCE: 73
caggtgaagc tgcaggagtc tggcgctgag ttggtgaaac ctggggcttc agtgaagatc 60
tcctgcaagg cttctggtta caccttcact gaccattcta ttcactgggt gaagcagaag 120
cctggacagg gcctagaatg gattggatat ctttttcccg gaaatggtaa ttttgaatat 180
aatgagaaat tcaagggcaa ggccacactg actgcagaca aatcctccag cactgcctac 240
atgcacctca acagcctgac atctgaggat tctgcagtgt atttctgtaa aaagatggac 300
tactggggcc aagggaccac ggtcaccgtc tcctca 336

<210> SEQ ID NO 74
<211> LENGTH: 112
<212> TYPE: PRT
<213> ORGANISM: Mus musculus

<400> SEQUENCE: 74

Gln Val Lys Leu Gln Glu Ser Gly Ala Glu Leu Val Lys Pro Gly Ala
1 5 10 15

Ser Val Lys Ile Ser Cys Lys Ala Ser Gly Tyr Thr Phe Thr Asp His
20 25 30

Ser Ile His Trp Val Lys Gln Lys Pro Gly Gln Gly Leu Glu Trp Ile
35 40 45

```
Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Ala Tyr
65                  70                  75                  80

Met His Leu Asn Ser Leu Thr Ser Glu Asp Ser Ala Val Tyr Phe Cys
                85                  90                  95

Lys Lys Met Asp Tyr Trp Gly Gln Gly Thr Thr Val Thr Val Ser Ser
            100                 105                 110


<210> SEQ ID NO 75
<211> LENGTH: 336
<212> TYPE: DNA
<213> ORGANISM: Mus musculus

<400> SEQUENCE: 75

caggttcagc tgcagcagtc cgacgctgag ttggtgaaac ctggggcttc agtgaagata      60

tcctgcaggg cttctggcta caccttcact gaccattcta ttcactgggt gaagcagcag     120

cctggccagg gcctggaatg gatcggatat atttttcccg gaaatggaaa tattgaatac     180

aatgacaaat tcaagggcaa ggccacactg actgcagaca aatcctccgg cactgcctac     240

atgcagctca acagcctgac atctgaggat tctgcagtgt atttctgtaa aaggatgggg     300

tactggggtc aaggaacctc agtcaccgtc tcctca                               336


<210> SEQ ID NO 76
<211> LENGTH: 112
<212> TYPE: PRT
<213> ORGANISM: Mus musculus

<400> SEQUENCE: 76

Gln Val Gln Leu Gln Gln Ser Asp Ala Glu Leu Val Lys Pro Gly Ala
 1               5                  10                  15

Ser Val Lys Ile Ser Cys Arg Ala Ser Gly Tyr Thr Phe Thr Asp His
            20                  25                  30

Ser Ile His Trp Val Lys Gln Gln Pro Gly Gln Gly Leu Glu Trp Ile
        35                  40                  45

Gly Tyr Ile Phe Pro Gly Asn Gly Asn Ile Glu Tyr Asn Asp Lys Phe
    50                  55                  60

Lys Gly Lys Ala Thr Leu Thr Ala Asp Lys Ser Ser Gly Thr Ala Tyr
65                  70                  75                  80

Met Gln Leu Asn Ser Leu Thr Ser Glu Asp Ser Ala Val Tyr Phe Cys
                85                  90                  95

Lys Arg Met Gly Tyr Trp Gly Gln Gly Thr Ser Val Thr Val Ser Ser
            100                 105                 110


<210> SEQ ID NO 77
<211> LENGTH: 336
<212> TYPE: DNA
<213> ORGANISM: Mus musculus

<400> SEQUENCE: 77

caggtcaagc tgcaggagtc tggcgctgag ttggtgaaac ctggggcttc agtgaagatc      60

tcctgcaagg cttctggcta caccttcact gaccattcta ttcactgggt gaagcagaag     120

cctggacagg gcctagaatg gattggatat ctttttcccg gaaatggtaa ttttgagtac     180

aatgaaaaat tcaagggcaa ggccacactg actgcagaca aatcctccag cactgtctac     240

atgtacctca acagcctgac atctgaggat tctgcagtgt atttctgtaa aaggatgggg     300
```

```
tactggggcc aagggaccac ggtcaccgtc tcctca                            336


<210> SEQ ID NO 78
<211> LENGTH: 112
<212> TYPE: PRT
<213> ORGANISM: Mus musculus

<400> SEQUENCE: 78

Gln Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
        35                  40                  45

Gly Tyr Leu Phe Pro Gly Asn Gly Asn Phe Glu Tyr Asn Glu Lys Phe
    50                  55                  60

Lys Gly Lys Ala Thr Leu Thr Ala Asp Lys Ser Ser Ser Thr Val Tyr
65                  70                  75                  80

Met Tyr Leu Asn Ser Leu Thr Ser Glu Asp Ser Ala Val Tyr Phe Cys
                85                  90                  95

Lys Arg Met Gly Tyr Trp Gly Gln Gly Thr Thr Val Thr Val Ser Ser
            100                 105                 110


<210> SEQ ID NO 79
<211> LENGTH: 336
<212> TYPE: DNA
<213> ORGANISM: Mus musculus

<400> SEQUENCE: 79

caggtcaagc tgcaggagtc tggacctgaa ctggtaaagc ctggggcttc agtgaagatg     60

tcctgcaagg cttctggata cacattcact aactatgtta tacactgggt gaagcaaaag    120

cctgggcagg gccttgagtg gattggatat attaatcctt acaatgatgg ctctaagtac    180

aatgagaagt tcaaaggcaa ggcctcactg acttcagaca aatcctccag cacagcctac    240

atggagctca gcagcctgac ctctgaggac tctgcggtct attactgtgc aagaatggac    300

tactggggcc aagggaccac ggtcaccgtc tcctca                            336


<210> SEQ ID NO 80
<211> LENGTH: 112
<212> TYPE: PRT
<213> ORGANISM: Mus musculus

<400> SEQUENCE: 80

Gln Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ser Lys Tyr Asn Glu Lys Phe
    50                  55                  60

Lys Gly Lys Ala Ser Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Met Asp Tyr Trp Gly Gln Gly Thr Thr Leu Thr Val Ser Ser
```

100 105 110

<210> SEQ ID NO 81
<211> LENGTH: 336
<212> TYPE: DNA
<213> ORGANISM: Mus musculus

<400> SEQUENCE: 81
caggtcaagc tgcaggagtc tggacctgaa ctggtaaagc ctggggcttc agtgaagatg 60
tcctgcaagg cttctggata cacattcact aactatgtta tacactgggt gaagcaaaag 120
cctgggcagg gccttgagtg gattggatat attaatcctt acaatgatgg ctctaagtac 180
aatgagaagt tcaaaggcaa ggcctcactg acttcagaca aatcctccag cacagcctac 240
atggagctca gcagcctgac ctctgaggac tctgcggtct attactgtgc aagaatgggg 300
tactggggcc aagggaccac ggtcaccgtc tcctca 336

<210> SEQ ID NO 82
<211> LENGTH: 112
<212> TYPE: PRT
<213> ORGANISM: Mus musculus

<400> SEQUENCE: 82

Gln Val Gln Leu Gln Glu Ser Gly Pro Glu Leu Val Lys Pro Gly Ala
1 5 10 15

Ser Val Lys Met Ser Cys Lys Ala Ser Gly Tyr Thr Phe Thr Asn Tyr
20 25 30

Val Ile His Trp Val Lys Gln Lys Pro Gly Gln Gly Leu Glu Trp Ile
35 40 45

Gly Tyr Ile Asn Pro Tyr Asn Asp Gly Ser Lys Tyr Asn Glu Lys Phe
50 55 60

Lys Gly Lys Ala Ser Leu Thr Ser Asp Lys Ser Ser Ser Thr Ala Tyr
65 70 75 80

Met Glu Leu Ser Ser Leu Thr Ser Glu Asp Ser Ala Val Tyr Tyr Cys
85 90 95

Ala Arg Met Gly Tyr Trp Gly Gln Gly Thr Thr Leu Thr Val Ser Ser
100 105 110

<210> SEQ ID NO 83
<211> LENGTH: 342
<212> TYPE: DNA
<213> ORGANISM: Mus musculus

<400> SEQUENCE: 83
gatgttttga tgacccaaac tccactctcc ctgcctgtca gtcttggaga tcaagcctcc 60
atctcttgca gatctagtca gagcattgta catagtaatg gaaacaccta tttagaatgg 120
tacctgcaga aaccaggcca gtctccaaag ctcctgatct acaaagtttc caaccgattt 180
tctggggtcc cagacaggtt cagtggcagt ggatcaggga cagatttcac actcaagatc 240
agcagagtgg aggctgagga tctgggagtt tattactgct ttcaaggttc acatgttcct 300
cctacgttcg gtgctgggac caagctggag ctgaaacggg ct 342

<210> SEQ ID NO 84
<211> LENGTH: 113
<212> TYPE: PRT
<213> ORGANISM: Mus musculus

<400> SEQUENCE: 84

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Ala Gly Thr Lys Leu Glu Leu Lys
            100                 105                 110

Arg


<210> SEQ ID NO 85
<211> LENGTH: 324
<212> TYPE: DNA
<213> ORGANISM: Mus musculus

<400> SEQUENCE: 85

gacatccaga tgactcagtc tccagcctcc ctatctgcat ctgtgggaga aactgtcacc      60

atcacatgtc gaacaactga aaatatttac agttattttg tatggtctca gcagagacag     120

ggaaaatctc ctcagctccg ggtctataat gcaaaatcct tagcagaagg tgtgccatca     180

agtttcaatg tcagtgtatc aggcacacag ttttctctga agatcaatag cctgcagcct     240

gaagattttg ggacttatca ctgtcaacac cattatggta ctccgtacac gttcggaggg     300

gggaccaggc tggaaataag acgg                                            324


<210> SEQ ID NO 86
<211> LENGTH: 108
<212> TYPE: PRT
<213> ORGANISM: Mus musculus

<400> SEQUENCE: 86

Asp Ile Gln Met Thr Gln Ser Pro Ala Ser Leu Ser Ala Ser Val Gly
 1               5                  10                  15

Glu Thr Val Thr Ile Thr Cys Arg Thr Thr Glu Asn Ile Tyr Ser Tyr
            20                  25                  30

Phe Val Trp Ser Gln Gln Arg Gln Gly Lys Ser Pro Gln Leu Arg Val
        35                  40                  45

Tyr Asn Ala Lys Ser Leu Ala Glu Gly Val Pro Ser Ser Phe Asn Val
    50                  55                  60

Ser Val Ser Gly Thr Gln Phe Ser Leu Lys Ile Asn Ser Leu Gln Pro
65                  70                  75                  80

Glu Asp Phe Gly Thr Tyr His Cys Gln His His Tyr Gly Thr Pro Tyr
                85                  90                  95

Thr Phe Gly Gly Gly Thr Arg Leu Glu Ile Arg Arg
            100                 105


<210> SEQ ID NO 87
<211> LENGTH: 339
<212> TYPE: DNA
<213> ORGANISM: Mus musculus

<400> SEQUENCE: 87
```

```
gatgttttg atgacccaaac tccactcact ttgtcggtta ccattggaca accagcttcc      60

atctcttgc aagtccagtca gagcctctta tatactaatg gaaaaaccta tttgacttgg     120

ttattccag aggccaggcca gtctccaaaa cgcctaatct atctggtgtc tgaattggac     180

tctggagtc cctgacaggtt cagtggcagt ggttcaggga cagatttcac actggaaatc     240

accagagtg gaggctgagga tttgggagtt tattactgct tgcagagtgc acattttcca     300

ttcacgttc ggctcgggcac caagctggaa atcaaacgg                            339


<210> SEQ ID NO 88
<211> LENGTH: 113
<212> TYPE: PRT
<213> ORGANISM: Mus musculus

<400> SEQUENCE: 88

Asp Val Leu Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Tyr Thr
            20                  25                  30

Asn Gly Lys Thr Tyr Leu Thr Trp Leu Phe Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Glu Ile
65                  70                  75                  80

Thr Arg Val Glu Ala Glu Asp Leu Gly Val Tyr Tyr Cys Leu Gln Ser
                85                  90                  95

Ala His Phe Pro Phe Thr Phe Gly Ser Gly Thr Lys Leu Glu Ile Lys
            100                 105                 110

Arg


<210> SEQ ID NO 89
<211> LENGTH: 339
<212> TYPE: DNA
<213> ORGANISM: Mus musculus

<400> SEQUENCE: 89

gatgttgtga tgacccaaac tccactcact ctgtcggtga ccattggaca accagcgttc      60

atctcttgca agtccagtca gagcctcttt aacactaatg gcaaaaccta tttgacttgg     120

ttaattcaga ggccaggcca gtctccacag cgcctgatct atctggtgtc caaattggac     180

tctggcgtcc cggacaggtt cagtggcagt ggctcaggga cagatttcac actgaaaatc     240

agcagagtgg aggctgagga tctgggagtt tattactgcc tgcagagtag ccattttccg     300

tttacgttcg gctcgggcac caagctggaa atcaaacgg                            339


<210> SEQ ID NO 90
<211> LENGTH: 113
<212> TYPE: PRT
<213> ORGANISM: Mus musculus

<400> SEQUENCE: 90

Asp Val Val Met Thr Gln Thr Pro Leu Thr Leu Ser Val Thr Ile Gly
 1               5                  10                  15

Gln Pro Ala Ser Ile Ser Cys Lys Ser Ser Gln Ser Leu Leu Asn Thr
            20                  25                  30

Asn Gly Lys Thr Tyr Leu Thr Trp Leu Ile Gln Arg Pro Gly Gln Ser
```

35 40 45

Pro Gln Arg Leu Ile Tyr Leu Val Ser Lys Leu Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Leu Gln Ser
85 90 95

Ser His Phe Pro Phe Thr Phe Gly Ser Gly Thr Lys Leu Glu Ile Lys
100 105 110

Arg

<210> SEQ ID NO 91
<211> LENGTH: 327
<212> TYPE: DNA
<213> ORGANISM: Mus musculus

<400> SEQUENCE: 91
gatgttgtgc taactcagtc tcctgccacc ctgtctgtga ctccaggaga tagagtcagt 60
ctttcctgca gggccagcca aaatattggc aactacctac actggtatca acagaaatca 120
catgagtctc caaggcttct catcaagtat gcttcccagt ccatctctgg gatcccctcc 180
aggttcagtg gcagtggatc agtcacagat ttcactctca atatcaacag tgtggagact 240
gaagattttg gaatgtattt ctgtcaacag agtgacacct ggcctctcac gttcggtgct 300
gggaccaagc tggagctgaa acgggct 327

<210> SEQ ID NO 92
<211> LENGTH: 108
<212> TYPE: PRT
<213> ORGANISM: Mus musculus

<400> SEQUENCE: 92

Asp Val Val Leu Thr Gln Ser Pro Ala Thr Leu Ser Val Thr Pro Gly
1 5 10 15

Asp Arg Val Ser Leu Ser Cys Arg Ala Ser Gln Asn Ile Gly Asn Tyr
20 25 30

Leu His Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Val Thr Asp Phe Thr Leu Asn Ile Asn Ser Val Glu Thr
65 70 75 80

Glu Asp Phe Gly Met Tyr Phe Cys Gln Gln Ser Asp Thr Trp Pro Leu
85 90 95

Thr Phe Gly Ala Gly Thr Lys Leu Glu Leu Lys Arg
100 105

<210> SEQ ID NO 93
<211> LENGTH: 8
<212> TYPE: PRT
<213> ORGANISM: Mus musculus

<400> SEQUENCE: 93

Thr Phe Thr Asp His Ser Ile His
1 5

<210> SEQ ID NO 94
<211> LENGTH: 8

<212> TYPE: PRT
<213> ORGANISM: Mus musculus

<400> SEQUENCE: 94

Thr Phe Thr Asn Tyr Val Ile His
1 5

<210> SEQ ID NO 95
<211> LENGTH: 8
<212> TYPE: PRT
<213> ORGANISM: Mus musculus

<400> SEQUENCE: 95

Ile Phe Thr Asp His Ala Leu His
1 5

<210> SEQ ID NO 96
<211> LENGTH: 17
<212> TYPE: PRT
<213> ORGANISM: Mus musculus

<400> SEQUENCE: 96

Tyr Ile Phe Pro Gly Asn Gly Asn Ile Glu Tyr Asn Asp Lys Phe Lys
1 5 10 15

Gly

<210> SEQ ID NO 97
<211> LENGTH: 17
<212> TYPE: PRT
<213> ORGANISM: Mus musculus

<400> SEQUENCE: 97

Tyr Leu Phe Pro Gly Asn Gly Asn Phe Glu Tyr Asn Glu Lys Phe Lys
1 5 10 15

Gly

<210> SEQ ID NO 98
<211> LENGTH: 17
<212> TYPE: PRT
<213> ORGANISM: Mus musculus

<400> SEQUENCE: 98

Tyr Ile Asn Pro Tyr Asn Asp Gly Ser Lys Tyr Asn Glu Lys Phe Lys
1 5 10 15

Gly

<210> SEQ ID NO 99
<211> LENGTH: 17
<212> TYPE: PRT
<213> ORGANISM: Mus musculus

<400> SEQUENCE: 99

Tyr Ile Phe Pro Gly Asn Gly Asn Ile Glu Tyr Asn Glu Lys Phe Lys
1 5 10 15

Gly

<210> SEQ ID NO 100
<211> LENGTH: 5
<212> TYPE: PRT
<213> ORGANISM: Mus musculus

<400> SEQUENCE: 100

-continued

```
Lys Arg Met Gly Tyr
 1              5


<210> SEQ ID NO 101
<211> LENGTH: 5
<212> TYPE: PRT
<213> ORGANISM: Mus musculus

<400> SEQUENCE: 101

Lys Lys Met Asp Tyr
 1              5


<210> SEQ ID NO 102
<211> LENGTH: 5
<212> TYPE: PRT
<213> ORGANISM: Mus musculus

<400> SEQUENCE: 102

Ala Arg Met Asp Tyr
 1              5


<210> SEQ ID NO 103
<211> LENGTH: 16
<212> TYPE: PRT
<213> ORGANISM: Mus musculus

<400> SEQUENCE: 103

Arg Ser Ser Gln Ser Ile Val His Ser Asn Gly Asn Thr Tyr Leu Glu
 1              5                   10                  15


<210> SEQ ID NO 104
<211> LENGTH: 11
<212> TYPE: PRT
<213> ORGANISM: Mus musculus

<400> SEQUENCE: 104

Arg Thr Thr Glu Asn Ile Tyr Ser Tyr Phe Val
 1              5                   10


<210> SEQ ID NO 105
<211> LENGTH: 16
<212> TYPE: PRT
<213> ORGANISM: Mus musculus

<400> SEQUENCE: 105

Lys Ser Ser Gln Ser Leu Leu Tyr Thr Asn Gly Lys Thr Tyr Leu Thr
 1              5                   10                  15


<210> SEQ ID NO 106
<211> LENGTH: 16
<212> TYPE: PRT
<213> ORGANISM: Mus musculus

<400> SEQUENCE: 106

Lys Ser Ser Gln Ser Leu Leu Asn Thr Asn Gly Lys Thr Tyr Leu Thr
 1              5                   10                  15


<210> SEQ ID NO 107
<211> LENGTH: 11
<212> TYPE: PRT
<213> ORGANISM: Mus musculus

<400> SEQUENCE: 107

Arg Ala Ser Gln Asn Ile Gly Asn Tyr Leu His
 1              5                   10
```

<210> SEQ ID NO 108
<211> LENGTH: 7
<212> TYPE: PRT
<213> ORGANISM: Mus musculus

<400> SEQUENCE: 108

Lys Val Ser Asn Arg Phe Ser
1 5

<210> SEQ ID NO 109
<211> LENGTH: 7
<212> TYPE: PRT
<213> ORGANISM: Mus musculus

<400> SEQUENCE: 109

Asn Ala Lys Ser Leu Ala Glu
1 5

<210> SEQ ID NO 110
<211> LENGTH: 7
<212> TYPE: PRT
<213> ORGANISM: Mus musculus

<400> SEQUENCE: 110

Leu Val Ser Glu Leu Asp Ser
1 5

<210> SEQ ID NO 111
<211> LENGTH: 7
<212> TYPE: PRT
<213> ORGANISM: Mus musculus

<400> SEQUENCE: 111

Leu Val Ser Lys Leu Asp Ser
1 5

<210> SEQ ID NO 112
<211> LENGTH: 7
<212> TYPE: PRT
<213> ORGANISM: Mus musculus

<400> SEQUENCE: 112

Tyr Ala Ser Gln Ser Ile Ser
1 5

<210> SEQ ID NO 113
<211> LENGTH: 9
<212> TYPE: PRT
<213> ORGANISM: Mus musculus

<400> SEQUENCE: 113

Phe Gln Gly Ser His Val Pro Pro Thr
1 5

<210> SEQ ID NO 114
<211> LENGTH: 9
<212> TYPE: PRT
<213> ORGANISM: Mus musculus

<400> SEQUENCE: 114

Gln His His Tyr Gly Thr Pro Tyr Thr
1 5

<210> SEQ ID NO 115
<211> LENGTH: 9
<212> TYPE: PRT
<213> ORGANISM: Mus musculus

<400> SEQUENCE: 115

Leu Gln Ser Ala His Phe Pro Phe Thr
1 5

<210> SEQ ID NO 116
<211> LENGTH: 9
<212> TYPE: PRT
<213> ORGANISM: Mus musculus

<400> SEQUENCE: 116

Leu Gln Ser Ser His Phe Pro Phe Thr
1 5

<210> SEQ ID NO 117
<211> LENGTH: 9
<212> TYPE: PRT
<213> ORGANISM: Mus musculus

<400> SEQUENCE: 117

Gln Gln Ser Asp Thr Trp Pro Leu Thr
1 5

<210> SEQ ID NO 118
<211> LENGTH: 5
<212> TYPE: PRT
<213> ORGANISM: Mus musculus

<400> SEQUENCE: 118

Asp His Ser Ile His
1 5

<210> SEQ ID NO 119
<211> LENGTH: 5
<212> TYPE: PRT
<213> ORGANISM: Mus musculus

<400> SEQUENCE: 119

Asn Tyr Val Ile His
1 5

<210> SEQ ID NO 120
<211> LENGTH: 5
<212> TYPE: PRT
<213> ORGANISM: Mus musculus

<400> SEQUENCE: 120

Asp His Ala Leu His
1 5

<210> SEQ ID NO 121
<211> LENGTH: 9
<212> TYPE: PRT
<213> ORGANISM: Mus musculus

<400> SEQUENCE: 121

Ile Phe Pro Gly Asn Gly Asn Ile Glu
1 5

<210> SEQ ID NO 122
<211> LENGTH: 9

<212> TYPE: PRT
<213> ORGANISM: Mus musculus

<400> SEQUENCE: 122

Leu Phe Pro Gly Asn Gly Asn Phe Glu
1 5

<210> SEQ ID NO 123
<211> LENGTH: 9
<212> TYPE: PRT
<213> ORGANISM: Mus musculus

<400> SEQUENCE: 123

Ile Asn Pro Tyr Asn Asp Gly Ser Lys
1 5

<210> SEQ ID NO 124
<211> LENGTH: 11
<212> TYPE: PRT
<213> ORGANISM: Mus musculus

<400> SEQUENCE: 124

His Leu Ala Asn Thr Tyr Tyr Tyr Phe Asp Tyr
1 5 10

<210> SEQ ID NO 125
<211> LENGTH: 5
<212> TYPE: PRT
<213> ORGANISM: Mus musculus

<400> SEQUENCE: 125

Ser Asn Gly Asn Thr
1 5

<210> SEQ ID NO 126
<211> LENGTH: 5
<212> TYPE: PRT
<213> ORGANISM: Mus musculus

<400> SEQUENCE: 126

Glu Asn Ile Tyr Ser
1 5

<210> SEQ ID NO 127
<211> LENGTH: 5
<212> TYPE: PRT
<213> ORGANISM: Mus musculus

<400> SEQUENCE: 127

Thr Ser Gly Tyr Ser
1 5

<210> SEQ ID NO 128
<211> LENGTH: 5
<212> TYPE: PRT
<213> ORGANISM: Mus musculus

<400> SEQUENCE: 128

Gln Asp Ile Lys Ser
1 5

<210> SEQ ID NO 129
<211> LENGTH: 5
<212> TYPE: PRT
<213> ORGANISM: Mus musculus

<400> SEQUENCE: 129

Gln Asn Ile Gly Asn
1 5

<210> SEQ ID NO 130
<211> LENGTH: 911
<212> TYPE: PRT
<213> ORGANISM: Artificial Sequence
<220> FEATURE:
<223> OTHER INFORMATION: Retargeted endopeptidase

<400> SEQUENCE: 130

Ile Ser Glu Phe Gly Ser Met Glu Phe Val Asn Lys Gln Phe Asn Tyr
1 5 10 15

Lys Asp Pro Val Asn Gly Val Asp Ile Ala Tyr Ile Lys Ile Pro Asn
20 25 30

Ala Gly Gln Met Gln Pro Val Lys Ala Phe Lys Ile His Asn Lys Ile
35 40 45

Trp Val Ile Pro Glu Arg Asp Thr Phe Thr Asn Pro Glu Glu Gly Asp
50 55 60

Leu Asn Pro Pro Pro Glu Ala Lys Gln Val Pro Val Ser Tyr Tyr Asp
65 70 75 80

Ser Thr Tyr Leu Ser Thr Asp Asn Glu Lys Asp Asn Tyr Leu Lys Gly
85 90 95

Val Thr Lys Leu Phe Glu Arg Ile Tyr Ser Thr Asp Leu Gly Arg Met
100 105 110

Leu Leu Thr Ser Ile Val Arg Gly Ile Pro Phe Trp Gly Gly Ser Thr
115 120 125

Ile Asp Thr Glu Leu Lys Val Ile Asp Thr Asn Cys Ile Asn Val Ile
130 135 140

Gln Pro Asp Gly Ser Tyr Arg Ser Glu Glu Leu Asn Leu Val Ile Ile
145 150 155 160

Gly Pro Ser Ala Asp Ile Ile Gln Phe Glu Cys Lys Ser Phe Gly His
165 170 175

Glu Val Leu Asn Leu Thr Arg Asn Gly Tyr Gly Ser Thr Gln Tyr Ile
180 185 190

Arg Phe Ser Pro Asp Phe Thr Phe Gly Phe Glu Glu Ser Leu Glu Val
195 200 205

Asp Thr Asn Pro Leu Leu Gly Ala Gly Lys Phe Ala Thr Asp Pro Ala
210 215 220

Val Thr Leu Ala His Glu Leu Ile His Ala Gly His Arg Leu Tyr Gly
225 230 235 240

Ile Ala Ile Asn Pro Asn Arg Val Phe Lys Val Asn Thr Asn Ala Tyr
245 250 255

Tyr Glu Met Ser Gly Leu Glu Val Ser Phe Glu Glu Leu Arg Thr Phe
260 265 270

Gly Gly His Asp Ala Lys Phe Ile Asp Ser Leu Gln Glu Asn Glu Phe
275 280 285

Arg Leu Tyr Tyr Tyr Asn Lys Phe Lys Asp Ile Ala Ser Thr Leu Asn
290 295 300

Lys Ala Lys Ser Ile Val Gly Thr Thr Ala Ser Leu Gln Tyr Met Lys
305 310 315 320

Asn Val Phe Lys Glu Lys Tyr Leu Leu Ser Glu Asp Thr Ser Gly Lys
325 330 335

-continued

```
Phe Ser Val Asp Lys Leu Lys Phe Asp Lys Leu Tyr Lys Met Leu Thr
            340                 345                 350

Glu Ile Tyr Thr Glu Asp Asn Phe Val Lys Phe Phe Lys Val Leu Asn
        355                 360                 365

Arg Lys Thr Tyr Leu Asn Phe Asp Lys Ala Val Phe Lys Ile Asn Ile
    370                 375                 380

Val Pro Lys Val Asn Tyr Thr Ile Tyr Asp Gly Phe Asn Leu Arg Asn
385                 390                 395                 400

Thr Asn Leu Ala Ala Asn Phe Asn Gly Gln Asn Thr Glu Ile Asn Asn
                405                 410                 415

Met Asn Phe Thr Lys Leu Lys Asn Phe Thr Gly Leu Phe Glu Phe Tyr
            420                 425                 430

Lys Leu Leu Cys Val Asp Gly Ile Ile Thr Ser Lys Thr Lys Ser Leu
        435                 440                 445

Ile Glu Gly Arg Phe Gly Gly Phe Thr Gly Ala Arg Lys Ser Ala Arg
    450                 455                 460

Lys Arg Lys Asn Gln Ala Leu Ala Gly Gly Gly Gly Ser Gly Gly Gly
465                 470                 475                 480

Gly Ser Gly Gly Gly Gly Ser Ala Leu Val Leu Gln Cys Ile Lys Val
                485                 490                 495

Asn Asn Trp Asp Leu Phe Phe Ser Pro Ser Glu Asp Asn Phe Thr Asn
            500                 505                 510

Asp Leu Asn Lys Gly Glu Glu Ile Thr Ser Asp Thr Asn Ile Glu Ala
        515                 520                 525

Ala Glu Glu Asn Ile Ser Leu Asp Leu Ile Gln Gln Tyr Tyr Leu Thr
    530                 535                 540

Phe Asn Phe Asp Asn Glu Pro Glu Asn Ile Ser Ile Glu Asn Leu Ser
545                 550                 555                 560

Ser Asp Ile Ile Gly Gln Leu Glu Leu Met Pro Asn Ile Glu Arg Phe
                565                 570                 575

Pro Asn Gly Lys Lys Tyr Glu Leu Asp Lys Tyr Thr Met Phe His Tyr
            580                 585                 590

Leu Arg Ala Gln Glu Phe Glu His Gly Lys Ser Arg Ile Ala Leu Thr
        595                 600                 605

Asn Ser Val Asn Glu Ala Leu Leu Asn Pro Ser Arg Val Tyr Thr Phe
    610                 615                 620

Phe Ser Ser Asp Tyr Val Lys Lys Val Asn Lys Ala Thr Glu Ala Ala
625                 630                 635                 640

Met Phe Leu Gly Trp Val Glu Gln Leu Val Tyr Asp Phe Thr Asp Glu
                645                 650                 655

Thr Ser Glu Val Ser Thr Thr Asp Lys Ile Ala Asp Ile Thr Ile Ile
            660                 665                 670

Ile Pro Tyr Ile Gly Pro Ala Leu Asn Ile Gly Asn Met Leu Tyr Lys
        675                 680                 685

Asp Asp Phe Val Gly Ala Leu Ile Phe Ser Gly Ala Val Ile Leu Leu
    690                 695                 700

Glu Phe Ile Pro Glu Ile Ala Ile Pro Val Leu Gly Thr Phe Ala Leu
705                 710                 715                 720

Val Ser Tyr Ile Ala Asn Lys Val Leu Thr Val Gln Thr Ile Asp Asn
                725                 730                 735

Ala Leu Ser Lys Arg Asn Glu Lys Trp Asp Glu Val Tyr Lys Tyr Ile
            740                 745                 750

Val Thr Asn Trp Leu Ala Lys Val Asn Thr Gln Ile Asp Leu Ile Arg
```

755 760 765

Lys Lys Met Lys Glu Ala Leu Glu Asn Gln Ala Glu Ala Thr Lys Ala
770 775 780

Ile Ile Asn Tyr Gln Tyr Asn Gln Tyr Thr Glu Glu Glu Lys Asn Asn
785 790 795 800

Ile Asn Phe Asn Ile Asp Asp Leu Ser Ser Lys Leu Asn Glu Ser Ile
805 810 815

Asn Lys Ala Met Ile Asn Ile Asn Lys Phe Leu Asn Gln Cys Ser Val
820 825 830

Ser Tyr Leu Met Asn Ser Met Ile Pro Tyr Gly Val Lys Arg Leu Glu
835 840 845

Asp Phe Asp Ala Ser Leu Lys Asp Ala Leu Leu Lys Tyr Ile Tyr Asp
850 855 860

Asn Arg Gly Thr Leu Ile Gly Gln Val Asp Arg Leu Lys Asp Lys Val
865 870 875 880

Asn Asn Thr Leu Ser Thr Asp Ile Pro Phe Gln Leu Ser Lys Tyr Val
885 890 895

Asp Asn Gln Arg Leu Leu Ser Thr Leu Glu Ala Leu Ala Ser Gly
900 905 910

<210> SEQ ID NO 131
<211> LENGTH: 904
<212> TYPE: PRT
<213> ORGANISM: Artificial Sequence
<220> FEATURE:
<223> OTHER INFORMATION: Retargeted endopeptidase

<400> SEQUENCE: 131

Met Gly Ser Met Glu Phe Val Asn Lys Gln Phe Asn Tyr Lys Asp Pro
1 5 10 15

Val Asn Gly Val Asp Ile Ala Tyr Ile Lys Ile Pro Asn Ala Gly Gln
20 25 30

Met Gln Pro Val Lys Ala Phe Lys Ile His Asn Lys Ile Trp Val Ile
35 40 45

Pro Glu Arg Asp Thr Phe Thr Asn Pro Glu Glu Gly Asp Leu Asn Pro
50 55 60

Pro Pro Glu Ala Lys Gln Val Pro Val Ser Tyr Tyr Asp Ser Thr Tyr
65 70 75 80

Leu Ser Thr Asp Asn Glu Lys Asp Asn Tyr Leu Lys Gly Val Thr Lys
85 90 95

Leu Phe Glu Arg Ile Tyr Ser Thr Asp Leu Gly Arg Met Leu Leu Thr
100 105 110

Ser Ile Val Arg Gly Ile Pro Phe Trp Gly Gly Ser Thr Ile Asp Thr
115 120 125

Glu Leu Lys Val Ile Asp Thr Asn Cys Ile Asn Val Ile Gln Pro Asp
130 135 140

Gly Ser Tyr Arg Ser Glu Glu Leu Asn Leu Val Ile Ile Gly Pro Ser
145 150 155 160

Ala Asp Ile Ile Gln Phe Glu Cys Lys Ser Phe Gly His Glu Val Leu
165 170 175

Asn Leu Thr Arg Asn Gly Tyr Gly Ser Thr Gln Tyr Ile Arg Phe Ser
180 185 190

Pro Asp Phe Thr Phe Gly Phe Glu Glu Ser Leu Glu Val Asp Thr Asn
195 200 205

Pro Leu Leu Gly Ala Gly Lys Phe Ala Thr Asp Pro Ala Val Thr Leu

-continued

```
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Gly Ser Ala Asp Asp Asp Asp Lys Gly Trp
        435                 440                 445

Thr Leu Asn Ser Ala Gly Tyr Leu Leu Gly Pro His Ala Val Ala Leu
    450                 455                 460

Ala Gly Gly Gly Gly Ser Gly Gly Gly Gly Ser Gly Gly Gly Gly Ser
465                 470                 475                 480

Ala Leu Val Leu Gln Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
            500                 505                 510

Ile Thr Ser Asp Thr Asn Ile Glu Ala Ala Glu Glu Asn Ile Ser Leu
        515                 520                 525

Asp Leu Ile Gln Gln Tyr Tyr Leu Thr Phe Asn Phe Asp Asn Glu Pro
    530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
            580                 585                 590

His Gly Lys Ser Arg Ile Ala Leu Thr Asn Ser Val Asn Glu Ala Leu
        595                 600                 605

Leu Asn Pro Ser Arg Val Tyr Thr Phe Phe Ser Ser Asp Tyr Val Lys
    610                 615                 620

Lys Val Asn Lys Ala Thr Glu Ala Ala Met Phe Leu Gly Trp Val Glu
625                 630                 635                 640
```

Gln Leu Val Tyr Asp Phe Thr Asp Glu Thr Ser Glu Val Ser Thr Thr
645 650 655

Asp Lys Ile Ala Asp Ile Thr Ile Ile Ile Pro Tyr Ile Gly Pro Ala
660 665 670

Leu Asn Ile Gly Asn Met Leu Tyr Lys Asp Asp Phe Val Gly Ala Leu
675 680 685

Ile Phe Ser Gly Ala Val Ile Leu Leu Glu Phe Ile Pro Glu Ile Ala
690 695 700

Ile Pro Val Leu Gly Thr Phe Ala Leu Val Ser Tyr Ile Ala Asn Lys
705 710 715 720

Val Leu Thr Val Gln Thr Ile Asp Asn Ala Leu Ser Lys Arg Asn Glu
725 730 735

Lys Trp Asp Glu Val Tyr Lys Tyr Ile Val Thr Asn Trp Leu Ala Lys
740 745 750

Val Asn Thr Gln Ile Asp Leu Ile Arg Lys Lys Met Lys Glu Ala Leu
755 760 765

Glu Asn Gln Ala Glu Ala Thr Lys Ala Ile Ile Asn Tyr Gln Tyr Asn
770 775 780

Gln Tyr Thr Glu Glu Glu Lys Asn Asn Ile Asn Phe Asn Ile Asp Asp
785 790 795 800

Leu Ser Ser Lys Leu Asn Glu Ser Ile Asn Lys Ala Met Ile Asn Ile
805 810 815

Asn Lys Phe Leu Asn Gln Cys Ser Val Ser Tyr Leu Met Asn Ser Met
820 825 830

Ile Pro Tyr Gly Val Lys Arg Leu Glu Asp Phe Asp Ala Ser Leu Lys
835 840 845

Asp Ala Leu Leu Lys Tyr Ile Tyr Asp Asn Arg Gly Thr Leu Ile Gly
850 855 860

Gln Val Asp Arg Leu Lys Asp Lys Val Asn Asn Thr Leu Ser Thr Asp
865 870 875 880

Ile Pro Phe Gln Leu Ser Lys Tyr Val Asp Asn Gln Arg Leu Leu Ser
885 890 895

Thr Leu Glu Ala Leu Ala Ser Gly
900

<210> SEQ ID NO 132
<211> LENGTH: 360
<212> TYPE: DNA
<213> ORGANISM: Mus musculus

<400> SEQUENCE: 132
caggtgaagc tgcaggagtc tggacctgaa ctggtaaagc ctggggcttc agtgaagatg 60
tcctgcaagg cttctggata cacattcact aactatgtta tacactgggt gaagcaaaag 120
cctgggcagg gccttgagtg gattggatat attaatcctt acaatgatgg ctctaagtac 180
aatgagaagt tcaaaggcaa ggcctcactg acttcagaca aatcctccag cacagcctac 240
atggagctca gcagcctgac ctctgaggac tctgcggtct attactgtgc aagacatctc 300
gctaatacct actactactt tgactactgg ggccaaggca ccactctcac agtctcctca 360

<210> SEQ ID NO 133
<211> LENGTH: 120
<212> TYPE: PRT
<213> ORGANISM: Mus musculus

<400> SEQUENCE: 133

```
Gln Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ser Lys Tyr Asn Glu Lys Phe
    50                  55                  60

Lys Gly Lys Ala Ser Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg His Leu Ala Asn Thr Tyr Tyr Tyr Phe Asp Tyr Trp Gly Gln
            100                 105                 110

Gly Thr Thr Leu Thr Val Ser Ser
        115                 120


<210> SEQ ID NO 134
<211> LENGTH: 5
<212> TYPE: PRT
<213> ORGANISM: Mus musculus

<400> SEQUENCE: 134

Ala Arg Met Gly Tyr
 1               5


<210> SEQ ID NO 135
<211> LENGTH: 13
<212> TYPE: PRT
<213> ORGANISM: Mus musculus

<400> SEQUENCE: 135

Ala Arg His Leu Ala Asn Thr Tyr Tyr Tyr Phe Asp Tyr
 1               5                  10


<210> SEQ ID NO 136
<211> LENGTH: 349
<212> TYPE: PRT
<213> ORGANISM: Homo sapiens

<400> SEQUENCE: 136

Met Glu Leu Ala Val Gly Asn Leu Ser Glu Gly Asn Ala Ser Trp Pro
 1               5                  10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
        35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125
```

```
Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
                165                 170                 175

Phe His Pro Arg Ala Ser Asn Gln Thr Phe Cys Trp Glu Gln Trp Pro
            180                 185                 190

Asp Pro Arg His Lys Lys Ala Tyr Val Val Cys Thr Phe Val Phe Gly
        195                 200                 205

Tyr Leu Leu Pro Leu Leu Leu Ile Cys Phe Cys Tyr Ala Lys Val Leu
    210                 215                 220

Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                245                 250                 255

Gly Ile Ser Trp Leu Pro His His Ile Ile His Leu Trp Ala Glu Phe
            260                 265                 270

Gly Val Phe Pro Leu Thr Pro Ala Ser Phe Leu Phe Arg Ile Thr Ala
        275                 280                 285

His Cys Leu Ala Tyr Ser Asn Ser Ser Val Asn Pro Ile Ile Tyr Ala
    290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
            340                 345


<210> SEQ ID NO 137
<211> LENGTH: 349
<212> TYPE: PRT
<213> ORGANISM: Homo sapiens

<400> SEQUENCE: 137

Met Glu Leu Ala Val Gly Asn Leu Ser Glu Gly Asn Ala Ser Trp Pro
 1               5                  10                  15

Glu Pro Pro Ala Pro Glu Pro Gly Pro Leu Phe Gly Ile Gly Val Glu
            20                  25                  30

Asn Phe Val Thr Leu Val Val Phe Gly Leu Ile Phe Ala Leu Gly Val
        35                  40                  45

Leu Gly Asn Ser Leu Val Ile Thr Val Leu Ala Arg Ser Lys Pro Gly
    50                  55                  60

Lys Pro Arg Ser Thr Thr Asn Leu Phe Ile Leu Asn Leu Ser Ile Ala
65                  70                  75                  80

Asp Leu Ala Tyr Leu Leu Phe Cys Ile Pro Phe Gln Ala Thr Val Tyr
                85                  90                  95

Ala Leu Pro Thr Trp Val Leu Gly Ala Phe Ile Cys Lys Phe Ile His
            100                 105                 110

Tyr Phe Phe Thr Val Ser Met Leu Val Ser Ile Phe Thr Leu Ala Ala
        115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160
```

Ala Leu Ser Ile Ala Met Ala Ser Pro Val Ala Tyr His Gln Gly Leu
165 170 175

Phe His Pro Arg Ala Ser Asn Gln Thr Phe Cys Trp Glu Gln Trp Pro
180 185 190

Asp Pro Arg His Lys Lys Ala Tyr Val Val Cys Thr Phe Val Phe Gly
195 200 205

Tyr Leu Leu Pro Leu Leu Leu Ile Cys Phe Cys Tyr Ala Lys Val Leu
210 215 220

Asn His Leu His Lys Lys Leu Lys Asn Met Ser Lys Lys Ser Glu Ala
225 230 235 240

Ser Lys Lys Lys Thr Ala Gln Thr Val Leu Val Val Val Val Val Phe
245 250 255

Gly Ile Ser Trp Leu Pro His His Ile Ile His Leu Trp Ala Glu Phe
260 265 270

Gly Val Phe Pro Leu Thr Pro Ala Ser Phe Leu Phe Arg Ile Thr Ala
275 280 285

His Cys Leu Ala Tyr Ser Asn Ser Ser Val Asn Pro Ile Ile Tyr Ala
290 295 300

Phe Leu Ser Glu Asn Phe Arg Lys Ala Tyr Lys Gln Val Phe Lys Cys
305 310 315 320

His Ile Arg Lys Asp Ser His Leu Ser Asp Thr Lys Glu Ser Lys Ser
325 330 335

Arg Ile Asp Thr Pro Pro Ser Thr Asn Cys Thr His Val
340 345

<210> SEQ ID NO 138
<211> LENGTH: 349
<212> TYPE: PRT
<213> ORGANISM: Homo sapiens

<400> SEQUENCE: 138

Met Glu Leu Ala Val Gly Asn Leu Ser Glu Gly Asn Ala Ser Cys Pro
1 5 10 15

Glu Pro Pro Ala Pro Glu Pro Gly Pro Leu Phe Gly Ile Gly Val Glu
20 25 30

Asn Phe Val Thr Leu Val Val Phe Gly Leu Ile Phe Ala Leu Gly Val
35 40 45

Leu Gly Asn Ser Leu Val Ile Thr Val Leu Ala Arg Ser Lys Pro Gly
50 55 60

Lys Pro Arg Ser Thr Thr Asn Leu Phe Ile Leu Asn Leu Ser Ile Ala
65 70 75 80

Asp Leu Ala Tyr Leu Leu Phe Cys Ile Pro Phe Gln Ala Thr Val Tyr
85 90 95

Ala Leu Pro Thr Trp Val Leu Gly Ala Phe Ile Cys Lys Phe Ile His
100 105 110

Tyr Phe Phe Thr Val Ser Met Leu Val Ser Ile Phe Thr Leu Ala Ala
115 120 125

Met Ser Val Asp Arg Tyr Val Ala Ile Val His Ser Arg Arg Ser Ser
130 135 140

Ser Leu Arg Val Ser Arg Asn Ala Leu Leu Gly Val Gly Cys Ile Trp
145 150 155 160

Ala Leu Ser Ile Ala Met Ala Ser Pro Val Ala Tyr His Gln Gly Leu
165 170 175

Phe His Pro Arg Ala Ser Asn Gln Thr Phe Cys Trp Glu Gln Trp Pro

```
            180                 185                 190

Asp Pro Arg His Lys Lys Ala Tyr Val Val Cys Thr Phe Val Phe Gly
        195                 200                 205

Tyr Leu Leu Pro Leu Leu Leu Ile Cys Phe Cys Tyr Ala Lys Val Leu
    210                 215                 220

Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                245                 250                 255

Gly Ile Ser Trp Leu Pro His His Ile Ile His Leu Trp Ala Glu Phe
            260                 265                 270

Gly Val Phe Pro Leu Thr Pro Ala Ser Phe Leu Phe Arg Ile Thr Ala
        275                 280                 285

His Cys Leu Ala Tyr Ser Asn Ser Ser Val Asn Pro Ile Ile Tyr Ala
    290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
            340                 345


<210> SEQ ID NO 139
<211> LENGTH: 387
<212> TYPE: PRT
<213> ORGANISM: Homo sapiens

<400> SEQUENCE: 139

Met Asn Val Ser Gly Cys Pro Gly Ala Gly Asn Ala Ser Gln Ala Gly
 1               5                  10                  15

Gly Gly Gly Gly Trp His Pro Glu Ala Val Ile Val Pro Leu Leu Phe
            20                  25                  30

Ala Leu Ile Phe Leu Val Gly Thr Val Gly Asn Thr Leu Val Leu Ala
        35                  40                  45

Val Leu Leu Arg Gly Gly Gln Ala Val Ser Thr Thr Asn Leu Phe Ile
    50                  55                  60

Leu Asn Leu Gly Val Ala Asp Leu Cys Phe Ile Leu Cys Cys Val Pro
65                  70                  75                  80

Phe Gln Ala Thr Ile Tyr Thr Leu Asp Gly Trp Val Phe Gly Ser Leu
                85                  90                  95

Leu Cys Lys Ala Val His Phe Leu Ile Phe Leu Thr Met His Ala Ser
            100                 105                 110

Ser Phe Thr Leu Ala Ala Val Ser Leu Asp Arg Tyr Leu Ala Ile Arg
        115                 120                 125

Tyr Pro Leu His Ser Arg Glu Leu Arg Thr Pro Arg Asn Ala Leu Ala
    130                 135                 140

Ala Ile Gly Leu Ile Trp Gly Leu Ser Leu Leu Phe Ser Gly Pro Tyr
145                 150                 155                 160

Leu Ser Tyr Tyr Arg Gln Ser Gln Leu Ala Asn Leu Thr Val Cys His
                165                 170                 175

Pro Ala Trp Ser Ala Pro Arg Arg Arg Ala Met Asp Ile Cys Thr Phe
            180                 185                 190

Val Phe Ser Tyr Leu Leu Pro Val Leu Val Leu Gly Leu Thr Tyr Ala
        195                 200                 205
```

-continued

```
Arg Thr Leu Arg Tyr Leu Trp Arg Ala Val Asp Pro Val Ala Ala Gly
    210                 215                 220

Ser Gly Ala Arg Arg Ala Lys Arg Lys Val Thr Arg Met Ile Leu Ile
225                 230                 235                 240

Val Ala Ala Leu Phe Cys Leu Cys Trp Met Pro His His Ala Leu Ile
                245                 250                 255

Leu Cys Val Trp Phe Gly Gln Phe Pro Leu Thr Arg Ala Thr Tyr Ala
            260                 265                 270

Leu Arg Ile Leu Ser His Leu Val Ser Tyr Ala Asn Ser Cys Val Asn
        275                 280                 285

Pro Ile Val Tyr Ala Leu Val Ser Lys His Phe Arg Lys Gly Phe Arg
    290                 295                 300

Thr Ile Cys Ala Gly Leu Leu Gly Arg Ala Pro Gly Arg Ala Ser Gly
305                 310                 315                 320

Arg Val Cys Ala Ala Ala Arg Gly Thr His Ser Gly Ser Val Leu Glu
                325                 330                 335

Arg Glu Ser Ser Asp Leu Leu His Met Ser Glu Ala Ala Gly Ala Leu
            340                 345                 350

Arg Pro Cys Pro Gly Ala Ser Gln Pro Cys Ile Leu Glu Pro Cys Pro
        355                 360                 365

Gly Pro Ser Trp Gln Gly Pro Lys Ala Gly Asp Ser Ile Leu Thr Val
    370                 375                 380

Asp Val Ala
385


<210> SEQ ID NO 140
<211> LENGTH: 368
<212> TYPE: PRT
<213> ORGANISM: Homo sapiens

<400> SEQUENCE: 140

Met Ala Asp Ala Gln Asn Ile Ser Leu Asp Ser Pro Gly Ser Val Gly
 1               5                  10                  15

Ala Val Ala Val Pro Val Val Phe Ala Leu Ile Phe Leu Leu Gly Thr
            20                  25                  30

Val Gly Asn Gly Leu Val Leu Ala Val Leu Leu Gln Pro Gly Pro Ser
        35                  40                  45

Ala Trp Gln Glu Pro Gly Ser Thr Thr Asp Leu Phe Ile Leu Asn Leu
    50                  55                  60

Ala Val Ala Asp Leu Cys Phe Ile Leu Cys Cys Val Pro Phe Gln Ala
65                  70                  75                  80

Thr Ile Tyr Thr Leu Asp Ala Trp Leu Phe Gly Ala Leu Val Cys Lys
                85                  90                  95

Ala Val His Leu Leu Ile Tyr Leu Thr Met Tyr Ala Ser Ser Phe Thr
            100                 105                 110

Leu Ala Ala Val Ser Val Asp Arg Tyr Leu Ala Val Arg His Pro Leu
        115                 120                 125

Arg Ser Arg Ala Leu Arg Thr Pro Arg Asn Ala Arg Ala Ala Val Gly
    130                 135                 140

Leu Val Trp Leu Leu Ala Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Trp
                165                 170                 175

Glu Asp Ala Arg Arg Arg Ala Leu Asp Val Ala Thr Phe Ala Ala Gly
            180                 185                 190
```

```
Tyr Leu Leu Pro Val Ala Val Val Ser Leu Ala Tyr Gly Arg Thr Leu
        195                 200                 205

Arg Phe Leu Trp Ala Ala Val Gly Pro Ala Gly Ala Ala Ala Ala Glu
    210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Cys
            260                 265                 270

Arg Leu Ala Ser His Cys Leu Ala Tyr Ala Asn Ser Cys Leu Asn Pro
        275                 280                 285

Leu Val Tyr Ala Leu Ala Ser Arg His Phe Arg Ala Arg Phe Arg Arg
    290                 295                 300

Leu Trp Pro Cys Gly Arg Arg Arg Arg His Arg Ala Arg Arg Ala Leu
305                 310                 315                 320

Arg Arg Val Arg Pro Ala Ser Ser Gly Pro Pro Gly Cys Pro Gly Asp
                325                 330                 335

Ala Arg Pro Ser Gly Arg Leu Leu Ala Gly Gly Gly Gln Gly Pro Glu
            340                 345                 350

Pro Arg Glu Gly Pro Val His Gly Gly Glu Ala Ala Arg Gly Pro Glu
        355                 360                 365
```

<210> SEQ ID NO 141
<211> LENGTH: 1050
<212> TYPE: DNA
<213> ORGANISM: Homo sapiens

<400> SEQUENCE: 141

```
atggagctgg cggtcgggaa cctcagcgag ggcaacgcga gctggccgga gcccccgcc      60

ccggagcccg ggccgctgtt cggcatcggc gtggagaact tcgtcacgct ggtggtgttc    120

ggcctgatct tcgcgctggg tgtgctgggc aacagcctag tgatcaccgt gctggcgcgc    180

agcaagccgg gcaagccgcg gagcaccacc aacctgttca tcctcaacct gagcatcgcc    240

gacctggcct acctgctctt ctgcatcccc ttccaggcca ccgtgtacgc gctgcccacc    300

tgggtgctgg gcgccttcat ctgcaagttc atccactact tcttcaccgt gtccatgctg    360

gtgagcatct tcaccctggc cgcgatgtcc gtggaccgct acgtggccat cgtgcactcg    420

cggcgctcct cctccctcag ggtgtcccgc aacgcgctgc tgggcgtggg ctgcatctgg    480

gcgctgtcca ttgccatggc ctcgcccgtg gcctaccacc agggcctctt ccacccgcgc    540

gccagcaacc agaccttctg ctgggagcag tggcccgacc ctcgccacaa gaaggcctac    600

gtggtgtgca ccttcgtctt cggctacctg ctgccgctcc tgctcatctg cttctgctat    660

gccaaggtcc ttaatcactt gcataaaaag ttgaagaaca tgtcaaagaa gtctgaagca    720

tccaagaaaa agactgcaca gacagttctg gtggtggttg tggtgtttgg aatctcctgg    780

ctgccgcacc acatcatcca tctctgggct gagtttggag ttttcccgct gacgccggct    840

tccttcctct tcagaatcac cgcccactgc ctggcgtaca gcaattcctc cgtgaatcct    900

atcatttatg catttctctc tgaaaatttc aggaaggcct ataaacaagt gttcaagtgt    960

cacattcgca aagattcaca cctgagtgat actaaagaaa ataaaagtcg aatagacacc   1020

ccaccatcaa ccaattgtac tcatgtgtga                                    1050
```

<210> SEQ ID NO 142
<211> LENGTH: 1050
<212> TYPE: DNA
<213> ORGANISM: Homo sapiens

<400> SEQUENCE: 142

```
atggagctgg cggtcgggaa cctcagcgag ggcaacgcga gctggccgga gccccccgcc     60
ccggagcccg ggccgctgtt cggcatcggc gtggagaact tcgtcacgct ggtggtgttc    120
ggcctgatct tcgcgctggg tgtgctgggc aacagcctag tgatcaccgt gctggcgcgc    180
agcaagccgg gcaagccgcg gagcaccacc aacctgttca tcctcaacct gagcatcgcc    240
gacctggcct acctgctctt ctgcatcccc ttccaggcca ccgtgtacgc gctgcccacc    300
tgggtgctgg gcgccttcat ctgcaagttc atccactact tcttcaccgt gtccatgctg    360
gtgagcatct tcaccctggc cgcgatgtcc gtggaccgct acgtggccat cgtgcactcg    420
cggcgctcct cctccctcag ggtgtcccgc aacgcgctgc tgggcgtggg ctgcatctgg    480
gcgctgtcca ttgccatggc ctcgcccgtg gcctaccacc agggcctctt ccacccgcgc    540
gccagcaacc agaccttctg ctgggagcag tggcccgacc ctcgccacaa gaaggcctac    600
gtggtgtgca ccttcgtctt cggctacctg ctgccgctcc tgctcatctg cttctgctat    660
gccaaggtcc ttaatcactt gcataaaaag ttgaagaaca tgtcaaagaa gtctgaagca    720
tccaagaaaa agactgcaca gacagttctg gtggtggttg tggtgtttgg aatctcctgg    780
ctgccgcacc acatcatcca tctctgggct gagtttggag ttttcccgct gacgccggct    840
tccttcctct tcagaatcac cgcccactgc ctggcgtaca gcaattcctc cgtgaatcct    900
atcatttatg catttctctc tgaaaatttc aggaaggcct ataaacaagt gttcaagtgt    960
cacattcgca aagattcaca cctgagtgat actaaagaaa gtaaaagtcg aatagacacc   1020
ccaccatcaa ccaattgtac tcatgtgtga                                    1050
```

<210> SEQ ID NO 143
<211> LENGTH: 1050
<212> TYPE: DNA
<213> ORGANISM: Homo sapiens

<400> SEQUENCE: 143

```
atggagctgg cggtcgggaa cctcagcgag ggcaacgcga gctgtccgga gccccccgcc     60
ccggagcccg ggccgctgtt cggcatcggc gtggagaact tcgtcacgct ggtggtgttc    120
ggcctgatct tcgcgctggg cgtgctgggc aacagcctag tgatcaccgt gctggcgcgc    180
agcaagccgg gcaagccgcg gagcaccacc aacctgttca tcctcaacct gagcatcgcc    240
gacctggcct acctgctctt ctgcatcccc ttccaggcca ccgtgtacgc gctgcccacc    300
tgggtgctgg gcgccttcat ctgcaagttc atccactact tcttcaccgt gtccatgctg    360
gtgagcatct tcaccctggc cgcgatgtcc gtggaccgct acgtggccat cgtgcactcg    420
cggcgctcct cctccctcag ggtgtcccgc aacgcgctgc tgggcgtggg ctgcatctgg    480
gcgctgtcca ttgccatggc ctcgcccgtg gcctaccacc agggcctctt ccacccgcgc    540
gccagcaacc agaccttctg ctgggagcag tggcccgacc ctcgccacaa gaaggcctac    600
gtggtgtgca ccttcgtctt cggctacctg ctgccgctcc tgctcatctg cttctgctat    660
gccaaggtcc ttaatcactt gcataaaaag ttgaagaaca tgtcaaagaa gtctgaagca    720
tccaagaaaa agactgcaca gacagttctg gtggtggttg tggtgtttgg aatctcctgg    780
ctgccgcacc acatcatcca tctctgggct gagtttggag ttttcccgct gacgccggct    840
```

tccttcctct tcagaatcac cgcccactgc ctggcgtaca gcaattcctc cgtgaatcct 900
atcatttatg catttctctc tgaaaatttc aggaaggcct ataaacaagt gttcaagtgt 960
cacattcgca aagattcaca cctgagtgat actaaagaaa ataaaagtcg aatagacacc 1020
ccaccatcaa ccaattgtac tcatgtgtga 1050

<210> SEQ ID NO 144
<211> LENGTH: 1164
<212> TYPE: DNA
<213> ORGANISM: Homo sapiens

<400> SEQUENCE: 144
atgaacgtct cgggctgccc aggggccggg aacgcgagcc aggcgggcgg cgggggaggc 60
tggcaccccg aggcggtcat cgtgcccctg ctcttcgcgc tcatcttcct cgtgggcacc 120
gtgggcaaca cgctggtgct ggcggtgctg ctgcgcggcg gccaggcggt cagcactacc 180
aacctgttca tccttaacct gggcgtggcc gacctgtgtt tcatcctgtg ctgcgtgccc 240
ttccaggcca ccatctacac cctggacggc tgggtgttcg gctcgctgct gtgcaaggcg 300
gtgcacttcc tcatcttcct caccatgcac gccagcagct tcacgctggc cgccgtctcc 360
ctggacaggt atctggccat ccgctacccg ctgcactccc gcgagctgcg cacgcctcga 420
aacgcgctgg cagccatcgg gctcatctgg gggctgtcgc tgctcttctc cgggccctac 480
ctgagctact accgccagtc gcagctggcc aacctgaccg tgtgccatcc cgcgtggagc 540
gcccctcgcc gccgcgccat ggacatctgc accttcgtct tcagctacct gcttcctgtg 600
ctggttctcg gcctgaccta cgcgcgcacc ttgcgctacc tctggcgcgc cgtcgacccg 660
gtggccgcgg gctcgggtgc ccggcgcgcc aagcgcaagg tgacacgcat gatcctcatc 720
gtggccgcgc tcttctgcct ctgctggatg ccccaccacg cgctcatcct ctgcgtgtgg 780
ttcggccagt tcccgctcac gcgcgccact tatgcgcttc gcatcctctc gcacctggtc 840
tcctacgcca actcctgcgt caaccccatc gtttacgcgc tggtctccaa gcacttccgc 900
aaaggcttcc gcacgatctg cgcgggcctg ctgggccgtg ccccaggccg agcctcgggc 960
cgtgtgtgcg ctgccgcgcg gggcacccac agtggcagcg tgttggagcg cgagtccagc 1020
gacctgttgc acatgagcga ggcggcgggg gcccttcgtc cctgccccgg cgcttcccag 1080
ccatgcatcc tcgagccctg tcctggcccg tcctggcagg gcccaaaggc aggcgacagc 1140
atcctgacgg ttgatgtggc ctga 1164

<210> SEQ ID NO 145
<211> LENGTH: 1107
<212> TYPE: DNA
<213> ORGANISM: Homo sapiens

<400> SEQUENCE: 145
atggctgatg cccagaacat ttcactggac agcccaggga gtgtgggggc cgtggcagtg 60
cctgtggtct ttgccctaat cttcctgctg ggcacagtgg gcaatgggct ggtgctggca 120
gtgctcctgc agcctggccc gagtgcctgg caggagcctg gcagcaccac ggacctgttc 180
atcctcaacc tggcggtggc tgacctctgc ttcatcctgt gctgcgtgcc cttccaggcc 240
accatctaca cgctggatgc ctggctcttt ggggccctcg tctgcaaggc cgtgcacctg 300
ctcatctacc tcaccatgta cgccagcagc tttacgctgg ctgctgtctc cgtggacagg 360
tacctggccg tgcggcaccc gctgcgctcg cgcgccctgc gcacgccgcg taacgcccgc 420
gccgcagtgg ggctggtgtg gctgctggcg gcgctcttct cggcgcccta cctcagctac 480

```
tacggcaccg tgcgctacgg cgcgctggag ctctgcgtgc ccgcctggga ggacgcgcgc    540

cgccgcgccc tggacgtggc caccttcgct gccggctacc tgctgcccgt ggctgtggtg    600

agcctggcct acgggcgcac gctgcgcttc ctgtgggccg ccgtgggtcc cgcgggcgcg    660

gcggcggccg aggcgcggcg gagggcgacg ggccgcgcgg ggcgcgccat gctggcggtg    720

gccgcgctct acgcgctctg ctggggtccg caccacgcgc tcatcctgtg cttctggtac    780

ggccgcttcg ccttcagccc ggccacctac gcctgccgcc tggcctcaca ctgcctggcc    840

tacgccaact cctgcctcaa cccgctcgtc tacgcgctcg cctcgcgcca cttccgcgcg    900

cgcttccgcc gcctgtggcc gtgcggccgc cgacgccgcc accgtgcccg ccgcgccttg    960

cgtcgcgtcc gccccgcgtc ctcgggccca cccggctgcc ccggagacgc ccggcctagc   1020

gggaggctgc tggctggtgg cggccagggc ccggagccca gggagggacc cgtccacggc   1080

ggagaggctg cccgaggacc ggaataa                                       1107
```

<210> SEQ ID NO 146
<211> LENGTH: 886
<212> TYPE: PRT
<213> ORGANISM: Artificial Sequence
<220> FEATURE:
<223> OTHER INFORMATION: LHn/A fragment

<400> SEQUENCE: 146

```
Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
```

-continued

```
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Gly Gly Gly Gly Glu Asn
        435                 440                 445

Leu Tyr Phe Gln Gly Gly Gly Gly Gly Asp Lys Gly Tyr Asn Lys Ala
    450                 455                 460

Phe Asn Asp Leu Cys Ile Lys Val Asn Asn Trp Asp Leu Phe Phe Ser
465                 470                 475                 480

Pro Ser Glu Asp Asn Phe Thr Asn Asp Leu Asn Lys Gly Glu Glu Ile
                485                 490                 495

Thr Ser Asp Thr Asn Ile Glu Ala Ala Glu Glu Asn Ile Ser Leu Asp
            500                 505                 510

Leu Ile Gln Gln Tyr Tyr Leu Thr Phe Asn Phe Asp Asn Glu Pro Glu
        515                 520                 525

Asn Ile Ser Ile Glu Asn Leu Ser Ser Asp Ile Ile Gly Gln Leu Glu
    530                 535                 540

Leu Met Pro Asn Ile Glu Arg Phe Pro Asn Gly Lys Lys Tyr Glu Leu
545                 550                 555                 560

Asp Lys Tyr Thr Met Phe His Tyr Leu Arg Ala Gln Glu Phe Glu His
                565                 570                 575

Gly Lys Ser Arg Ile Ala Leu Thr Asn Ser Val Asn Glu Ala Leu Leu
            580                 585                 590

Asn Pro Ser Arg Val Tyr Thr Phe Phe Ser Ser Asp Tyr Val Lys Lys
        595                 600                 605

Val Asn Lys Ala Thr Glu Ala Ala Met Phe Leu Gly Trp Val Glu Gln
    610                 615                 620

Leu Val Tyr Asp Phe Thr Asp Glu Thr Ser Glu Val Ser Thr Thr Asp
625                 630                 635                 640

Lys Ile Ala Asp Ile Thr Ile Ile Ile Pro Tyr Ile Gly Pro Ala Leu
                645                 650                 655

Asn Ile Gly Asn Met Leu Tyr Lys Asp Asp Phe Val Gly Ala Leu Ile
            660                 665                 670
```

```
Phe Ser Gly Ala Val Ile Leu Leu Glu Phe Ile Pro Glu Ile Ala Ile
        675                 680                 685

Pro Val Leu Gly Thr Phe Ala Leu Val Ser Tyr Ile Ala Asn Lys Val
    690                 695                 700

Leu Thr Val Gln Thr Ile Asp Asn Ala Leu Ser Lys Arg Asn Glu Lys
705                 710                 715                 720

Trp Asp Glu Val Tyr Lys Tyr Ile Val Thr Asn Trp Leu Ala Lys Val
                725                 730                 735

Asn Thr Gln Ile Asp Leu Ile Arg Lys Lys Met Lys Glu Ala Leu Glu
            740                 745                 750

Asn Gln Ala Glu Ala Thr Lys Ala Ile Ile Asn Tyr Gln Tyr Asn Gln
        755                 760                 765

Tyr Thr Glu Glu Glu Lys Asn Asn Ile Asn Phe Asn Ile Asp Asp Leu
    770                 775                 780

Ser Ser Lys Leu Asn Glu Ser Ile Asn Lys Ala Met Ile Asn Ile Asn
785                 790                 795                 800

Lys Phe Leu Asn Gln Cys Ser Val Ser Tyr Leu Met Asn Ser Met Ile
                805                 810                 815

Pro Tyr Gly Val Lys Arg Leu Glu Asp Phe Asp Ala Ser Leu Lys Asp
            820                 825                 830

Ala Leu Leu Lys Tyr Ile Tyr Asp Asn Arg Gly Thr Leu Ile Gly Gln
        835                 840                 845

Val Asp Arg Leu Lys Asp Lys Val Asn Asn Thr Leu Ser Thr Asp Ile
    850                 855                 860

Pro Phe Gln Leu Ser Lys Tyr Val Asp Asn Gln Arg Leu Leu Ser Thr
865                 870                 875                 880

His His His His His His
                885
```

<210> SEQ ID NO 147
<211> LENGTH: 2661
<212> TYPE: DNA
<213> ORGANISM: Artificial Sequence
<220> FEATURE:
<223> OTHER INFORMATION: LHn/A fragment

<400> SEQUENCE: 147

```
atgccgttcg taaacaaaca gttcaactat aaagacccag tcaacggcgt ggacattgcc      60

tatatcaaaa tcccgaatgc gggtcaaatg cagcccgtga aagcatttaa aatccataac     120

aaaatttggg tgatcccgga gcgcgatacg ttcacgaacc cggaagaagg agatttaaac     180

ccaccgcctg aggctaaaca ggtcccggtg tcttactatg atagcacata cctgagtacc     240

gacaatgaaa aggacaacta cctgaaaggt gttaccaaac tgttcgagcg catttattcg     300

acagatctcg gtcgcatgtt gctgacttct attgtgcgcg gcattccgtt ttggggtggt     360

agcaccatcg atacagaact caaagtgatt gacaccaact gcatcaatgt gattcagcct     420

gatgggagct accggtccga agagcttaac ctcgtaatca ttggcccgag cgcggatatt     480

atccaattcg aatgtaaatc ttttgggcat gaagtcctga atctgacgcg gaatggctat     540

ggatcgacgc agtatattcg tttttctcca gatttcacat ttggatttga agaaagcctc     600

gaagttgata cgaaccctct tttaggcgcg ggaaaattcg cgacggaccc agcggtgacc     660

ttggcacatg aacttattca tgccgggcat cgcttgtatg gaatcgccat taacccgaac     720

cgtgttttca aggtgaatac gaacgcgtat tacgagatgt cgggcttaga agtgtccttt     780
```

-continued

```
gaagaactgc gcacgtttgg cggtcatgat gcaaaattta ttgatagtct gcaagaaaac    840
gaatttcggc tgtactatta caataaattc aaagacattg catcaacctt aaacaaggcg    900
aaaagcattg tgggtaccac ggctagctta caatatatga aaacgtttt caaagaaaaa    960
tacctcctta gcgaagacac ttccggcaaa ttctctgtcg ataaactgaa atttgataaa   1020
ctgtataaaa tgctcaccga gatctacaca gaggataact ttgtcaaatt cttcaaggtc   1080
ttgaatcgga aaacctatct gaacttcgat aaagccgtct ttaagatcaa catcgtaccg   1140
aaagttaact acaccatcta tgatggcttt aatctgcgca atacgaatct ggcggcgaac   1200
tttaacggcc agaacaccga aatcaacaac atgaacttta ctaaactgaa aaattttacc   1260
ggcttgtttg aattctataa gctcctgtgt gtccgcggta ttatcaccag caaaaccaaa   1320
tccttgggcg gtggtggcga aaacctgtac ttccagggcg gtggcggtgg tgataagggc   1380
tataacaagg ccttcaatga tttatgcatc aaggtgaaca actgggactt gtttttctct   1440
ccatctgaag ataattttac taacgacttg aacaaaggag aggaaattac ttccgatacc   1500
aacatcgaag cagcggaaga gaatattagt ctagatctta ttcaacaata ttacctgacc   1560
tttaattttg ataacgagcc tgagaacatt tccattgaga atctcagctc tgacatcatc   1620
ggccagctgg aactgatgcc gaatatcgaa cgctttccta atggaaagaa atatgaattg   1680
gacaaataca ccatgttcca ctatctccgc gcgcaggagt ttgagcacgg caagtctcgt   1740
attgctctga ccaattcggt aaacgaagcc cttttaaatc cttcgcgtgt gtacaccttt   1800
ttctcaagcg attatgttaa aaaagtgaac aaggcgaccg aagcggcgat gtttttggga   1860
tgggtggaac aactggtata tgactttacg gatgaaactt ctgaagtctc gaccaccgac   1920
aaaattgccg atattaccat tatcattccc tatattggcc ctgcactgaa cattggtaac   1980
atgctgtata aagatgattt tgtgggcgcc ctgatctttt caggcgctgt tatcctgctg   2040
gaatttatcc cggaaatcgc cattccagta ctcggtacct ttgcgctggt gtcctatatc   2100
gcaaacaaag ttttgactgt ccagacgatc gacaacgcgc tcagtaaacg taacgaaaaa   2160
tgggatgagg tgtataagta tattgttacc aactggctcg ctaaagtaaa cacccagatt   2220
gacctgattc gcaagaagat gaaagaagcg ctggaaaacc aagcagaagc gaccaaagct   2280
attatcaact atcaatataa ccagtacaca gaggaagaaa agaataacat caacttcaac   2340
atcgacgact tatcttcaaa gctgaatgaa tctattaaca aagcgatgat taatattaac   2400
aagttcttga accaatgtag tgtcagctat ctgatgaact cgatgatccc ttacggtgtg   2460
aaacgtctgg aagacttcga tgcaagcctt aaagatgccc ttctgaagta tatttacgat   2520
aatcgcggaa ctcttattgg ccaagtggat cgcttaaaag ataaagtcaa caacacgctg   2580
agtacagaca tccctttca gctgtctaaa tatgtggaca atcagcgcct gctgtccacg   2640
caccatcacc atcaccacta a                                             2661
```

<210> SEQ ID NO 148
<211> LENGTH: 20
<212> TYPE: DNA
<213> ORGANISM: Artificial Sequence
<220> FEATURE:
<223> OTHER INFORMATION: ORL-1 forward oligonucleotide primer

<400> SEQUENCE: 148

```
cactcggctg gtgctggtgg                                                 20
```

<210> SEQ ID NO 149
<211> LENGTH: 20

-continued

```
<212> TYPE: DNA
<213> ORGANISM: Artificial Sequence
<220> FEATURE:
<223> OTHER INFORMATION: ORL-1 reverse oligonucleotide primer

<400> SEQUENCE: 149

aatggccacg gcagtctcgc                                              20


<210> SEQ ID NO 150
<211> LENGTH: 20
<212> TYPE: DNA
<213> ORGANISM: Artificial Sequence
<220> FEATURE:
<223> OTHER INFORMATION: Galanin receptor 1 forward oligonucleotide
      primer

<400> SEQUENCE: 150

ccccatcatg tcatccacct                                              20


<210> SEQ ID NO 151
<211> LENGTH: 20
<212> TYPE: DNA
<213> ORGANISM: Artificial Sequence
<220> FEATURE:
<223> OTHER INFORMATION: Galanin receptor 1 reverse oligonucleotide
      primer

<400> SEQUENCE: 151

atggggttca ccgaggagtt                                              20


<210> SEQ ID NO 152
<211> LENGTH: 18
<212> TYPE: DNA
<213> ORGANISM: Artificial Sequence
<220> FEATURE:
<223> OTHER INFORMATION: Galanin receptor 2 forward oligonucleotide
      primer

<400> SEQUENCE: 152

catcgtggcg gtgctttt                                                18


<210> SEQ ID NO 153
<211> LENGTH: 18
<212> TYPE: DNA
<213> ORGANISM: Artificial Sequence
<220> FEATURE:
<223> OTHER INFORMATION: Galanin receptor 2 reverse oligonucleotide
      primer

<400> SEQUENCE: 153

agcgggaagc gaccaaac                                                18
```

We claim:

1. A method of detecting the activity of retargeted endopeptidase in a sample, wherein the retargeted endopeptidase comprises an enzymatic domain, the method comprising (a) contacting a cell with a sample suspected of comprising a retargeted endopeptidase, wherein the cell is from an established cell line expressing a SNAP-25 polypeptide consisting essentially of at least a portion of human SNAP-25 comprising SEQ ID NO:5 cleavage by the enzymatic domain, and wherein the established cell line is susceptible to intoxication by the retargeted endopeptidase at about or less than 50 nmol per liter culture medium, as indicated by the enzymatic cleavage of the SNAP-25 polypeptide by the enzymatic domain to yield a fragment of said SNAP-25 polypeptide comprising the amino acid sequence of SEQ ID NO:38;

(b) isolating polypeptides from the cell;

(c) contacting the polypeptides with an antibody selected from the group consisting of 1D3B8 having a heavy chain variable region comprising amino acid sequence of SEQ ID NO: 72 and a light chain variable region comprising the amino acid sequence of SEQ ID NO: 84, 2E2A6 having a heavy chain variable region comprising amino acid sequence SEQ ID NO: 76 and a light chain variable region comprising the amino acid sequence of SEQ ID NO: 88, 3C1A5 having a heavy chain variable region comprising the amino acid sequence of SEQ ID NO: 78 and a light chain variable region comprising the amino acid sequence SEQ ID NO: 90, and 3C3E2 having a heavy chain variable region comprising amino acid sequence of SEQ ID NO: 80 or SEQ ID NO: 82 and a light chain variable region comprising the amino acid sequence of SEQ ID NO: 92; and (d) detecting the presence of the antibody-polypeptide complex, wherein a higher amount of the antibody-polypeptide complex detected correlates to a higher amount of activity of the retargeted endopeptidase in the sample.

2. The method of claim 1, wherein the antibody is 2E2A6 having a heavy chain variable region comprising amino acid sequence SEQ ID NO: 76 and a light chain variable region comprising the amino acid sequence of SEQ ID NO: 88.

3. The method of claim 1, wherein the antibody is 3C1A5 having a heavy chain variable region comprising the amino acid sequence of SEQ ID NO: 78 and a light chain variable region comprising the amino acid sequence SEQ ID NO: 90.

4. A method of detecting the activity of retargeted endopeptidase in a sample, wherein the retargeted endopeptidase comprises an enzymatic domain, the method comprising (a) contacting a cell with a sample suspected of comprising a retargeted endopeptidase, wherein the cell is from an established cell line expressing a SNAP-25 polypeptide consisting essentially of at least a portion of human SNAP-25 comprising SEQ ID NO:5 cleavage by the enzymatic domain, and wherein the established cell line is susceptible to intoxication by the retargeted endopeptidase at about or less than 50 nmol per liter culture medium, as indicated by the enzymatic cleavage of the SNAP-25 polypeptide by the enzymatic domain to yield a fragment of said SNAP-25 polypeptide comprising the amino acid sequence of SEQ ID NO:38;

(b) isolating polypeptides from the cell;

(c) contacting the polypeptides with an antibody comprising a heavy chain variable region comprising complementary determining regions (CDRs) comprising the amino acid sequences of at least one of SEQ ID NOs: 95, 99 and 101 and a light chain variable region comprising CDRs comprising the amino acid sequences of at least one of SEQ ID NOs: 103, 108 and 113; a heavy chain variable region comprising complementary determining regions (CDRs) comprising the amino acid sequences of at least one of SEQ ID NOs: 93, 96 and 100 and a light chain variable region comprising CDRs comprising the amino acid sequences of at least one of SEQ ID NOs: 105, 110 and 115; a heavy chain variable region comprising complementary determining regions (CDRs) comprising the amino acid sequences of at least one of SEQ ID NOs: 93, 97 and 100 and a light chain variable region comprising CDRs comprising the amino acid sequences of at least one of SEQ ID NOs: 106, 111 and 116; or a heavy chain variable region comprising complementary determining regions (CDRs) comprising the amino acid sequences of at least one of SEQ ID NOs: 94, 98 and 102, 134 or 135 and a light chain variable region comprising CDRs comprising the amino acid sequences of at least one of SEQ ID NOs: 107, 112 and 117; and (d) detecting the presence of the antibody-polypeptide complex, wherein a higher amount of the antibody-polypeptide complex detected correlates to a higher amount of activity of the retargeted endopeptidase in the sample.

* * * * *